(12) United States Patent
Heinemann et al.

(10) Patent No.: US 11,497,212 B2
(45) Date of Patent: Nov. 15, 2022

(54) SUBSTITUTED THIOPHENYL URACILS, SALTS THEREOF AND THE USE THEREOF AS HERBICIDAL AGENTS

(71) Applicant: Syngenta Crop Protection AG, Basel (CH)

(72) Inventors: Ines Heinemann, Hofheim (DE); Jens Frackenpohl, Frankfurt (DE); Lothar Willms, Hillscheid (DE); Roland Beffa, Liederbach (DE); Hansjörg Dietrich, Liederbach am Taunus (DE); Elmar Gatzweiler, Bad Nauheim (DE); Anu Bheemaiah Machettira, Frankfurt am Main (DE); Christopher Hugh Rosinger, Hofheim (DE); Peter Lümmen, Idstein (DE); Elisabeth Asmus, Hösbach (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/955,554

(22) PCT Filed: Dec. 17, 2018

(86) PCT No.: PCT/EP2018/085263
§ 371 (c)(1),
(2) Date: Jun. 18, 2020

(87) PCT Pub. No.: WO2019/121544
PCT Pub. Date: Jun. 27, 2019

(65) Prior Publication Data
US 2020/0315174 A1   Oct. 8, 2020

(30) Foreign Application Priority Data
Dec. 19, 2017   (EP) .................... EP17208490

(51) Int. Cl.
| C07D 405/12 | (2006.01) |
| A01N 43/54 | (2006.01) |
| C07D 409/12 | (2006.01) |
| C07D 493/08 | (2006.01) |
| C07D 493/04 | (2006.01) |

(52) U.S. Cl.
CPC ........... *A01N 43/54* (2013.01); *C07D 405/12* (2013.01); *C07D 409/12* (2013.01); *C07D 493/04* (2013.01); *C07D 493/08* (2013.01)

(58) Field of Classification Search
CPC .. C07D 405/12; C07D 409/12; C07D 239/54; C07D 493/04; C07D 493/08; A01N 43/54
See application file for complete search history.

(56) References Cited

U.S. PATENT DOCUMENTS

| 4,943,309 A | 7/1990 | Bell |
| 5,084,084 A | 1/1992 | Satow et al. |
| 5,127,935 A | 7/1992 | Satow et al. |
| 6,403,534 B1 | 6/2002 | Komori et al. |
| 2013/0154396 A1 | 6/2013 | Chou |

FOREIGN PATENT DOCUMENTS

| DE | 4437197 A1 | 4/1996 |
| EP | 408382 A2 | 1/1991 |
| EP | 473551 A1 | 3/1992 |
| EP | 648749 A2 | 4/1995 |
| EP | 714602 A1 | 6/1996 |
| JP | 09188676 A * | 7/1997 |
| JP | 2000302764 A | 10/2000 |
| JP | 2001055382 A * | 2/2001 |
| JP | 2001172265 A | 6/2001 |
| JP | 2009188676 A | 8/2009 |
| JP | 2011189506 A | 9/2011 |
| KR | 20110110420 A | 10/2011 |
| KR | 101402876 B1 * | 6/2014 |
| WO | 9100278 A1 | 1/1991 |
| WO | 9529168 A1 | 11/1995 |
| WO | 9530661 A1 | 11/1995 |
| WO | 9607323 A1 | 3/1996 |
| WO | 9608151 A1 | 3/1996 |

(Continued)

OTHER PUBLICATIONS

Machine English translations of JP1997-1188676, no pagination, 1997.*

(Continued)

*Primary Examiner* — Erin E Hirt
(74) *Attorney, Agent, or Firm* — BakerHostetler; Toni-Junell Herbert

(57) ABSTRACT

The invention relates to substituted thiophenyl uracils of general formula (I) or the salts (I) thereof, wherein the groups in general formula (I) are as defined in the description, and to the use thereof as herbicides, in particular for controlling weeds and/or weed grasses in crops of cultivated plants and/or as plant growth regulators for influencing the growth of crops of cultivated plants.

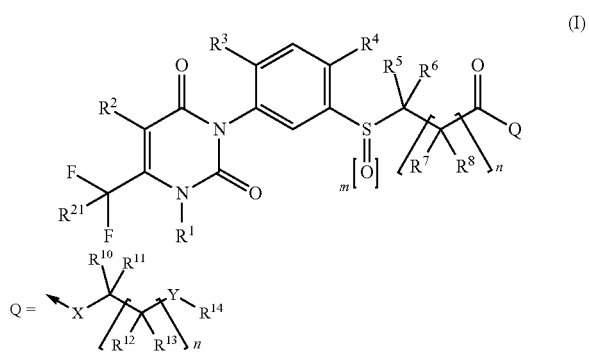

4 Claims, No Drawings

(56) References Cited

FOREIGN PATENT DOCUMENTS

| | | |
|---|---|---|
| WO | 9635679 A1 | 11/1996 |
| WO | 9701541 A1 | 1/1997 |
| WO | 9825909 A1 | 6/1998 |
| WO | 2001039597 A2 | 6/2001 |
| WO | 2010038953 A2 | 4/2010 |
| WO | 2013154396 A1 | 10/2013 |

OTHER PUBLICATIONS

Love to Know "How to Kill Weeds" https://web.archive.org/web/20070817202338/https://garden.lovetoknow.com/wiki/How_to_Kill_Weeds, wayback machine cached Aug. 17, 2007, no pagination. (Year: 2007).*

TAMU "Calculating Dilutions and site size" cached wayback machine, May 17, 2002, https://web.archive.org/web/20020517125641/http://hortipm.tamu.edu/ipmguide/ento/chapters/dilution.html, no pagination. (Year: 2002).*

EPA fact sheet of glyphosate (https://www3.epa.gov/pesticides/chem_search/reg_actions/reregistration/fs_PC-417300_1-Sep-93.pdf, p. 1-7, Dated Sep. 1993.*

Patani, G. A. et al. "Bioisosterism: A rational approach in drug design" Chemical Reviews, 1996, 96(8), 3147-3176.*

* cited by examiner

SUBSTITUTED THIOPHENYL URACILS, SALTS THEREOF AND THE USE THEREOF AS HERBICIDAL AGENTS

CROSS-REFERENCE TO RELATED APPLICATIONS

This application is a 371 National Stage application of International Application No. PCT/EP2018/085263 filed Dec. 17, 2018 which claims priority to EP 17208490.7, filed Dec. 19, 2017, the entire contents of which applications are hereby incorporated by reference.

The invention relates to the technical field of crop protection products, especially that of the herbicides for selective control of broad-leaved weeds and weed grasses in crops of useful plants.

Specifically, this invention relates to substituted thiophenyluracils and salts thereof, to processes for preparation thereof and to the use thereof as herbicides, especially for control of broad-leaved weeds and/or weed grasses in crops of useful plants and/or as plant growth regulators for influencing the growth of crops of useful plants.

Crop protection products known to date for selective control of harmful plants in crops of useful plants or active ingredients for control of unwanted plant growth have some disadvantages on employment, whether in that they have (a) no or else inadequate herbicidal action against particular harmful plants, (b) too small a spectrum of harmful plants that can be controlled by an active ingredient, (c) too low a selectivity in crops of useful plants and/or (d) a toxicologically unfavorable profile. Furthermore, some active ingredients that can be used as plant growth regulators for some useful plants lead to undesirably reduced harvest yields for other useful plants, or are compatible with the crop plant only within a narrow range of application rates, if at all. Some of the known active ingredients cannot be produced economically on an industrial scale owing to the difficulty of obtaining precursors and reagents, or have only inadequate chemical stabilities. For other active ingredients, the effect depends too significantly on environmental conditions, such as weather and soil conditions.

The herbicidal action of these known compounds, especially at low application rates, and compatibility thereof with crop plants remain in need of improvement.

It is known from various documents that particular substituted N-linked aryluracils can be used as active herbicidal ingredients (cf. EP408382, EP473551, EP648749, U.S. Pat. Nos. 4,943,309, 5,084,084, 5,127,935, WO91/00278, WO95/29168, WO95/30661, WO96/35679, WO97/01541, WO98/25909, WO2001/39597). However, the known aryluracils have a number of gaps in their action, particularly against monocotyledonous weeds. A number of active herbicidal ingredient combinations based on N-linked aryluracils have likewise become known (cf. DE4437197, EP714602, WO96/07323, WO96/08151, JP11189506). However, the properties of these combinations of active ingredients were not satisfactory in all aspects.

It is also known that particular N-aryluracils having optionally further-substituted lactic acid groups can also be used as active herbicidal ingredients (cf. JP2000/302764, JP2001/172265, U.S. Pat. No. 6,403,534, EP408382). It is additionally known that N-aryluracils having specific, optionally further-substituted thiolactic acid groups likewise show herbicidal effects (cf. WO2010/038953, KR2011110420). Particular substituted tetrahydrofuryl esters of N-aryluracils having optionally further-substituted thiolactic acid groups are described in JP09188676.

Substituted thiophenyluracils, by contrast, are essentially yet to be described. It has now been found that, surprisingly, particular substitute thiophenyluracils or salts thereof have good suitability as herbicides and can be used particularly advantageously as active ingredients for control of monocotyledonous and dicotyledonous weeds in crops of useful plants.

The present invention thus provides substituted thiophenyluracils of the general formula (I) or salts thereof

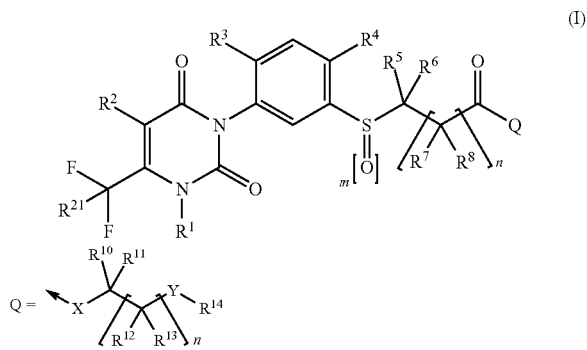

in which
$R^1$ is $(C_1-C_8)$-alkyl, amino, $NR^{17}R^{18}$,
$R^2$ is hydrogen, $(C_1-C_8)$-alkyl,
$R^3$ is hydrogen, halogen, $(C_1-C_8)$-alkoxy,
$R^4$ is halogen, cyano, $NO_2$, $C(O)NH_2$, $C(S)NH_2$, $(C_1-C_8)$-haloalkyl, $(C_2-C_8)$-alkynyl,
$R^5$ and $R^6$ are independently hydrogen, halogen, $(C_1-C_8)$-alkyl, $(C_3-C_8)$-cycloalkyl, $(C_3-C_8)$-cycloalkyl-$(C_1-C_5)$-alkyl, $(C_2-C_8)$-alkenyl, $(C_2-C_8)$-alkynyl, $(C_1-C_{10})$-haloalkyl, $(C_2-C_8)$-haloalkenyl, $(C_2-C_8)$-haloalkynyl, $(C_3-C_{10})$-halocycloalkyl, $(C_4-C_{10})$-cycloalkenyl, $(C_4-C_{10})$-halocycloalkenyl, $(C_1-C_8)$-alkoxy, $(C_1-C_8)$-alkoxy-$(C_1-C_8)$-alkyl, $(C_1-C_8)$-alkoxy-$(C_1-C_8)$-haloalkyl, $(C_1-C_8)$-haloalkoxy-$(C_1-C_8)$-haloalkyl, $(C_1-C_8)$-haloalkoxy-$(C_1-C_8)$-alkyl, aryl, aryl-$(C_1-C_8)$-alkyl, heteroaryl, heteroaryl-$(C_1-C_8)$-alkyl, $(C_4-C_{10})$-cycloalkenyl-$(C_1-C_8)$-alkyl, heterocyclyl, heterocyclyl-$(C_1-C_8)$-alkyl, $(C_1-C_8)$-alkylthio-$(C_1-C_8)$-alkyl, $(C_1-C_8)$-haloalkylthio-$(C_1-C_8)$-alkyl, $(C_1-C_8)$-alkylcarbonyl-$(C_1-C_8)$-alkyl, $C(O)OR^{19}$, $C(O)NR^{17}R^{18}$, $C(O)R^{19}$, $R^{19}O(O)C$—$(C_1-C_8)$-alkyl, $R^{17}R^{18}N(O)C$—$(C_1-C_8)$-alkyl, $R^{17}R^{18}N$—$(C_1-C_8)$-alkyl, or $R^5$ and $R^6$ together with the carbon atom to which they are bonded form a fully saturated or partly saturated 3- to 10-membered monocyclic or bicyclic ring optionally interrupted by heteroatoms and optionally having further substitution, or $R^5$ and $R^6$ together with the carbon atom to which they are bonded form a double bond optionally substituted by $R^{22}$ and $R^{23}$, according to formula (I') below

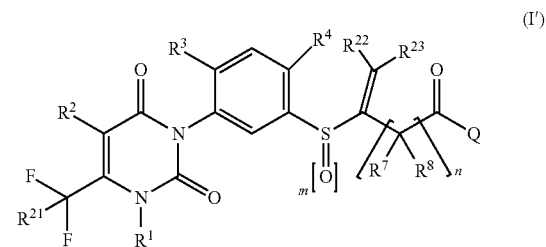

-continued

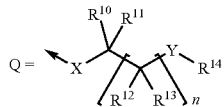

$R^7$ and $R^8$ are independently hydrogen, halogen, $(C_1-C_8)$-alkyl, $(C_3-C_8)$-cycloalkyl, $(C_3-C_8)$-cycloalkyl-$(C_1-C_8)$-alkyl, $(C_2-C_8)$-alkenyl, $(C_2-C_8)$-alkynyl, $(C_1-C_{10})$-haloalkyl, $(C_2-C_8)$-haloalkenyl, $(C_2-C_8)$-haloalkynyl, $(C_3-C_{10})$-halocycloalkyl, $(C_1-C_8)$-alkoxy-$(C_1-C_8)$-alkyl, $(C_1-C_8)$-alkoxy-$(C_1-C_8)$-haloalkyl, $(C_1-C_5)$-haloalkoxy-$(C_1-C_5)$-haloalkyl, $(C_1-C_5)$-haloalkoxy-$(C_1-C_8)$-alkyl, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, $(C_1-C_5)$-alkylthio-$(C_1-C_8)$-alkyl, $(C_1-C_5)$-haloalkylthio-$(C_1-C_8)$-alkyl, $C(O)OR^{19}$, $C(O)NR^{17}R^{18}$, $C(O)R^{19}$, $R^{19}O(O)C—(C_1-C_8)$-alkyl, $R^{17}R^{18}N(O)C—(C_1-C_8)$-alkyl, $R^{17}R^{18}N—(C_1-C_8)$-alkyl, or $R^7$ and $R^8$ together with the carbon atom to which they are bonded form a fully saturated or partly saturated 3- to 10-membered monocyclic or bicyclic ring optionally interrupted by heteroatoms and optionally having further substitution, or $R^7$ and $R^8$ together with the carbon atom to which they are bonded form a double bond optionally substituted by $R^{22}$ and $R^{23}$, according to formula (I″) below

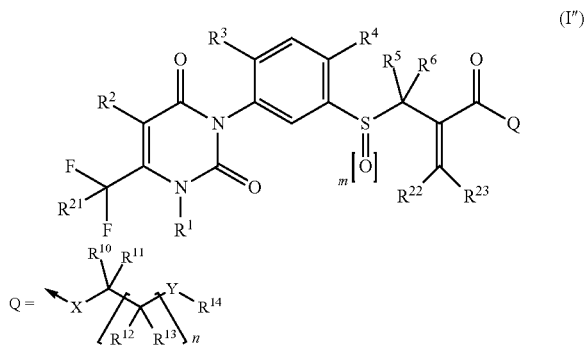

(I″)

m is 0, 1, 2,
n is 0, 1, 2, 3, 4, 5, 6,
p is 1, 2, 3,
X is O (oxygen), N (nitrogen) or the N—$R^{15}$ or N—O—$R^{16}$ moieties, and where $R^{15}$ and $R^{16}$ in the N—$R^{15}$ and N—O—$R^{16}$ moiety independently have the meanings according to the definitions below,
Y is O (oxygen) or S (sulfur), SO, $SO_2$,
$R^{10}$ and $R^{11}$ are independently hydrogen, fluorine, cyano, $(C_1-C_8)$-alkyl, $(C_3-C_8)$-cycloalkyl, $(C_3-C_8)$-cycloalkyl-$(C_1-C_8)$-alkyl, $(C_2-C_8)$-alkenyl, $(C_2-C_8)$-alkynyl, $(C_1-C_{10})$-haloalkyl, aryl, aryl-$(C_1-C_8)$-alkyl, heteroaryl, heteroaryl-$(C_1-C_8)$-alkyl, $(C_4-C_{10})$-cycloalkenyl-$(C_1-C_8)$-alkyl, heterocyclyl, heterocyclyl-$(C_1-C_8)$-alkyl, $R^{19}O—(C_1-C_8)$-alkyl, $R^{20}S—(C_1-C_8)$-alkyl, $R^{20}SO_2—(C_1-C_8)$-alkyl, or $R^{10}$ and $R^{11}$ together with the carbon atom to which they are bonded form a fully saturated or partly saturated 3- to 10-membered monocyclic or bicyclic ring optionally interrupted by heteroatoms and optionally having further substitution, $R^{12}$ and $R^{13}$ are independently hydrogen, fluorine, $(C_1-C_8)$-alkyl, $(C_3-C_8)$-cycloalkyl, $(C_3-C_8)$-cycloalkyl-$(C_1-C_8)$-alkyl, $(C_2-C_8)$-alkenyl, $(C_2-C_8)$-alkynyl, $(C_1-C_{10})$-haloalkyl, $(C_2-C_8)$-haloalkenyl, $(C_2-C_8)$-haloalkynyl, $(C_3-C_{10})$-halocycloalkyl, $(C_4-C_{10})$-cycloalkenyl, $(C_4-C_{10})$-halocycloalkenyl, $(C_1-C_8)$-alkoxy-$(C_1-C_8)$-haloalkyl, $(C_1-C_8)$-haloalkoxy-$(C_1-C_8)$-haloalkyl, aryl, aryl-$(C_1-C_8)$-alkyl, heteroaryl, heteroaryl-$(C_1-C_8)$-alkyl, $(C_4-C_{10})$-cycloalkenyl-$(C_1-C_8)$-alkyl, heterocyclyl, heterocyclyl-$(C_1-C_8)$-alkyl, $R^{19}O—(C_1-C_8)$-alkyl, $R^{20}S—(C_1-C_8)$-alkyl, $R^{20}SO_2—(C_1-C_8)$-alkyl, $R^{17}R^{18}N—(C_1-C_8)$-alkyl, or $R^{12}$ and $R^{13}$ together with the carbon atom to which they are bonded form a fully saturated or partly saturated 3- to 10-membered monocyclic or bicyclic ring optionally interrupted by heteroatoms and optionally having further substitution, or $R^{14}$ is $(C_1-C_8)$-alkyl, $(C_1-C_8)$-haloalkyl, $(C_3-C_8)$-cycloalkyl, $(C_3-C_8)$-cycloalkyl-$(C_1-C_8)$-alkyl, $(C_2-C_8)$-alkenyl, $(C_2-C_8)$-alkynyl, $(C_1-C_8)$-alkoxy-$(C_1-C_8)$-alkyl, $(C_1-C_8)$-haloalkoxy-$(C_1-C_8)$-alkyl, aryl, aryl-$(C_1-C_8)$-alkyl, heteroaryl, heteroaryl-$(C_1-C_8)$-alkyl, heterocyclyl, heterocyclyl-$(C_1-C_8)$-alkyl, $(C_1-C_8)$-alkylthio-$(C_1-C_8)$-alkyl, $(C_1-C_8)$-haloalkylthio-$(C_1-C_8)$-alkyl, $R^{17}R^{18}N—(C_1-C_8)$-alkyl, cyano-$(C_1-C_8)$-alkyl, or $R^{10}$ and $R^{14}$ together with the carbon atoms to which they are bonded form a fully saturated or partly saturated 3- to 10-membered monocyclic or bicyclic ring optionally interrupted by heteroatoms and optionally having further substitution, or $R^{12}$ and $R^{14}$ together with the carbon atoms to which they are bonded form a fully saturated or partly saturated 3- to 10-membered monocyclic or bicyclic ring optionally interrupted by heteroatoms and optionally having further substitution, $R^{15}$ is hydrogen, $(C_1-C_8)$-alkyl, $(C_3-C_8)$-cycloalkyl, cyano-$(C_1-C_8)$-alkyl, $(C_3-C_8)$-cycloalkyl-$(C_1-C_8)$-alkyl, $(C_1-C_8)$-alkylsulfonyl, arylsulfonyl, heteroarylsulfonyl, $(C_3-C_8)$-cycloalkylsulfonyl, heterocyclylsulfonyl, aryl-$(C_1-C_8)$-alkylsulfonyl, $(C_1-C_8)$-alkylcarbonyl, arylcarbonyl, heteroarylcarbonyl, $(C_3-C_8)$-cycloalkylcarbonyl, heterocyclylcarbonyl, $(C_1-C_8)$-alkoxycarbonyl, $(C_1-C_8)$-alkoxy, $(C_2-C_8)$-alkenyloxy, aryl-$(C_1-C_8)$-alkoxycarbonyl, $(C_1-C_8)$-haloalkylcarbonyl, $(C_2-C_8)$-alkenyl, $(C_2-C_8)$-alkynyl, $(C_1-C_8)$-haloalkyl, halo-$(C_2-C_8)$-alkynyl, halo-$(C_2-C_8)$-alkenyl, $(C_1-C_8)$-alkoxy-$(C_1-C_8)$-alkyl, amino, $(C_1-C_8)$-alkylamino, bis[$(C_1-C_8)$-alkyl]amino, $(C_1-C_8)$-alkoxy-$(C_1-C_8)$-alkoxy-$(C_1-C_8)$-alkyl, heteroaryl-$(C_1-C_8)$-alkylsulfonyl, heterocyclyl-$(C_1-C_8)$-alkylsulfonyl, $(C_2-C_8)$-alkenyloxycarbonyl, $(C_2-C_8)$-alkynyloxycarbonyl, $(C_1-C_8)$-alkylaminocarbonyl, $(C_3-C_8)$-cycloalkylaminocarbonyl, bis-[$(C_1-C_8)$-alkyl]aminocarbonyl, $R^{16}$ is hydrogen, $(C_1-C_8)$-alkyl, $(C_3-C_8)$-cycloalkyl-$(C_1-C_8)$-alkyl, $(C_2-C_8)$-alkenyl, $(C_2-C_8)$-alkynyl, $(C_1-C_8)$-alkoxy-$(C_1-C_8)$-alkyl, aryl, aryl-$(C_1-C_8)$-alkyl, $R^{19}O(O)C—(C_1-C_8)$-alkyl, $R^{17}R^{18}N(O)C—(C_1-C_8)$-alkyl, $R^{17}$ and $R^{18}$ are the same or different and are independently hydrogen, $(C_1-C_8)$-alkyl, $(C_2-C_8)$-alkenyl, $(C_2-C_8)$-alkynyl, $(C_1-C_8)$-cyanoalkyl, $(C_1-C_{10})$-haloalkyl, $(C_2-C_8)$-haloalkenyl, $(C_2-C_8)$-haloalkynyl, $(C_3-C_{10})$-cycloalkyl, $(C_3-C_{10})$-halocycloalkyl, $(C_4-C_{10})$-cycloalkenyl, $(C_4-C_{10})$-halocycloalkenyl, $(C_1-C_8)$-alkoxy-$(C_1-C_8)$-alkyl, $(C_1-C_8)$-haloalkoxy-$(C_1-C_8)$-alkyl, $(C_1-C_8)$-alkylthio-$(C_1-C_8)$-alkyl, $(C_1-C_8)$-haloalkylthio-$(C_1-C_8)$-alkyl, $(C_1-C_8)$-alkoxy-$(C_1-C_8)$-haloalkyl, aryl, aryl-$(C_1-C_8)$-alkyl, heteroaryl, heteroaryl-$(C_1-C_8)$-alkyl, $(C_3-C_8)$-cycloalkyl-$(C_1-C_8)$-alkyl, $(C_4-C_{10})$-cycloalkenyl-$(C_1-C_8)$-alkyl, COR$^{19}$, SO$_2$R$^{20}$, (C$_1$-C$_8$)-alkyl-HNO$_2$S—, (C$_3$-C$_8$)-cycloalkyl-HNO$_2$S—, heterocyclyl, (C$_1$-C$_8$)-alkoxycarbonyl-(C$_1$-C$_8$)-alkyl, (C$_1$-C$_8$)-alkoxycarbonyl, aryl-(C$_1$-C$_8$)-alkoxycarbonyl-(C$_1$-C$_8$)-alkyl, aryl-(C$_1$-C$_8$)-alkoxycarbonyl, heteroaryl-(C$_1$-C$_8$)-alkoxycarbonyl, (C$_2$-C$_8$)-alkenyloxycarbonyl, (C$_2$-C$_8$)-alkynyloxycarbonyl, heterocyclyl-(C$_1$-C$_8$)-alkyl, R$^{19}$ is hydrogen, (C$_1$-C$_8$)-alkyl, (C$_2$-C$_8$)-alkenyl, (C$_2$-C$_8$)-alkynyl, (C$_1$-C$_8$)-cyanoalkyl, (C$_1$-C$_{10}$)-haloalkyl, (C$_2$-C$_8$)-haloalkenyl, (C$_2$-C$_8$)-haloalkynyl, (C$_3$-C$_{10}$)-cycloalkyl, (C$_3$-C$_{10}$)-halocycloalkyl, (C$_4$-C$_{10}$)-cycloalkenyl, (C$_4$-C$_{10}$)-halocycloalkenyl, (C$_1$-C$_8$)-alkoxy-(C$_1$-C$_8$)-alkyl, (C$_1$-C$_8$)-alkoxy-(C$_1$-C$_8$)-haloalkyl, aryl, aryl-(C$_1$-C$_8$)-alkyl, heteroaryl, heteroaryl-(C$_1$-C$_8$)-alkyl, (C$_3$-C$_8$)-cycloalkyl-(C$_1$-C$_8$)-alkyl, (C$_4$-C$_{10}$)-cycloalkenyl-(C$_1$-C$_8$)-alkyl, (C$_1$-C$_8$)-alkoxycarbonyl-(C$_1$-C$_8$)-alkyl, (C$_2$-C$_8$)-alkenyloxycarbonyl-(C$_1$-C$_8$)-alkyl, aryl-(C$_1$-C$_8$)-alkoxycarbonyl-(C$_1$-C$_8$)-alkyl, hydroxycarbonyl-(C$_1$-C$_8$)-alkyl, heterocyclyl, heterocyclyl-(C$_1$-C$_8$)-alkyl, R$^{20}$ is hydrogen, (C$_1$-C$_8$)-alkyl, (C$_2$-C$_8$)-alkenyl, (C$_2$-C$_8$)-alkynyl, (C$_1$-C$_8$)-cyanoalkyl, (C$_1$-C$_{10}$)-haloalkyl, (C$_2$-C$_8$)-haloalkenyl, (C$_2$-C$_8$)-haloalkynyl, (C$_3$-C$_{10}$)-cycloalkyl, (C$_3$-C$_{10}$)-halocycloalkyl, (C$_4$-C$_{10}$)-cycloalkenyl, (C$_4$-C$_{10}$)-halocycloalkenyl, (C$_1$-C$_8$)-alkoxy-(C$_1$-C$_8$)-alkyl, (C$_1$-C$_8$)-alkoxy-(C$_1$-C$_8$)-haloalkyl, aryl, aryl-(C$_1$-C$_8$)-alkyl, heteroaryl, heteroaryl-(C$_1$-C$_8$)-alkyl, heterocyclyl-(C$_1$-C$_8$)-alkyl, (C$_3$-C$_8$)-cycloalkyl-(C$_1$-C$_8$)-alkyl, (C$_4$-C$_{10}$)-cycloalkenyl-(C$_1$-C$_8$)-alkyl, NR$^{17}$R$^{18}$, R$^{21}$ is hydrogen, fluorine, chlorine, bromine, trifluoromethyl, (C$_1$-C$_8$)-alkoxy and R$^{22}$ and R$^{23}$ are independently hydrogen, halogen, (C$_1$-C$_8$)-alkyl, (C$_3$-C$_8$)-cycloalkyl, (C$_2$-C$_8$)-alkenyl, (C$_2$-C$_8$)-alkynyl, (C$_1$-C$_{10}$)-haloalkyl, aryl, or R$^{22}$ and R$^{23}$ together with the carbon atom to which they are bonded form a 3- to 10-membered monocyclic or bicyclic ring which is saturated or optionally interrupted by heteroatoms and optionally has further substitution.

The compounds of the general formula (I) can form salts by addition of a suitable inorganic or organic acid, for example mineral acids, for example HCl, HBr, H$_2$SO$_4$, H$_3$PO$_4$ or HNO$_3$, or organic acids, e.g. carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts contain the conjugate base of the acid as anion. Suitable substituents in deprotonated form, for example sulfonic acids, particular sulfonamides or carboxylic acids, may form internal salts with groups that are protonatable in turn, such as amino groups. Salts can also be formed by the action of a base on compounds of the general formula (I). Suitable bases are, for example, organic amines such as trialkylamines, morpholine, piperidine and pyridine, and ammonium, alkali metal or alkaline earth metal hydroxides, carbonates and hydrogencarbonates, especially sodium hydroxide and potassium hydroxide, sodium carbonate and potassium carbonate, and sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NR$^a$R$^b$R$^c$R$^d$] in which R$^a$ to R$^d$ are independently an organic radical, especially alkyl, aryl, aralkyl or alkylaryl.

Also useful are alkylsulfonium and alkylsulfoxonium salts, such as (C$_1$-C$_4$)-trialkylsulfonium and (C$_1$-C$_4$)-trialkylsulfoxonium salts.

The compounds of the formula (I) used in accordance with the invention and salts thereof are referred to hereinafter as "compounds of the general formula (I)".

The invention preferably provides compounds of the general formula (I) in which

R$^1$ is (C$_1$-C$_7$)-alkyl, amino, NR$^{17}$R$^{18}$,

R$^2$ is hydrogen, (C$_1$-C$_7$)-alkyl,

R$^3$ is hydrogen, halogen, (C$_1$-C$_7$)-alkoxy,

R$^4$ is halogen, cyano, NO$_2$, C(O)NH$_2$, C(S)NH$_2$, (C$_1$-C$_7$)-haloalkyl, (C$_2$-C$_7$)-alkynyl, R$^5$ and R$^6$ are independently hydrogen, halogen, (C$_1$-C$_7$)-alkyl, (C$_3$-C$_7$)-cycloalkyl, (C$_3$-C$_7$)-cycloalkyl-(C$_1$-C$_7$)-alkyl, (C$_2$-C$_7$)-alkenyl, (C$_2$-C$_7$)-alkynyl, (C$_1$-C$_7$)-haloalkyl, (C$_2$-C$_7$)-haloalkenyl, (C$_2$-C$_7$)-haloalkynyl, (C$_3$-C$_7$)-halocycloalkyl, (C$_4$-C$_7$)-cycloalkenyl, (C$_4$-C$_7$)-halocycloalkenyl, (C$_1$-C$_7$)-alkoxy, (C$_1$-C$_7$)-alkoxy-(C$_1$-C$_7$)-alkyl, (C$_1$-C$_7$)-alkoxy-(C$_1$-C$_7$)-haloalkyl, (C$_1$-C$_7$)-haloalkoxy-(C$_1$-C$_7$)-haloalkyl, (C$_1$-C$_7$)-haloalkoxy-(C$_1$-C$_7$)-alkyl, aryl, aryl-(C$_1$-C$_7$)-alkyl, heteroaryl, heteroaryl-(C$_1$-C$_7$)-alkyl, (C$_4$-C$_7$)-cycloalkenyl-(C$_1$-C$_7$)-alkyl, heterocyclyl, heterocyclyl-(C$_1$-C$_7$)-alkyl, (C$_1$-C$_7$)-alkylthio-(C$_1$-C$_7$)-alkyl, (C$_1$-C$_7$)-haloalkylthio-(C$_1$-C$_7$)-alkyl, (C$_1$-C$_7$)-alkylcarbonyl-(C$_1$-C$_7$)-alkyl, C(O)OR$^{19}$, C(O)NR$^{17}$R$^{18}$, C(O)R$^{19}$, R$^{19}$O(O)C—(C$_1$-C$_7$)-alkyl, R$^{17}$R$^{18}$N(O)C—(C$_1$-C$_7$)-alkyl, R$^{17}$R$^{18}$N—(C$_1$-C$_7$)-alkyl, or R$^5$ and R$^6$ together with the carbon atom to which they are bonded form a fully saturated or partly saturated 3- to 10-membered monocyclic or bicyclic ring optionally interrupted by heteroatoms and optionally having further substitution, or R$^5$ and R$^6$ together with the carbon atom to which they are bonded form a double bond optionally substituted by R$^{22}$ and R$^{23}$, according to formula (I') below

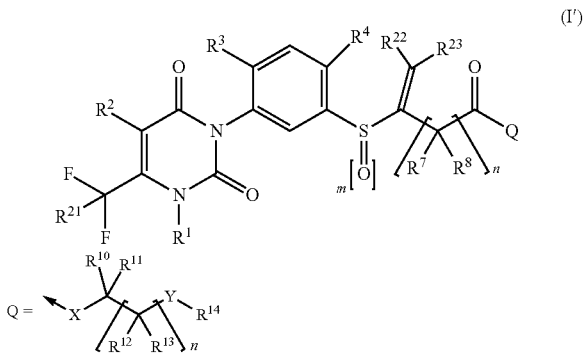

(I')

R$^7$ and R$^8$ are independently hydrogen, halogen, (C$_1$-C$_7$)-alkyl, (C$_3$-C$_7$)-cycloalkyl, (C$_3$-C$_7$)-cycloalkyl-(C$_1$-C$_7$)-alkyl, (C$_2$-C$_7$)-alkenyl, (C$_2$-C$_7$)-alkynyl, (C$_1$-C$_7$)-haloalkyl, (C$_2$-C$_7$)-haloalkenyl, (C$_2$-C$_7$)-haloalkynyl, (C$_3$-C$_7$)-halocycloalkyl, (C$_1$-C$_7$)-alkoxy-(C$_1$-C$_7$)-alkyl, (C$_1$-C$_7$)-alkoxy-(C$_1$-C$_7$)-haloalkyl, (C$_1$-C$_7$)-haloalkoxy-(C$_1$-C$_7$)-haloalkyl, (C$_1$-C$_7$)-haloalkoxy-(C$_1$-C$_7$)-alkyl, aryl, aryl-(C$_1$-C$_7$)-alkyl, heteroaryl, heteroaryl-(C$_1$-C$_7$)-alkyl, heterocyclyl, heterocyclyl-(C$_1$-C$_7$)-alkyl, (C$_1$-C$_7$)-alkylthio-(C$_1$-C$_7$)-alkyl, (C$_1$-C$_7$)-haloalkylthio-(C$_1$-C$_7$)-alkyl, C(O)OR$^{19}$, C(O)NR$^{17}$R$^{18}$, C(O)R$^{19}$, R$^{19}$O(O)C—(C$_1$-C$_7$)-alkyl, R$^{17}$R$^{18}$N(O)C—(C$_1$-C$_7$)-alkyl, R$^{17}$R$^{18}$N—(C$_1$-C$_7$)-alkyl, or $R^7$ and $R^8$ together with the carbon atom to which they are bonded form a fully saturated or partly saturated 3- to 10-membered monocyclic or bicyclic ring optionally interrupted by heteroatoms and optionally having further substitution, or $R^7$ and $R^8$ together with the carbon atom to which they are bonded form a double bond optionally substituted by $R^{22}$ and $R^{23}$, according to formula (I″) below

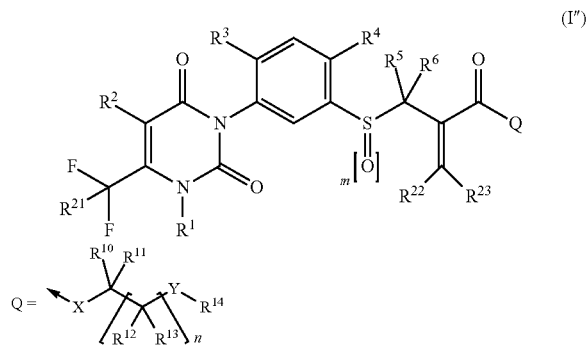

m is 0, 1, 2,
n is 0, 1, 2, 3, 4, 5, 6,
p is 1, 2, 3,
X is O (oxygen), N (nitrogen) or the N—$R^{15}$ or N—O—$R^{16}$ moieties, and where $R^{15}$ and $R^{16}$ in the N—$R^{15}$ and N—O—$R^{16}$ moiety independently have the meanings according to the definitions below,
Y is O (oxygen) or S (sulfur), SO, $SO_2$,
$R^{10}$ and $R^{11}$ are independently hydrogen, fluorine, cyano, ($C_1$-$C_7$)-alkyl, ($C_3$-$C_7$)-cycloalkyl, ($C_3$-$C_7$)-cycloalkyl-($C_1$-$C_7$)-alkyl, ($C_2$-$C_7$)-alkenyl, ($C_2$-$C_7$)-alkynyl, ($C_1$-$C_7$)-haloalkyl, aryl, aryl-($C_1$-$C_7$)-alkyl, heteroaryl, heteroaryl-($C_1$-$C_7$)-alkyl, ($C_4$-$C_7$)-cycloalkenyl-($C_1$-$C_7$)-alkyl, heterocyclyl, heterocyclyl-($C_1$-$C_7$)-alkyl, $R^{19}$O—($C_1$-$C_7$)-alkyl, $R^{20}$S—($C_1$-$C_7$)-alkyl, $R^{20}SO_2$—($C_1$-$C_7$)-alkyl, or $R^{10}$ and $R^{11}$ together with the carbon atom to which they are bonded form a fully saturated or partly saturated 3- to 10-membered monocyclic or bicyclic ring optionally interrupted by heteroatoms and optionally having further substitution, $R^{12}$ and $R^{13}$ are independently hydrogen, fluorine, ($C_1$-$C_7$)-alkyl, ($C_3$-$C_7$)-cycloalkyl, ($C_3$-$C_7$)-cycloalkyl-($C_1$-$C_7$)-alkyl, ($C_2$-$C_7$)-alkenyl, ($C_2$-$C_7$)-alkynyl, ($C_1$-$C_7$)-haloalkyl, ($C_2$-$C_7$)-haloalkenyl, ($C_2$-$C_7$)-haloalkynyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-haloalkyl, ($C_1$-$C_7$)-haloalkoxy-($C_1$-$C_7$)-haloalkyl, aryl, aryl-($C_1$-$C_7$)-alkyl, heteroaryl, heteroaryl-($C_1$-$C_7$)-alkyl, ($C_4$-$C_{10}$)-cycloalkenyl-($C_1$-$C_7$)-alkyl, heterocyclyl, heterocyclyl-($C_1$-$C_7$)-alkyl, $R^{19}$O—($C_1$-$C_7$)-alkyl, $R^{20}$S—($C_1$-$C_7$)-alkyl, $R^{20}SO_2$—($C_1$-$C_7$)-alkyl, $R^{17}R^{18}$N—($C_1$-$C_7$)-alkyl, or $R^{12}$ and $R^{13}$ together with the carbon atom to which they are bonded form a fully saturated or partly saturated 3- to 10-membered monocyclic or bicyclic ring optionally interrupted by heteroatoms and optionally having further substitution, or $R^{14}$ is ($C_1$-$C_7$)-alkyl, ($C_1$-$C_7$)-haloalkyl, ($C_3$-$C_7$)-cycloalkyl, ($C_3$-$C_7$)-cycloalkyl-($C_1$-$C_7$)-alkyl, ($C_2$-$C_7$)-alkenyl, ($C_2$-$C_7$)-alkynyl, ($C_1$-$C_7$)-alkoxy-($C_1$-$C_7$)-alkyl, ($C_1$-$C_7$)-haloalkoxy-($C_1$-$C_7$)-alkyl, aryl, aryl-($C_1$-$C_7$)-alkyl, heteroaryl, heteroaryl-($C_1$-$C_7$)-alkyl, heterocyclyl, heterocyclyl-($C_1$-$C_7$)-alkyl, ($C_1$-$C_7$)-alkylthio-($C_1$-$C_7$)-alkyl, ($C_1$-$C_7$)-haloalkylthio-($C_1$-$C_7$)-alkyl, $R^{17}R^{18}$N—($C_1$-$C_7$)-alkyl, cyano-($C_1$-$C_7$)-alkyl, or $R^{10}$ and $R^{14}$ together with the carbon atoms to which they are bonded form a fully saturated or partly saturated 3- to 10-membered monocyclic or bicyclic ring optionally interrupted by heteroatoms and optionally having further substitution, or $R^{12}$ and $R^{14}$ together with the carbon atoms to which they are bonded form a fully saturated or partly saturated 3- to 10-membered monocyclic or bicyclic ring optionally interrupted by heteroatoms and optionally having further substitution, $R^{15}$ is hydrogen, ($C_1$-$C_7$)-alkyl, ($C_3$-$C_7$)-cycloalkyl, cyano-($C_1$-$C_7$)-alkyl, ($C_3$-$C_7$)-cycloalkyl-($C_1$-$C_7$)-alkyl, ($C_1$-$C_7$)-alkylsulfonyl, arylsulfonyl, heteroarylsulfonyl, ($C_3$-$C_7$)-cycloalkylsulfonyl, heterocyclylsulfonyl, aryl-($C_1$-$C_7$)-alkylsulfonyl, ($C_1$-$C_7$)-alkylcarbonyl, arylcarbonyl, heteroarylcarbonyl, ($C_3$-$C_7$)-cycloalkylcarbonyl, heterocyclylcarbonyl, ($C_1$-$C_7$)-alkoxycarbonyl, ($C_1$-$C_7$)-alkoxy, ($C_2$-$C_7$)-alkenyloxy, aryl-($C_1$-$C_7$)-alkoxycarbonyl, ($C_1$-$C_7$)-haloalkylcarbonyl, ($C_2$-$C_7$)-alkenyl, ($C_2$-$C_7$)-alkynyl, ($C_1$-$C_7$)-haloalkyl, halo-($C_2$-$C_7$)-alkynyl, halo-($C_2$-$C_7$)-alkenyl, ($C_1$-$C_7$)-alkoxy-($C_1$-$C_7$)-alkyl, amino, ($C_1$-$C_7$)-alkylamino, bis[($C_1$-$C_7$)-alkyl]amino, ($C_1$-$C_7$)-alkoxy-($C_1$-$C_7$)-alkoxy-($C_1$-$C_7$)-alkyl, heteroaryl-($C_1$-$C_7$)-alkylsulfonyl, heterocyclyl-($C_1$-$C_7$)-alkylsulfonyl, ($C_2$-$C_7$)-alkenyloxycarbonyl, ($C_2$-$C_7$)-alkynyloxycarbonyl, ($C_1$-$C_7$)-alkylaminocarbonyl, ($C_3$-$C_7$)-cycloalkylaminocarbonyl, bis[($C_1$-$C_7$)-alkyl]aminocarbonyl, $R^{16}$ is hydrogen, ($C_1$-$C_7$)-alkyl, ($C_3$-$C_7$)-cycloalkyl-($C_1$-$C_7$)-alkyl, ($C_2$-$C_7$)-alkenyl, ($C_2$-$C_7$)-alkynyl, ($C_1$-$C_7$)-alkoxy-($C_1$-$C_7$)-alkyl, aryl, aryl-($C_1$-$C_7$)-alkyl, $R^{19}$O(O)C—($C_1$-$C_7$)-alkyl, $R^{17}R^{18}$N(O)C—($C_1$-$C_7$)-alkyl, $R^{17}$ and $R^{18}$ are the same or different and are independently hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_7$)-haloalkyl, ($C_2$-$C_7$)-haloalkenyl, ($C_2$-$C_7$)-haloalkynyl, ($C_3$-$C_7$)-cycloalkyl, ($C_3$-$C_7$)-halocycloalkyl, ($C_4$-$C_{10}$)-cycloalkenyl, ($C_4$-$C_7$)-halocycloalkenyl, ($C_1$-$C_7$)-alkoxy-($C_1$-$C_7$)-alkyl, ($C_1$-$C_7$)-haloalkoxy-($C_1$-$C_7$)-alkyl, ($C_1$-$C_7$)-alkylthio-($C_1$-$C_7$)-alkyl, ($C_1$-$C_7$)-haloalkylthio-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, $COR^{19}$, $SO_2R^{20}$, ($C_1$-$C_7$)-alkyl-$HNO_2S$—, ($C_3$-$C_7$)-cycloalkyl-$HNO_2S$—, heterocyclyl, ($C_1$-$C_7$)-alkoxycarbonyl-($C_1$-$C_7$)-alkyl, ($C_1$-$C_7$)-alkoxycarbonyl, aryl-($C_1$-$C_7$)-alkoxycarbonyl-($C_1$-$C_7$)-alkyl, aryl-($C_1$-$C_7$)-alkoxycarbonyl, heteroaryl-($C_1$-$C_7$)-alkoxycarbonyl, ($C_2$-$C_7$)-alkenyloxycarbonyl, ($C_2$-$C_7$)-alkynyloxycarbonyl, heterocyclyl-($C_1$-$C_7$)-alkyl, $R^{19}$ is hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_{10}$)-haloalkyl, ($C_2$-$C_7$)-haloalkenyl, ($C_2$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, ($C_1$-$C_7$)-alkoxycarbonyl-($C_1$-$C_7$)-alkyl, ($C_2$-$C_7$)-alkenyloxycarbonyl-($C_1$-$C_7$)-alkyl, aryl-($C_1$-$C_7$)-alkoxycarbonyl-($C_1$-$C_7$)-alkyl, hydroxycarbonyl-($C_1$-$C_7$)-alkyl, heterocyclyl, heterocyclyl-($C_1$-$C_7$)-alkyl, $R^{20}$ is hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_7$)-haloalkyl, ($C_2$-$C_7$)-haloalkenyl, ($C_2$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, heterocyclyl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, $NR^{17}R^{18}$, $R^{21}$ is hydrogen, fluorine, chlorine, bromine, trifluoromethyl, ($C_1$-$C_7$)-alkoxy
and
$R^{22}$ and $R^{23}$ are independently hydrogen, halogen, ($C_1$-$C_7$)-alkyl, ($C_3$-$C_7$)-cycloalkyl, ($C_2$-$C_7$)-alkenyl, ($C_2$-$C_7$)-alkynyl, ($C_1$-$C_7$)-haloalkyl, aryl, or
$R^{22}$ and $R^{23}$ together with the carbon atom to which they are bonded form a 3- to 10-membered monocyclic or bicyclic ring which is saturated or optionally interrupted by heteroatoms and optionally has further substitution.

The invention more preferably provides compounds of the general formula (I) in which
$R^1$ is ($C_1$-$C_6$)-alkyl, amino, $NR^{17}R^{18}$,
$R^2$ is hydrogen, ($C_1$-$C_6$)-alkyl,
$R^3$ is hydrogen, halogen, ($C_1$-$C_6$)-alkoxy,
$R^4$ is halogen, cyano, $NO_2$, $C(O)NH_2$, $C(S)NH_2$, ($C_1$-$C_6$)-haloalkyl, ($C_2$-$C_6$)-alkynyl,
$R^5$ and $R^6$ are independently hydrogen, halogen, ($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_1$-$C_6$)-haloalkyl, ($C_2$-$C_6$)-haloalkenyl, ($C_2$-$C_6$)-haloalkynyl, ($C_3$-$C_6$)-halocycloalkyl, ($C_1$-$C_6$)-alkoxy, ($C_1$-$C_6$)-alkoxy-($C_1$-$C_6$)-alkyl, ($C_1$-$C_6$)-alkoxy-($C_1$-$C_6$)-haloalkyl, ($C_1$-$C_6$)-haloalkoxy-($C_1$-$C_6$)-haloalkyl, ($C_1$-$C_6$)-haloalkoxy-($C_1$-$C_6$)-alkyl, aryl, aryl-($C_1$-$C_6$)-alkyl, heteroaryl, heteroaryl-($C_1$-$C_6$)-alkyl, heterocyclyl, heterocyclyl-($C_1$-$C_6$)-alkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylcarbonyl-($C_1$-$C_6$)-alkyl, $C(O)OR^{19}$, $C(O)NR^{17}R^{18}$, $C(O)R^{19}$, $R^{19}O(O)C$—($C_1$-$C_6$)-alkyl, $R^{17}R^{18}N(O)C$—($C_1$-$C_6$)-alkyl, $R^{17}R^{18}N$—($C_1$-$C_6$)-alkyl, or
$R^5$ and $R^6$ together with the carbon atom to which they are bonded form a fully saturated or partly saturated 3- to 10-membered monocyclic or bicyclic ring optionally interrupted by heteroatoms and optionally having further substitution, or
$R^5$ and $R^6$ together with the carbon atom to which they are bonded form a double bond optionally substituted by $R^{22}$ and $R^{23}$, according to formula (I') below

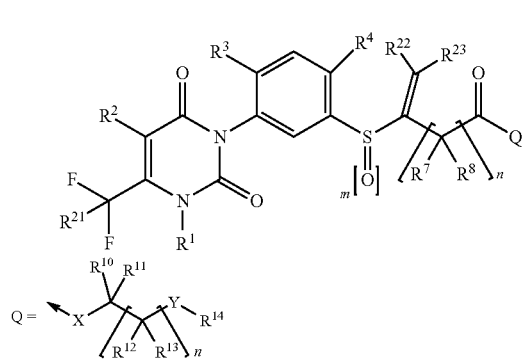

(I')

$R^7$ and $R^8$ are independently hydrogen, halogen, ($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_1$-$C_6$)-haloalkyl, ($C_2$-$C_6$)-haloalkenyl, ($C_2$-$C_6$)-haloalkynyl, ($C_3$-$C_6$)-halocycloalkyl, ($C_1$-$C_6$)-alkoxy-($C_1$-$C_6$)-alkyl, ($C_1$-$C_6$)-alkoxy-($C_1$-$C_6$)-haloalkyl, ($C_1$-$C_6$)-haloalkoxy-($C_1$-$C_6$)-haloalkyl, ($C_1$-$C_6$)-haloalkoxy-($C_1$-$C_6$)-alkyl, aryl, aryl-($C_1$-$C_6$)-alkyl, heteroaryl, heteroaryl-($C_1$-$C_6$)-alkyl, heterocyclyl, heterocyclyl-($C_1$-$C_6$)-alkyl, ($C_1$-$C_6$)-alkylthio-($C_1$-$C_6$)-alkyl, ($C_1$-$C_6$)-haloalkylthio-($C_1$-$C_6$)-alkyl, $C(O)OR^{19}$, $C(O)NR^{17}R^{18}$, $C(O)R^{19}$, $R^{19}O(O)C$—($C_1$-$C_6$)-alkyl, $R^{17}R^{18}N(O)C$—($C_1$-$C_6$)-alkyl, $R^{17}R^{18}N$—($C_1$-$C_6$)-alkyl, or
$R^7$ and $R^8$ together with the carbon atom to which they are bonded form a fully saturated or partly saturated 3- to 10-membered monocyclic or bicyclic ring optionally interrupted by heteroatoms and optionally having further substitution, or
$R^7$ and $R^8$ together with the carbon atom to which they are bonded form a double bond optionally substituted by $R^{22}$ and $R^{23}$, according to formula (I") below

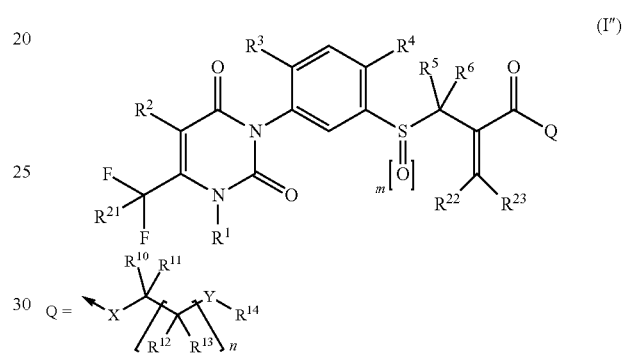

(I")

m is 0, 1, 2,
n is 0, 1, 2, 3, 4, 5, 6,
p is 1, 2, 3,
X is O (oxygen), N (nitrogen) or the N—$R^{15}$ or N—O—$R^{16}$ moieties, and where $R^{15}$ and $R^{16}$ in the N—$R^{15}$ and N—O—$R^{16}$ moiety independently have the meanings according to the definitions below,
Y is O (oxygen) or S (sulfur), SO, $SO_2$,
$R^{10}$ and $R^{11}$ are independently hydrogen, fluorine, cyano, ($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_1$-$C_6$)-haloalkyl, aryl, aryl-($C_1$-$C_6$)-alkyl, heteroaryl, heteroaryl-($C_1$-$C_6$)-alkyl, ($C_4$-$C_6$)-cycloalkenyl-($C_1$-$C_6$)-alkyl, heterocyclyl, heterocyclyl-($C_1$-$C_6$)-alkyl, $R^{19}O$—($C_1$-$C_6$)-alkyl, $R^{20}S$—($C_1$-$C_6$)-alkyl, $R^{20}SO_2$—($C_1$-$C_6$)-alkyl, or
$R^{10}$ and $R^{11}$ together with the carbon atom to which they are bonded form a fully saturated or partly saturated 3- to 10-membered monocyclic or bicyclic ring optionally interrupted by heteroatoms and optionally having further substitution,
$R^{12}$ and $R^{13}$ are independently hydrogen, fluorine, ($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_1$-$C_6$)-haloalkyl, ($C_2$-$C_6$)-haloalkenyl, ($C_2$-$C_6$)-haloalkynyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-haloalkyl, ($C_1$-$C_6$)-haloalkoxy-($C_1$-$C_6$)-haloalkyl, aryl, aryl-($C_1$-$C_6$)-alkyl, heteroaryl, heteroaryl-($C_1$-$C_6$)-alkyl, ($C_4$-$C_{10}$)-cycloalkenyl-($C_1$-$C_6$)-alkyl, heterocyclyl, heterocyclyl-($C_1$-$C_6$)-alkyl, $R^{19}O$—($C_1$-$C_6$)-alkyl, $R^{20}S$—($C_1$-$C_6$)-alkyl, $R^{20}SO_2$—($C_1$-$C_6$)-alkyl, $R^{17}R^{18}N$—($C_1$-$C_8$)-alkyl, or
$R^{12}$ and $R^{13}$ together with the carbon atom to which they are bonded form a fully saturated or partly saturated 3- to 10-membered monocyclic or bicyclic ring optionally interrupted by heteroatoms and optionally having further substitution, $R^{14}$ is $(C_1-C_6)$-alkyl, $(C_1-C_6)$-haloalkyl, $(C_3-C_6)$-cycloalkyl, $(C_3-C_6)$-cycloalkyl-$(C_1-C_6)$-alkyl, $(C_2-C_6)$-alkenyl, $(C_2-C_6)$-alkynyl, $(C_1-C_6)$-alkoxy-$(C_1-C_6)$-alkyl, $(C_1-C_6)$-haloalkoxy-$(C_1-C_6)$-alkyl, aryl, aryl-$(C_1-C_6)$-alkyl, heteroaryl, heteroaryl-$(C_1-C_6)$-alkyl, heterocyclyl, heterocyclyl-$(C_1-C_6)$-alkyl, $(C_1-C_6)$-alkylthio-$(C_1-C_6)$-alkyl, $(C_1-C_6)$-haloalkylthio-$(C_1-C_6)$-alkyl, $R^{17}R^{18}N$—$(C_1-C_6)$-alkyl, cyano-$(C_1-C_6)$-alkyl, or $R^{10}$ and $R^{14}$ together with the carbon atoms to which they are bonded form a fully saturated or partly saturated 3- to 10-membered monocyclic or bicyclic ring optionally interrupted by heteroatoms and optionally having further substitution, or $R^{12}$ and $R^{14}$ together with the carbon atoms to which they are bonded form a fully saturated or partly saturated 3- to 10-membered monocyclic or bicyclic ring optionally interrupted by heteroatoms and optionally having further substitution, $R^{15}$ is hydrogen, $(C_1-C_6)$-alkyl, $(C_3-C_6)$-cycloalkyl, cyano-$(C_1-C_6)$-alkyl, $(C_3-C_6)$-cycloalkyl-$(C_1-C_6)$-alkyl, $(C_1-C_6)$-alkylsulfonyl, arylsulfonyl, heteroarylsulfonyl, $(C_3-C_6)$-cycloalkylsulfonyl, heterocyclylsulfonyl, aryl-$(C_1-C_6)$-alkylsulfonyl, $(C_1-C_6)$-alkylcarbonyl, arylcarbonyl, heteroarylcarbonyl, $(C_3-C_6)$-cycloalkylcarbonyl, heterocyclylcarbonyl, $(C_1-C_6)$-alkoxycarbonyl, $(C_1-C_6)$-alkoxy, $(C_2-C_6)$-alkenyloxy, aryl-$(C_1-C_6)$-alkoxycarbonyl, $(C_1-C_6)$-haloalkylcarbonyl, $(C_2-C_6)$-alkenyl, $(C_2-C_6)$-alkynyl, $(C_1-C_6)$-haloalkyl, halo-$(C_2-C_6)$-alkynyl, halo-$(C_2-C_6)$-alkenyl, $(C_1-C_6)$-alkoxy-$(C_1-C_6)$-alkyl, amino, $(C_1-C_6)$-alkylamino, bis[$(C_1-C_6)$-alkyl]amino, $(C_1-C_6)$-alkoxy-$(C_1-C_6)$-alkoxy-$(C_1-C_6)$-alkyl, heteroaryl-$(C_1-C_6)$-alkylsulfonyl, heterocyclyl-$(C_1-C_6)$-alkylsulfonyl, $(C_2-C_6)$-alkenyloxycarbonyl, $(C_2-C_6)$-alkynyloxycarbonyl, $(C_1-C_6)$-alkylaminocarbonyl, $(C_3-C_6)$-cycloalkylaminocarbonyl, bis[$(C_1-C_6)$-alkyl]aminocarbonyl, $R^{16}$ is hydrogen, $(C_1-C_6)$-alkyl, $(C_3-C_6)$-cycloalkyl-$(C_1-C_6)$-alkyl, $(C_2-C_6)$-alkenyl, $(C_2-C_6)$-alkynyl, $(C_1-C_6)$-alkoxy-$(C_1-C_6)$-alkyl, aryl, aryl-$(C_1-C_6)$-alkyl, $R^{19}O(O)C$—$(C_1-C_6)$-alkyl, $R^{17}R^{18}N(O)C$—$(C_1-C_6)$-alkyl, $R^{17}$ and $R^{18}$ are the same or different and are independently hydrogen, $(C_1-C_6)$-alkyl, $(C_2-C_6)$-alkenyl, $(C_2-C_6)$-alkynyl, $(C_1-C_6)$-cyanoalkyl, $(C_1-C_6)$-haloalkyl, $(C_2-C_6)$-haloalkenyl, $(C_2-C_6)$-haloalkynyl, $(C_3-C_6)$-cycloalkyl, $(C_3-C_6)$-halocycloalkyl, $(C_4-C_{10})$-cycloalkenyl, $(C_4-C_6)$-halocycloalkenyl, $(C_1-C_6)$-alkoxy-$(C_1-C_6)$-alkyl, $(C_1-C_6)$-haloalkoxy-$(C_1-C_6)$-alkyl, $(C_1-C_6)$-alkylthio-$(C_1-C_6)$-alkyl, $(C_1-C_6)$-haloalkylthio-$(C_1-C_6)$-alkyl, $(C_1-C_6)$-alkoxy-$(C_1-C_6)$-haloalkyl, aryl, aryl-$(C_1-C_6)$-alkyl, heteroaryl, heteroaryl-$(C_1-C_6)$-alkyl, $(C_3-C_6)$-cycloalkyl-$(C_1-C_6)$-alkyl, $(C_4-C_6)$-cycloalkenyl-$(C_1-C_6)$-alkyl, $COR^{19}$, $SO_2R^{20}$, $(C_1-C_6)$-alkyl-$HNO_2S$—, $(C_3-C_6)$-cycloalkyl-$HNO_2S$—, heterocyclyl, $(C_1-C_6)$-alkoxycarbonyl-$(C_1-C_6)$-alkyl, $(C_1-C_6)$-alkoxycarbonyl, aryl-$(C_1-C_6)$-alkoxycarbonyl-$(C_1-C_6)$-alkyl, aryl-$(C_1-C_6)$-alkoxycarbonyl, heteroaryl-$(C_1-C_6)$-alkoxycarbonyl, $(C_2-C_6)$-alkenyloxycarbonyl, $(C_2-C_6)$-alkynyloxycarbonyl, heterocyclyl-$(C_1-C_6)$-alkyl, $R^{19}$ is hydrogen, $(C_1-C_6)$-alkyl, $(C_2-C_6)$-alkenyl, $(C_2-C_6)$-alkynyl, $(C_1-C_6)$-cyanoalkyl, $(C_1-C_{10})$-haloalkyl, $(C_2-C_6)$-haloalkenyl, $(C_2-C_6)$-haloalkynyl, $(C_3-C_6)$-cycloalkyl, $(C_3-C_6)$-halocycloalkyl, $(C_4-C_6)$-cycloalkenyl, $(C_4-C_6)$-halocycloalkenyl, $(C_1-C_6)$-alkoxy-$(C_1-C_6)$-alkyl, $(C_1-C_6)$-alkoxy-$(C_1-C_6)$-haloalkyl, aryl, aryl-$(C_1-C_6)$-alkyl, heteroaryl, heteroaryl-$(C_1-C_6)$-alkyl, $(C_3-C_6)$-cycloalkyl-$(C_1-C_6)$-alkyl, $(C_4-C_6)$-cycloalkenyl-$(C_1-C_6)$-alkyl, $(C_1-C_6)$-alkoxycarbonyl-$(C_1-C_6)$-alkyl, $(C_2-C_6)$-alkenyloxycarbonyl-$(C_1-C_6)$-alkyl, aryl-$(C_1-C_6)$-alkoxycarbonyl-$(C_1-C_6)$-alkyl, hydroxycarbonyl-$(C_1-C_6)$-alkyl, heterocyclyl, heterocyclyl-$(C_1-C_6)$-alkyl, $R^{20}$ is hydrogen, $(C_1-C_6)$-alkyl, $(C_2-C_6)$-alkenyl, $(C_2-C_6)$-alkynyl, $(C_1-C_6)$-cyanoalkyl, $(C_1-C_6)$-haloalkyl, $(C_2-C_6)$-haloalkenyl, $(C_2-C_6)$-haloalkynyl, $(C_3-C_6)$-cycloalkyl, $(C_3-C_6)$-halocycloalkyl, $(C_4-C_6)$-cycloalkenyl, $(C_4-C_6)$-halocycloalkenyl, $(C_1-C_6)$-alkoxy-$(C_1-C_6)$-alkyl, $(C_1-C_6)$-alkoxy-$(C_1-C_6)$-haloalkyl, aryl, aryl-$(C_1-C_6)$-alkyl, heteroaryl, heteroaryl-$(C_1-C_6)$-alkyl, heterocyclyl-$(C_1-C_6)$-alkyl, $(C_3-C_6)$-cycloalkyl-$(C_1-C_6)$-alkyl, $(C_4-C_6)$-cycloalkenyl-$(C_1-C_6)$-alkyl, $NR^{17}R^{18}$, $R^{21}$ is hydrogen, fluorine, chlorine, bromine, trifluoromethyl, $(C_1-C_6)$-alkoxy and $R^{22}$ and $R^{23}$ are independently hydrogen, halogen, $(C_1-C_6)$-alkyl, $(C_3-C_6)$-cycloalkyl, $(C_2-C_6)$-alkenyl, $(C_2-C_6)$-alkynyl, $(C_1-C_6)$-haloalkyl, aryl, or $R^{22}$ and $R^{23}$ together with the carbon atom to which they are bonded form a 3- to 10-membered monocyclic or bicyclic ring which is saturated or optionally interrupted by heteroatoms and optionally has further substitution.

The invention even more preferably provides compounds of the general formula (I) in which $R^1$ is methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, amino, dimethylamino, diethylamino, methyl(ethyl)amino, methyl(n-propyl)amino, $R^2$ is hydrogen, methyl, ethyl, n-propyl, isopropyl, $R^3$ is hydrogen, fluorine, chlorine, bromine, methoxy, ethoxy, $R^4$ is halogen, cyano, $NO_2$, $C(O)NH_2$, $C(S)NH_2$, difluoromethyl, trifluoromethyl, ethynyl, propyn-1-yl, 1-butyn-1-yl, pentyn-1-yl, hexyn-1-yl, $R^5$ and $R^6$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, spiro[2.2]pent-1-yl, spiro[2.3]hex-1-yl, spiro[2.3]hex-4-yl, 3-spiro[2.3]hex-5-yl, bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, 1-methylcyclopropyl, 2-methylcyclopropyl, 2,2-dimethylcyclopropyl, 2,3-dimethylcyclopropyl, 1,1'-bi(cyclopropyl)-1-yl, 1,1'-bi(cyclopropyl)-2-yl, 2'-methyl-1,1'-bi(cyclopropyl)-2-yl, 1-cyanocyclopropyl, 2-cyanocyclopropyl, 1-methylcyclobutyl, 2-methylcyclobutyl, 3-methylcyclobutyl, 3,3-dimethylcyclobut-1-yl, 1-cyanocyclobutyl, 2-cyanocyclobutyl, 3-cyanocyclobutyl, 3,3-difluorocyclobut-1-yl, 3-fluorocyclobut-1-yl, 2,2-difluorocycloprop-1-yl, 1-fluorocycloprop-1-yl, 2-fluorocycloprop-1-yl, 1-allylcyclopropyl, 1-vinylcyclobutyl, 1-vinylcyclopropyl, 1-ethylcyclopropyl, 1-methylcyclohexyl, 2-methylcyclohexyl, 3-methylcyclohexyl, 1-methoxycyclohexyl, 2-methoxycyclohexyl, 3-methoxycyclohexyl, 2-fluorocycloprop-1-yl, 4-fluorocyclohexyl, 4,4-difluorocyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, difluoro-tert-butyl, chloromethyl, bromomethyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, methoxydifluoromethyl, ethoxydifluoromethyl, n-propyloxydifluoromethyl, n-butyloxydifluoromethyl, trifluoromethoxymethyl, trifluoromethoxyethyl, trifluoromethoxy-n-propyl, phenyl, 2-fluorophenyl, 3-fluorophenyl, 4-fluorophenyl, 2,4-difluorophenyl, 2,5-difluorophenyl, 2,6-difluorophenyl, 2,3-difluorophenyl, 3,4-difluorophenyl, 3,5-difluorophenyl, 2,4,5-trifluorophenyl, 3,4,5-trifluorophenyl, 2-chlorophenyl, 3-chlorophenyl, 4-chlorophenyl, 2,4-dichlorophenyl, 2,5-dichlorophenyl, 2,6-dichlorophenyl, 2,3-dichlorophenyl, 3,4-dichlorophenyl, 3,5-dichlorophenyl, 2,4,5-trichlorophenyl, 3,4,5-trichlorophenyl, 2,4,6-trichlorophenyl, 2-bromophenyl, 3-bromophenyl, 4-bromophenyl, 2-iodophenyl, 3-iodophenyl, 4-iodophenyl, 2-bromo-4-fluorophenyl, 2-bromo-4-chlorophenyl, 3-bromo-4-fluorophenyl, 3-bromo-4-chlorophenyl, 3-bromo-5-fluorophenyl, 3-bromo-5-chlorophenyl, 2-fluoro-4-bromophenyl, 2-chloro-4-bromophenyl, 3-fluoro-4-bromophenyl, 3-chloro-4-bromophenyl, 2-chloro-4-fluorophenyl, 3-chloro-4-fluorophenyl, 2-fluoro-3-chlorophenyl, 2-fluoro-4-chlorophenyl, 2-fluoro-5-chlorophenyl, 3-fluoro-4-chlorophenyl, 3-fluoro-5-chlorophenyl, 2-fluoro-6-chlorophenyl, 2-methylphenyl, 3-methylphenyl, 4-methylphenyl, 2,4-dimethylphenyl, 2,5-dimethylphenyl, 2,6-dimethylphenyl, 2,3-dimethylphenyl, 3,4-dimethylphenyl, 3,5-dimethylphenyl, 2,4,5-trimethylphenyl, 3,4,5-trimethylphenyl, 2,4,6-trimethylphenyl, 2-methoxyphenyl, 3-methoxyphenyl, 4-methoxyphenyl, 2,4-dimethoxyphenyl, 2,5-dimethoxyphenyl, 2,6-dimethoxyphenyl, 2,3-dimethoxyphenyl, 3,4-dimethoxyphenyl, 3,5-dimethoxyphenyl, 2,4,5-trimethoxyphenyl, 3,4,5-trimethoxyphenyl, 2,4,6-trimethoxyphenyl, 2-trifluoromethoxyphenyl, 3-trifluoromethoxyphenyl, 4-trifluoromethoxyphenyl, 2-difluoromethoxyphenyl, 3-difluoromethoxyphenyl, 4-difluoromethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 3,5-bis(trifluoromethyl)phenyl, 3-trifluoromethyl-5-fluorophenyl, 3-trifluoromethyl-5-chlorophenyl, 3-methyl-5-fluorophenyl, 3-methyl-5-chlorophenyl, 3-methoxy-5-fluorophenyl, 3-methoxy-5-chlorophenyl, 3-trifluoromethoxy-5-chlorophenyl, 2-ethoxyphenyl, 3-ethoxyphenyl, 4-ethoxyphenyl, 2-methylthiophenyl, 3-methylthiophenyl, 4-methylthiophenyl, 2-trifluoromethylthiophenyl, 3-trifluoromethylthiophenyl, 4-trifluoromethylthiophenyl, 2-ethylphenyl, 3-ethylphenyl, 4-ethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, pyridin-2-yl, pyridin-3-yl, pyridin-4-yl, pyrazin-2-yl, pyridazin-3-yl, pyridazin-4-yl, pyrimidin-2-yl, pyrimidin-5-yl, pyrimidin-4-yl, pyridazin-3-ylmethyl, pyridazin-4-ylmethyl, pyrimidin-2-ylmethyl, pyrimidin-5-ylmethyl, pyrimidin-4-ylmethyl, pyrazin-2-ylmethyl, 3-chloropyrazin-2-yl, 3-bromopyrazin-2-yl, 3-methoxypyrazin-2-yl, 3-ethoxypyrazin-2-yl, 3-trifluoromethylpyrazin-2-yl, 3-cyanopyrazin-2-yl, naphth-2-yl, naphth-1-yl, quinolin-4-yl, quinolin-6-yl, quinolin-8-yl, quinolin-2-yl, quinoxalin-2-yl, 2-naphthylmethyl, 1-naphthylmethyl, quinolin-4-ylmethyl, quinolin-6-ylmethyl, quinolin-8-ylmethyl, quinolin-2-ylmethyl, quinoxalin-2-ylmethyl, pyrazin-2-ylmethyl, 4-chloropyridin-2-yl, 3-chloropyridin-4-yl, 2-chloropyridin-3-yl, 2-chloropyridin-4-yl, 2-chloropyridin-5-yl, 2,6-dichloropyridin-4-yl, 3-chloropyridin-5-yl, 3,5-dichloropyridin-2-yl, 3-chloro-5-trifluoromethylpyridin-2-yl, (4-chloropyridin-2-yl)methyl, (3-chloropyridin-4-yl)methyl, (2-chloropyridin-3-yl)methyl, (2-chloropyridin-4-yl)methyl, (2-chloropyridin-5-yl)methyl, (2,6-dichloropyridin-4-yl)methyl, (3-chloropyridin-5-yl)methyl, (3,5-dichloropyridin-2-yl)methyl, thiophen-2-yl, thiophen-3-yl, 5-methylthiophen-2-yl, 5-ethylthiophen-2- yl, 5-chlorothiophen-2-yl, 5-bromothiophen-2-yl, 4-methylthiophen-2-yl, 3-methylthiophen-2-yl, 5-fluorothiophen-3-yl, 3,5-dimethylthiophen-2-yl, 3-ethylthiophen-2-yl, 4,5-dimethylthiophen-2-yl, 3,4-dimethylthiophen-2-yl, 4-chlorothiophen-2-yl, furan-2-yl, 5-methylfuran-2-yl, 5-ethylfuran-2-yl, 5-methoxycarbonylfuran-2-yl, 5-chlorofuran-2-yl, 5-bromofuran-2-yl, thiophan-2-yl, thiophan-3-yl, sulfolan-2-yl, sulfolan-3-yl, tetrahydrothiopyran-4-yl, tetrahydropyran-4-yl, tetrahydrofuran-2-yl, tetrahydrofuran-3-yl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (2,4,5-trifluorophenyl)methyl, (2,4,6-trifluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, (2,6-dichlorophenyl)methyl, (2,4,5-trichlorophenyl)methyl, (2,4,6-trichlorophenyl)methyl, (4-bromophenyl)methyl, (3-bromophenyl)methyl, (2-bromophenyl)methyl, (4-iodophenyl)methyl, (3-iodophenyl)methyl, (2-iodophenyl)methyl, (3-chloro-5-trifluoromethylpyridin-2-yl)methyl, (2-bromo-4-fluorophenyl)methyl, (2-bromo-4-chlorophenyl)methyl, (3-bromo-4-fluorophenyl)methyl, (3-bromo-4-chlorophenyl)methyl, (3-bromo-5-fluorophenyl)methyl, (3-bromo-5-chlorophenyl)methyl, (2-fluoro-4-bromophenyl)methyl, (2-chloro-4-bromophenyl)methyl, (3-fluoro-4-bromophenyl)methyl, (3-chloro-4-bromophenyl)methyl, (2-chloro-4-fluorophenyl)methyl, (3-chloro-4-fluorophenyl)methyl, (2-fluoro-3-chlorophenyl)methyl, (2-fluoro-4-chlorophenyl)methyl, (2-fluoro-5-chlorophenyl)methyl, (3-fluoro-4-chlorophenyl)methyl, (3-fluoro-5-chlorophenyl)methyl, (2-fluoro-6-chlorophenyl)methyl, 2-phenyleth-1-yl, 3-trifluoromethyl-4-chlorophenyl, 3-chloro-4-trifluoromethylphenyl, 2-chloro-4-trifluoromethylphenyl, 3,5-difluoropyridin-2-yl, (3,6-dichloropyridin-2-yl)methyl, (4-trifluoromethylphenyl)methyl, (3-trifluoromethylphenyl)methyl, (2-trifluoromethylphenyl)methyl, (4-trifluoromethoxyphenyl)methyl, (3-trifluoromethoxyphenyl)methyl, (2-trifluoromethoxyphenyl)methyl, (4-methoxyphenyl)methyl, (3-methoxyphenyl)methyl, (2-methoxyphenyl)methyl, (4-methylphenyl)methyl, (3-methylphenyl)methyl, (2-methylphenyl)methyl, (4-cyanophenyl)methyl, (3-cyanophenyl)methyl, (2-cyanophenyl)methyl, (2,4-diethylphenyl)methyl, (3,5-diethylphenyl)methyl, (3,4-dimethylphenyl)methyl, (3,5-dimethoxyphenyl)methyl, 1-phenyleth-1-yl, 1-(o-chlorophenyl)eth-1-yl, 1,3-thiazol-2-yl, 4-methyl-1,3-thiazol-2-yl, 1,3-thiazol-2-yl, methylthiomethyl, ethylthiomethyl, ethylthioethyl, methylthioethyl, n-propylthiomethyl, isopropylthiomethyl, trifluoromethylthiomethyl, trifluoromethylthioethyl, $R^5$ and $R^6$ together with the carbon atom to which they are bonded form a fully saturated or partly saturated 3- to 10-membered monocyclic or bicyclic ring optionally interrupted by heteroatoms and optionally having further substitution, or $R^5$ and $R^6$ together with the carbon atom to which they are bonded form a double bond optionally substituted by $R^{22}$ and $R^{23}$, according to formula (I') below

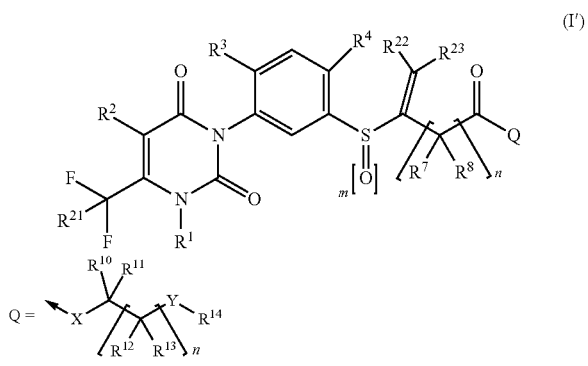

$R^7$ and $R^8$ are independently hydrogen, fluorine, chlorine, bromine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, 1-methylcyclopropyl, 2-methylcyclopropyl, 2,2-dimethylcyclopropyl, 2,3-dimethylcyclopropyl, 1-methylcyclobutyl, 2-methylcyclobutyl, 3-methylcyclobutyl, 3,3-dimethylcyclobut-1-yl, 1-cyanocyclobutyl, 2-cyanocyclobutyl, 3-cyanocyclobutyl, 3,3-difluorocyclobut-1-yl, 3-fluorocyclobut-1-yl, 2,2-difluorocycloprop-1-yl, 1-fluorocycloprop-1-yl, 2-fluorocycloprop-1-yl, 1-allylcyclopropyl, 1-vinylcyclobutyl, 1-vinylcyclopropyl, 1-ethylcyclopropyl, 1-methylcyclohexyl, 2-methylcyclohexyl, 3-methylcyclohexyl, 1-methoxycyclohexyl, 2-methoxycyclohexyl, 3-methoxycyclohexyl, 2-fluorocycloprop-1-yl, 4-fluorocyclohexyl, 4,4-difluorocyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1- butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, difluoro-tert-butyl, chloromethyl, bromomethyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, methoxydifluoromethyl, ethoxydifluoromethyl, n-propyloxydifluoromethyl, n-butyloxydifluoromethyl, trifluoromethoxymethyl, trifluoromethoxyethyl, trifluoromethoxy-n-propyl, phenyl, 2-fluorophenyl, 3-fluorophenyl, 4-fluorophenyl, 2,4-difluorophenyl, 2,5-difluorophenyl, 2,6-difluorophenyl, 2,3-difluorophenyl, 3,4-difluorophenyl, 3,5-difluorophenyl, 2,4,5-trifluorophenyl, 3,4,5-trifluorophenyl, 2-chlorophenyl, 3-chlorophenyl, 4-chlorophenyl, 2,4-dichlorophenyl, 2,5-dichlorophenyl, 2,6-dichlorophenyl, 2,3-dichlorophenyl, 3,4-dichlorophenyl, 3,5-dichlorophenyl, 2,4,5-trichlorophenyl, 3,4,5-trichlorophenyl, 2,4,6-trichlorophenyl, 2-bromophenyl, 3-bromophenyl, 4-bromophenyl, 2-iodophenyl, 3-iodophenyl, 4-iodophenyl, 2-bromo-4-fluorophenyl, 2-bromo-4-chlorophenyl, 3-bromo-4-fluorophenyl, 3-bromo-4-chlorophenyl, 3-bromo-5-fluorophenyl, 3-bromo-5-chlorophenyl, 2-fluoro-4-bromophenyl, 2-chloro-4-bromophenyl, 3-fluoro-4-bromophenyl, 3-chloro-4-bromophenyl, 2-chloro-4-fluorophenyl, 3-chloro-4-fluorophenyl, 2-fluoro-3-chlorophenyl, 2-fluoro-4-chlorophenyl, 2-fluoro-5-chlorophenyl, 3-fluoro-4-chlorophenyl, 3-fluoro-5-chlorophenyl, 2-fluoro-6-chlorophenyl, 2-methylphenyl, 3-methylphenyl, 4-methylphenyl, 2,4-dimethylphenyl, 2,5-dimethylphenyl, 2,6-dimethylphenyl, 2,3-dimethylphenyl, 3,4-dimethylphenyl, 3,5-dimethylphenyl, 2,4,5-trimethylphenyl, 3,4,5-trimethylphenyl, 2,4,6-trimethylphenyl, 2-methoxyphenyl, 3-methoxyphenyl, 4-methoxyphenyl, 2,4-dimethoxyphenyl, 2,5-dimethoxyphenyl, 2,6-dimethoxyphenyl, 2,3-dimethoxyphenyl, 3,4-dimethoxyphenyl, 3,5-dimethoxyphenyl, 2,4,5-trimethoxyphenyl, 3,4,5-trimethoxyphenyl, 2,4,6-trimethoxyphenyl, 2-trifluoromethoxyphenyl, 3-trifluoromethoxyphenyl, 4-trifluoromethoxyphenyl, 2-difluoromethoxyphenyl, 3-difluoromethoxyphenyl, 4-difluoromethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 3,5-bis(trifluoromethyl)phenyl, 3-trifluoromethyl-5-fluorophenyl, 3-trifluoromethyl-5-chlorophenyl, 3-methyl-5-fluorophenyl, 3-methyl-5-chlorophenyl, 3-methoxy-5-fluorophenyl, 3-methoxy-5-chlorophenyl, 3-trifluoromethoxy-5-chlorophenyl, 2-ethoxyphenyl, 3-ethoxyphenyl, 4-ethoxyphenyl, 2-methylthiophenyl, 3-methylthiophenyl, 4-methylthiophenyl, 2-trifluoromethylthiophenyl, 3-trifluoromethylthiophenyl, 4-trifluoromethylthiophenyl, 2-ethylphenyl, 3-ethylphenyl, 4-ethylphenyl, 2-methoxycarbonylphenyl, 3-methoxycarbonylphenyl, 4-methoxycarbonylphenyl, 2-ethoxycarbonylphenyl, 3-ethoxycarbonylphenyl, 4-ethoxycarbonylphenyl, pyridin-2-yl, pyridin-3-yl, pyridin-4-yl, pyrazin-2-yl, pyridazin-3-yl, pyridazin-4-yl, pyrimidin-2-yl, pyrimidin-5-yl, pyrimidin-4-yl, pyridazin-3-ylmethyl, pyridazin-4-ylmethyl, pyrimidin-2-ylmethyl, pyrimidin-5-ylmethyl, pyrimidin-4-ylmethyl, pyrazin-2-ylmethyl, 3-chloropyrazin-2-yl, 3-bromopyrazin-2-yl, 3-methoxypyrazin-2-yl, 3-ethoxypyrazin-2-yl, 3-trifluoromethylpyrazin-2-yl, 3-cyanopyrazin-2-yl, naphth-2-yl, naphth-1-yl, quinolin-4-yl, quinolin-6-yl, quinolin-8-yl, quinolin-2-yl, quinoxalin-2-yl, 2-naphthylmethyl, 1-naphthylmethyl, quinolin-4-ylmethyl, quinolin-6-ylmethyl, quinolin-8-ylmethyl, quinolin-2-ylmethyl, quinoxalin-2-ylmethyl, pyrazin-2-ylmethyl, 4-chloropyridin-2-yl, 3-chloropyridin-4-yl, 2-chloropyridin-3-yl, 2-chloropyridin-4-yl, 2-chloropyridin-5-yl, 2,6-dichloropyridin-4-yl, 3-chloropyridin-5-yl, 3,5-dichloropyridin-2-yl, 3-chloro-5-trifluoromethylpyridin-2-yl, (4-chloropyridin-2-yl)methyl, (3-chloropyridin-4-yl)methyl, (2-chloropyridin-3-yl)methyl, (2-chloropyridin-4-yl)methyl, (2-chloropyridin-5-yl)methyl, (2,6-dichloropyridin-4-yl)methyl, (3-chloropyridin-5-yl)methyl, (3,5-dichloropyridin-2-yl)methyl, thiophen-2-yl, thiophen-3-yl, 5-methylthiophen-2-yl, 5-ethylthiophen-2-yl, 5-chlorothiophen-2-yl, 5-bromothiophen-2-yl, 4-methylthiophen-2-yl, 3-methylthiophen-2-yl, 5-fluorothiophen-3-yl, 3,5-dimethylthiophen-2-yl, 3-ethylthiophen-2-yl, 4,5-dimethylthiophen-2-yl, 3,4-dimethylthiophen-2-yl, 4-chlorothiophen-2-yl, furan-2-yl, 5-methylfuran-2-yl, 5-ethylfuran-2-yl, 5-methoxycarbonylfuran-2-yl, 5-chlorofuran-2-yl, 5-bromofuran-2-yl, thiophan-2-yl, thiophan-3-yl, sulfolan-2-yl, sulfolan-3-yl, tetrahydrothiopyran-4-yl, tetrahydropyran-4-yl, tetrahydrofuran-2-yl, tetrahydrofuran-3-yl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (2,4,5-trifluorophenyl)methyl, (2,4,6-trifluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, (2,6-dichlorophenyl)methyl, (2,4,5-trichlorophenyl)methyl, (2,4,6-trichlorophenyl)methyl, (4-bromophenyl)methyl, (3-bromophenyl)methyl, (2-bromophenyl)methyl, (4-iodophenyl)methyl, (3-iodophenyl)methyl, (2-iodophenyl)methyl, (3-chloro-5-trifluoromethylpyridin-2-yl)methyl, (2-bromo-4-fluorophenyl)methyl, (2-bromo-4-chlorophenyl)methyl, (3-bromo-4-fluorophenyl)methyl, (3-bromo-4-chlorophenyl)methyl, (3-bromo-5-fluorophenyl)methyl, (3-bromo-5-chlorophenyl)methyl, (2-fluoro-4-bromophenyl)methyl, (2-chloro-4-bromophenyl)methyl, (3-fluoro-4-bromophenyl)methyl, (3-chloro-4-bromophenyl)methyl, (2-chloro-4-fluorophenyl)methyl, (3-chloro-4-fluorophenyl)methyl, (2-fluoro-3-chlorophenyl)methyl, (2-fluoro-4-chlorophenyl)

methyl, (2-fluoro-5-chlorophenyl)methyl, (3-fluoro-4-chlorophenyl)methyl, (3-fluoro-5-chlorophenyl)methyl, (2-fluoro-6-chlorophenyl)methyl, 2-phenyleth-1-yl, 3-trifluoromethyl-4-chlorophenyl, 3-chloro-4-trifluoromethylphenyl, 2-chloro-4-trifluoromethylphenyl, 3,5-difluoropyridin-2-yl, (3,6-dichloropyridin-2-yl)methyl, (4-trifluoromethylphenyl)methyl, (3-trifluoromethylphenyl)methyl, (2-trifluoromethylphenyl)methyl, (4-trifluoromethoxyphenyl)methyl, (3-trifluoromethoxyphenyl)methyl, (2-trifluoromethoxyphenyl)methyl, (4-methoxyphenyl)methyl, (3-methoxyphenyl)methyl, (2-methoxyphenyl)methyl, (4-methylphenyl)methyl, (3-methylphenyl)methyl, (2-methylphenyl)methyl, (4-cyanophenyl)methyl, (3-cyanophenyl)methyl, (2-cyanophenyl)methyl, (2,4-diethylphenyl)methyl, (3,5-diethylphenyl)methyl, (3,4-dimethylphenyl)methyl, (3,5-dimethoxyphenyl)methyl, 1-phenyleth-1-yl, 1-(o-chlorophenyl)eth-1-yl, 1,3-thiazol-2-yl, 4-methyl-1,3-thiazol-2-yl, 1,3-thiazol-2-yl, methylthiomethyl, ethylthiomethyl, ethylthioethyl, methylthioethyl, n-propylthiomethyl, isopropylthiomethyl, trifluoromethylthiomethyl, trifluoromethylthioethyl, hydroxycarbonyl, methoxycarbonyl, ethoxycarbonyl, n-propyloxycarbonyl, isopropyloxycarbonyl, n-butyloxycarbonyl, tert-butyloxycarbonyl, allyloxycarbonyl, benzyloxycarbonyl, aminocarbonyl, methylaminocarbonyl, ethylaminocarbonyl, n-propylaminocarbonyl, isopropylaminocarbonyl, dimethylaminocarbonyl, diethylaminocarbonyl, methyl(ethyl)aminocarbonyl, cyclopropylaminocarbonyl, cyclobutylaminocarbonyl, cyclopentylaminocarbonyl, cyclohexylaminocarbonyl, allylaminocarbonyl, benzylaminocarbonyl, tert-butyloxycarbonylaminocarbonyl, hydroxycarbonylmethyl, methoxycarbonylmethyl, ethoxycarbonylmethyl, n-propyloxycarbonylmethyl, isopropyloxycarbonylmethyl, n-butyloxycarbonylmethyl, tert-butyloxycarbonylmethyl, allyloxycarbonylmethyl, benzyloxycarbonylmethyl, aminocarbonylmethyl, methylaminocarbonylmethyl, ethylaminocarbonylmethyl, n-propylaminocarbonylmethyl, isopropylaminocarbonylmethyl, dimethylaminocarbonylmethyl, diethylaminocarbonylmethyl, methyl(ethyl)aminocarbonylmethyl, cyclopropylaminocarbonylmethyl, cyclobutylaminocarbonylmethyl, cyclopentylaminocarbonylmethyl, cyclohexylaminocarbonylmethyl, allylaminocarbonylmethyl, benzylaminocarbonylmethyl, aminomethyl, 2-aminoeth-1-yl, 1-aminoeth-1-yl, 1-aminoprop-1-yl, 3-aminoprop-1-yl, methylaminomethyl, dimethylaminomethyl, diethylaminomethyl, ethylaminomethyl, isopropylaminomethyl, cyclopropylaminomethyl, cyclobutylaminomethyl, cyclopentylaminomethyl, cyclohexylaminomethyl, methoxycarbonylaminomethyl, ethoxycarbonylaminomethyl, tert-butyloxycarbonylaminomethyl, or $R^7$ and $R^8$ together with the carbon atom to which they are bonded form a fully saturated or partly saturated 3- to 10-membered monocyclic or bicyclic ring optionally interrupted by heteroatoms and optionally having further substitution, or $R^7$ and $R^8$ together with the carbon atom to which they are bonded form a double bond optionally substituted by $R^{22}$ and $R^{23}$, according to formula (I″) below

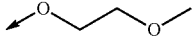

m is 0, 1, 2, n is 0, 1, 2, 3, 4, 5, 6, $R^{21}$ is hydrogen, fluorine, chlorine, bromine, trifluoromethyl, methoxy, ethoxy, n-propyloxy, n-butyloxy, $R^{22}$ and $R^{23}$ are independently hydrogen, fluorine, chlorine, bromine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, cyclopropyl, cyclobutyl, cyclopentyl, cyclohexyl, trifluoromethyl, difluoromethyl, pentafluoroethyl, ethenyl, 1-propenyl, 1-methylethenyl, 1-butenyl, phenyl, or $R^{22}$ and $R^{23}$ together with the carbon atom to which they are bonded forma 3- to 10-membered monocyclic or bicyclic ring which is saturated or optionally interrupted by heteroatoms and optionally has further substitution and Q is one of the moieties Q-1 to Q-345 specified below:

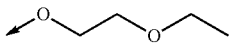 Q-1

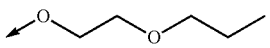 Q-2

 Q-3

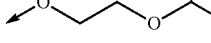 Q-4

 Q-5

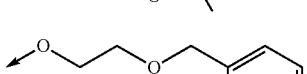 Q-6

 Q-7

Q-8

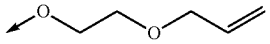 Q-9

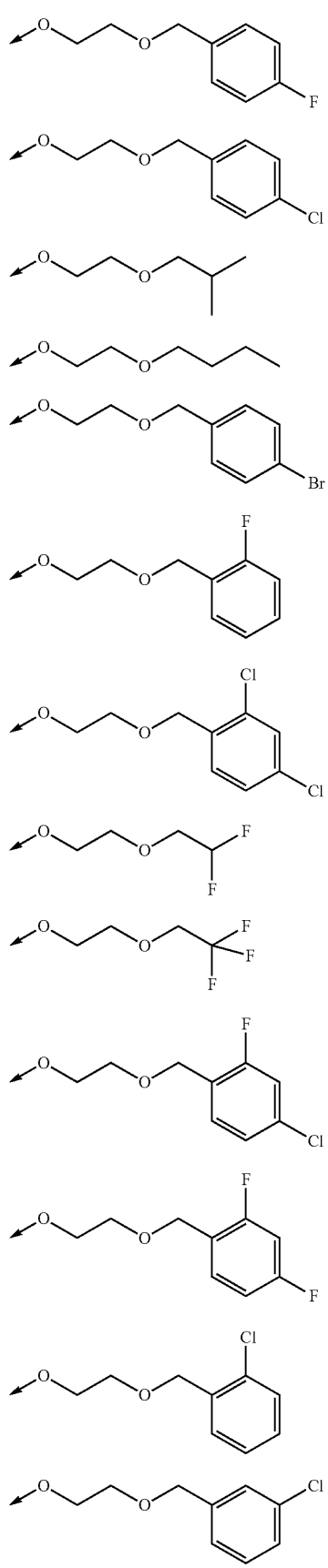
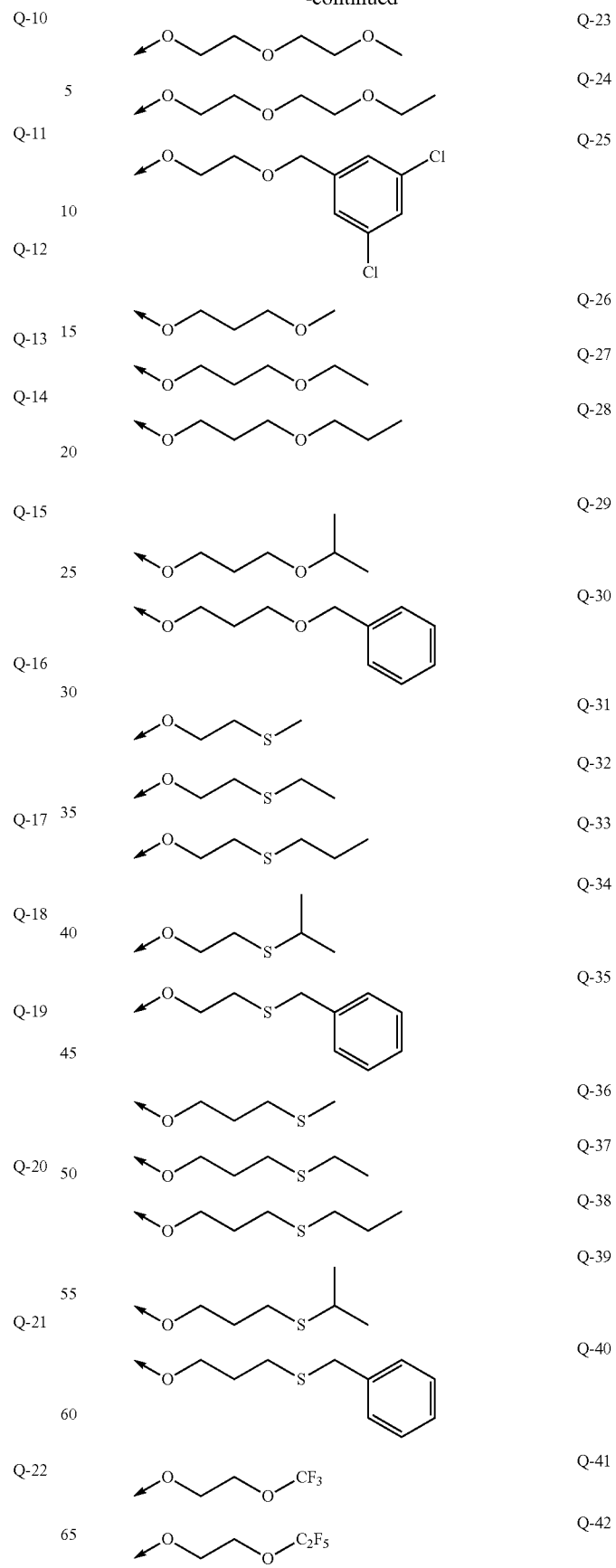

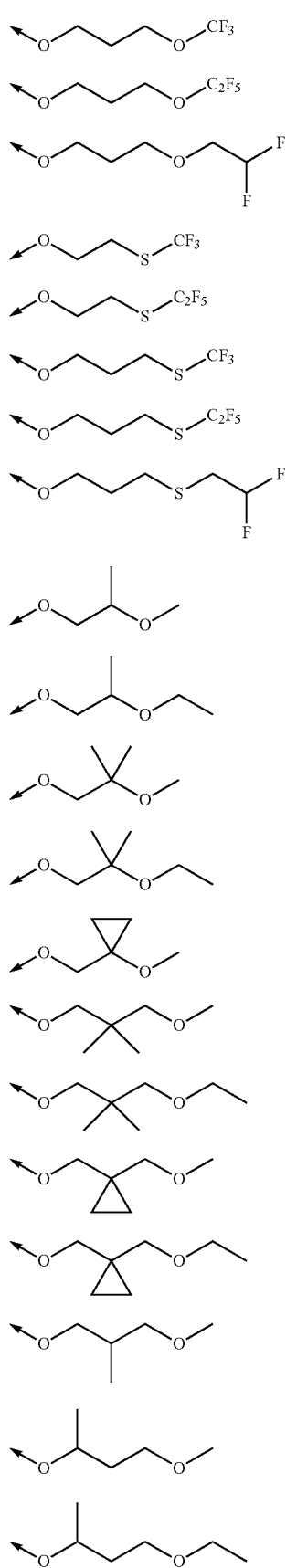
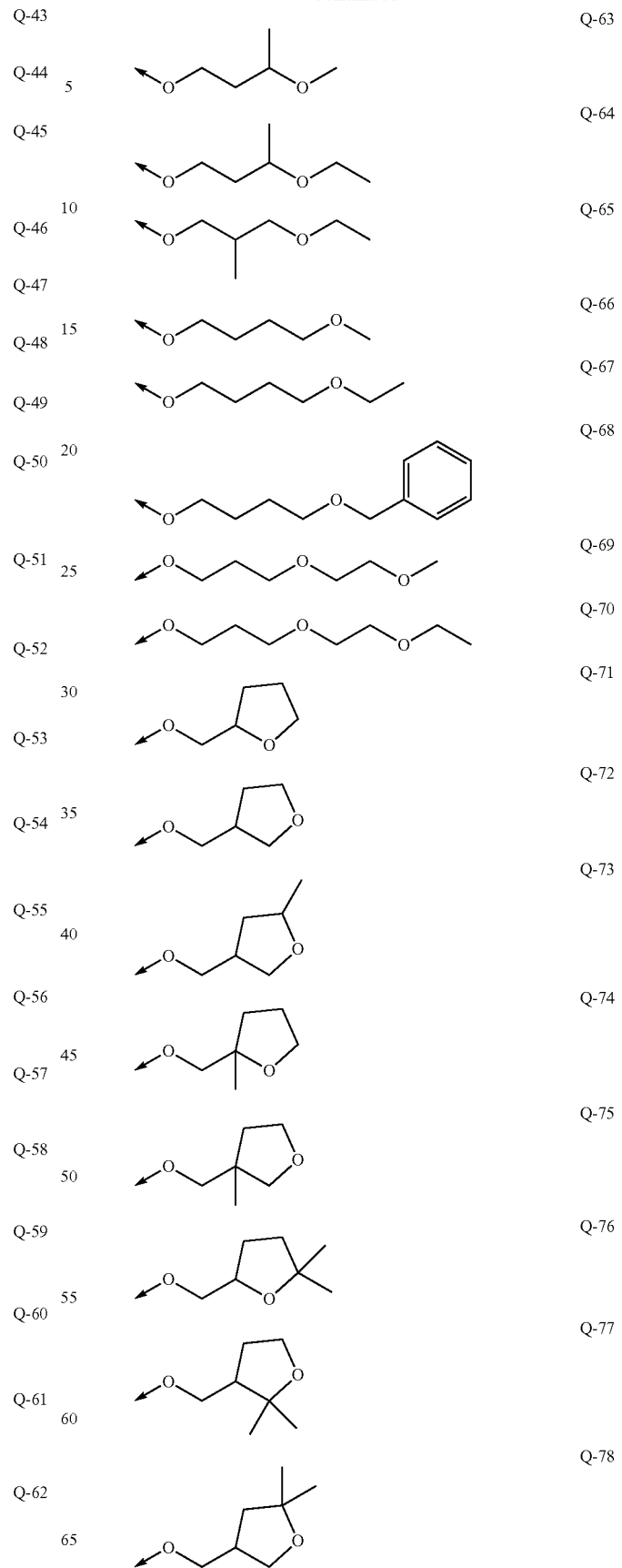

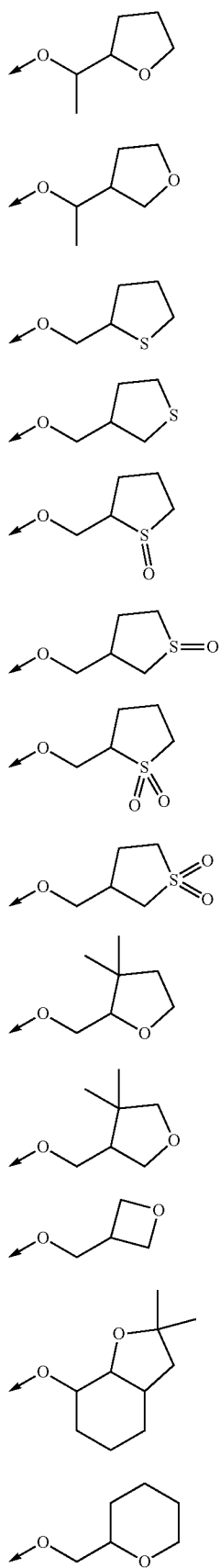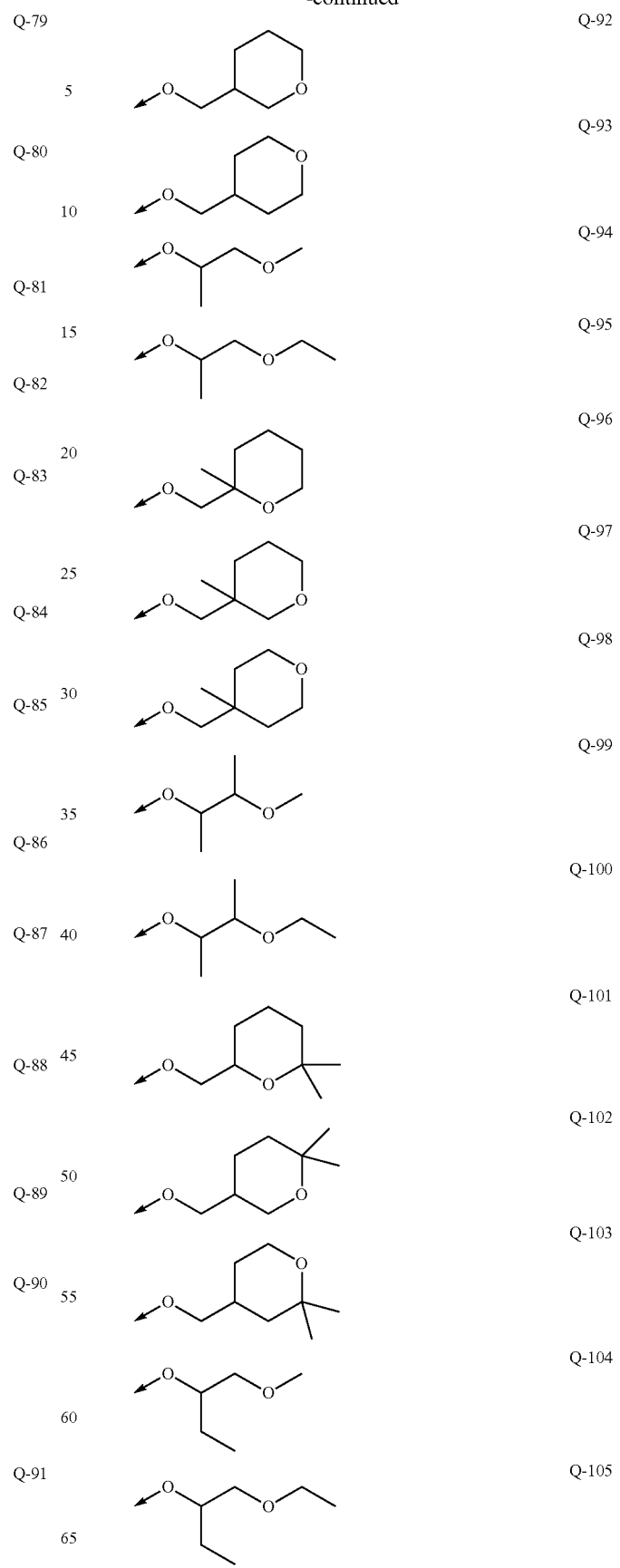

Q-106 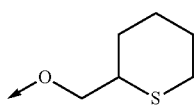
Q-107 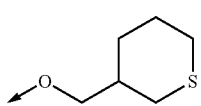
Q-108 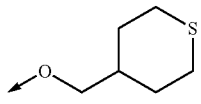
Q-109 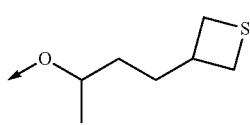
Q-110 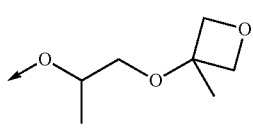
Q-111 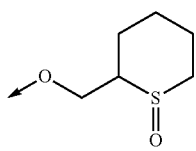
Q-112 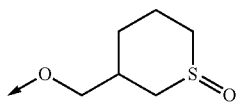
Q-113 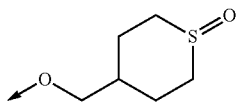
Q-114 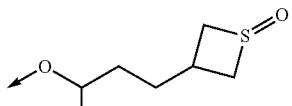
Q-115 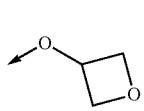
Q-116 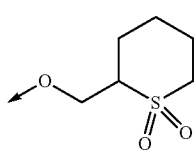
Q-117 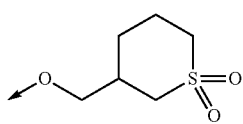
Q-118 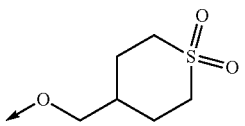
Q-119 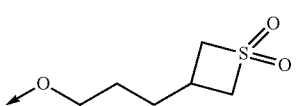
Q-120 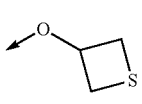
Q-121 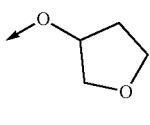
Q-122 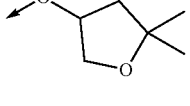
Q-123 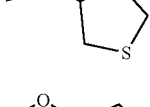
Q-124 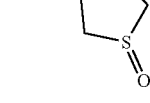
Q-125 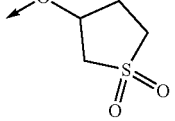
Q-126 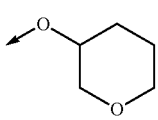
Q-127 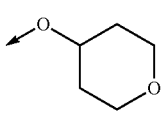
Q-128 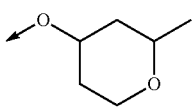
Q-129 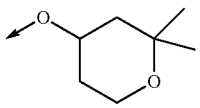
Q-130 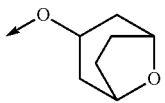

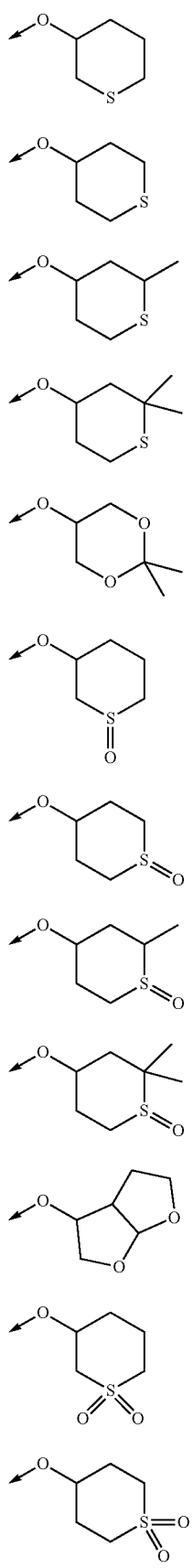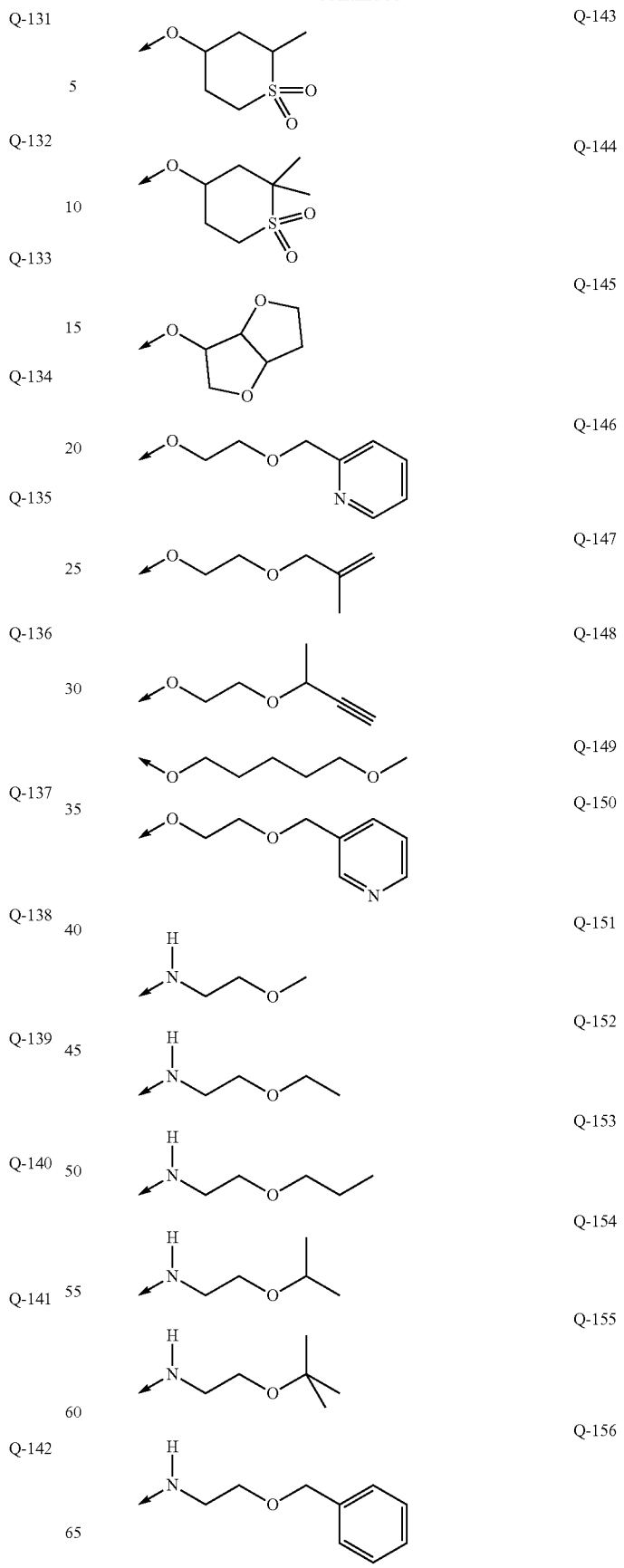

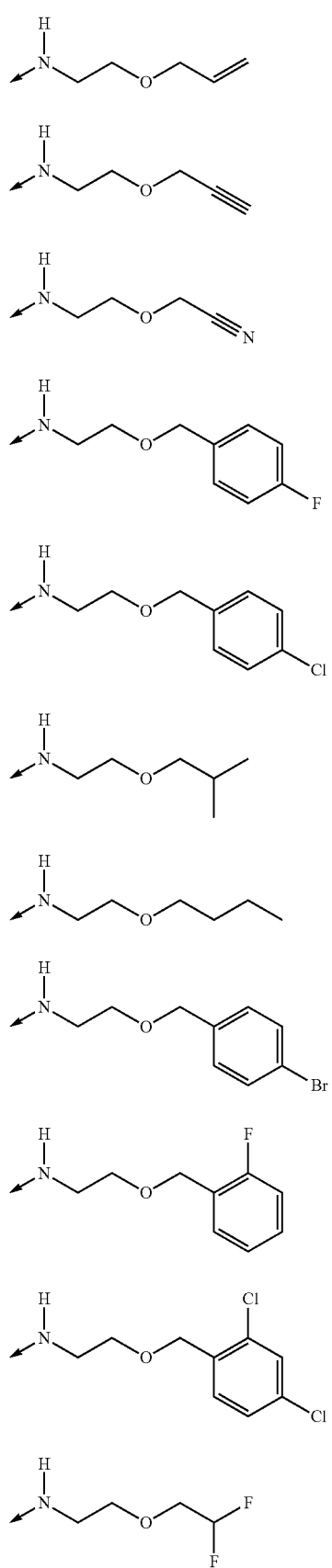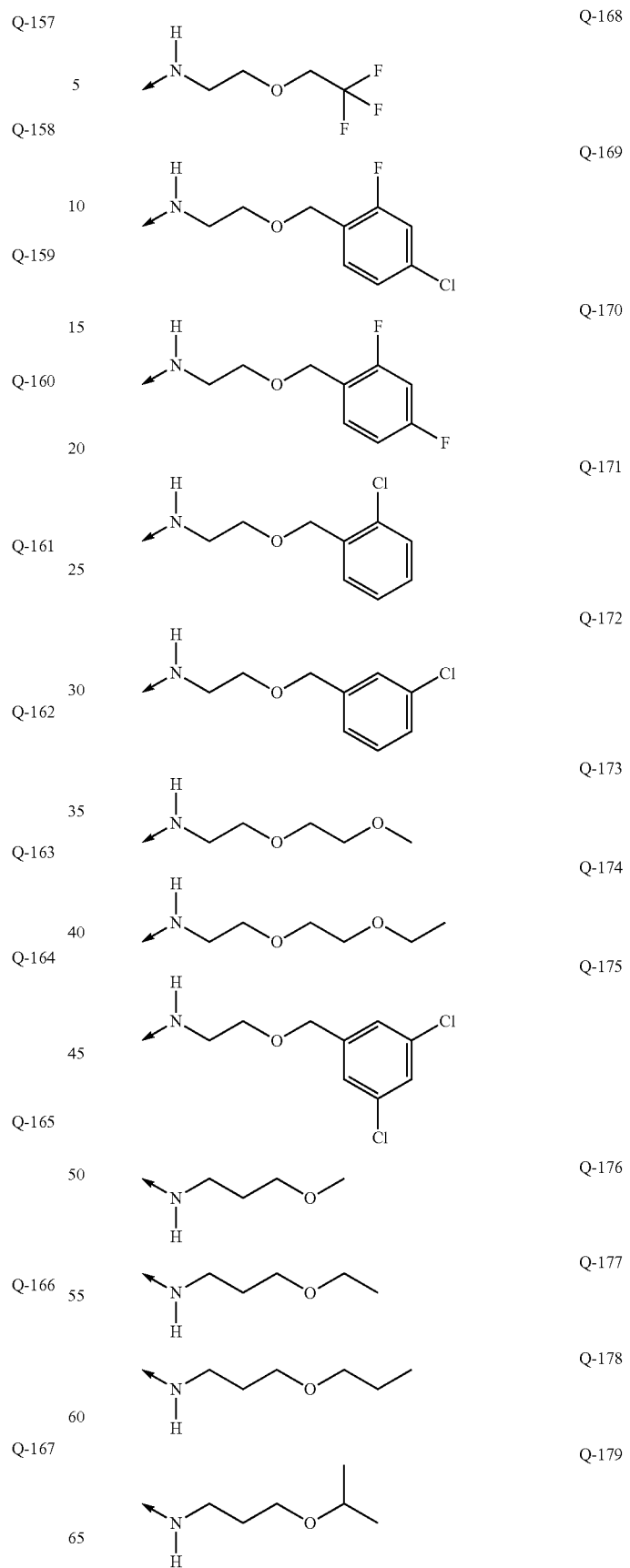

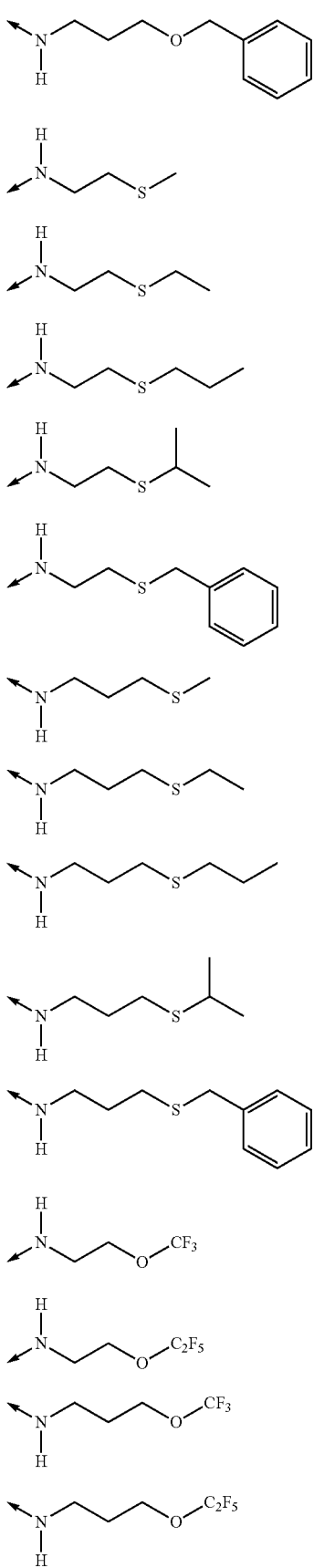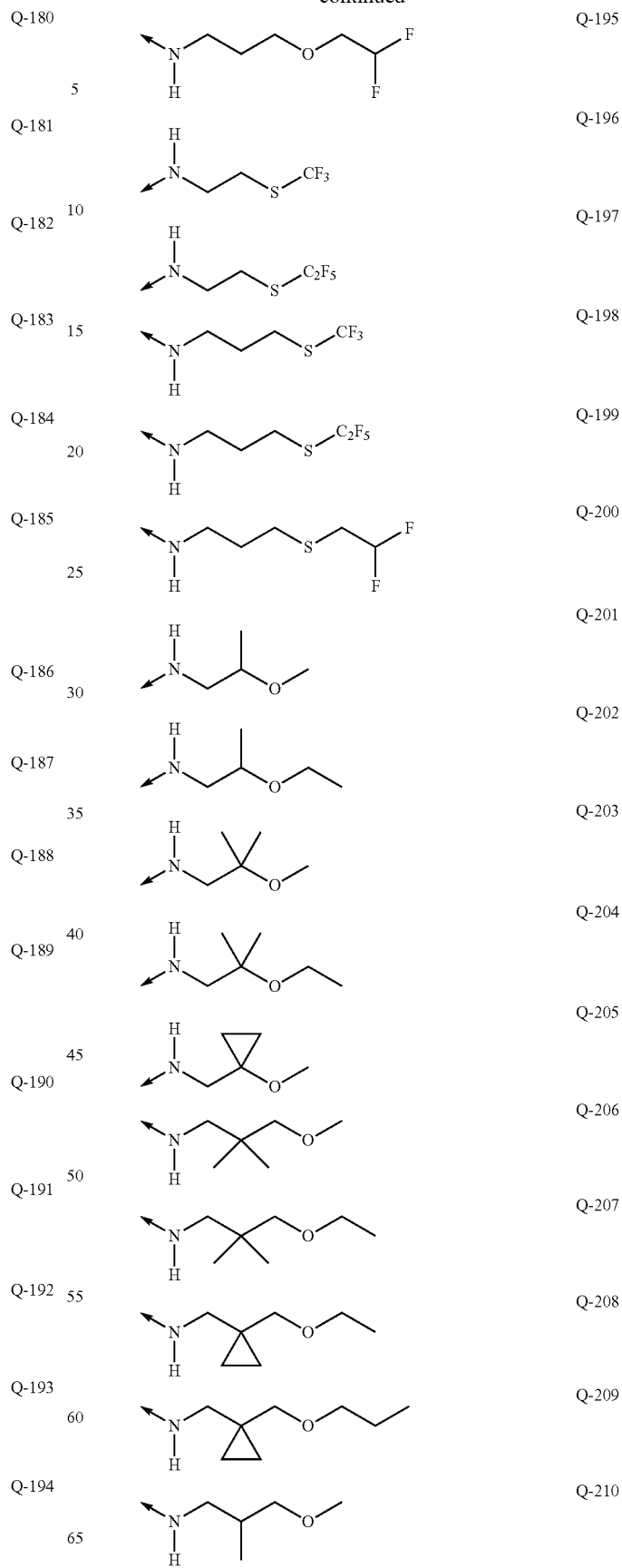

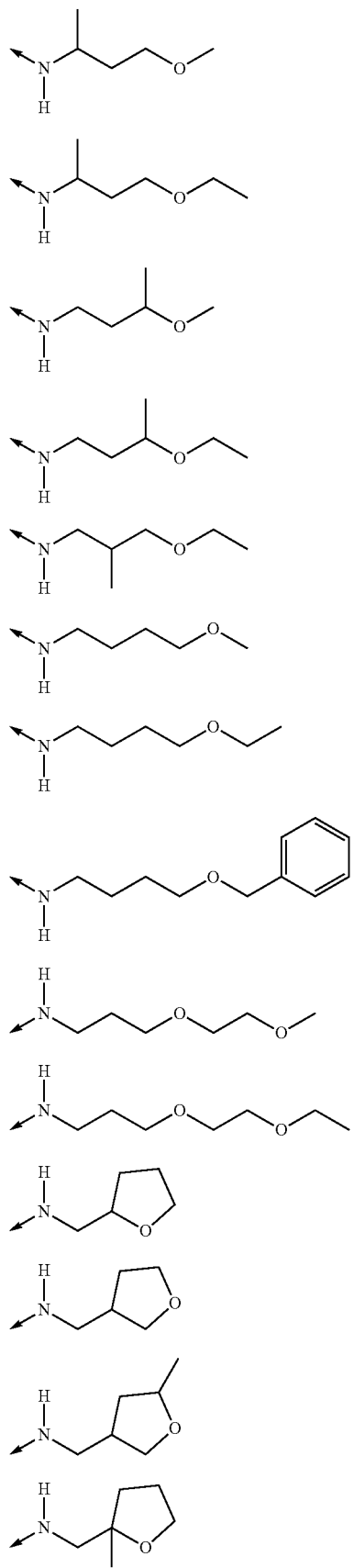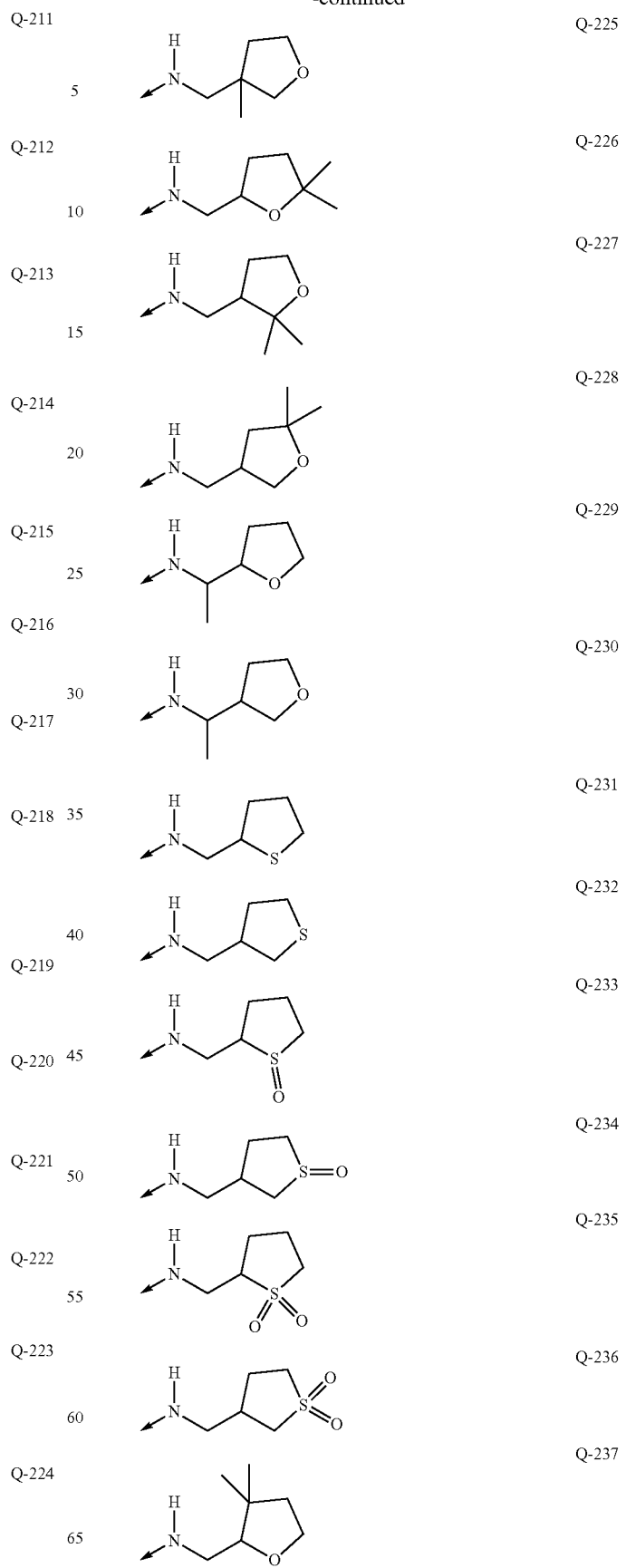

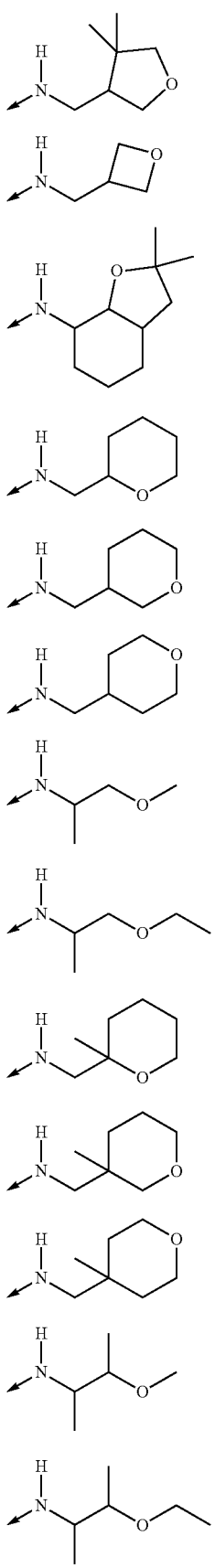
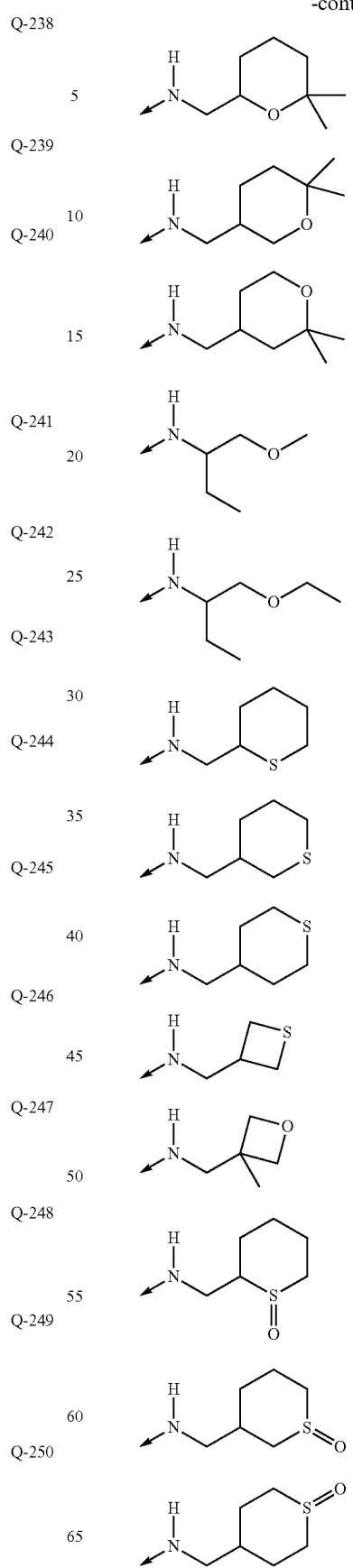

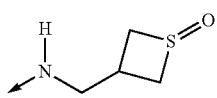
Q-264
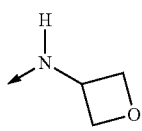
Q-265
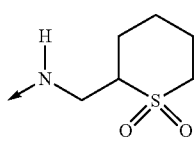
Q-266
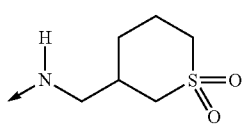
Q-267
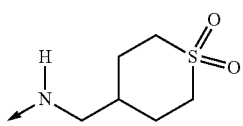
Q-268
Q-269
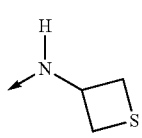
Q-270
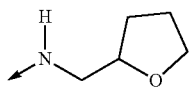
Q-271
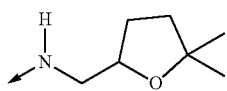
Q-272
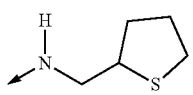
Q-273
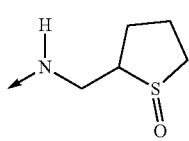
Q-274
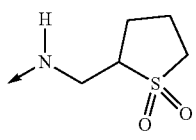
Q-275
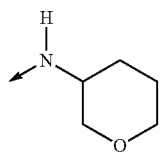
Q-276
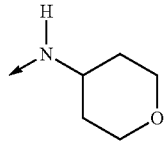
Q-277
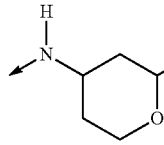
Q-278
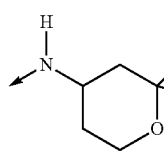
Q-279
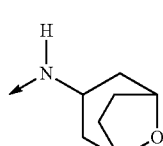
Q-280
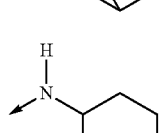
Q-281
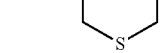
Q-282
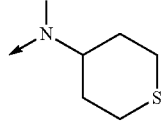
Q-282
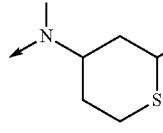
Q-283
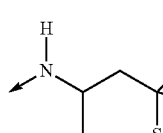
Q-284
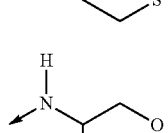
Q-285
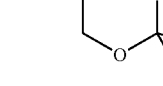

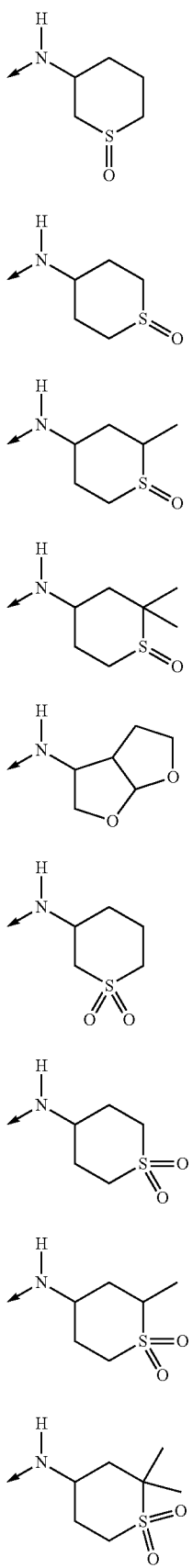
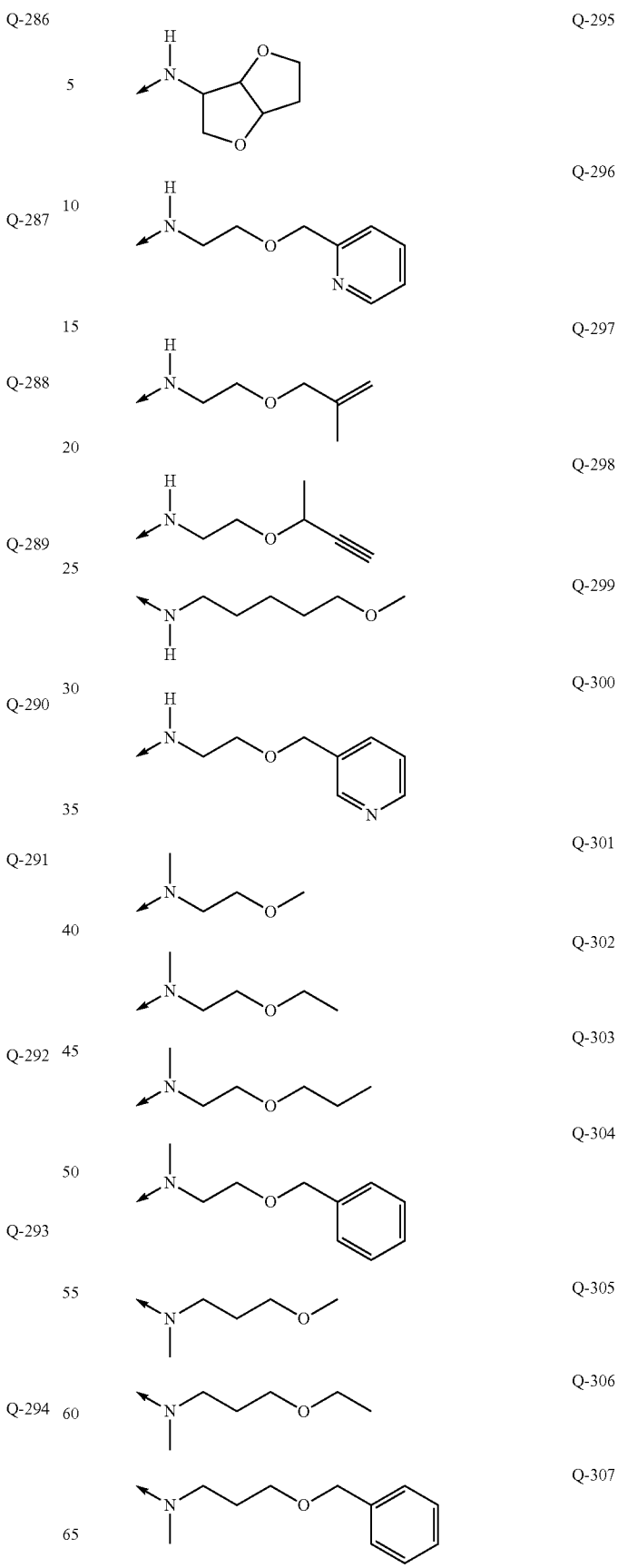

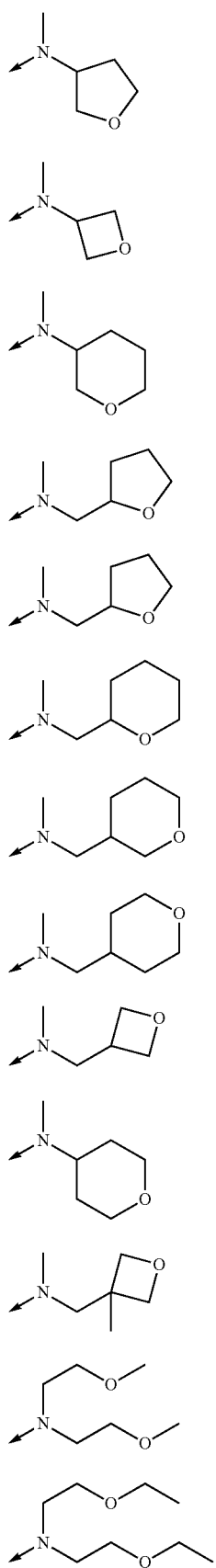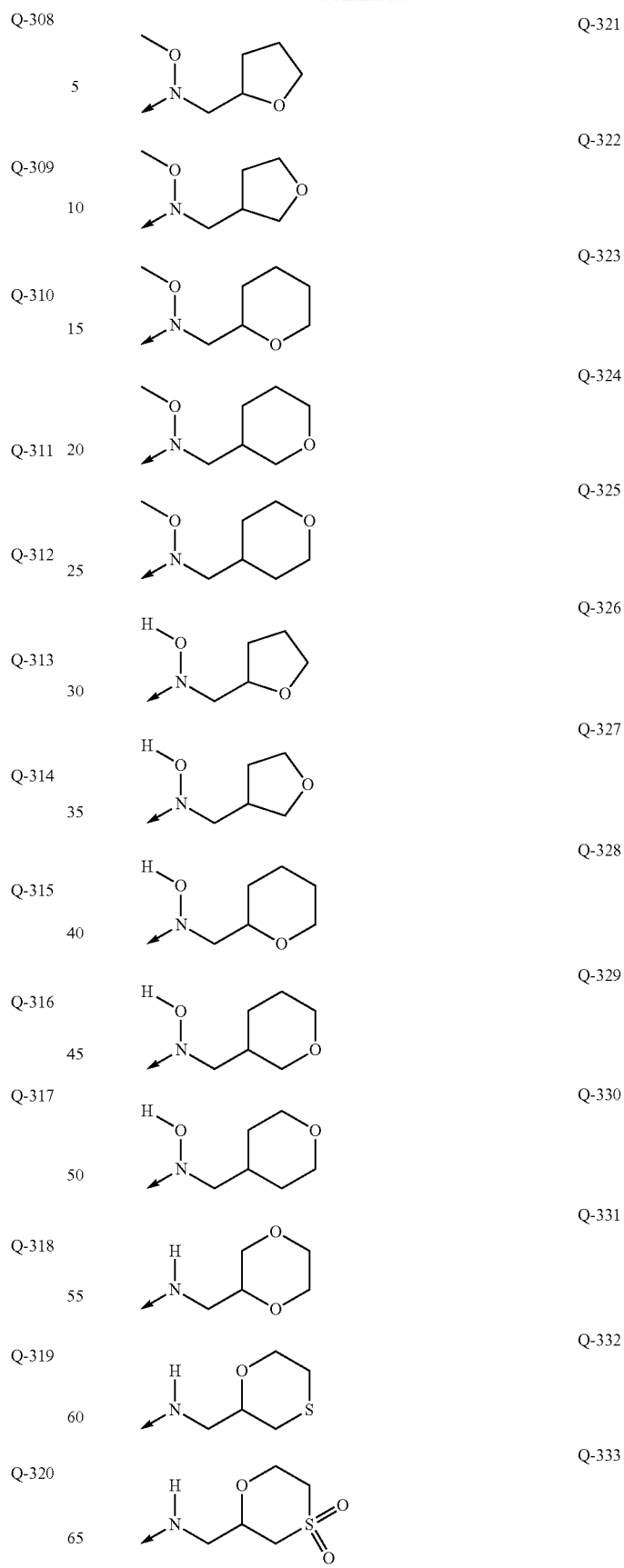

-continued

Q-334 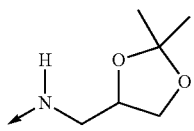

Q-335 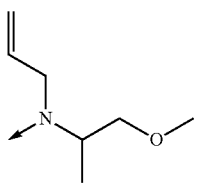

Q-336 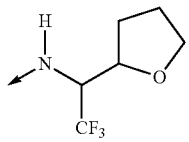

Q-337 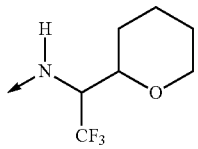

Q-338 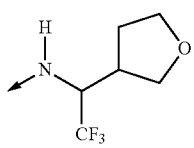

Q-339 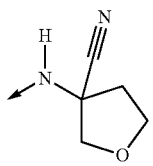

Q-340 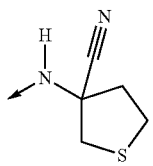

Q-341 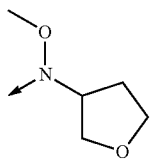

Q-342 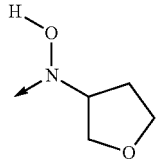

Q-343 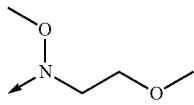

-continued

Q-344 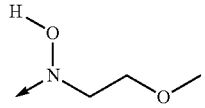

Q-345 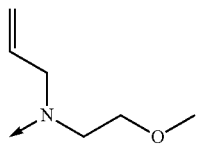

The invention especially preferably provides compounds of the general formula (I), in which $R^1$ is methyl, ethyl, n-propyl, 1-methylethyl, n-butyl, 1-methylpropyl, 2-methylpropyl, 1,1-dimethylethyl, n-pentyl, amino, dimethylamino, diethylamino, $R^2$ is hydrogen, methyl, ethyl, n-propyl, isopropyl, $R^3$ is hydrogen, fluorine, chlorine, bromine, methoxy, ethoxy, $R^4$ is halogen, cyano, C(O)NH$_2$, C(S)NH$_2$, difluoromethyl, trifluoromethyl, ethynyl, propyn-1-yl, $R^5$ and $R^6$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, ethynyl, 1-propynyl, 2-propynyl, 1-butynyl, 2-butynyl, 3-butynyl, trifluoromethyl, pentafluoroethyl, 1,1,2,2-tetrafluoroethyl, heptafluoropropyl, nonafluorobutyl, difluoromethyl, 2,2-difluoroethyl, 2,2,2-trifluoroethyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, phenyl, 2-fluorophenyl, 3-fluorophenyl, 4-fluorophenyl, 2,4-difluorophenyl, 2-chlorophenyl, 3-chlorophenyl, 4-chlorophenyl, 2,4-dichlorophenyl, 2,5-dichlorophenyl, 3,4-dichlorophenyl, 3,5-dichlorophenyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, phenylethyl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, methylthiomethyl, ethylthiomethyl, ethylthioethyl, methylthioethyl, n-propylthioethyl, isopropylthiomethyl, trifluoromethylthiomethyl, trifluoromethylthioethyl, or $R^5$ and $R^6$ together with the carbon atom to which they are bonded form a fully saturated or partly saturated 3- to 10-membered monocyclic or bicyclic ring optionally interrupted by heteroatoms and optionally having further substitution, or $R^5$ and $R^6$ together with the carbon atom to which they are bonded form a double bond optionally substituted by $R^{22}$ and $R^{23}$, according to formula (I') below

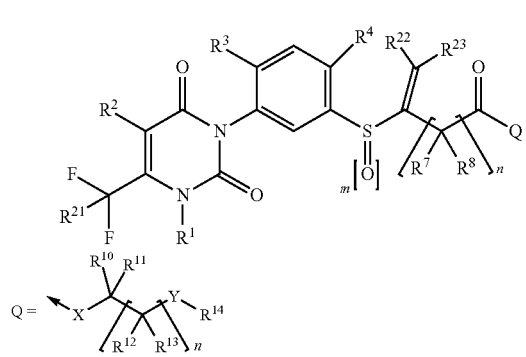

$R^7$ and $R^8$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, trifluoromethyl, pentafluoroethyl, 1,1,2,2-tetrafluoroethyl, heptafluoropropyl, difluoromethyl, 2,2-difluoroethyl, 2,2,2-trifluoroethyl, difluoro-tert-butyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, 2-fluorophenyl, 3-fluorophenyl, 4-fluorophenyl, 2,4-difluorophenyl, 2,5-difluorophenyl, 2,6-difluorophenyl, 2,3-difluorophenyl, 3,4-difluorophenyl, 3,5-difluorophenyl, 2,4,5-trifluorophenyl, 3,4,5-trifluorophenyl, 2-chlorophenyl, 3-chlorophenyl, 4-chlorophenyl, 2,4-dichlorophenyl, 2,5-dichlorophenyl, 2,6-dichlorophenyl, 2,3-dichlorophenyl, 3,4-dichlorophenyl, 3,5-dichlorophenyl, 2,4,5-trichlorophenyl, 3,4,5-trichlorophenyl, 2,4,6-trichlorophenyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (2,4,5-trifluorophenyl)methyl, (2,4,6-trifluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, (2,6-dichlorophenyl)methyl, (2,4,5-trichlorophenyl)methyl, (2,4,6-trichlorophenyl)methyl, methylthiomethyl, ethylthiomethyl, ethylthioethyl, methylthioethyl, n-propylthiomethyl, isopropylthiomethyl, trifluoromethylthiomethyl, trifluoromethylthioethyl, or $R^7$ and $R^8$ together with the carbon atom to which they are bonded form a fully saturated or partly saturated 3- to 10-membered monocyclic or bicyclic ring optionally interrupted by heteroatoms and optionally having further substitution, or $R^7$ and $R^8$ together with the carbon atom to which they are bonded form a double bond optionally substituted by $R^{22}$ and $R^{23}$, according to formula (I") below

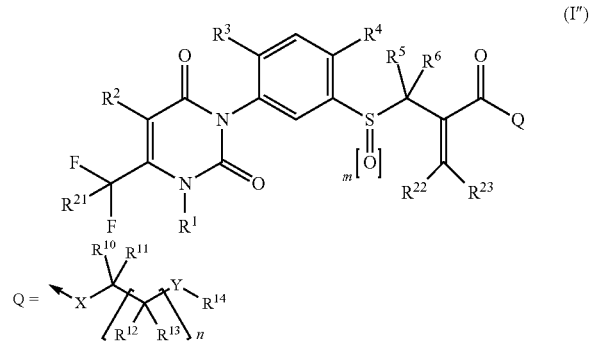

m is 0, 1, 2, n is 0, 1, 2, 3, $R^{21}$ is hydrogen, fluorine, chlorine, bromine, trifluoromethyl, methoxy, ethoxy, n-propyloxy, n-butyloxy, $R^{22}$ and $R^{23}$ are independently hydrogen, fluorine, chlorine, bromine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, cyclopropyl, cyclobutyl, cyclopentyl, cyclohexyl, trifluoromethyl, difluoromethyl, pentafluoroethyl, ethenyl, 1-propenyl, 1-methylethenyl, 1-butenyl, phenyl, or $R^{22}$ and $R^{23}$ together with the carbon atom to which they are bonded forma 3- to 10-membered monocyclic or bicyclic ring which is saturated or optionally interrupted by heteroatoms and optionally has further substitution and Q is one of the moieties Q-1 to Q-345 specified above.

The invention very especially preferably provides compounds of the general formula (I) in which $R^1$ is methyl, ethyl, n-propyl, 1-methylethyl, n-butyl, amino, dimethylamino, $R^2$ is hydrogen, methyl, ethyl, $R^3$ is hydrogen, fluorine, chlorine, bromine, methoxy, ethoxy, $R^4$ is fluorine, chlorine, bromine, cyano, C(O)NH$_2$, C(S)NH$_2$, difluoromethyl, trifluoromethyl, ethynyl, propyn-1-yl, $R^5$ and $R^6$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, ethynyl, 1-propynyl, 2-propynyl, 1-butynyl, 2-butynyl, 3-butynyl, trifluoromethyl, pentafluoroethyl, 1,1,2,2-tetrafluoroethyl, heptafluoropropyl, nonafluorobutyl, difluoromethyl, 2,2-difluoroethyl, 2,2,2-trifluoroethyl, methoxy, ethoxy, n-propyloxy, isopropyloxy, n-butyloxy, methoxymethyl, ethoxymethyl, n-propyloxymethyl, isopropyloxymethyl, methoxyethyl, ethoxyethyl, n-propyloxyethyl, methoxy-n-propyl, phenyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, phenylethyl, benzyl, methylthiomethyl, ethylthiomethyl, ethylthioethyl, methylthioethyl, n-propylthiomethyl, isopropylthiomethyl, trifluoromethylthiomethyl, trifluoromethylthioethyl, or $R^5$ and $R^6$ together with the carbon atom to which they are bonded form a fully saturated or partly saturated 3- to 10-membered monocyclic or bicyclic ring optionally interrupted by heteroatoms and optionally having further substitution, or $R^5$ and $R^6$ together with the carbon atom to which they are bonded form a double bond optionally substituted by $R^{22}$ and $R^{23}$, according to formula (I') below

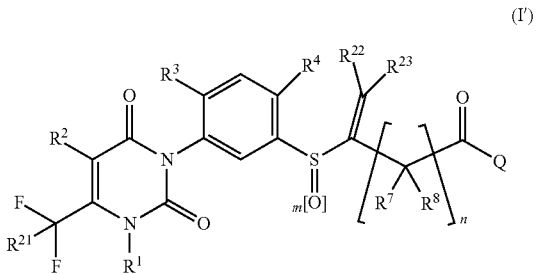

(I')

$R^7$ and $R^8$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, trifluoromethyl, pentafluoroethyl, 1,1,2,2-tetrafluoroethyl, heptafluoropropyl, difluoromethyl, 2,2-difluoroethyl, 2,2,2-trifluoroethyl, methoxy, ethoxy, n-propyloxy, isopropyloxy, n-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, benzyl, methylthiomethyl, ethylthiomethyl, ethylthioethyl, methylthioethyl, n-propylthiomethyl, isopropylthiomethyl, trifluoromethylthiomethyl, trifluoromethylthioethyl or $R^7$ and $R^8$ together with the carbon atom to which they are bonded form a fully saturated or partly saturated 3- to 10-membered monocyclic or bicyclic ring optionally interrupted by heteroatoms and optionally having further substitution, or $R^7$ and $R^8$ together with the carbon atom to which they are bonded form a double bond optionally substituted by $R^{22}$ and $R^{23}$, according to formula (I'') below

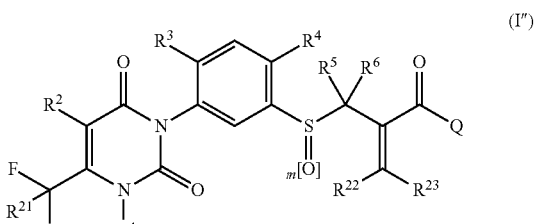

(I'')

m is 0, 1, 2, n is 0, 1, 2, 3, $R^{21}$ is hydrogen, fluorine, chlorine, bromine, trifluoromethyl, methoxy, ethoxy, $R^{22}$ and $R^{23}$ are independently hydrogen, fluorine, chlorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, cyclopropyl, cyclobutyl, cyclopentyl, cyclohexyl, trifluoromethyl, difluoromethyl, pentafluoroethyl, ethenyl, 1-propenyl, 1-methylethenyl, 1-butenyl, phenyl, or $R^{22}$ and $R^{23}$ together with the carbon atom to which they are bonded form a 3- to 10-membered monocyclic or bicyclic ring which is saturated or optionally interrupted by heteroatoms and optionally has further substitution and Q is one of the following moieties: Q-1, Q-2, Q-3, Q-6, Q-7, Q-8, Q-10, Q-11, Q-18, Q-23, Q-24, Q-26, Q-27, Q-28, Q-30, Q-31, Q-32, Q-36, Q-41, Q-42, Q-46, Q-48, Q-51, Q-52, Q-71, Q-72, Q-73, Q-74, Q-79, Q-80, Q-81, Q-82, Q-89, Q-91, Q-92, Q-93, Q-94, Q-95, Q-106, Q-108, Q-115, Q-117, Q-118, Q-121, Q-123, Q-126, Q-127, Q-132, Q-142, Q-151, Q-152, Q-153, Q-156, Q-157, Q-158, Q-176, Q-177, Q-180, Q-181, Q-216, Q-221, Q-224, Q-229, Q-239, Q-241, Q-242, Q-243, Q-271, Q-273, Q-275, Q-276, Q-277, Q-285, Q-301, Q-302, Q-308, Q-311, Q-312, Q-331, Q-333, Q-334, Q-335, Q-336, Q-340, Q-341.

The abovementioned radical definitions given in general terms or listed within areas of preference apply both to the end products of the formula (I) and correspondingly to the starting materials or intermediates required in each case for the production. These radical definitions can be combined with one another as desired, i.e. including combinations between the stated ranges of preference.

Primarily for reasons of higher herbicidal activity, better selectivity and/or better preparability, particular interest is attached to inventive compounds of the specified formula (I) or salts thereof or use thereof according to the invention in which individual radicals have one of the preferred meanings already specified or specified hereinafter, or in particular to those in which one or more of the preferred meanings already specified or specified hereinafter occur in combination.

When the compounds can form, by a hydrogen shift, tautomers having structures that would not be covered by the formula (I) in a formal sense, these tautomers are nevertheless encompassed by the definition of the inventive compounds of the formula (I), unless a particular tautomer is under consideration. For example, many carbonyl compounds may be present either in the keto form or in the enol form, both forms being encompassed by the definition of the compound of the formula (I).

Depending on the nature of the substituents and the manner in which they are attached, the compounds of the general formula (I) may exist as stereoisomers. The possible stereoisomers defined by their specific three-dimensional shape, such as enantiomers, diastereomers and Z and E isomers, are all encompassed by the formula (I). If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. Chromatographic separation can be effected either on the analytical scale to determine the enantiomeric excess or diastereomeric excess or on the preparative scale for preparation of test specimens for biological testing. It is likewise possible to selectively prepare stereoisomers by using stereoselective reactions with use of optically active starting materials and/or auxiliaries. The invention thus also relates to all stereoisomers that are encompassed by the general formula (I) but are not defined with their specific stereometric form, as well as mixtures thereof.

If the compounds are obtained in solid form, purification can also be effected by recrystallization or digestion. If individual compounds (I) are unobtainable satisfactorily by the routes described hereinafter, they can be prepared by derivatization of other compounds (I).

Useful isolation, purification and stereoisomer separation processes for compounds of the formula (I) include methods known in general terms to a person skilled in the art from analogous cases, for example by physical processes such as crystallization, chromatography methods, particularly column chromatography and HPLC (high-pressure liquid chromatography), distillation, optionally under reduced pressure, extraction and other processes; any remaining mixtures can generally be separated by chromatographic separation, for example on solid chiral phases. For preparative amounts or on the industrial scale, useful processes include crystallization, for example of diastereomeric salts that can be obtained from the diastereomer mixtures with optically active acids and, if appropriate, in the presence of acidic groups, with optically active bases.

With regard to the compounds of the invention, the designations used above and further down are elucidated. These are familiar to the person skilled in the art and especially have the meanings elucidated hereinafter:

Unless defined differently, it is generally the case in respect of the designation of chemical groups that the binding to the skeleton or the rest of the molecule is via the last structural element mentioned in the chemical group in question, i.e., for example, via the oxygen atom in the case of $(C_2-C_8)$-alkenyloxy, and via the respective carbon atom of the alkyl group in the case of heterocyclyl-$(C_1-C_8)$-alkyl or $R^{17}O(O)C-(C_1-C_8)$-alkyl.

According to the invention, "alkylsulfonyl"—on its own or as part of a chemical group—represents straight-chain or branched alkylsulfonyl, preferably having 1 to 8, or having 1 to 6, carbon atoms, for example (but not limited to) $(C_1-C_6)$-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

According to the invention, "heteroarylsulfonyl" represents optionally substituted pyridylsulfonyl, pyrimidinylsulfonyl, pyrazinylsulfonyl or optionally substituted polycyclic heteroarylsulfonyl, here especially optionally substituted quinolinylsulfonyl, for example substituted by fluorine, chlorine, bromine, iodine, cyano, nitro, or alkyl, haloalkyl, haloalkoxy, amino, alkylamino, alkylcarbonylamino, dialkylamino or alkoxy groups.

According to the invention, "alkylthio"—on its own or as part of a chemical group—is straight-chain or branched S-alkyl, preferably having 1 to 8, or having 1 to 6, carbon atoms, such as $(C_1-C_{10})$-, $(C_1-C_6)$- or $(C_1-C_4)$-alkylthio, for example (but not limited to) $(C_1-C_6)$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

According to the invention, "alkenylthio" means an alkenyl radical bonded via a sulfur atom, alkynylthio means an alkynyl radical bonded via a sulfur atom, cycloalkylthio means a cycloalkyl radical bonded via a sulfur atom, and cycloalkenylthio means a cycloalkenyl radical bonded via a sulfur atom.

"Alkylsulfinyl (alkyl-S(=O)—)", unless defined differently elsewhere, according to the invention, represents alkyl radicals bonded to the skeleton via —S(=O)—, such as $(C_1-C_{10})$-, $(C_1-C_6)$- or $(C_1-C_4)$-alkylsulfinyl, for example (but not limited to) $(C_1-C_6)$-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

Analogously, "alkenylsulfinyl" and "alkynylsulfinyl" are respectively defined in accordance with the invention as alkenyl and alkynyl radicals bonded to the skeleton via —S(=O)—, such as $(C_2-C_{10})$-, $(C_2-C_6)$- or $(C_2-C_4)$-alkenylsulfinyl and $(C_3-C_{10})$-, $(C_3-C_6)$- or $(C_3-C_4)$-alkynylsulfinyl.

Analogously, "alkenylsulfonyl" and "alkynylsulfonyl" are respectively defined in accordance with the invention as alkenyl and alkynyl radicals bonded to the skeleton via —S(=O)$_2$—, such as $(C_2-C_{10})$-, $(C_2-C_6)$- or $(C_2-C_4)$-alkenylsulfonyl and $(C_3-C_{10})$-, $(C_3-C_6)$- or $(C_3-C_4)$-alkynylsulfonyl.

"Alkoxy" means an alkyl radical bonded via an oxygen atom, for example (but not limited to) $(C_1-C_6)$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Alkenyloxy means an alkenyl radical bonded via an oxygen atom, alkynyloxy means an alkynyl radical bonded via an oxygen atom, such as $(C_2-C_{10})$-, $(C_2-C_6)$- or $(C_2-C_4)$-alkenyloxy or $(C_3-C_{10})$-, $(C_3-C_6)$- or $(C_3-C_4)$-alkynyloxy.

"Cycloalkyloxy" means a cycloalkyl radical bonded via an oxygen atom, and cycloalkenyloxy means a cycloalkenyl radical bonded via an oxygen atom.

"Alkylcarbonyl" (alkyl-C(=O)—), unless defined differently elsewhere, according to the invention, represents alkyl radicals bonded to the skeleton via —C(=O)—, such as $(C_1-C_{10})$-, $(C_1-C_6)$- or $(C_1-C_4)$-alkylcarbonyl. The number of carbon atoms relates here to the alkyl radical in the alkylcarbonyl group.

Analogously, "alkenylcarbonyl" and "alkynylcarbonyl", unless defined differently elsewhere, according to the invention, represent alkenyl and alkynyl radicals bonded to the skeleton via —C(=O)—, such as $(C_2-C_{10})$-, $(C_2-C_6)$- or $(C_2-C_4)$-alkenylcarbonyl and $(C_2-C_{10})$-, $(C_2-C_6)$- or $(C_2-C_4)$-alkynylcarbonyl. The number of carbon atoms relates here to the alkenyl or alkynyl radical in the alkenyl- or alkynylcarbonyl group.

"Alkoxycarbonyl (alkyl-O—C(=O)—)", unless defined differently elsewhere: alkyl radicals bonded to the skeleton via —O—C(=O)—, such as $(C_1-C_{10})$-, $(C_1-C_6)$- or $(C_1-C_4)$-alkoxycarbonyl. The number of carbon atoms relates here to the alkyl radical in the alkoxycarbonyl group. Analogously, "alkenyloxycarbonyl" and "alkynyloxycarbonyl", unless defined differently elsewhere, according to the invention, represent alkenyl and alkynyl radicals bonded to the skeleton via —O—C(=O)—, such as $(C_2-C_{10})$-, $(C_2-C_6)$- or $(C_2-C_4)$-alkenyloxycarbonyl and $(C_3-C_{10})$-, $(C_3-C_6)$- or $(C_3-C_4)$-alkynyloxycarbonyl. The number of carbon atoms relates here to the alkenyl or alkynyl radical in the alkenyl- or alkynyloxycarbonyl group.

According to the invention, the term "alkylcarbonyloxy" (alkyl-C(=O)—O—), unless defined differently elsewhere, represents alkyl radicals bonded to the skeleton via a carbonyloxy group (—C(=O)—O—) by the oxygen, such as $(C_1-C_{10})$-, $(C_1-C_6)$- or $(C_1-C_4)$-alkylcarbonyloxy. The number of carbon atoms relates here to the alkyl radical in the alkylcarbonyloxy group.

Analogously, "alkenylcarbonyloxy" and "alkynylcarbonyloxy" are respectively defined in accordance with the invention as alkenyl and alkynyl radicals bonded to the skeleton via (—C(=O)—O—) by the oxygen, such as $(C_2-C_{10})$-, $(C_2-C_6)$- or $(C_2-C_4)$-alkenylcarbonyloxy and $(C_2-C_{10})$-, $(C_2-C_6)$- or $(C_2-C_4)$-alkynylcarbonyloxy. The number of carbon atoms relates here to the alkenyl or alkynyl radical in the alkenyl- or alkynylcarbonyloxy group.

In abbreviated forms such as C(O)R, C(O)OR$^{17}$, OC(O)NR$^{15}$R$^{16}$, or C(O)NR$^{15}$R$^{16}$, for example, the abbreviation O listed between brackets represents an oxygen atom bonded to the adjacent carbon atom via a double bond.

In abbreviated forms such as OC(S)OR$^{17}$, OC(S)SR$^{18}$, OC(S)NR$^{15}$R$^{16}$, for example, the abbreviation S listed between brackets represents a sulfur atom bonded to the adjacent carbon atom via a double bond.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems such as tetrahydronaphtyl, indenyl, indanyl, fluorenyl, biphenylyl, where the bonding site is on the aromatic system. In systematic terms, "aryl" is generally also encompassed by the term "optionally substituted phenyl". Preferred aryl substituents here are, for example, hydrogen, halogen, alkyl, cycloalkyl, cycloalkylalkyl, cycloalkenyl, halocycloalkyl, alkenyl, alkynyl, aryl, arylalkyl, arylalkenyl, heteroaryl, heteroarylalkyl, heterocyclyl, heterocyclylalkyl, alkoxyalkyl, alkylthio, haloalkylthio, haloalkyl, alkoxy, haloalkoxy, cycloalkoxy, cycloalkylalkoxy, aryloxy, heteroaryloxy, alkoxyalkoxy, alkynylalkoxy, alkenyloxy, bisalkylaminoalkoxy, tris[alkyl]silyl, bis[alkyl]arylsilyl, bis[alkyl]alkylsilyl, tris[alkyl]silylalkynyl, arylalkynyl, heteroarylalkynyl, alkylalkynyl, cycloalkylalkynyl, haloalkylalkynyl, heterocyclyl-N-alkoxy, nitro, cyano, amino, alkylamino, bisalkylamino, alkylcarbonylamino, cycloalkylcarbonylamino, arylcarbonylamino, alkoxycarbonylamino, alkoxycarbonylalkylamino, arylalkoxycarbonylalkylamino, hydroxycarbonyl, alkoxycarbonyl, aminocarbonyl, alkylaminocarbonyl, cycloalkylaminocarbonyl, bisalkylaminocarbonyl, heteroarylalkoxy, arylalkoxy.

A heterocyclic radical (heterocyclyl) contains at least one heterocyclic ring (=carbocyclic ring in which at least one carbon atom is replaced by a heteroatom, preferably by a heteroatom from the group of N, O, S, P) which is saturated, unsaturated, partly saturated or heteroaromatic and may be unsubstituted or substituted, where the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. In the case of optionally substituted heterocyclyl, spirocyclic systems are also included, for example 1-oxa-5-azaspiro[2.3]hexyl. Unless defined differently, the heterocyclic ring preferably contains 3 to 9 ring atoms, especially 3 to 6 ring atoms, and one or more, preferably 1 to 4, especially 1, 2 or 3, heteroatoms in the heterocyclic ring, preferably from the group of N, O and S, although no two oxygen atoms should be directly adjacent, for example with one heteroatom from the group of N, O and S: 1- or 2- or 3-pyrrolidinyl; 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl. Preferred 3- and 4-membered heterocyclic rings are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partially or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyriazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of "heterocyclyl" are a partially or fully hydrogenated heterocyclic radical having 3 heteroatoms from the group of N, O and S, for example 1,4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl. Structure examples of optionally further-substituted heterocycles are also listed below:

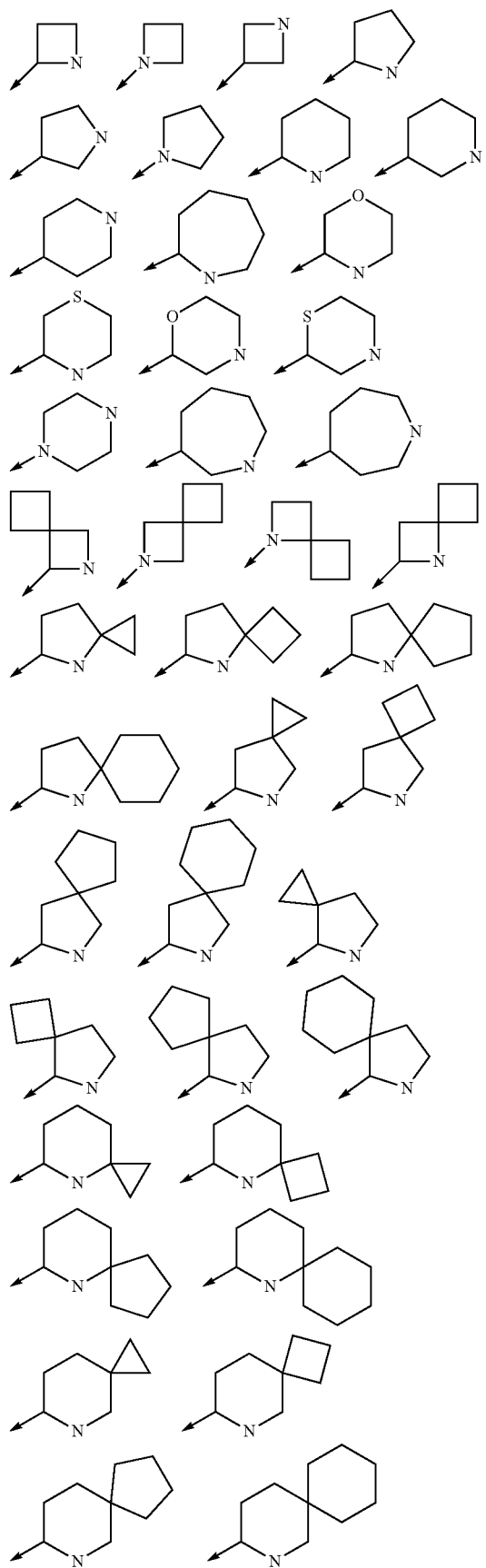

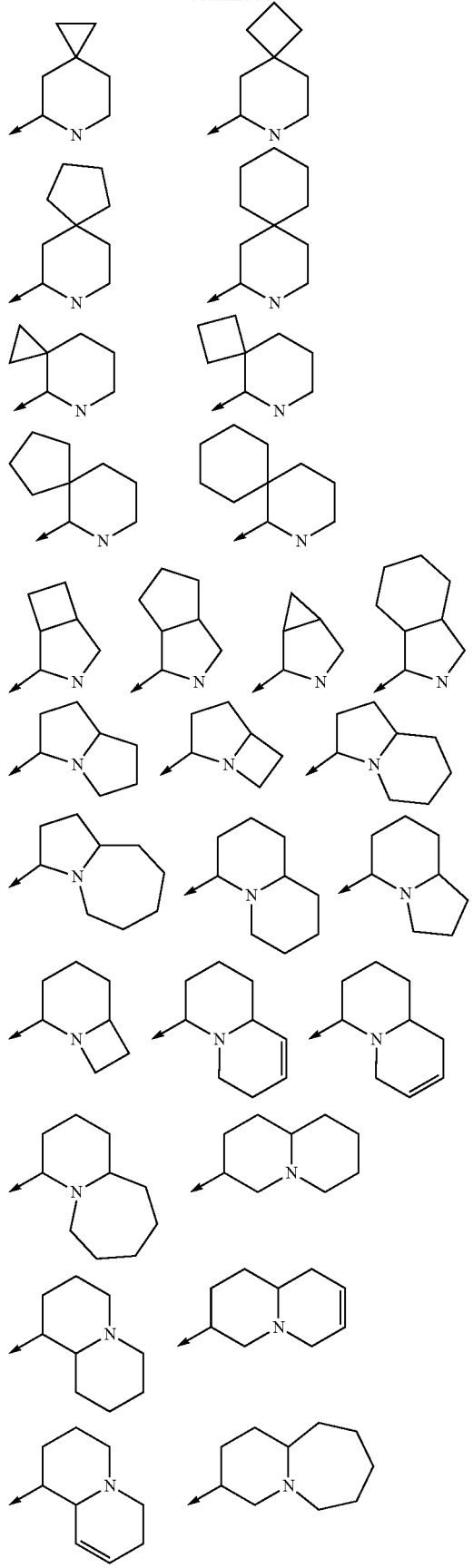
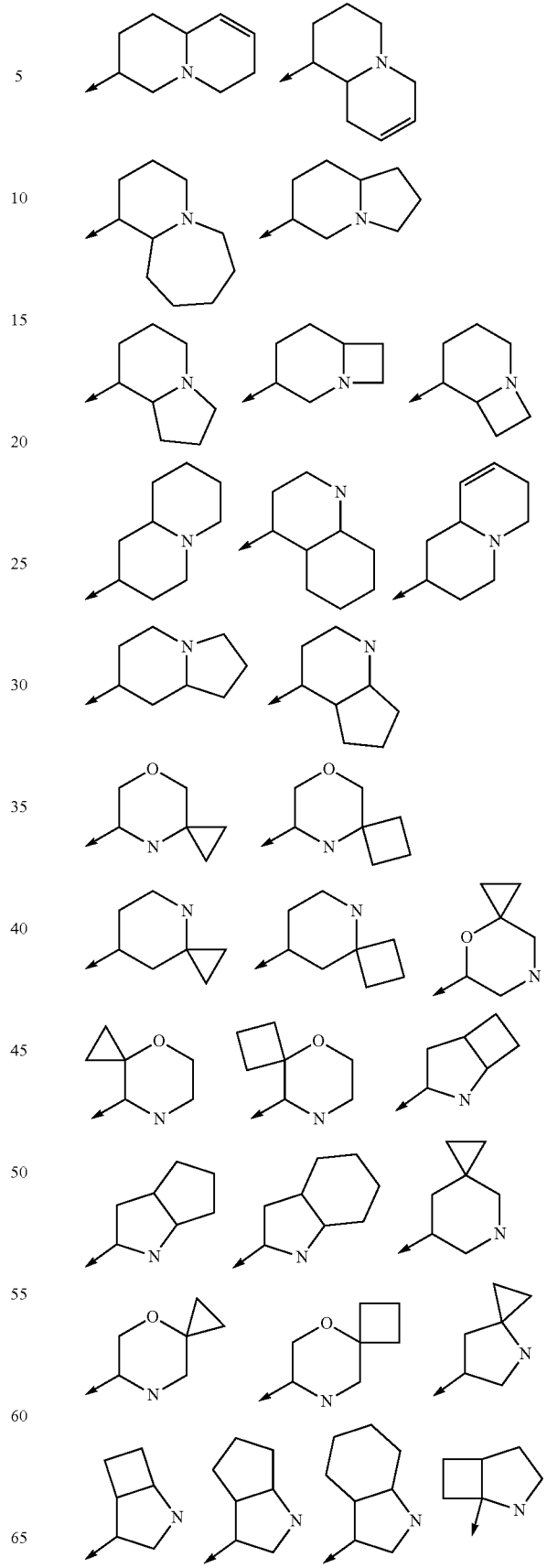

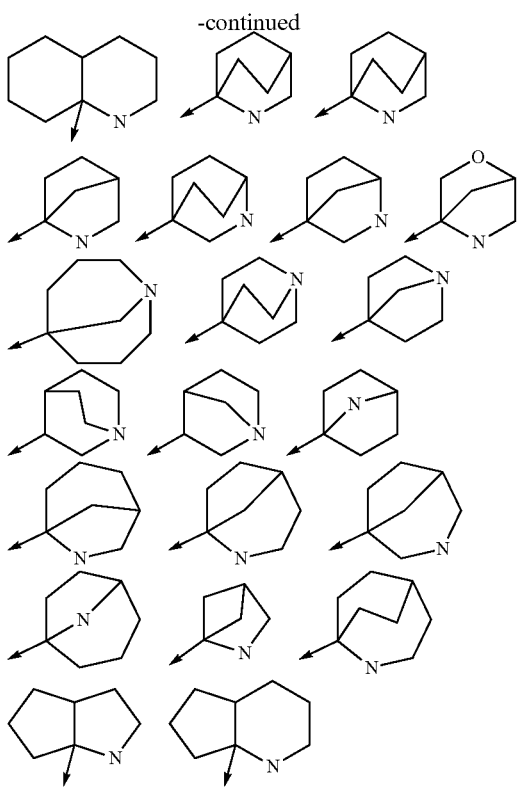

The heterocycles listed above are preferably substituted, for example, by hydrogen, halogen, alkyl, haloalkyl, hydroxy, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a main structure is substituted "by one or more radicals" from an enumeration of radicals (=group) or a generically defined group of radicals, this in each case includes simultaneous substitution by multiple identical and/or structurally different radicals.

In the case of a partly or fully saturated nitrogen heterocycle, this may be joined to the rest of the molecule either via carbon or via the nitrogen.

Useful substituents for a substituted heterocyclic radical include the substituents mentioned further down, and additionally also oxo and thioxo. The oxo group as substituent on a ring carbon atom in that case means, for example, a carbonyl group in the heterocyclic ring. As a result, lactones and lactams are preferably also encompassed. The oxo group may also occur on the ring heteroatoms that can exist in different oxidation states, for example in the case of N and S, and in that case form the divalent groups N(O), S(O) (also SO for short) and $S(O)_2$ (also $SO_2$ for short) in the heterocyclic ring. In the case of —N(O)— and —S(O)— groups, both enantiomers are encompassed in each case.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Heteroaryls according to the invention are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups of the invention may also be substituted by one or more identical or different radicals. If two adjacent carbon atoms are part of a further aromatic ring, this results in fused heteroaromatic systems, such as benzofused or polyfused heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol- 4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched, open-chain, saturated, hydrocarbyl radical which is optionally mono- or polysubstituted, and in the latter case is referred to as "substituted alkyl". Preferred substituents are halogen atoms or alkoxy, haloalkoxy, cyano, alkylthio, haloalkylthio, amino or nitro groups, more preferably methoxy, methyl, fluoroalkyl, cyano, nitro, fluorine, chlorine, bromine or iodine. The prefix "bis" also includes the combination of different alkyl radicals, e.g. methyl (ethyl) or ethyl(methyl).

"Haloalkyl", "-alkenyl" and "-alkynyl" respectively mean alkyl, alkenyl and alkynyl partly or fully substituted by identical or different halogen atoms, e.g. monohaloalkyl, for example $CH_2CH_2Cl$, $CH_2CH_2Br$, $CHClCH_3$, $CH_2Cl$, $CH_2F$; perhaloalkyl, for example $CCl_3$, $CCF_2$, $CFCl_2$, $CF_2CCF_2$, $CF_2CClFCF_3$; polyhaloalkyl, for example $CH_2CHFCl$, $CF_2CClFH$, $CF_2CBrFH$, $CH_2CF_3$; the term perhaloalkyl also includes the term perfluoroalkyl.

"Partly fluorinated alkyl" means a straight-chain or branched, saturated hydrocarbon mono- or polysubstituted by fluorine, where the corresponding fluorine atoms may be present as substituents on one or more different carbon atoms of the straight-chain or branched hydrocarbon chain, for example $CHFCH_3$, $CH_2CH_2F$, $CH_2CH_2CF_3$, $CHF_2$, $CH_2F$, $CHFCF_2CF_3$.

"Partly fluorinated haloalkyl" means a straight-chain or branched, saturated hydrocarbon substituted by various halogen atoms with at least one fluorine atom, where any other halogen atoms present are selected from the group of fluorine, chlorine or bromine, iodine. The corresponding halogen atoms may be present here as substituents on one or more different carbon atoms of the straight-chain or branched hydrocarbon chain. Party fluorinated haloalkyl also includes the complete substitution of the straight-chain or branched chain by halogen with involvement of at least one fluorine atom.

"Haloalkoxy" is, for example, $OCF_3$, $OCHF_2$, $OCH_2F$, $OCF_2CF_3$, $OCH_2CF_3$ and $OCH_2CH_2Cl$; the same applies to haloalkenyl and other halogen-substituted radicals.

The expression "$(C_1-C_4)$-alkyl" cited by way of example here is a brief notation for straight-chain or branched alkyl having one to 4 carbon atoms in accordance with the stated range for carbon atoms, i.e. includes the methyl, ethyl, 1-propyl, 2-propyl, 1-butyl, 2-butyl, 2-butylpropyl or tert-butyl radicals. General alkyl radicals having a greater specified range of carbon atoms, e.g. "$(C_1-C_6)$-alkyl", also correspondingly include straight-chain or branched alkyl radicals having a greater number of carbon atoms, i.e., according to the example, also the alkyl radicals having 5 and 6 carbon atoms.

Unless stated specifically, in the case of the hydrocarbyl radicals such as alkyl, alkenyl and alkynyl radicals, preference is given to the lower carbon skeletons in composite radicals too, for example having 1 to 6 carbon atoms, or in the case of unsaturated groups having 2 to 6 carbon atoms. Alkyl radicals, including in the composite radicals such as alkoxy, haloalkyl etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals are defined as the possible unsaturated radicals corresponding to the alkyl radicals, where at least one double bond/triple bond is present. Preference is given to radicals having one double bond/triple bond.

The term "alkenyl" especially also includes straight-chain or branched open-chain hydrocarbyl radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl that may optionally be substituted by further alkyl radicals, for example (but not limited to) $(C_2-C_6)$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-Trimethyl-2-propenyl, 1-ethyl-1-methyl-2-propenyl, 1-ethyl-2-methyl-1-propenyl and 1-ethyl-2-methyl-2-propenyl.

The term "alkynyl" especially also includes straight-chain or branched open-chain hydrocarbyl radicals having more than one triple bond or else having one or more triple bonds and one or more double bonds, for example 1,3-butatrienyl or 3-penten-1-yn-1-yl. $(C_2-C_6)$-Alkynyl is, for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The term "cycloalkyl" means a carbocyclic saturated ring system having preferably 3-8 ring carbon atoms, e.g. cyclopropyl, cyclobutyl, cyclopentyl or cyclohexyl, and optionally having further substitution, preferably by hydrogen, alkyl, alkoxy, cyano, nitro, alkylthio, haloalkylthio, halogen, alkenyl, alkynyl, haloalkyl, amino, alkylamino, bisalkylamino, alkoxycarbonyl, hydroxycarbonyl, arylalkoxycarbonyl, aminocarbonyl, alkylaminocarbonyl, cycloalkylaminocarbonyl. In the case of optionally substituted cycloalkyl, cyclic systems having substituents are included, also including substituents having a double bond on the cycloalkyl radical, for example an alkylidene group such as methylidene. In the case of optionally substituted cycloalkyl, polycyclic aliphatic systems are also included, for example bicyclo[0.1.0]butan-1-yl, bicyclo[0.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl and adamantan-2-yl, but also systems such as, for example, 1,1'-bi(cyclopropyl)-1-yl, 1,1'-bi(cyclopropyl)-2-yl. The expression "$(C_3-C_7)$-cycloalkyl" is a brief notation for cycloalkyl having three to 7 carbon atoms in accordance with the stated range for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl.

"Cycloalkenyl" means a carbocyclic, nonaromatic, partially unsaturated ring system having preferably 4-8 atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents having a double bond on the cycloalkenyl radical, for example an alkylidene group such as methylidene. In the case of optionally substituted cycloalkenyl, the elucidations for substituted cycloalkyl are correspondingly applicable.

The term "alkylidene", for example including in the $(C_1-C_{10})$-alkylidene form, means the remainder of a straight-chain or branched open-chain hydrocarbyl radical bonded via a double bond. Possible bonding sites for alkylidene naturally include solely positions on the main structure where two hydrogen atoms can be replaced by the double bond; radicals are, for example, =$CH_2$, =CH—$CH_3$, =C($CH_3$)—$CH_3$, =C($CH_3$)—$C_2H_5$ or =C($C_2H_5$)—$C_2H_5$. Cycloalkylidene is a carbocyclic radical bonded via a double bond.

"Cycloalkylalkyloxy" means a cycloalkylalkyl radical bonded via an oxygen atom, and "arylalkyloxy" means an arylalkyl radical bonded via an oxygen atom.

"Alkoxyalkyl" means an alkoxy radical bonded via an alkyl group, and "alkoxyalkoxy" means an alkoxyalkyl radical bonded via an oxygen atom, for example (but not limited to) methoxymethoxy, methoxyethoxy, ethoxyethoxy, methoxy-n-propyloxy.

"Alkylthioalkyl" is an alkylthio radical bonded via an alkyl group, and "alkylthioalkylthio" means an alkylthioalkyl radical bonded via an oxygen atom.

"Arylalkoxyalkyl" is an aryloxy radical bonded via an alkyl group, and "heteroaryloxyalkyl" means a heteroaryloxy radical bonded via an alkyl group.

"Haloalkoxyalkyl" is a bound haloalkoxy radical, and "haloalkylthioalkyl" means a haloalkylthio radical bonded via an alkyl group.

"Arylalkyl" is an aryl radical bonded via an alkyl group, "heteroarylalkyl" is a heteroaryl radical bonded via an alkyl group, and "heterocyclylalkyl" is a heterocyclyl radical bonded via an alkyl group.

"Cycloalkylalkyl" is a cycloalkyl radical bonded via an alkyl group, for example (but not limited to) cyclopropylmethyl, cyclobutylmethyl, cyclopentylmethyl, cyclohexylmethyl, 1-cyclopropyleth-1-yl, 2-cyclopropyleth-1-yl, 1-cyclopropylprop-1-yl, 3-cyclopropylprop-1-yl.

"Arylalkenyl" is an aryl radical bonded via an alkenyl group, "heteroarylalkenyl" is a heteroaryl radical bonded via an alkenyl group, and "heterocyclylalkenyl" is a heterocyclyl radical bonded via an alkenyl group.

"Arylalkynyl" is an aryl radical bonded via an alkynyl group, "heteroarylalkynyl" is a heteroaryl radical bonded via an alkynyl group, and "heterocyclylalkynyl" is a heterocyclyl radical bonded via an alkynyl group.

According to the invention, "haloalkylthio"—on its own or as part of a chemical group—represents straight-chain or branched S-haloalkyl, preferably having 1 to 8, or having 1 to 6, carbon atoms, such as $(C_1-C_8)$-, $(C_1-C_6)$- or $(C_1-C_4)$-haloalkylthio, for example (but not limited to) trifluoromethylthio, pentafluoroethylthio, difluoromethyl, 2,2-difluoroeth-1-ylthio, 2,2,2-difluoroeth-1-ylthio, 3,3,3-prop-1-ylthio.

"Halocycloalkyl" and "halocycloalkenyl" mean cycloalkyl or cycloalkenyl partly or fully substituted by identical or different halogen atoms, for example F, Cl and Br, or by haloalkyl, for example trifluoromethyl or difluoromethyl, for example 1-fluorocycloprop-1-yl, 2-fluorocycloprop-1-yl, 2,2-difluorocycloprop-1-yl, 1-fluorocyclobut-1-yl, 1-trifluoromethylcycloprop-1-yl, 2-trifluoromethylcycloprop-1-yl, 1-chlorocycloprop-1-yl, 2-chlorocycloprop-1-yl, 2,2-dichlorocycloprop-1-yl, 3,3-difluorocyclobutyl.

According to the invention, "trialkylsilyl"—on its own or as part of a chemical group—represents straight-chain or branched Si-alkyl, preferably having 1 to 8, or having 1 to 6, carbon atoms, such as tri-$[(C_1-C_8)$-, $(C_1-C_6)$- or $(C_1-C_4)$-alkyl]silyl, for example (but not limited to) trimethylsilyl, triethylsilyl, tri-(n-propyl)silyl, tri(isopropyl)silyl, tri(n-butyl)silyl, tri(1-methylprop-1-yl)silyl, tri-(2-methylprop-1-yl)silyl, tri(1,1-dimethyleth-1-yl)silyl, tri(2,2-dimethyleth-1-yl)silyl.

"Trialkylsilylalkynyl" is a trialkylsilyl radical bonded via an alkynyl group.

Synthesis of Substituted Thiophenyluracils of the General Formula (I)

The inventive substituted thiophenyluracils of the general formula (I) can be prepared proceeding from known processes. The synthesis routes used and examined proceed from commercially available or readily preparable heteroaromatic amines and from appropriately substituted hydroxy esters. The Q, $R^1$, $R^2$, $R^3$, $R^4$, $R^5$, $R^6$, $R^7$, $R^8$ and $R^{21}$ moieties in the general formula (I), in the schemes below, have the meanings defined above, unless illustrative but nonlimiting definitions are made. The first key intermediate prepared for the synthesis of the inventive compounds of the general formula (I) is an optionally further-substituted mercaptophenyl-1H-pyrimidine-2,4-dione. By way of example but without limitation, this is shown for the synthesis of 3-(4-chloro-2-fluoro-5-mercaptophenyl)-1-methyl-6-trifluoromethyl-1H-pyrimidine-2,4-dione (IIa) (scheme 1). For this purpose, a suitable substituted aniline, 2-fluoro-4-chloroaniline by way of example but without limitation, is converted to the corresponding isocyanate with a suitable reagent (e.g. triphosgene) in a suitable polar aprotic solvent (e.g. dichloromethane), and the isocyanate is converted in the next step by reaction with a suitable aminoacrylic ester, using a suitable base (e.g. sodium hydride or potassium tert-butoxide), in a suitable polar aprotic solvent (e.g. N,N-dimethylformamide), to the corresponding, optionally further-substituted pyrimidine-2,4-dione, by way of example but without limitation 3-(4-chloro-2-fluorophenyl)-1-methyl-6-trifluoromethyl-1H-pyrimidine-2,4-dione (scheme 1). By subsequent sulfochlorination with a suitable reagent (e.g. chlorosulfonic acid), followed by reduction with a suitable reducing agent (e.g. Zn in EtOH and HCl, tin(II) chloride hydrate or triphenylphosphine), it is possible to prepare the desired further-substituted mercaptophenyl-1H-pyrimidine-2,4-dione, by way of example but without limitation 3-(4-chloro-2-fluoro-5-mercaptophenyl)-1-methyl-6-trifluoromethyl-1H-pyrimidine-2,4-dione (IIa) (cf. KR1345394; EP1122244; EP408382; WO 2003/029226; WO2010/038953; US2011/0224083; KR2011/110420). In scheme 1 below, $R^1$, by way of example but without limitation, is $CH_3$, $R^2$, by way of example but without limitation, is hydrogen, $R^3$, by way of example but without limitation, is fluorine, $R^4$, by way of example but without limitation, is chlorine, and $R^{21}$, by way of example but without limitation, is fluorine.

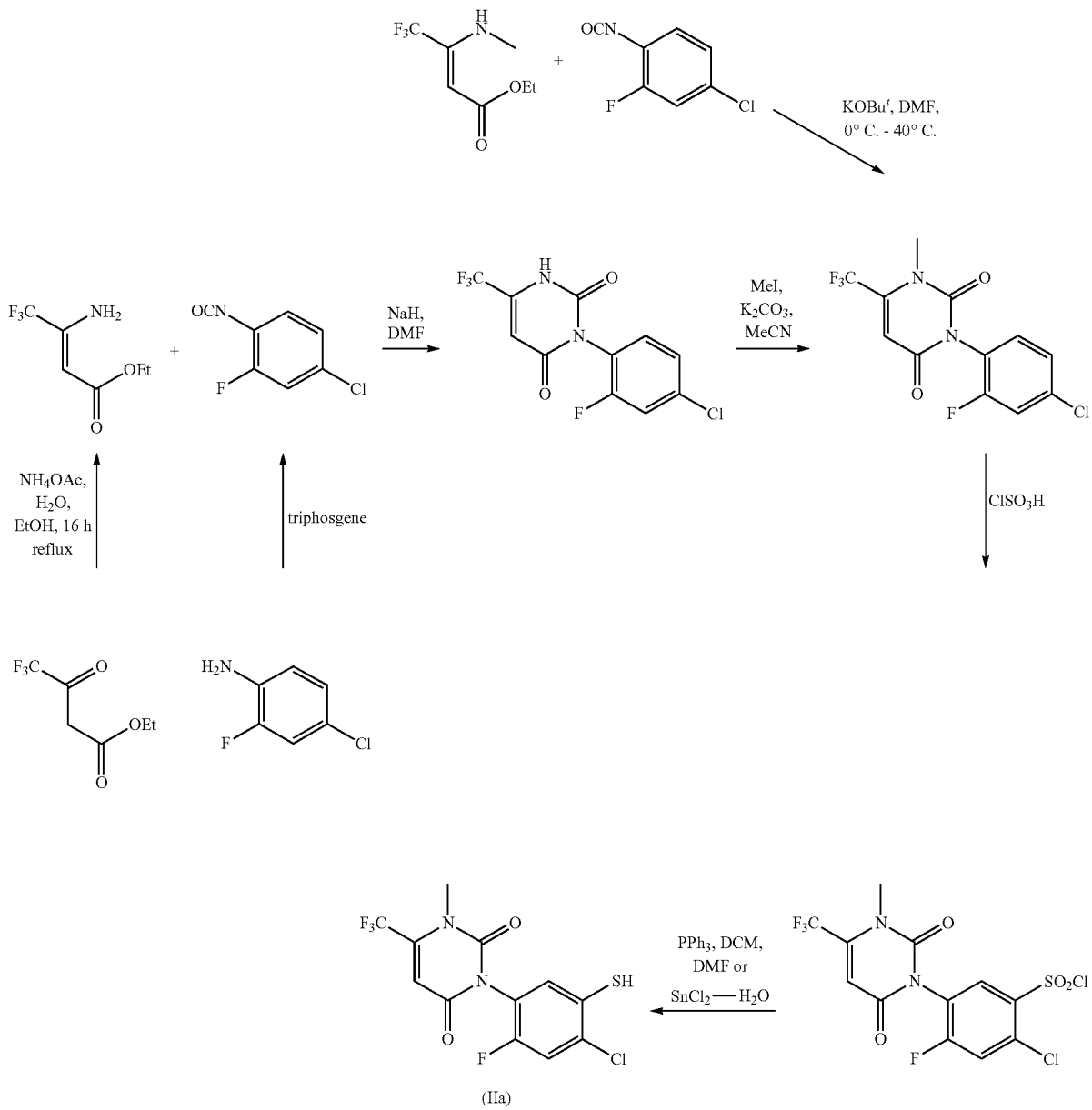

The synthesis of the key intermediate (IIa) described in scheme 1 can also be applied to the preparation of similar intermediates, e.g. 3-(4-chloro-2-fluoro-5-mercaptophenyl)-1,5-dimethyl-6-trifluoromethyl-1H-pyrimidine-2,4-dione (IIb). In scheme 2 below, $R^1$, by way of example but without limitation, is $CH_3$, $R^2$, by way of example but without limitation, is methyl, $R^3$, by way of example but without limitation, is fluorine, $R^4$, by way of example but without limitation, is chlorine, and $R^{21}$, by way of example but without limitation, is fluorine.

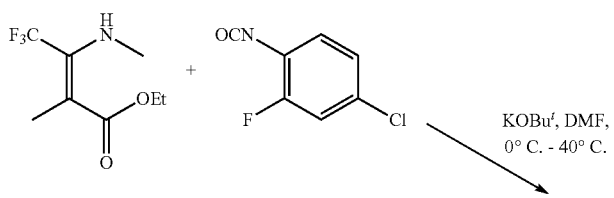

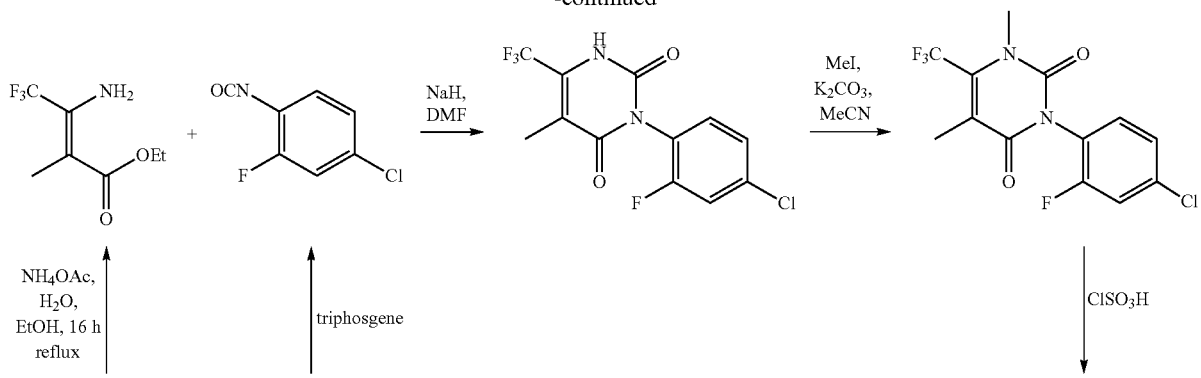

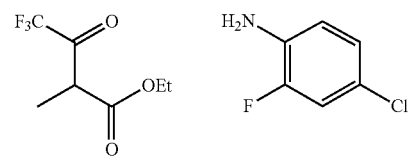

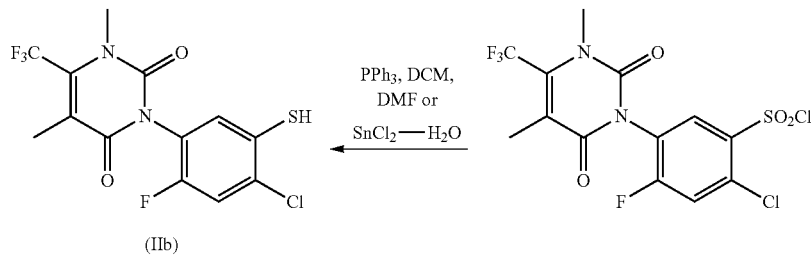

(IIb)

The synthesis of the key intermediate (IIa) described in scheme 1 can additionally be applied to the preparation of intermediates in which the $R^1$ group is an amino group, e.g. 3-(4-chloro-2-fluoro-5-mercaptophenyl)-1,5-dimethyl-6-trifluoromethyl-1H-pyrimidine-2,4-dione (IIc). A suitable phthalimide is used here as protecting group for the amino group. In scheme 3 below, $R^1$, by way of example but without limitation, is $NH_2$, $R^2$, by way of example but without limitation, is hydrogen, $R^3$, by way of example but without limitation, is fluorine, $R^4$, by way of example but without limitation, is chlorine, and $R^{21}$, by way of example but without limitation, is fluorine.

Scheme 3.

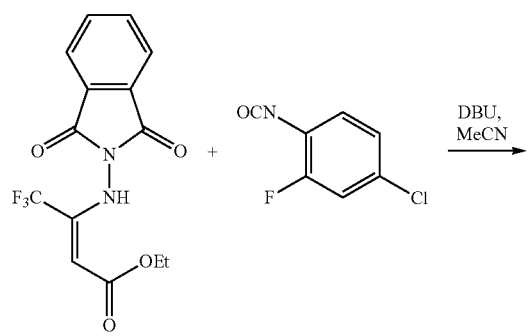

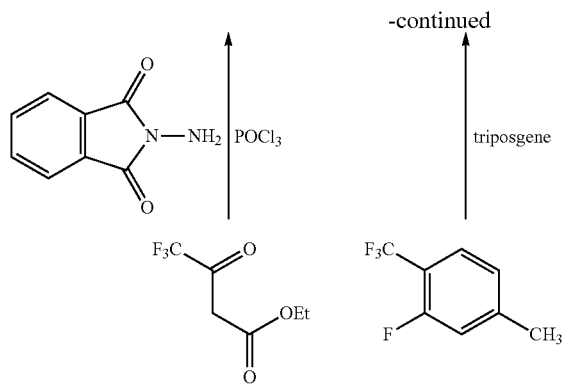

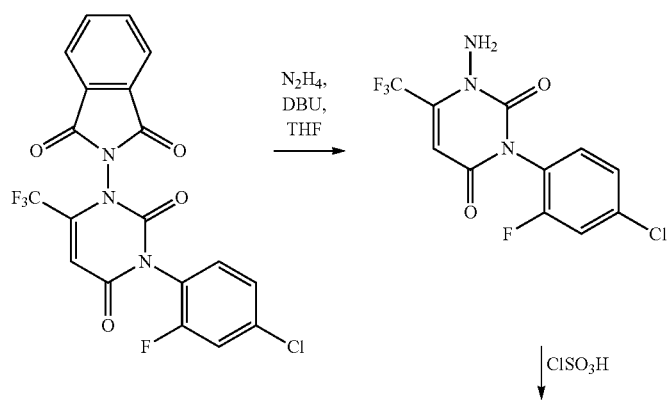

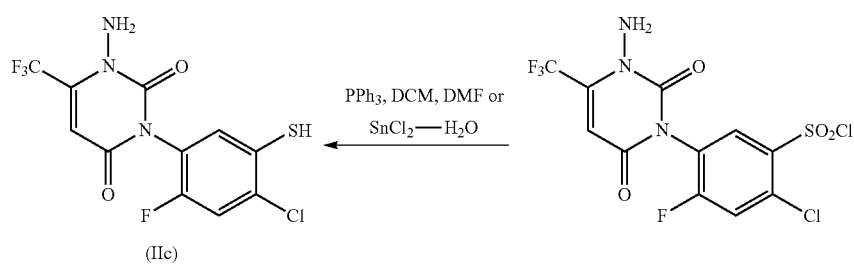

The intermediate further-substituted 5-mercaptophenyl-1H-pyrimidine-2,4-diones (II) in question can then be converted to the desired inventive compounds of the general formula (I) by two different routes (scheme 4): (i) by reaction with a suitable, optionally further-substituted 2-haloalkyl carboxylate (III) using a suitable base (e.g. potassium carbonate, cesium carbonate or sodium carbonate) in a suitable polar aprotic solvent, or (ii) by reaction of the intermediates (II) with a suitable, optionally further-substituted 2-haloalkanecarboxylic acid to give a corresponding thioalkanecarboxylic acid intermediate (IV) using a suitable base (e.g. potassium carbonate, cesium carbonate) and subsequent reaction of the corresponding intermediate (IV) with a suitable, optionally further-substituted hydroxyalkyl ether or hydroxyalkyl thioether using suitable coupling reagents (e.g. HOBt=1-hydroxybenzotriazole, EDC=1-ethyl-3-(3-dimethylaminopropyl)carbodiimide, HATU=O-(7-azabenzotriazol-1-yl)-N,N,N',N'-tetramethyluronium hexafluorophosphate, T3P=2,4,6-tripropyl-1,3,5,2,4,6-trioxatriphosphorinane 2,4,6-trioxide) and suitable bases (e.g. diisopropylethylamine, triethylamine) in a suitable polar aprotic solvent (e.g. dichloromethane, chloroform). In scheme 4 below, $R^2$ and $R^6$, by way of example but without limitation, are hydrogen, $R^{21}$, by way of example but without limitation, is fluorine, n and m, by way of example but without limitation, are 0, and Q, by way of example but without limitation, is the moieties Q-21 and Q-26.

Scheme 4.

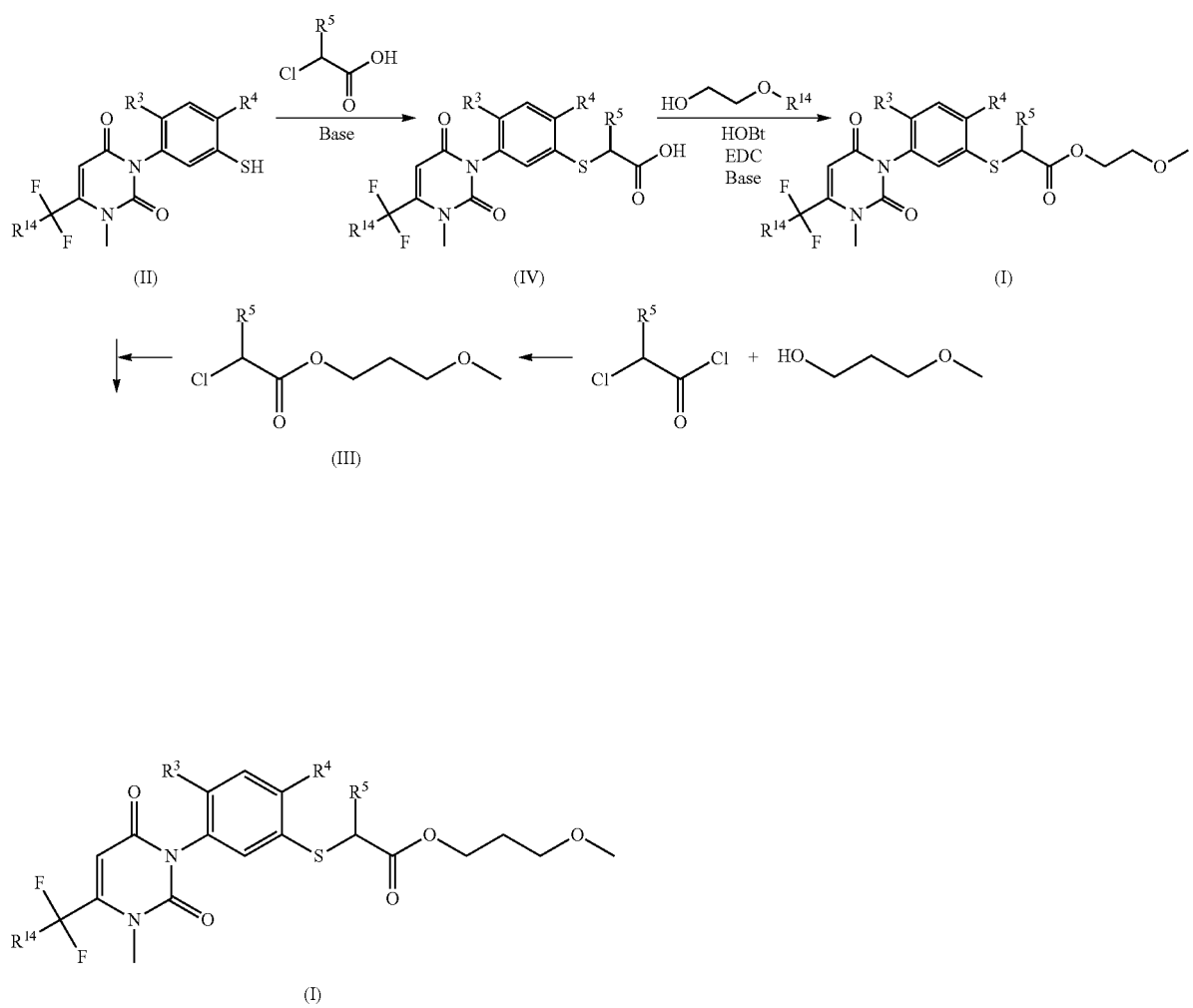

(I)

Selected detailed synthesis examples for the inventive compounds of the general formula (I) are adduced below. The example numbers specified correspond to the numbering given in tables I.1 to I.60 below. The $^1$H NMR, $^{13}$C NMR and $^{19}$F NMR spectroscopy data reported for the chemical examples described in the paragraphs that follow (400 MHz in the case of $^1$H NMR and 150 MHz in the case of $^{13}$C NMR and 375 MHz in the case of $^{19}$F NMR, solvent: CDCl$_3$, CD$_3$OD or d$_6$-DMSO, internal standard: tetramethylsilane δ=0.00 ppm) were obtained with a Bruker instrument, and the signals identified have the following definitions: br=broad; s=singlet, d=doublet, t=triplet, dd=double doublet, ddd=doublet of a double doublet, m=multiplet, q=quartet, quint=quintet, sext=sextet, sept=septet, dq=double quartet, dt=double triplet. In the case of diastereomer mixtures, either the respective significant signals for both diastereomers or the characteristic signal of the main diastereomer are reported. The abbreviations used for chemical groups have the following meanings, for example: Me=CH$_3$, Et=CH$_2$CH$_3$, t-Hex=C(CH$_3$)$_2$CH(CH$_3$)$_2$, t-Bu=C(CH$_3$)$_3$, n-Bu=unbranched butyl, n-Pr=unbranched propyl, i-Pr=branched propyl, c-Pr=cyclopropyl, c-Hex= cyclohexyl.

SYNTHESIS EXAMPLES

No. I.2-72: Tetrahydrofuran-3-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate

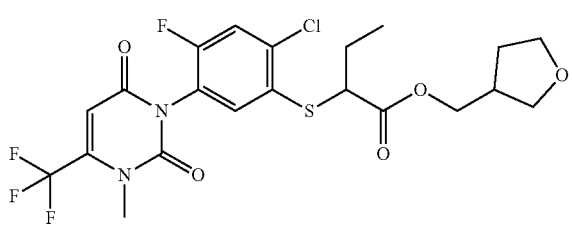 [SMILES: CCC(Sc1cc(-n2c(=O)cc(C(F)(F)F)n(C)c2=O)c(F)cc1Cl)C(=O)OCC1CCOC1]

2-Fluoro-4-chloroaniline (145 g, 996 mmol) and triethylamine (202 g, 2000 mmol) were successively added cautiously to a solution of triphosgene (119 g, 401 mmol) in abs. dichloromethane (1000 mL), in such a way that the temperature of the resulting reaction mixture remained below 20° C. After the end of the addition, the reaction mixture was stirred at room temperature overnight and then washed with water (3×500 mL) and 1N hydrochloric acid (500 mL), dried over sodium sulfate, filtered and concentrated under reduced pressure. The 2-fluoro-4-chlorophenyl isocyanate was used in the next step without further purification. Sodium hydride (5.60 g, 140 mmol, 60% dispersion in mineral oil) was suspended in abs. N,N-dimethylformamide, and ethyl (2E)-3-amino-4,4,4-trifluorobut-2-enoate (14.2 g, 77.5 mmol) was added. The reaction mixture was stirred at room temperature for 1 h, then cooled down to a temperature of −30° C., and 2-fluoro-4-chlorophenyl isocyanate (12.0 g, 70.0 mmol) was added. On completion of addition, the resulting reaction mixture was stirred at room temperature for a further 4 h and then added to ice-water. After the addition of ethyl acetate and acidification with 1N hydrochloric acid, the aqueous phase was extracted thoroughly with ethyl acetate. The combined organic phases were washed with water, dried over sodium sulfate, filtered and concentrated under reduced pressure. In this way, 3-(4-chloro-2-fluorophenyl)-6-(trifluoromethyl)pyrimidine-2,4(1H,3H)-dione (15.2 g, 50.2 mmol, 65%) was obtained, which was used in the next step without further purification. It was also possible to repeat this reaction step successfully on a larger scale. To a solution of 3-(4-chloro-2-fluorophenyl)-6-(trifluoromethyl)pyrimidine-2,4(1H,3H)-dione (238 g, 770 mmol) in abs. N,N-dimethylformamide (800 mL) was added potassium carbonate (117 g, 850 mmol). Thereafter, a solution of methyl iodide (120 g, 850 mmol) in abs. N,N-dimethylformamide (100 mL) was added and the resulting reaction mixture was stirred at room temperature for a further 1 h. On completion of conversion, the reaction mixture was cooled to a temperature of 0° C., water (2000 mL) was added cautiously, and then the mixture was extracted thoroughly with dichloromethane. The combined organic phases were dried over sodium sulfate, filtered and concentrated under reduced pressure. In this way, 3-(4-chloro-2-fluorophenyl)-1-methyl-6-(trifluoromethyl)pyrimidine-2,4(1H,3H)-dione (241 g, 747 mmol, 97% of theory) was obtained, which was converted in the next step without further purification. 3-(4-Chloro-2-fluorophenyl)-1-methyl-6-(trifluoromethyl)pyrimidine-2,4(1H,3H)-dione (100 g, 310 mmol) was then added stepwise to chlorosulfonic acid in a baked-out round-bottom flask. The resulting reaction mixture was then stirred at a temperature of 110° C. for 20 h and, after cooling to room temperature, added to ice-water and extracted repeatedly with ethyl acetate (3×300 mL). The combined organic phases were dried over sodium sulfate, filtered and concentrated under reduced pressure. This gave 2-chloro-4-fluoro-5-[3-methyl-2,6-dioxo-4-(trifluoromethyl)-3,6-dihydropyrimidin-1(2H)-yl]benzenesulfonyl chloride (75.0 g, 178 mmol, 57% of theory), which was used in the next step without further purification. To an initial charge of 2-chloro-4-fluoro-5-[3-methyl-2,6-dioxo-4-(trifluoromethyl)-3,6-dihydropyrimidin-1(2H)-yl]sulfonyl chloride (100.0 g, 237 mmol) in a round-bottom flask were successively added hydrochloric acid (500 mL), acetic acid (500 mL) and tin dichloride dihydrate (270 g, 1197 mmol). The resulting reaction mixture was stirred at a temperature of 100° C. for 10 h, after cooling to room temperature added to ice-water, and extracted thoroughly with dichloromethane (3×400 mL). The combined organic phases were dried over sodium sulfate, filtered and concentrated under reduced pressure. Final column chromatography purification afforded 3-(4-chloro-2-fluoro-5-sulfanylphenyl)-1-methyl-6-(trifluoromethyl)pyrimidine-2,4(1H,3H)-dione (73.0 g, 206 mmol, 83% of theory) in the form of a colorless solid. 2-Chlorobutanecarboxylic acid (691 mg, 5.64 mmol) was dissolved in abs. acetonitrile under argon in a baked-out round-bottom flask, and then cesium carbonate (3.67 g, 11.28 mmol) and 3-(4-chloro-2-fluoro-5-sulfanylphenyl)-1-methyl-6-(trifluoromethyl)pyrimidine-2,4(1H,3H)-dione (2.0 g, 5.64 mmol) were added. The resulting reaction mixture was stirred at a temperature of 50° C. for 1 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 2-({2-chloro-4-fluoro-5-[3-methyl-2,6-dioxo-4-(trifluoromethyl)-3,6-dihydropyrimidin-1(2H)-yl]phenyl}sulfanyl)butanoic acid (2.0 g, 80% of theory) was obtained in the form of a colorless solid. $^1$H-NMR (CDCl$_3$ δ, ppm) 7.53 (d, 1H), 7.38 (d, 1H), 6.36 (d, 1H), 3.68 (m, 1H), 3.55 (s, 3H), 2.05-1.95 (m, 1H), 1.93-1.82 (m, 1H), 1.09 (t, 3H). 2-({2-Chloro-4-fluoro-5-[3-methyl-2,6-dioxo-4-(trifluoromethyl)-3,6-dihydropyrimidin-1(2H)-yl]phenyl}sulfanyl)butanoic acid (90 mg, 0.20 mmol), 1-hydroxy-1H-benzotriazole (36 mg, 0.27 mmol) and 1-(3-dimethylaminopropyl)-3-ethylcarbodiimide hydrochloride (51 mg, 0.27 mmol) were dissolved in abs. dichloromethane in a baked-out round-bottom flask under argon and, after stirring at room temperature for 5 minutes, tetrahydro-3-furanmethanol (27 mg, 0.28 mmol) and triethylamine (0.04 mL, 0.27 mmol) were added. The resulting reaction mixture was stirred at room temperature for 6 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydrofuran-3-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate (83 mg, 77% of theory) was obtained in the form of a highly viscous, colorless oil. $^1$H-NMR (CDCl$_3$ δ, ppm) 7.47 (m, 1H), 7.37 (d, 1H), 6.35 (d, 1H), 4.13-3.89 (m, 2H), 3.83-3.67 (m, 4H), 3.55 (s, 3H), 3.47-3.43 (m, 1H), 2.53-2.40 (m, 1H), 2.02-1.90 (m, 2H), 1.89-1.79 (m, 1H), 1.59-1.49 (m, 1H), 1.07 (t, 3H).

No. I.2-91: Tetrahydro-2H-pyran-2-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate

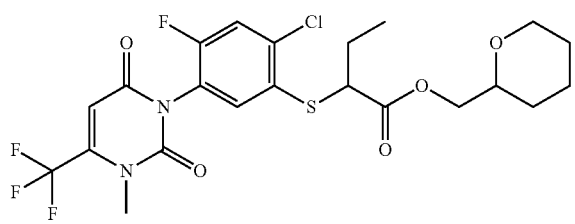 [SMILES: CCC(Sc1cc(-n2c(=O)cc(C(F)(F)F)n(C)c2=O)c(F)cc1Cl)C(=O)OCC1CCCCO1]

2-({2-Chloro-4-fluoro-5-[3-methyl-2,6-dioxo-4-(trifluoromethyl)-3,6-dihydropyrimidin-1(2H)-yl]phenyl}sulfanyl)butanoic acid (100 mg, 0.23 mmol), 1-hydroxy-1H-benzotriazole (40 mg, 0.29 mmol) and 1-(3-dimethylaminopropyl)-3-ethylcarbodiimide hydrochloride (57 mg, 0.29 mmol) were dissolved in abs. dichloromethane in a baked-out round-bottom flask under argon and, after stirring at room temperature for 5 minutes, 2-(hydroxymethyl)tetrahydropyran (34 mg, 0.29 mmol) and triethylamine (0.04 mL, 0.29 mmol) were added. The resulting reaction mixture was stirred at room temperature for 2 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydro-2H-pyran-2-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate (38 mg, 31% of theory) was obtained in the form of a highly viscous, colorless oil. $^1$H-NMR (CDCl$_3$ δ, ppm) 7.53 (m, 1H), 7.35 (m, 1H), 6.35 (m, 1H), 4.12-3.88 (m, 3H), 3.76-3.71 (m, 1H), 3.55 (s, 3H), 3.47-3.32 (m, 2H), 2.03-1.92 (m, 1H), 1.89-1.78 (m, 2H), 1.62-1.42 (m, 5H), 1.08 (t, 3H).

No. I.2-92: Tetrahydro-2H-pyran-3-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate

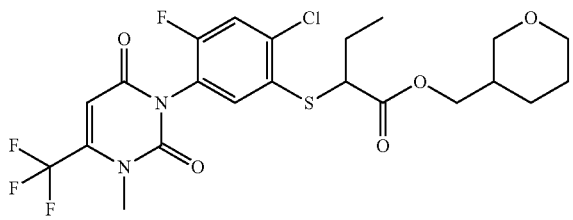 [SMILES: CCC(Sc1cc(-n2c(=O)cc(C(F)(F)F)n(C)c2=O)c(F)cc1Cl)C(=O)OCC1CCCOC1]

2-({2-Chloro-4-fluoro-5-[3-methyl-2,6-dioxo-4-(trifluoromethyl)-3,6-dihydropyrimidin-1(2H)-yl]phenyl}sulfanyl)butanoic acid (100 mg, 0.23 mmol), 1-hydroxy-1H-benzotriazole (40 mg, 0.29 mmol) and 1-(3-dimethylaminopropyl)-3-ethylcarbodiimide hydrochloride (57 mg, 0.29 mmol) were dissolved in abs. dichloromethane in a baked-out round-bottom flask under argon and, after stirring at room temperature for 5 minutes, 3-(hydroxymethyl)tetrahydropyran (34 mg, 0.29 mmol) and triethylamine (0.04 ml, 0.29 mmol) were added. The resulting reaction mixture was stirred at room temperature for 2 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydro-2H-pyran-3-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)butanoate (25 mg, 20% of theory) was obtained in the form of a highly viscous, colorless oil. $^1$H-NMR (CDCl$_3$ δ, ppm) 7.52 (m, 1H), 7.37 (m, 1H), 6.35 (m, 1H), 4.03-3.97 (m, 1H), 3.96-3.87 (m, 1H), 3.85-3.77 (m, 1H), 3.72-3.68 (m, 1H), 3.55 (s, 3H), 3.41-3.34 (m, 1H), 3.17-3.10 (m, 1H), 2.03-1.92 (m, 1H), 1.89-1.78 (m, 2H), 1.62-1.42 (m, 5H), 1.08 (t, 3H).

No. I.4-91: Tetrahydro-2H-pyran-2-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)-4-methylpentanoate

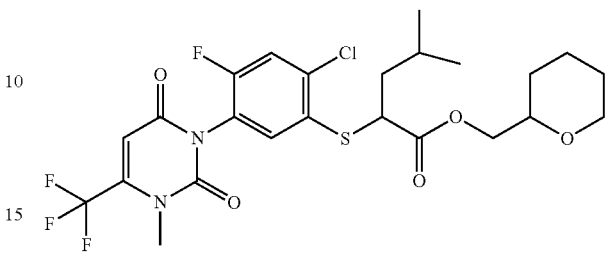

2-Chloro-4-methylpentanecarboxylic acid (849 mg, 5.64 mmol) was dissolved in abs. acetonitrile under argon in a baked-out round-bottom flask, and then cesium carbonate (3.67 g, 11.28 mmol) and 3-(4-chloro-2-fluoro-5-sulfanylphenyl)-1-methyl-6-(trifluoromethyl)pyrimidine-2,4(1H,3H)-dione (2.0 g, 5.64 mmol) were added. The resulting reaction mixture was stirred at a temperature of 50° C. for 1 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 2-({2-chloro-4-fluoro-5-[3-methyl-2,6-dioxo-4-(trifluoromethyl)-3,6-dihydropyrimidin-1(2H)-yl]phenyl}sulfanyl)-4-methylpentanoic acid (1.62 g, 61% of theory) was obtained in the form of a colorless solid. $^1$H-NMR (CDCl$_3$ δ, ppm) 7.53 (d, 1H), 7.37 (d, 1H), 6.37 (m, 1H), 3.82-3.78 (m, 1H), 3.55 (s, 3H), 1.90-1.78 (m, 2H), 1.73-1.65 (m, 1H), 0.99-0.92 (m, 6H). 2-({2-Chloro-4-fluoro-5-[3-methyl-2,6-dioxo-4-(trifluoromethyl)-3,6-dihydropyrimidin-1(2H)-yl]phenyl}sulfanyl)-4-methylpentanoic acid (120 mg, 0.26 mmol), 1-hydroxy-1H-benzotriazole (45 mg, 0.33 mmol) and 1-(3-dimethylaminopropyl)-3-ethylcarbodiimide hydrochloride (66 mg, 0.33 mmol) were dissolved in abs. dichloromethane in a baked-out round-bottom flask under argon and, after stirring at room temperature for 5 minutes, 2-(hydroxymethyl)tetrahydropyran (39 mg, 0.33 mmol) and triethylamine (0.05 mL, 0.33 mmol) were added. The resulting reaction mixture was stirred at room temperature for 2 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydro-2H-pyran-2-ylmethyl 2-({2-chloro-4-fluoro-5-[3-methyl-2,6-dioxo-4-(trifluoromethyl)-3,6-dihydropyrimidin-1(2H)-yl]phenyl}sulfanyl)-4-methylpentanoate (81 mg, 56% of theory) was obtained in the form of a highly viscous, colorless oil. $^1$H-NMR (CDCl$_3$ δ, ppm) 7.53 (m, 1H), 7.35 (m, 1H), 6.35 (d, 1H), 4.08-3.98 (m, 1H), 3.94-3.84 (m, 3H), 3.55 (s, 3H), 3.48-3.33 (m, 2H), 1.90-1.76 (m, 3H) 1.71-1.63 (m, 1H), 1.57-1.43 (m, 5H), 1.28-1.17 (m, 1H), 0.96-0.93 (m, 6H), 0.90-0.84 (m, 1H).

No. I.6-221: 2-({2-Chloro-4-fluoro-5-[3-methyl-2,6-dioxo-4-(trifluoromethyl)-3,6-dihydropyrimidin-1(2H)-yl]phenyl}sulfanyl)-3-methyl-N-(tetrahydrofuran-2-ylmethyl)butanamide No. I.12-72: Tetrahydrofuran-3-ylmethyl 2-({2-chloro-4-fluoro-5-[3,5-dimethyl-2,6-dioxo-4-(trifluoromethyl)-3,6-dihydropyrimidin-1(2H)-yl]phenyl}sulfanyl)butanoate

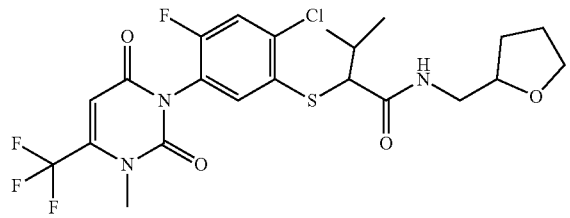 [SMILES: CC(C)C(Sc1cc(-n2c(=O)cc(C(F)(F)F)n(C)c2=O)c(F)cc1Cl)C(=O)NCC1CCCO1]

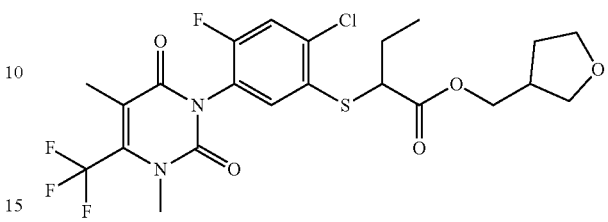

2-Chloro-3-methylbutanecarboxylic acid (770 mg, 5.64 mmol) was dissolved in abs. acetonitrile under argon in a baked-out round-bottom flask, and then cesium carbonate (3.67 g, 11.28 mmol) and 3-(4-chloro-2-fluoro-5-sulfanylphenyl)-1-methyl-6-(trifluoromethyl)pyrimidine-2,4(1H, 3H)-dione (2.0 g, 5.64 mmol) were added. The resulting reaction mixture was stirred at a temperature of 50° C. for 1 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 2-({2-chloro-4-fluoro-5-[3-methyl-2,6-dioxo-4-(trifluoromethyl)-3,6-dihydropyrimidin-1(2H)-yl]phenyl}sulfanyl)-3-methylbutanoic acid (0.47 g, 21% of theory) was obtained in the form of a colorless solid. $^1$H-NMR (CDCl$_3$ δ, ppm) 7.49 (d, 1H), 7.37 (d, 1H), 6.33 (m, 1H), 3.58-3.48 (m, 1H), 3.53 (s, 3H), 2.25-2.17 (m, 1H), 1.18 (d, 3H), 1.11 (d, 3H). 2-({2-Chloro-4-fluoro-5-[3-methyl-2,6-dioxo-4-(trifluoromethyl)-3,6-dihydropyrimidin-1(2H)-yl]phenyl}sulfanyl)-3-methylbutanoic acid (100 mg, 0.22 mmol), 1-hydroxy-1H-benzotriazole (39 mg, 0.29 mmol) and 1-(3-dimethylaminopropyl)-3-ethylcarbodiimide hydrochloride (65 mg, 0.29 mmol) were dissolved in abs. dichloromethane in a baked-out round-bottom flask under argon and, after stirring at room temperature for 5 minutes, 2-(aminomethyl)tetrahydrofuran (29 mg, 0.29 mmol) and triethylamine (0.04 ml, 0.29 mmol) were added. The resulting reaction mixture was stirred at room temperature for 2 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and 2-({2-chloro-4-fluoro-5-[3-methyl-2,6-dioxo-4-(trifluoromethyl)-3,6-dihydropyrimidin-1(2H)-yl]phenyl}sulfanyl)-3-methyl-N-(tetrahydrofuran-2-ylmethyl)butanamide (44 mg, 37% of theory) was obtained in the form of a highly viscous, colorless oil. $^1$H-NMR (CDCl$_3$ δ, ppm) 7.36 (m, 1H), 7.28 (m, 1H), 6.91-6.81 (m, 1H, NH), 6.34 (m, 1H), 3.90-3.61 (m, 3H), 3.58-3.56 (m, 1H), 3.54 (s, 3H), 3.50-3.42 (m, 1H), 3.20-3.06 (m, 1H), 2.42-2.33 (m, 1H), 1.92-1.68 (m, 3H), 1.48-1.42/1.33-1.28 (m, 1H), 1.15 (d, 3H), 1.11 (d, 3H).

A solution of n-butyllithium in hexane (2.5M, 240 mL) was added to a solution, cooled to −10° C., of diisopropylamine (61.0 g, 603 mmol) in abs. tetrahydrofuran (300 mL). The resulting reaction mixture was stirred at a temperature of −10° C. for 30 minutes and then cooled further to −78° C. This was followed by cautious addition of ethyl propionate (51.0 g, 499 mmol). The reaction mixture was stirred at −78° C. for 1 h, 2,2,2-trifluoroethyl trifluoroacetate (147 g, 750 mmol) was added and, finally, the mixture was stirred at room temperature overnight. On completion of conversion, the mixture was acidified with dil. hydrochloric acid (1M) and repeatedly extracted thoroughly with ethyl acetate. These combined organic phases were dried over sodium sulfate, filtered and concentrated under reduced pressure, and the ethyl 4,4,4-trifluoro-2-methyl-3-oxobutanoate (62.0 g, 63% of theory) obtained in this way was, as a portion (49.5 g, 250 mmol), without further purification, dissolved in toluene (400 mL) in a round-bottom flask and admixed with ammonium acetate (96.0 g, 1245 mmol) and acetic acid (15 mL). The resulting reaction mixture was stirred under reflux conditions with use of a water separator for several hours until no further water was separated out. After cooling to room temperature, the reaction mixture was concentrated under reduced pressure and then the residue was taken up with ethyl acetate and water. The water phase was then extracted thoroughly with ethyl acetate, and the combined organic phases were dried over sodium sulfate, filtered and concentrated under reduced pressure. Distillative purification of the residue obtained afforded ethyl (2Z)-3-amino-4,4,4-trifluoro-2-methylbut-2-enoate (31.0 g, 62% of theory). 2-Fluoro-4-chloroaniline (145 g, 996 mmol) and triethylamine (202 g, 2000 mmol) were successively added cautiously to a solution of triphosgene (119 g, 401 mmol) in abs. dichloromethane (1000 mL), in such a way that the temperature of the resulting reaction mixture remained below 20° C. After the end of the addition, the reaction mixture was stirred at room temperature overnight and then washed with water (3×500 mL) and 1N hydrochloric acid (500 mL), dried over sodium sulfate, filtered and concentrated under reduced pressure. The 2-fluoro-4-chlorophenyl isocyanate obtained was used in the next step without further purification. Sodium hydride (5.60 g, 140 mmol, 60% dispersion in mineral oil) was suspended in abs. N,N-dimethylformamide, and ethyl (2Z)-3-amino-4,4,4-trifluoro-2-methylbut-2-enoate (14.2 g, 72.1 mmol) was added. The reaction mixture was stirred at room temperature for 1 h, then cooled down to a temperature of −30° C., and 2-fluoro-4-chlorophenyl isocyanate (12.0 g, 70.0 mmol) was added. On completion of addition, the resulting reaction mixture was stirred at room temperature for a further 4 h and then added to ice-water. After the addition of ethyl acetate and acidification with 1N hydrochloric acid, the aqueous phase was extracted thoroughly with ethyl acetate. The combined organic phases were washed with water, dried over sodium sulfate, filtered and concentrated under reduced pressure. In this way, 3-(4-chloro-2-fluorophenyl) 5-methyl-6-(trifluoromethyl)pyrimidine-2,4(1H,3H)-dione (15.5 g, 48.1 mmol, 66%) was obtained, which was used in the next step without further purification. To a solution of 3-(4-chloro-2-fluorophenyl)-5-methyl-6-(trifluoromethyl)pyrimidine-2,4(1H,3H)-dione (23.8 g, 73.8 mmol) in abs. N,N-dimethylformamide (80 mL) was added potassium carbonate (11.7 g, 84.7 mmol). Thereafter, a solution of methyl iodide (12.0 g, 84.5 mmol) in abs. N,N-dimethylformamide (10 mL) was added and the resulting reaction mixture was stirred at room temperature for a further 1 h. On completion of conversion, the reaction mixture was cooled to a temperature of 0° C., water (200 mL) was added cautiously, and then the mixture was extracted thoroughly with dichloromethane. The combined organic phases were dried over sodium sulfate, filtered and concentrated under reduced pressure. In this way, 3-(4-chloro-2-fluorophenyl)-1,5-dimethyl-6-(trifluoromethyl)pyrimidine-2,4(1H,3H)-dione (24.1 g, 71.6 mmol, 97% of theory) was obtained, which was converted in the next step without further purification. 3-(4-Chloro-2-fluorophenyl)-1,5-dimethyl-6-(trifluoromethyl)pyrimidine-2,4(1H,3H)-dione (10.0 g, 29.7 mmol) was then added stepwise to chlorosulfonic acid (200 mL) in a baked-out round-bottom flask. The resulting reaction mixture was then stirred at a temperature of 110° C. for 20 h and, after cooling to room temperature, added to ice-water and extracted repeatedly with ethyl acetate (3×300 mL). The combined organic phases were dried over sodium sulfate, filtered and concentrated under reduced pressure. This gave 2-chloro-4-fluoro-5-[3,5-dimethyl-2,6-dioxo-4-(trifluoromethyl)-3,6-dihydropyrimidin-1(2H)-yl]benzenesulfonyl chloride (7.74 g, 17.8 mmol, 60% of theory), which was used in the next step without further purification. To an initial charge of 2-chloro-4-fluoro-5-[3,5-dimethyl-2,6-dioxo-4-(trifluoromethyl)-3,6-dihydropyrimidin-1(2H)-yl] sulfonyl chloride (10.0 g, 23.0 mmol) in around-bottom flask were successively added hydrochloric acid (50 mL), acetic acid (50 mL) and tin dichloride dihydrate (27.0 g, 120 mmol). The resulting reaction mixture was stirred at a temperature of 100° C. for 10 h, after cooling to room temperature added to ice-water, and extracted thoroughly with dichloromethane (3×400 mL). The combined organic phases were dried over sodium sulfate, filtered and concentrated under reduced pressure. Final column chromatography purification afforded 3-(4-chloro-2-fluoro-5-sulfanylphenyl)-1,5-dimethyl-6-(trifluoromethyl)pyrimidine-2,4(1H,3H)-dione (7.6 g, 20.6 mmol, 89% of theory) in the form of a colorless solid. 2-Chlorobutanecarboxylic acid (332 mg, 2.71 mmol) was dissolved in abs. acetonitrile under argon in a baked-out round-bottom flask, and then cesium carbonate (1.77 g, 5.42 mmol) and 3-(4-chloro-2-fluoro-5-sulfanylphenyl)-1,5-dimethyl-6-(trifluoromethyl)pyrimidine-2,4(1H,3H)-dione (1.0 g, 2.71 mmol) were added. The resulting reaction mixture was stirred at a temperature of 50° C. for 1 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 2-({2-chloro-5-[3,5-methyl-2,6-dioxo-4-(trifluoromethyl)-3,6-dihydropyrimidin-1(2H)-yl]-4-fluorophenyl}sulfanyl)butanoic acid (1.42 g, 80% of theory) was obtained in the form of a colorless solid. $^1$H-NMR (CDCl$_3$ δ, ppm) 7.55 (d, 1H), 7.37 (d, 1H), 3.68 (m, 1H), 3.55 (s, 3H), 2.28-2.21 (m, 3H), 2.05-1.91 (m, 1H), 1.90-1.78 (m, 1H), 1.10 (t, 3H). 2-({2-Chloro-5-[3,5-dimethyl-2,6-dioxo-4-(trifluoromethyl)-3,6-dihydropyrimidin-1(2H)-yl]-4-fluorophenyl}sulfanyl)butanoic acid (160 mg, 0.35 mmol), 1-hydroxy-1H-benzotriazole (62 mg, 0.46 mmol) and 1-(3-dimethylaminopropyl)-3-ethylcarbodiimide hydrochloride (88 mg, 0.46 mmol) were dissolved in abs. dichloromethane in a baked-out round-bottom flask under argon and, after stirring at room temperature for 5 minutes, 3-(hydroxymethyl)tetrahydrofuran (47 mg, 0.46 mmol) and triethylamine (0.12 mL, 0.84 mmol) were added. The resulting reaction mixture was stirred at room temperature for 6 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydrofuran-3-ylmethyl 2-({2-chloro-4-fluoro-5-[3,5-dimethyl-2,6-dioxo-4-(trifluoromethyl)-3,6-dihydropyrimidin-1(2H)-yl]phenyl}sulfanyl)butanoate (171 mg, 75% of theory) was obtained in the form of a highly viscous, colorless oil. $^1$H-NMR (CDCl$_3$ δ, ppm) 7.47 (m, 1H), 7.37 (d, 1H), 4.13-3.89 (m, 2H), 3.83-3.67 (m, 4H), 3.55 (s, 3H), 3.49-3.43 (m, 1H), 2.53-2.44 (m, 1H), 2.26-2.21 (m, 3H), 2.02-1.92 (m, 2H), 1.90-1.82 (m, 1H), 1.59-1.49 (m, 1H), 1.07 (t, 3H).

No. I.44-71: Tetrahydrofuran-2-ylmethyl ({2-chloro-4-fluoro-5-[3-methyl-2,6-dioxo-4-(trifluoromethyl)-3,6-dihydropyrimidin-1(2H)-yl]phenyl}sulfanyl)(cyclopropyl)acetate

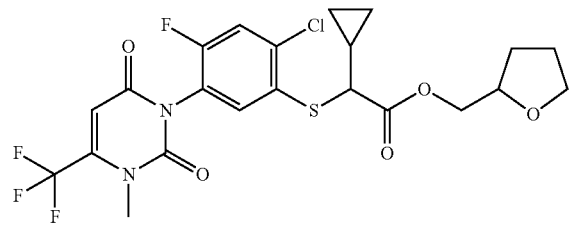 [SMILES: Cn1c(C(F)(F)F)cc(=O)n(-c2cc(SC(C(=O)OCC3CCCO3)C3CC3)c(Cl)cc2F)c1=O]

Ethyl chloro(cyclopropyl)acetate (409 mg, 1.97 mmol) was dissolved in abs. acetonitrile under argon in a baked-out round-bottom flask, and then cesium carbonate (273 mg, 1.97 mmol) and 3-(4-chloro-2-fluoro-5-sulfanylphenyl)-1-methyl-6-(trifluoromethyl)pyrimidine-2,4(1H,3H)-dione (700 mg, 1.97 mmol) were added. The resulting reaction mixture was stirred at a temperature of 50° C. for 2 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and ethyl ({2-chloro-4-fluoro-5-[3-methyl-2,6-dioxo-4-(trifluoromethyl)-3,6-dihydropyrimidin-1(2H)-yl]phenyl}sulfanyl)(cyclopropyl)acetate (940 mg, 99% of theory) was obtained in the form of a colorless solid. ¹H-NMR (CDCl₃ δ, ppm) 7.51 (d, 1H), 7.35 (d, 1H), 6.34 (s, 1H), 4.18-4.05 (m, 2H), 3.53 (s, 3H), 3.13-3.10 (m, 1H), 1.33-1.26 (m, 1H), 1.15 (t, 3H), 0.75-0.66 (m, 2H), 0.48-0.44 (m, 1H), 0.42-0.36 (m, 1H). Ethyl ({2-chloro-4-fluoro-5-[3-methyl-2,6-dioxo-4-(trifluoromethyl)-3,6-dihydropyrimidin-1(2H)-yl]phenyl}sulfanyl)(cyclopropyl)acetate (160 mg, 0.33 mmol) was then dissolved in ethyl acetate, and 6N HCl was added. The reaction mixture obtained was stirred at a temperature of 100° C. for 3 h, after cooling to room temperature admixed with water, and extracted thoroughly with abs. dichloromethane. The combined organic phases were dried over sodium sulfate, filtered and concentrated under reduced pressure. The crude product was then purified by column chromatography (ethyl acetate/heptane gradient), and ({2-chloro-4-fluoro-5-[3-methyl-2,6-dioxo-4-(trifluoromethyl)-3,6-dihydropyrimidin-1(2H)-yl]phenyl}sulfanyl)(cyclopropyl)acetic acid (120 mg, 79% of theory) was obtained in the form of a colorless solid. ¹H-NMR (CDCl₃ δ, ppm) 7.54 (dd, 1H), 7.36 (d, 1H), 6.34 (m, 1H), 3.55 (s, 3H), 3.11-3.08 (m, 1H), 1.32-1.24 (m, 1H), 0.77-0.69 (m, 2H), 0.52-0.38 (m, 2H).2-({2-Chloro-4-fluoro-5-[3-methyl-2,6-dioxo-4-(trifluoromethyl)-3,6-dihydropyrimidin-1(2H)-yl]phenyl}sulfanyl)(cyclopropyl)acetic acid (120 mg, 0.27 mmol), 1-hydroxy-1H-benzotriazole (47 mg, 0.35 mmol) and 1-(3-dimethylaminopropyl)-3-ethylcarbodiimide hydrochloride (66 mg, 0.35 mmol) were dissolved in abs. dichloromethane in a baked-out round-bottom flask under argon and, after stirring at room temperature for 5 minutes, 2-(hydroxymethyl)tetrahydrofuran (35 mg, 0.35 mmol) and triethylamine (0.09 mL, 0.64 mmol) were added. The resulting reaction mixture was stirred at room temperature for 2 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydrofuran-2-ylmethyl ({2-chloro-4-fluoro-5-[3-methyl-2,6-dioxo-4-(trifluoromethyl)-3,6-dihydropyrimidin-1(2H)-yl]phenyl}sulfanyl)(cyclopropyl)acetate (81 mg, 54% of theory) was obtained in the form of a highly viscous, colorless oil. ¹H-NMR (d₆δ, ppm) 7.83 (d, 1H), 7.72/7.68 (m, 1H), 6.62 (m, 1H), 4.06-3.99 (m, 1H), 3.97-3.85 (m, 2H), 3.70-3.64 (m, 1H), 3.62-3.56 (m, 1H), 3.48-3.34 (m, 4H), 1.90-1.68 (m, 3H) 1.53-1.40 (m, 1H), 1.30-1.13 (m, 1H), 0.69-0.58 (m, 2H), 0.48-0.35 (m 2H).

No. I.48-82:Tetrahydrothiophen-3-ylmethyl 3-({2-chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoate

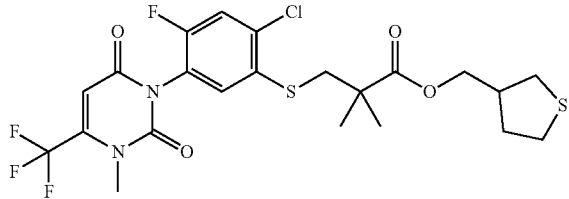 [SMILES: Cn1c(C(F)(F)F)cc(=O)n(-c2cc(SCC(C)(C)C(=O)OCC3CCSC3)c(Cl)cc2F)c1=O]

3-Chloropivalic acid (778 mg, 5.64 mmol) was dissolved in abs. acetonitrile (30 mL) under argon in a baked-out round-bottom flask, and then potassium carbonate (1.64 g, 11.28 mmol) and 3-(4-chloro-2-fluoro-5-sulfanylphenyl)-1-methyl-6-(trifluoromethyl)pyrimidine-2,4(1H,3H)-dione (2.0 g, 5.64 mmol) were added. The resulting reaction mixture was stirred at a temperature of 45° C. for 2 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 3-({2-chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoic acid (2.35 g, 87% of theory) was obtained in the form of a colorless solid. ¹H-NMR (CDCl₃ δ, ppm) 7.49 (d, 1H), 7.37 (d, 1H), 6.39 (s, 1H), 3.57 (s, 3H), 3.02 (s, 2H), 1.29 (s, 6H). 3-({2-Chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoic acid (200 mg, 0.44 mmol), 1-hydroxy-1H-benzotriazole (77 mg, 0.57 mmol) and 1-(3-dimethylaminopropyl)-3-ethylcarbodiimide hydrochloride (110 mg, 0.57 mmol) were dissolved in abs. dichloromethane in a baked-out round-bottom flask under argon and, after stirring at room temperature for 5 minutes, tetrahydrothiophen-3-ylmethanol (68 mg, 0.57 mmol) and triethylamine (0.15 mL, 1.06 mmol) were added. The resulting reaction mixture was stirred at room temperature for 3 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydrothiophen-3-ylmethyl 3-({2-chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoate (128 mg, 52% of theory) was obtained in the form of a highly viscous, colorless oil. ¹H-NMR (CDCl₃ δ, ppm) 7.34 (d, 1H), 7.30 (d, 1H), 6.36 (m, 1H), 4.12-4.08 (m, 1H), 4.06-4.00 (m, 1H), 3.56 (s, 3H), 3.12 (s, 2H), 2.93-2.85 (m, 3H) 2.64-2.58 (m, 1H), 2.56-2.48 (m 1H), 2.13-2.09 (m 1H), 1.78-1.69 (m 1H), 1.32 (s, 6H).

No. I.48-92: Tetrahydro-2H-pyran-3-ylmethyl 3-({2-chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoate

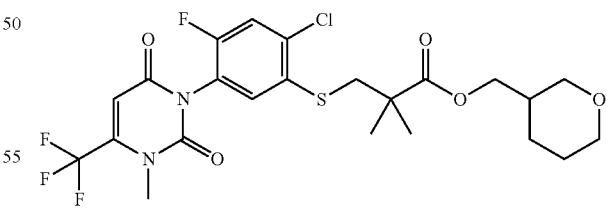

3-({2-Chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoic acid (200 mg, 0.44 mmol), 1-hydroxy-1H-benzotriazole (77 mg, 0.57 mmol) and 1-(3-dimethylaminopropyl)-3-ethylcarbodiimide hydrochloride (110 mg, 0.57 mmol) were dissolved in abs. dichloromethane in a baked-out round-bottom flask under argon and, after stirring at room temperature for 5 minutes, tetrahydro-2H-pyran-3-ylmethanol (66 mg, 0.57 mmol) and triethylamine (0.15 mL, 1.06 mmol) were added. The resulting reaction mixture was stirred at room temperature for 3 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydro-2H-pyran-3-ylmethyl 3-({2-chloro-4-fluoro-5-[3-methyl-2,6-dioxo-4-(trifluoromethyl)-3,6-dihydropyrimidin-1(2H)-yl]phenyl}sulfanyl)-2,2-dimethylpropanoate (149 mg, 61% of theory) was obtained in the form of a highly viscous, colorless oil. $^1$H-NMR (CDCl$_3$ δ, ppm) 7.34 (d, 1H), 7.31 (m, 1H), 6.36 (m, 1H), 4.02-3.95 (m, 1H), 3.92-3.70 (m, 3H), 3.56 (s, 3H), 3.43-3.37 (m, 1H), 3.27-3.19 (m, 1H), 3.11 (s, 2H), 1.99-1.91 (m, 1H), 1.84-1.77 (m, 1H), 1.66-1.59 (m, 2H), 1.33-1.27 (m, 1H), 1.31 (s, 6H).

No. I.60-71: Tetrahydrofuran-2-ylmethyl 2-({2-chloro-5-[5-ethyl-3-methyl-2,6-dioxo-4-(trifluoromethyl)-3,6-dihydropyrimidin-1(2H)-yl]-4-fluorophenyl}sulfanyl)propanoate

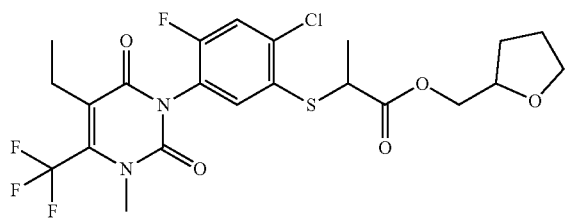 [SMILES: CCc1c(C(F)(F)F)n(C)c(=O)n(-c2cc(SC(C)C(=O)OCC3CCCO3)c(Cl)cc2F)c1=O]

Analogously to the synthesis of example No. I.12-72, a solution of n-butyllithium in hexane was added to a solution, cooled to −10° C., of diisopropylamine in abs. tetrahydrofuran. The resulting reaction mixture was stirred at a temperature of −10° C. for 40 minutes and then cooled further to −78° C. Then ethyl butanoate was added cautiously. The reaction mixture was stirred at −78° C. for 1 h, a suitable amount of 2,2,2-trifluoroethyl trifluoroacetate was added and, finally, the mixture was stirred at room temperature overnight. On completion of conversion, the mixture was acidified with dil. hydrochloric acid (1M) and repeatedly extracted thoroughly with ethyl acetate. These combined organic phases were dried over sodium sulfate, filtered and concentrated under reduced pressure, and the ethyl 4,4,4-trifluoro-2-ethyl-3-oxobutanoate (67% of theory) obtained in this way, without further purification, was dissolved in toluene in a round-bottom flask and admixed with ammonium acetate and acetic acid. The resulting reaction mixture was stirred under reflux conditions with use of a water separator for several hours until no further water was separated out. After cooling to room temperature, the reaction mixture was concentrated under reduced pressure and then the residue was taken up with ethyl acetate and water. The water phase was then extracted thoroughly with ethyl acetate, and the combined organic phases were dried over sodium sulfate, filtered and concentrated under reduced pressure. Distillative purification of the residue obtained afforded ethyl (2Z)-3-amino-4,4,4-trifluoro-2-ethylbut-2-enoate (58% of theory). 2-Fluoro-4-chloroaniline and triethylamine were successively added cautiously to a solution of triphosgene in abs. dichloromethane, in such a way that the temperature of the resulting reaction mixture remained below 20° C. After the end of the addition, the reaction mixture was stirred at room temperature overnight and then washed with water and 1N hydrochloric acid, dried over sodium sulfate, filtered and concentrated under reduced pressure. The 2-fluoro-4-chlorophenyl isocyanate was used in the next step without further purification. Sodium hydride (60% dispersion in mineral oil) was suspended in abs. N,N-dimethylformamide, and ethyl (2Z)-3-amino-4,4,4-trifluoro-2-ethylbut-2-enoate was added. The reaction mixture was stirred at room temperature for 1 h, then cooled down to a temperature of −30° C., and 2-fluoro-4-chlorophenyl isocyanate was added. On completion of addition, the resulting reaction mixture was stirred at room temperature for a further 4 h and then added to ice-water. After the addition of ethyl acetate and acidification with 1N hydrochloric acid, the aqueous phase was extracted thoroughly with ethyl acetate. The combined organic phases were washed with water, dried over sodium sulfate, filtered and concentrated under reduced pressure. In this way, 3-(4-chloro-2-fluorophenyl)-5-ethyl-6-(trifluoromethyl)pyrimidine-2,4(1H,3H)-dione (66%) was obtained, which was used in the next step without further purification. To a solution of 3-(4-chloro-2-fluorophenyl)-5-methyl-6-(trifluoromethyl)pyrimidine-2,4(1H,3H)-dione (1 equiv.) in abs. N,N-dimethylformamide was added potassium carbonate (1.2 equiv). Thereafter, a solution of methyl iodide (1.2 equiv.) in abs. N,N-dimethylformamide was added and the resulting reaction mixture was stirred at room temperature for a further 1 h. On completion of conversion, the reaction mixture was cooled to a temperature of 0° C., water was added cautiously, and then the mixture was extracted thoroughly with dichloromethane. The combined organic phases were dried over sodium sulfate, filtered and concentrated under reduced pressure. In this way, 3-(4-chloro-2-fluorophenyl)-5-ethyl-1-methyl-6-(trifluoromethyl)pyrimidine-2,4(1H,3H)-dione (97% of theory) was obtained, which was converted in the next step without further purification. 3-(4-Chloro-2-fluorophenyl)-5-ethyl-1-methyl-6-(trifluoromethyl)pyrimidine-2,4(1H,3H)-dione was then added stepwise to chlorosulfonic acid in a baked-out round-bottom flask. The resulting reaction mixture was then stirred at a temperature of 110° C. for 20 h and, after cooling to room temperature, added to ice-water and extracted repeatedly with ethyl acetate. The combined organic phases were dried over sodium sulfate, filtered and concentrated under reduced pressure. This gave 2-chloro-4-fluoro-5-[5-ethyl-3-methyl-2,6-dioxo-4-(trifluoromethyl)-3,6-dihydropyrimidin-1(2H)-yl]benzenesulfonyl chloride (54% of theory), which was used in the next step without further purification. To an initial charge of 2-chloro-4-fluoro-5-[5-ethyl-3-methyl-2,6-dioxo-4-(trifluoromethyl)-3,6-dihydropyrimidin-1(2H)-yl]sulfonyl chloride (1 equiv.) in a round-bottom flask were successively added hydrochloric acid (2 mL/mmol), acetic acid (2.5 mL/mmol) and tin dichloride dihydrate (3 equiv). The resulting reaction mixture was stirred at a temperature of 100° C. for 10 h, after cooling to room temperature added to ice-water, and extracted thoroughly with dichloromethane. The combined organic phases were dried over sodium sulfate, filtered and concentrated under reduced pressure. Final column chromatography purification afforded 3-(4-chloro-2-fluoro-5-sulfanylphenyl)-5-ethyl-1-methyl-6-(trifluoromethyl)pyrimidine-2,4(1H,3H)-dione (84% of theory) in the form of a colorless solid. 2-Chloropropanecarboxylic acid (567 mg, 5.23 mmol) was dissolved in abs. acetonitrile under argon in a baked-out round-bottom flask, and then cesium carbonate (3.41 g, 10.45 mmol) and 3-(4-chloro-2-fluoro-5-sulfanylphenyl)-5-ethyl-1-methyl-6-(trifluoromethyl)pyrimidine-2,4(1H,3H)-dione (2.0 g, 5.23 mmol) were added. The resulting reaction mixture was stirred at a temperature of 50° C. for 1 h and, after cooling to room temperature, admixed with water and dichloromethane and extracted thoroughly. The aqueous phase was then acidified with 10% hydrochloric acid and again extracted repeatedly with dichloromethane. The combined organic phases were dried over sodium sulfate, filtered and concentrated under reduced pressure. The crude product was then purified by column chromatography (ethyl acetate/heptane gradient), and 2-({2-chloro-5-[5-ethyl-3-methyl-2,6-dioxo-4-(trifluoromethyl)-3,6-dihydropyrimidin-1(2H)-yl]-4-fluorophenyl}sulfanyl)propanoic acid (1.30 g, 54% of theory) was obtained in the form of a colorless solid. $^{1}$H-NMR (CDCl$_3$ δ, ppm) 7.54 (d, 1H), 7.39 (d, 1H), 3.90-3.83 (m, 1H), 3.54 (s, 3H), 2.72-2.69 (m, 2H), 1.55 (d, 3H), 1.13 (t, 3H). 2-({2-Chloro-5-[5-ethyl-3-dimethyl-2,6-dioxo-4-(trifluoromethyl)-3,6-dihydropyrimidin-1(2H)-yl]-4-fluorophenyl}sulfanyl)propanoic acid (110 mg, 0.24 mmol), 1-hydroxy-1H-benzotriazole (42 mg, 0.31 mmol) and 1-(3-dimethylaminopropyl)-3-ethylcarbodiimide hydrochloride (60 mg, 0.31 mmol) were dissolved in abs. dichloromethane in a baked-out round-bottom flask under argon and, after stirring at room temperature for 5 minutes, 2-(hydroxymethyl)tetrahydrofuran (32 mg, 0.31 mmol) and triethylamine (0.08 mL, 0.61 mmol) were added. The resulting reaction mixture was stirred at room temperature for 6 h, then admixed with water and dichloromethane and extracted thoroughly with dichloromethane. The combined organic phases were dried over sodium sulfate, filtered and concentrated under reduced pressure. The crude product was then purified by column chromatography (ethyl acetate/heptane gradient), and tetrahydrofuran-2-ylmethyl 2-({2-chloro-5-[5-ethyl-3-methyl-2,6-dioxo-4-(trifluoromethyl)-3,6-dihydropyrimidin-1(2H)-yl]-4-fluorophenyl}sulfanyl)propanoate (58 mg, 43% of theory) was obtained in the form of a highly viscous, colorless oil. $^{1}$H-NMR (CDCl$_3$ δ, ppm) 7.56-7.52 (m, 1H), 7.38-7.33 (m, 1H), 4.18-3.88 (m, 4H), 3.83-3.68 (m, 2H), 3.54 (s, 3H), 2.74-2.68 (m, 2H), 2.01-1.82 (m 3H), 1.64-1.50 (m 4H), 1.13 (t. 3H).

In analogy to the above-cited preparation examples that have been recited at the corresponding point, and taking account of the general details of the preparation of substituted N-heterocyclyl- and N-heteroaryltetrahydropyrimidinones, the compounds cited below are obtained. When a structural element in table 1 is defined by a structural formula containing a dotted line, this dotted line means that the group in question is connected to the rest of the molecule at that position. When a structural element in table 1 is defined by a structural formula containing an arrow, the arrow represents a bond of the respective Q group to the carbonyl group in the general formula (I).

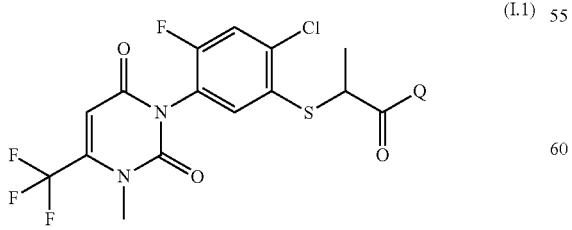

(I.1)

Table I.1: Preferred compounds of the formula (I.1) are the compounds I.1-1 to I.1-345 in which Q has the definitions from table 1 that are given in the respective line. The compounds I.1-1 to I.1-345 from table I.1 are thus defined by the meaning of the respective entries No. 1 to 345 for Q from table 1.

TABLE 1

| No. | Q |
|---|---|
| 1 | Q-1 |
| 2 | Q-2 |
| 3 | Q-3 |
| 4 | Q-4 |
| 5 | Q-5 |
| 6 | Q-6 |
| 7 | Q-7 |
| 8 | Q-8 |
| 9 | Q-9 |
| 10 | Q-10 |
| 11 | Q-11 |
| 12 | Q-12 |
| 13 | Q-13 |
| 14 | Q-14 |
| 15 | Q-15 |
| 16 | Q-16 |
| 17 | Q-17 |
| 18 | Q-18 |
| 19 | Q-19 |
| 20 | Q-20 |
| 21 | Q-21 |
| 22 | Q-22 |
| 23 | Q-23 |
| 24 | Q-24 |
| 25 | Q-25 |
| 26 | Q-26 |
| 27 | Q-27 |
| 28 | Q-28 |
| 29 | Q-29 |
| 30 | Q-30 |
| 31 | Q-31 |
| 32 | Q-32 |
| 33 | Q-33 |
| 34 | Q-34 |
| 35 | Q-35 |
| 36 | Q-36 |
| 37 | Q-37 |
| 38 | Q-38 |
| 39 | Q-39 |
| 40 | Q-40 |
| 41 | Q-41 |
| 42 | Q-42 |
| 43 | Q-43 |
| 44 | Q-44 |
| 45 | Q-45 |
| 46 | Q-46 |
| 47 | Q-47 |
| 48 | Q-48 |
| 49 | Q-49 |
| 50 | Q-50 |
| 51 | Q-51 |
| 52 | Q-52 |
| 53 | Q-53 |
| 54 | Q-54 |
| 55 | Q-55 |
| 56 | Q-56 |
| 57 | Q-57 |
| 58 | Q-58 |
| 59 | Q-59 |
| 60 | Q-60 |
| 61 | Q-61 |
| 62 | Q-62 |
| 63 | Q-63 |
| 64 | Q-64 |
| 65 | Q-65 |
| 66 | Q-66 |
| 67 | Q-67 |
| 68 | Q-68 |
| 69 | Q-69 |
| 70 | Q-70 |
| 71 | Q-71 |
| 72 | Q-72 |
| 73 | Q-73 |

TABLE 1-continued

| No. | Q |
|---|---|
| 74 | Q-74 |
| 75 | Q-75 |
| 76 | Q-76 |
| 77 | Q-77 |
| 78 | Q-78 |
| 79 | Q-79 |
| 80 | Q-80 |
| 81 | Q-81 |
| 82 | Q-82 |
| 83 | Q-83 |
| 84 | Q-84 |
| 85 | Q-85 |
| 86 | Q-86 |
| 87 | Q-87 |
| 88 | Q-88 |
| 89 | Q-89 |
| 90 | Q-90 |
| 91 | Q-91 |
| 92 | Q-92 |
| 93 | Q-93 |
| 94 | Q-94 |
| 95 | Q-95 |
| 96 | Q-96 |
| 97 | Q-97 |
| 98 | Q-98 |
| 99 | Q-99 |
| 100 | Q-100 |
| 101 | Q-101 |
| 102 | Q-102 |
| 103 | Q-103 |
| 104 | Q-104 |
| 105 | Q-105 |
| 106 | Q-106 |
| 107 | Q-107 |
| 108 | Q-108 |
| 109 | Q-109 |
| 110 | Q-110 |
| 111 | Q-111 |
| 112 | Q-112 |
| 113 | Q-113 |
| 114 | Q-114 |
| 115 | Q-115 |
| 116 | Q-116 |
| 117 | Q-117 |
| 118 | Q-118 |
| 119 | Q-119 |
| 120 | Q-120 |
| 121 | Q-121 |
| 122 | Q-122 |
| 123 | Q-123 |
| 124 | Q-124 |
| 125 | Q-125 |
| 126 | Q-126 |
| 127 | Q-127 |
| 128 | Q-128 |
| 129 | Q-129 |
| 130 | Q-130 |
| 131 | Q-131 |
| 132 | Q-132 |
| 133 | Q-133 |
| 134 | Q-134 |
| 135 | Q-135 |
| 136 | Q-136 |
| 137 | Q-137 |
| 138 | Q-138 |
| 139 | Q-139 |
| 140 | Q-140 |
| 141 | Q-141 |
| 142 | Q-142 |
| 143 | Q-143 |
| 144 | Q-144 |
| 145 | Q-145 |
| 146 | Q-146 |
| 147 | Q-147 |
| 148 | Q-148 |
| 149 | Q-149 |
| 150 | Q-150 |
| 151 | Q-151 |
| 152 | Q-152 |
| 153 | Q-153 |
| 154 | Q-154 |
| 155 | Q-155 |
| 156 | Q-156 |
| 157 | Q-157 |
| 158 | Q-158 |
| 159 | Q-159 |
| 160 | Q-160 |
| 161 | Q-161 |
| 162 | Q-162 |
| 163 | Q-163 |
| 164 | Q-164 |
| 165 | Q-165 |
| 166 | Q-166 |
| 167 | Q-167 |
| 168 | Q-168 |
| 169 | Q-169 |
| 170 | Q-170 |
| 171 | Q-171 |
| 172 | Q-172 |
| 173 | Q-173 |
| 174 | Q-174 |
| 175 | Q-175 |
| 176 | Q-176 |
| 177 | Q-177 |
| 178 | Q-178 |
| 179 | Q-179 |
| 180 | Q-180 |
| 181 | Q-181 |
| 182 | Q-182 |
| 183 | Q-183 |
| 184 | Q-184 |
| 185 | Q-185 |
| 186 | Q-186 |
| 187 | Q-187 |
| 188 | Q-188 |
| 189 | Q-189 |
| 190 | Q-190 |
| 191 | Q-191 |
| 192 | Q-192 |
| 193 | Q-193 |
| 194 | Q-194 |
| 195 | Q-195 |
| 196 | Q-196 |
| 197 | Q-197 |
| 198 | Q-198 |
| 199 | Q-199 |
| 200 | Q-200 |
| 201 | Q-201 |
| 202 | Q-202 |
| 203 | Q-203 |
| 204 | Q-204 |
| 205 | Q-205 |
| 206 | Q-206 |
| 207 | Q-207 |
| 208 | Q-208 |
| 209 | Q-209 |
| 210 | Q-210 |
| 211 | Q-211 |
| 212 | Q-212 |
| 213 | Q-213 |
| 214 | Q-214 |
| 215 | Q-215 |
| 216 | Q-216 |
| 217 | Q-217 |
| 218 | Q-218 |
| 219 | Q-219 |
| 220 | Q-220 |
| 221 | Q-221 |
| 222 | Q-222 |
| 223 | Q-223 |
| 224 | Q-224 |
| 225 | Q-225 |
| 226 | Q-226 |
| 227 | Q-227 |
| 228 | Q-228 |
| 229 | Q-229 |

TABLE 1-continued

| No. | Q |
|---|---|
| 230 | Q-230 |
| 231 | Q-231 |
| 232 | Q-232 |
| 233 | Q-233 |
| 234 | Q-234 |
| 235 | Q-235 |
| 236 | Q-236 |
| 237 | Q-237 |
| 238 | Q-238 |
| 239 | Q-239 |
| 240 | Q-240 |
| 241 | Q-241 |
| 242 | Q-242 |
| 243 | Q-243 |
| 244 | Q-244 |
| 245 | Q-245 |
| 246 | Q-246 |
| 247 | Q-247 |
| 248 | Q-248 |
| 249 | Q-249 |
| 250 | Q-250 |
| 251 | Q-251 |
| 252 | Q-252 |
| 253 | Q-253 |
| 254 | Q-254 |
| 255 | Q-255 |
| 256 | Q-256 |
| 257 | Q-257 |
| 258 | Q-258 |
| 259 | Q-259 |
| 260 | Q-260 |
| 261 | Q-261 |
| 262 | Q-262 |
| 263 | Q-263 |
| 264 | Q-264 |
| 265 | Q-265 |
| 266 | Q-266 |
| 267 | Q-267 |
| 268 | Q-268 |
| 269 | Q-269 |
| 270 | Q-270 |
| 271 | Q-271 |
| 272 | Q-272 |
| 273 | Q-273 |
| 274 | Q-274 |
| 275 | Q-275 |
| 276 | Q-276 |
| 277 | Q-277 |
| 278 | Q-278 |
| 279 | Q-279 |
| 280 | Q-280 |
| 281 | Q-281 |
| 282 | Q-282 |
| 283 | Q-283 |
| 284 | Q-284 |
| 285 | Q-285 |
| 286 | Q-286 |
| 287 | Q-287 |
| 288 | Q-288 |
| 289 | Q-289 |
| 290 | Q-290 |
| 291 | Q-291 |
| 292 | Q-292 |
| 293 | Q-293 |
| 294 | Q-294 |
| 295 | Q-295 |
| 296 | Q-296 |
| 297 | Q-297 |
| 298 | Q-298 |
| 299 | Q-299 |
| 300 | Q-300 |
| 301 | Q-301 |
| 302 | Q-302 |
| 303 | Q-303 |
| 304 | Q-304 |
| 305 | Q-305 |
| 306 | Q-306 |
| 307 | Q-307 |
| 308 | Q-308 |
| 309 | Q-309 |
| 310 | Q-310 |
| 311 | Q-311 |
| 312 | Q-312 |
| 313 | Q-313 |
| 314 | Q-314 |
| 315 | Q-315 |
| 316 | Q-316 |
| 317 | Q-317 |
| 318 | Q-318 |
| 319 | Q-319 |
| 320 | Q-320 |
| 321 | Q-321 |
| 322 | Q-322 |
| 323 | Q-323 |
| 324 | Q-324 |
| 325 | Q-325 |
| 326 | Q-326 |
| 327 | Q-327 |
| 328 | Q-328 |
| 329 | Q-329 |
| 330 | Q-330 |
| 331 | Q-331 |
| 332 | Q-332 |
| 333 | Q-333 |
| 334 | Q-334 |
| 335 | Q-335 |
| 336 | Q-336 |
| 337 | Q-337 |
| 338 | Q-338 |
| 339 | Q-339 |
| 340 | Q-340 |
| 341 | Q-341 |
| 342 | Q-342 |
| 343 | Q-343 |
| 344 | Q-344 |
| 345 | Q-345 |

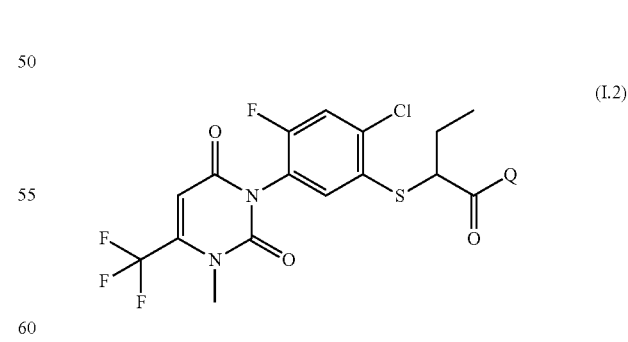

(I.2)

Table I.2: Preferred compounds of the formula (I.2) are the compounds I.2-1 to I.2-345 in which Q has the definitions from table 1 that are given in the respective line. The compounds I.2-1 to I.2-345 from table I.2 are thus defined by the meaning of the respective entries No. 1 to 345 for Q from table 1.

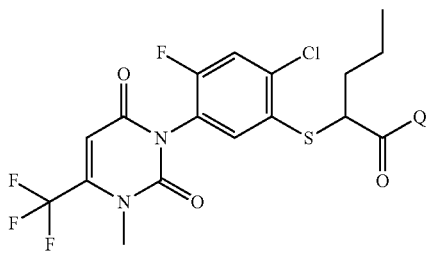

(I.3)

Table I.3: Preferred compounds of the formula (I.3) are the compounds I.3-1 to I.3-345 in which Q has the definitions from table 1 that are given in the respective line. The compounds I.3-1 to I.3-345 from table I.3 are thus defined by the meaning of the respective entries No. 1 to 345 for Q from table 1.

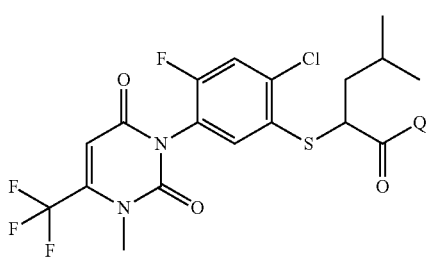

(I.4)

Table I.4: Preferred compounds of the formula (I.4) are the compounds I.4-1 to I.4-345 in which Q has the definitions from table 1 that are given in the respective line. The compounds I.4-1 to I.4-345 from table I.4 are thus defined by the meaning of the respective entries No. 1 to 345 for Q from table 1.

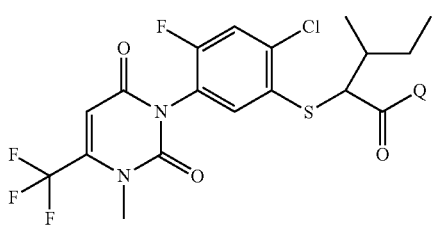

(I.5)

Table I.5: Preferred compounds of the formula (I.5) are the compounds I.5-1 to I.5-345 in which Q has the definitions from table 1 that are given in the respective line. The compounds I.5-1 to I.5-345 from table I.5 are thus defined by the meaning of the respective entries No. 1 to 345 for Q from table 1.

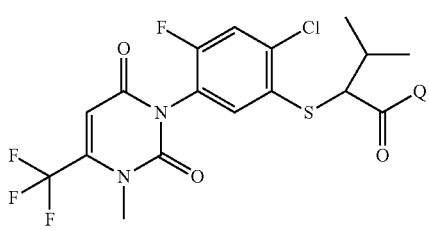

(I.6)

Table I.6: Preferred compounds of the formula (I.6) are the compounds I.6-1 to I.6-345 in which Q has the definitions from table 1 that are given in the respective line. The compounds I.6-1 to I.6-345 from table I.6 are thus defined by the meaning of the respective entries No. 1 to 345 for Q from table 1.

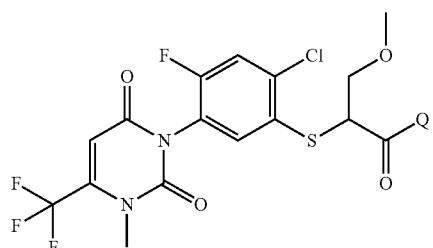

(I.7)

Table I.7: Preferred compounds of the formula (I.7) are the compounds I.7-1 to I.7-345 in which Q has the definitions from table 1 that are given in the respective line. The compounds I.7-1 to I.7-345 from table I.7 are thus defined by the meaning of the respective entries No. 1 to 345 for Q from table 1.

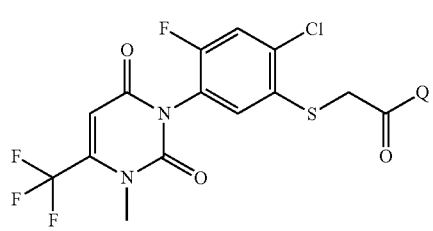

(I.8)

Table I.8: Preferred compounds of the formula (I.8) are the compounds I.8-1 to I.8-345 in which Q has the definitions from table 1 that are given in the respective line. The compounds I.8-1 to I.8-345 from table I.8 are thus defined by the meaning of the respective entries No. 1 to 345 for Q from table 1.

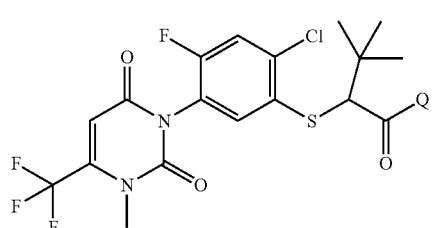

(I.9)

Table I.9: Preferred compounds of the formula (I.9) are the compounds I.9-1 to I.9-345 in which Q has the definitions from table 1 that are given in the respective line. The compounds I.9-1 to I.9-345 from table I.9 are thus defined by the meaning of the respective entries No. 1 to 345 for Q from table 1.

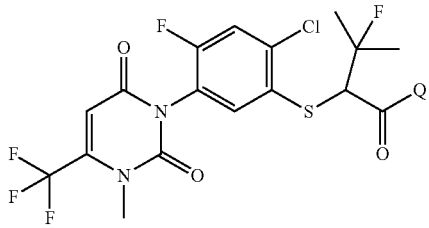
(I.10)

Table I.10: Preferred compounds of the formula (I.10) are the compounds I.10-1 to I.10-345 in which Q has the definitions from table 1 that are given in the respective line. The compounds I.10-1 to I.10-345 from table I.10 are thus defined by the meaning of the respective entries No. 1 to 345 for Q from table 1.

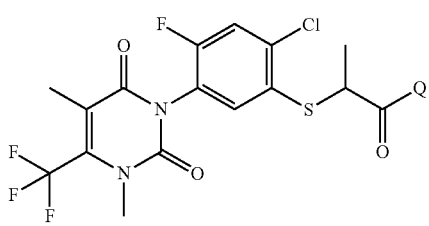
(I.11)

Table I.11: Preferred compounds of the formula (I.11) are the compounds I.11-1 to I.11-345 in which Q has the definitions from table 1 that are given in the respective line. The compounds I.11-1 to I.11-345 from table I.11 are thus defined by the meaning of the respective entries No. 1 to 345 for Q from table 1.

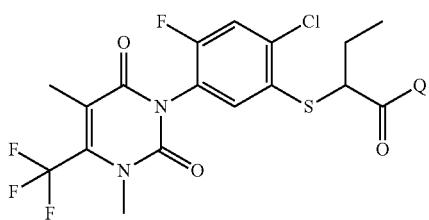
(I.12)

Table I.12: Preferred compounds of the formula (I.12) are the compounds I.12-1 to I.12-345 in which Q has the definitions from table 1 that are given in the respective line. The compounds I.12-1 to I.12-345 from table I.12 are thus defined by the meaning of the respective entries No. 1 to 345 for Q from table 1.

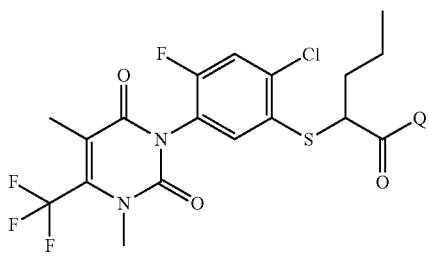
(I.13)

Table I.13: Preferred compounds of the formula (I.13) are the compounds I.13-1 to I.13-345 in which Q has the definitions from table 1 that are given in the respective line. The compounds I.13-1 to I.13-345 from table I.13 are thus defined by the meaning of the respective entries No. 1 to 345 for Q from table 1.

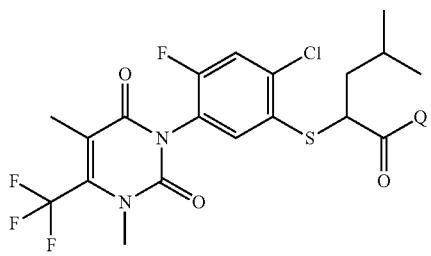
(I.14)

Table I.14: Preferred compounds of the formula (I.14) are the compounds I.14-1 to I.14-345 in which Q has the definitions from table 1 that are given in the respective line. The compounds I.14-1 to I.14-345 from table I.14 are thus defined by the meaning of the respective entries No. 1 to 345 for Q from table 1.

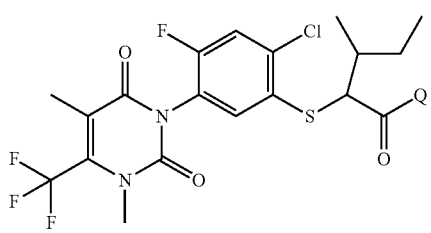
(I.15)

Table I.15: Preferred compounds of the formula (I.15) are the compounds I.15-1 to I.15-345 in which Q has the definitions from table 1 that are given in the respective line. The compounds I.15-1 to I.15-345 from table I.15 are thus defined by the meaning of the respective entries No. 1 to 345 for Q from table 1.

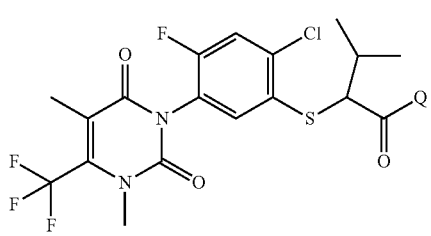
(I.16)

Table I.16: Preferred compounds of the formula (I.16) are the compounds I.16-1 to I.16-345 in which Q has the definitions from table 1 that are given in the respective line. The compounds I.16-1 to I.16-345 from table I.16 are thus defined by the meaning of the respective entries No. 1 to 345 for Q from table 1.

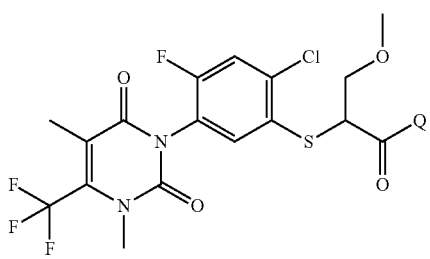

(I.17)

Table I.17: Preferred compounds of the formula (I.17) are the compounds I.17-1 to I.17-345 in which Q has the definitions from table 1 that are given in the respective line. The compounds I.17-1 to I.17-345 from table I.17 are thus defined by the meaning of the respective entries No. 1 to 345 for Q from table 1.

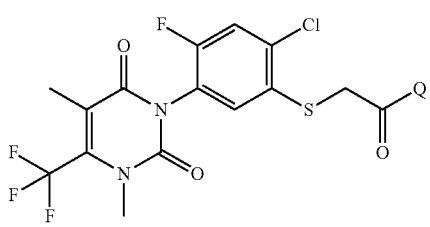

(I.18)

Table I.18: Preferred compounds of the formula (I.18) are the compounds I.18-1 to I.18-345 in which Q has the definitions from table 1 that are given in the respective line. The compounds I.18-1 to I.18-345 from table I.18 are thus defined by the meaning of the respective entries No. 1 to 345 for Q from table 1.

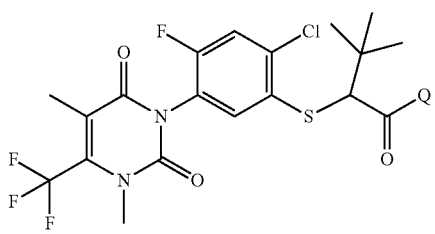

(I.19)

Table I.19: Preferred compounds of the formula (I.19) are the compounds I.19-1 to I.19-345 in which Q has the definitions from table 1 that are given in the respective line. The compounds I.19-1 to I.19-345 from table I.19 are thus defined by the meaning of the respective entries No. 1 to 345 for Q from table 1.

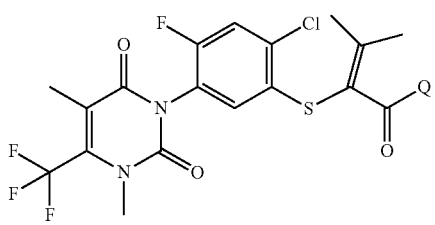

(I.20)

Table I.20: Preferred compounds of the formula (I.20) are the compounds I.20-1 to I.20-345 in which Q has the definitions from table 1 that are given in the respective line. The compounds I.20-1 to I.20-345 from table I.20 are thus defined by the meaning of the respective entries No. 1 to 345 for Q from table 1.

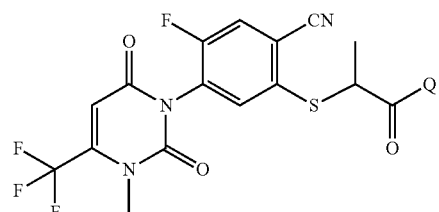

(I.21)

Table I.21: Preferred compounds of the formula (I.21) are the compounds I.21-1 to I.21-345 in which Q has the definitions from table 1 that are given in the respective line. The compounds I.21-1 to I.21-345 from table I.21 are thus defined by the meaning of the respective entries No. 1 to 345 for Q from table 1.

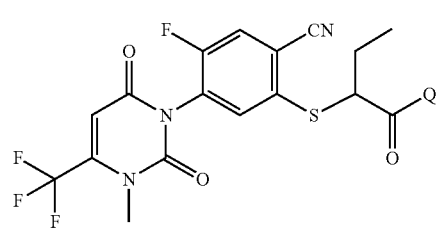

(I.22)

Table I.22: Preferred compounds of the formula (I.22) are the compounds I.22-1 to I.22-345 in which Q has the definitions from table 1 that are given in the respective line. The compounds I.22-1 to I.22-345 from table I.22 are thus defined by the meaning of the respective entries No. 1 to 345 for Q from table 1.

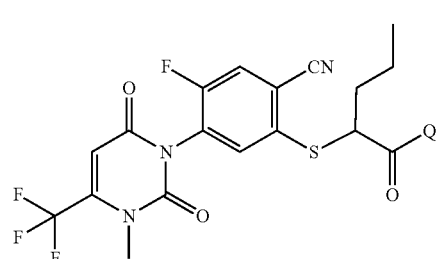

(I.23)

Table I.23: Preferred compounds of the formula (I.23) are the compounds I.23-1 to I.23-345 in which Q has the definitions from table 1 that are given in the respective line. The compounds I.23-1 to I.23-345 from table I.23 are thus defined by the meaning of the respective entries No. 1 to 345 for Q from table 1.

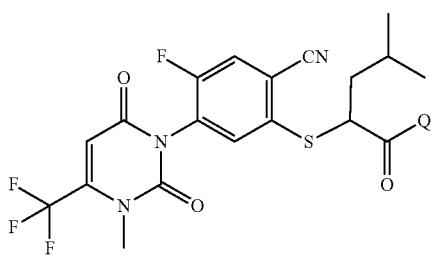

(I.24)

Table I.24: Preferred compounds of the formula (I.24) are the compounds I.24-1 to I.24-345 in which Q has the definitions from table 1 that are given in the respective line. The compounds I.24-1 to I.24-345 from table I.24 are thus defined by the meaning of the respective entries No. 1 to 345 for Q from table 1.

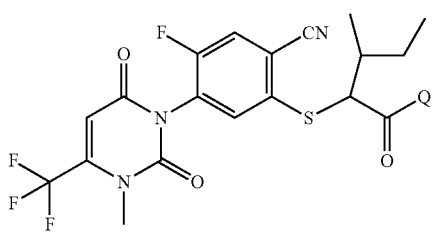

(I.25)

Table I.25: Preferred compounds of the formula (I.25) are the compounds I.25-1 to I.25-345 in which Q has the definitions from table 1 that are given in the respective line. The compounds I.25-1 to I.25-345 from table I.25 are thus defined by the meaning of the respective entries No. 1 to 345 for Q from table 1.

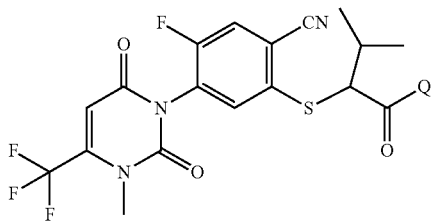

(I.26)

Table I.26: Preferred compounds of the formula (I.26) are the compounds I.26-1 to I.26-345 in which Q has the definitions from table 1 that are given in the respective line. The compounds I.26-1 to I.26-345 from table I.26 are thus defined by the meaning of the respective entries No. 1 to 345 for Q from table 1.

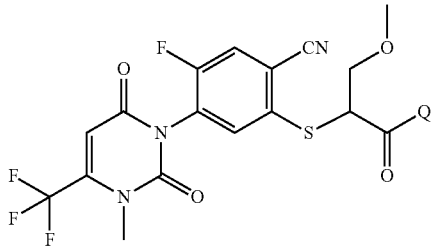

(I.27)

Table I.27: Preferred compounds of the formula (I.27) are the compounds I.27-1 to I.27-345 in which Q has the definitions from table 1 that are given in the respective line. The compounds I.27-1 to I.27-345 from table I.27 are thus defined by the meaning of the respective entries No. 1 to 345 for Q from table 1.

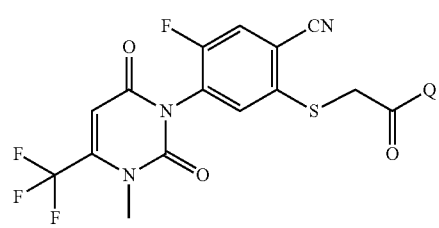

(I.28)

Table I.28: Preferred compounds of the formula (I.28) are the compounds I.28-1 to I.28-345 in which Q has the definitions from table 1 that are given in the respective line. The compounds I.28-1 to I.28-345 from table I.28 are thus defined by the meaning of the respective entries No. 1 to 345 for Q from table 1.

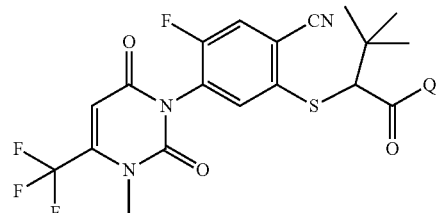

(I.29)

Table I.29: Preferred compounds of the formula (I.29) are the compounds I.29-1 to I.29-345 in which Q has the definitions from table 1 that are given in the respective line. The compounds I.29-1 to I.29-345 from table I.29 are thus defined by the meaning of the respective entries No. 1 to 345 for Q from table 1.

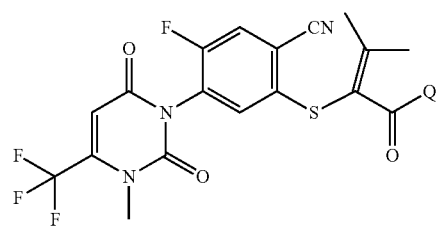

(I.30)

Table I.30: Preferred compounds of the formula (I.30) are the compounds I.30-1 to I.30-345 in which Q has the definitions from table 1 that are given in the respective line. The compounds I.30-1 to I.30-345 from table I.30 are thus defined by the meaning of the respective entries No. 1 to 345 for Q from table 1.

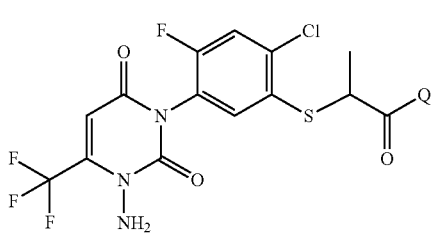

(I.31)

Table I.31: Preferred compounds of the formula (I.31) are the compounds I.31-1 to I.31-345 in which Q has the definitions from table 1 that are given in the respective line. The compounds I.31-1 to I.31-345 from table I.31 are thus defined by the meaning of the respective entries No. 1 to 345 for Q from table 1.

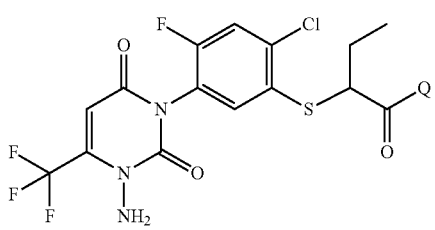

(I.32)

Table I.32: Preferred compounds of the formula (I.32) are the compounds I.32-1 to I.32-345 in which Q has the definitions from table 1 that are given in the respective line. The compounds I.32-1 to I.32-345 from table I.32 are thus defined by the meaning of the respective entries No. 1 to 345 for Q from table 1.

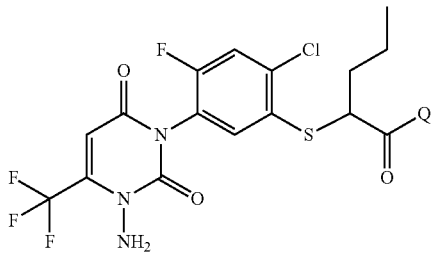

(I.33)

Table I.33: Preferred compounds of the formula (I.33) are the compounds I.33-1 to I.33-345 in which Q has the definitions from table 1 that are given in the respective line. The compounds I.33-1 to I.33-345 from table I.33 are thus defined by the meaning of the respective entries No. 1 to 345 for Q from table 1.

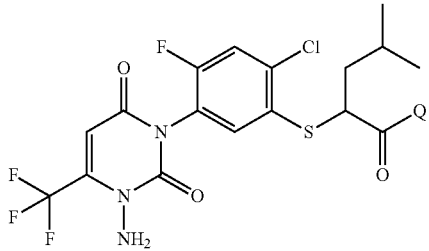

(I.34)

Table I.34: Preferred compounds of the formula (I.34) are the compounds I.34-1 to I.34-345 in which Q has the definitions from table 1 that are given in the respective line. The compounds I.34-1 to I.34-345 from table I.34 are thus defined by the meaning of the respective entries No. 1 to 345 for Q from table 1.

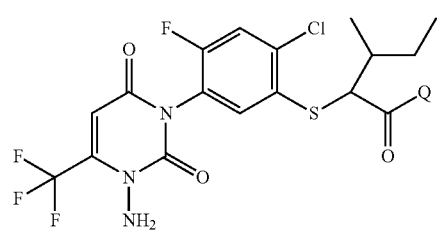

(I.35)

Table I.35: Preferred compounds of the formula (I.35) are the compounds I.35-1 to I.35-345 in which Q has the definitions from table 1 that are given in the respective line. The compounds I.35-1 to I.35-345 from table I.35 are thus defined by the meaning of the respective entries No. 1 to 345 for Q from table 1.

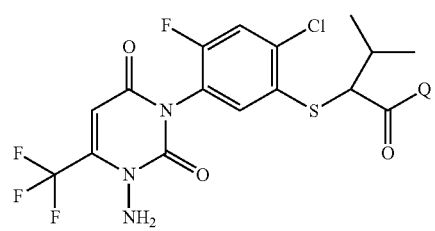

(I.36)

Table I.36: Preferred compounds of the formula (I.36) are the compounds I.36-1 to I.36-345 in which Q has the definitions from table 1 that are given in the respective line. The compounds I.36-1 to I.36-345 from table I.36 are thus defined by the meaning of the respective entries No. 1 to 345 for Q from table 1.

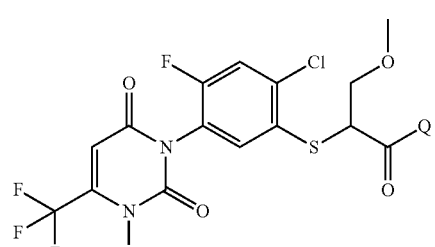

(I.37)

Table I.37: Preferred compounds of the formula (I.37) are the compounds I.37-1 to I.37-345 in which Q has the definitions from table 1 that are given in the respective line. The compounds I.37-1 to I.37-345 from table I.37 are thus defined by the meaning of the respective entries No. 1 to 345 for Q from table 1.

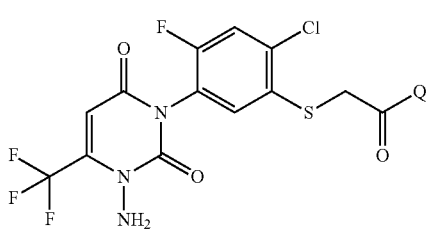

(I.38)

Table I.38: Preferred compounds of the formula (I.38) are the compounds I.38-1 to I.38-345 in which Q has the definitions from table 1 that are given in the respective line. The compounds I.38-1 to I.38-345 from table I.38 are thus defined by the meaning of the respective entries No. 1 to 345 for Q from table 1.

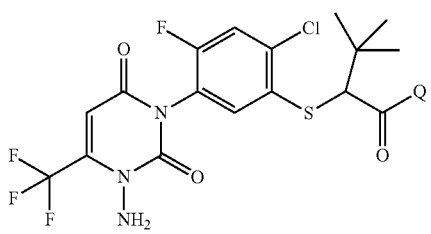

(I.39)

Table I.39: Preferred compounds of the formula (I.39) are the compounds I.39-1 to I.39-345 in which Q has the definitions from table 1 that are given in the respective line. The compounds I.39-1 to I.39-345 from table I.39 are thus defined by the meaning of the respective entries No. 1 to 345 for Q from table 1.

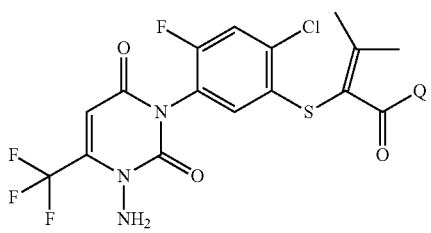

(I.40)

Table I.40: Preferred compounds of the formula (I.40) are the compounds I.40-1 to I.40-345 in which Q has the definitions from table 1 that are given in the respective line. The compounds I.40-1 to I.40-345 from table I.40 are thus defined by the meaning of the respective entries No. 1 to 345 for Q from table 1.

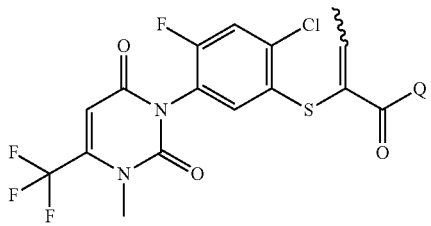

(I.41)

Table I.41: Preferred compounds of the formula (I.41) are the compounds I.41-1 to I.41-345 in which Q has the definitions from table 1 that are given in the respective line. The compounds I.41-1 to I.41-345 from table I.41 are thus defined by the meaning of the respective entries No. 1 to 345 for Q from table 1.

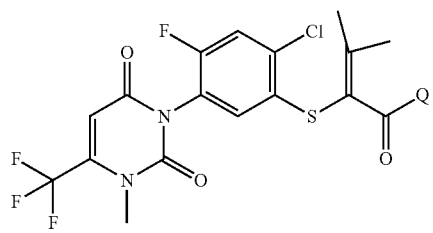

(I.42)

Table I.42: Preferred compounds of the formula (I.42) are the compounds I.42-1 to I.42-345 in which Q has the definitions from table 1 that are given in the respective line. The compounds I.42-1 to I.42-345 from table I.42 are thus defined by the meaning of the respective entries No. 1 to 345 for Q from table 1.

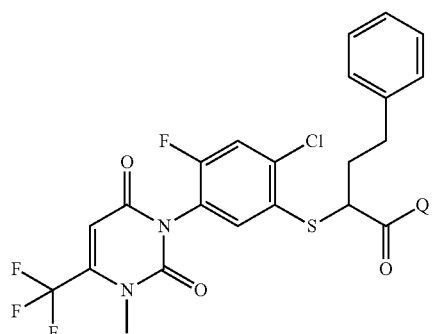

(I.43)

Table I.43: Preferred compounds of the formula (I.43) are the compounds I.43-1 to I.43-345 in which Q has the definitions from table 1 that are given in the respective line. The compounds I.43-1 to I.43-345 from table I.43 are thus defined by the meaning of the respective entries No. 1 to 345 for Q from table 1.

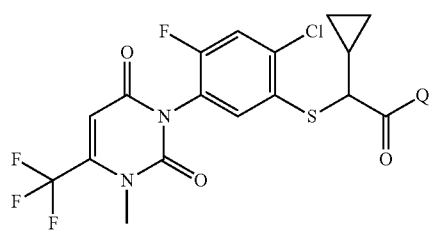

(I.44)

Table I.44: Preferred compounds of the formula (I.44) are the compounds I.44-1 to I.44-345 in which Q has the definitions from table 1 that are given in the respective line. The compounds I.44-1 to I.44-345 from table I.44 are thus defined by the meaning of the respective entries No. 1 to 345 for Q from table 1.

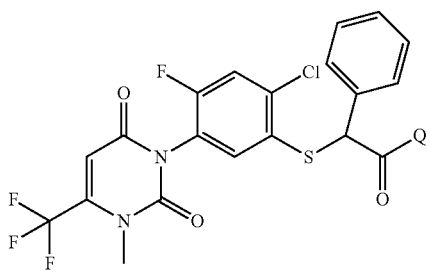
(I.45)

Table I.45: Preferred compounds of the formula (I.45) are the compounds I.45-1 to I.45-345 in which Q has the definitions from table 1 that are given in the respective line. The compounds I.45-1 to I.45-345 from table I.45 are thus defined by the meaning of the respective entries No. 1 to 345 for Q from table 1.

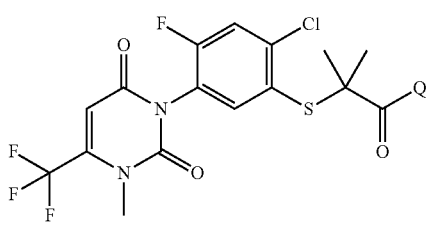
(I.46)

Table I.46: Preferred compounds of the formula (I.46) are the compounds I.46-1 to I.46-345 in which Q has the definitions from table 1 that are given in the respective line. The compounds I.46-1 to I.46-345 from table I.46 are thus defined by the meaning of the respective entries No. 1 to 345 for Q from table 1.

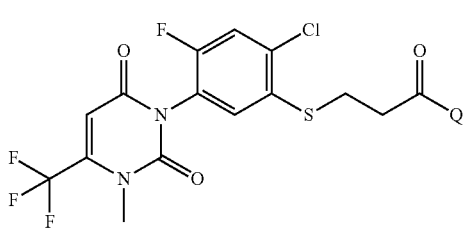
(I.47)

Table I.47: Preferred compounds of the formula (I.47) are the compounds I.47-1 to I.47-345 in which Q has the definitions from table 1 that are given in the respective line. The compounds I.47-1 to I.47-345 from table I.47 are thus defined by the meaning of the respective entries No. 1 to 345 for Q from table 1.

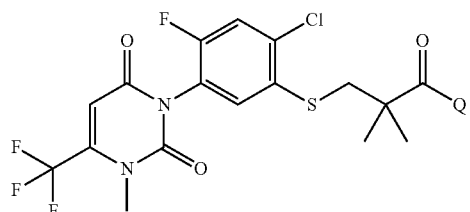
(I.48)

Table I.48: Preferred compounds of the formula (I.48) are the compounds I.48-1 to I.48-345 in which Q has the definitions from table 1 that are given in the respective line. The compounds I.48-1 to I.48-345 from table I.48 are thus defined by the meaning of the respective entries No. 1 to 345 for Q from table 1.

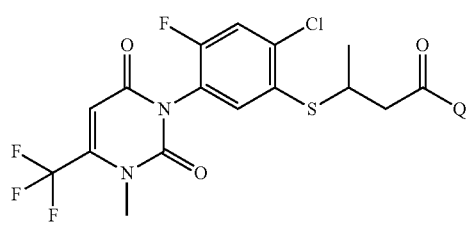
(I.49)

Table I.49: Preferred compounds of the formula (I.49) are the compounds I.49-1 to I.49-345 in which Q has the definitions from table 1 that are given in the respective line. The compounds I.49-1 to I.49-345 from table I.49 are thus defined by the meaning of the respective entries No. 1 to 345 for Q from table 1.

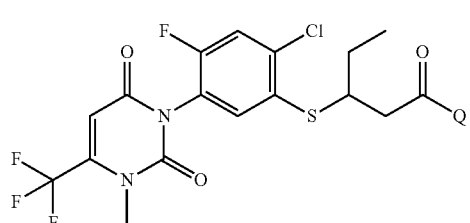
(I.50)

Table I.50: Preferred compounds of the formula (I.50) are the compounds I.50-1 to I.50-345 in which Q has the definitions from table 1 that are given in the respective line. The compounds I.50-1 to I.50-345 from table I.50 are thus defined by the meaning of the respective entries No. 1 to 345 for Q from table 1.

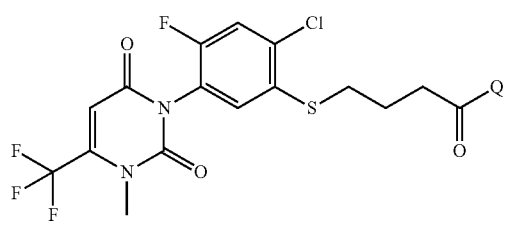
(I.51)

Table I.51: Preferred compounds of the formula (I.51) are the compounds I.51-1 to I.51-345 in which Q has the definitions from table 1 that are given in the respective line. The compounds 0.51-1 to I.51-345 from table I.51 are thus defined by the meaning of the respective entries No. 1 to 345 for Q from table 1.

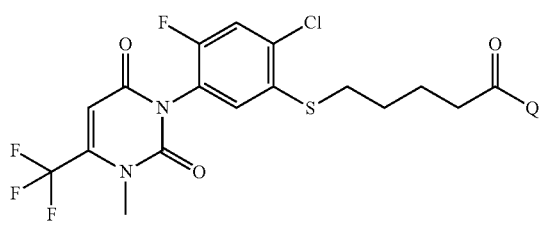
(I.52)

Table I.52: Preferred compounds of the formula (I.52) are the compounds I.52-1 to I.52-345 in which Q has the definitions from table 1 that are given in the respective line. The compounds I.52-1 to I.52-345 from table I.52 are thus defined by the meaning of the respective entries No. 1 to 345 for Q from table 1.

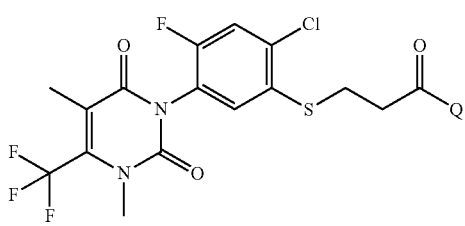
(I.53)

Table I.53: Preferred compounds of the formula (I.53) are the compounds I.53-1 to I.53-345 in which Q has the definitions from table 1 that are given in the respective line. The compounds I.53-1 to I.53-345 from table I.53 are thus defined by the meaning of the respective entries No. 1 to 345 for Q from table 1.

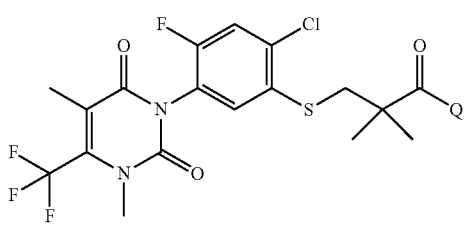
(I.54)

Table I.54: Preferred compounds of the formula (I.54) are the compounds I.54-1 to I.54-345 in which Q has the definitions from table 1 that are given in the respective line. The compounds I.54-1 to I.54-345 from table I.54 are thus defined by the meaning of the respective entries No. 1 to 345 for Q from table 1.

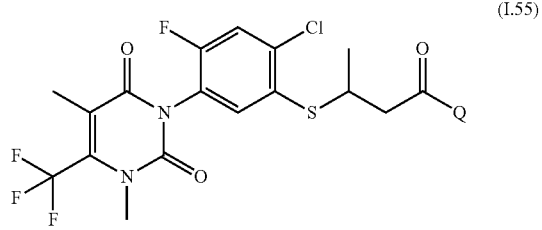
(I.55)

Table I.55: Preferred compounds of the formula (I.55) are the compounds I.55-1 to I.55-345 in which Q has the definitions from table 1 that are given in the respective line. The compounds I.55-1 to I.55-345 from table I.55 are thus defined by the meaning of the respective entries No. 1 to 345 for Q from table 1.

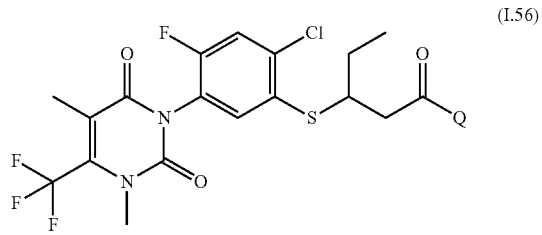
(I.56)

Table I.56: Preferred compounds of the formula (I.56) are the compounds I.56-1 to I.56-345 in which Q has the definitions from table 1 that are given in the respective line. The compounds I.56-1 to I.56-345 from table I.56 are thus defined by the meaning of the respective entries No. 1 to 345 for Q from table 1.

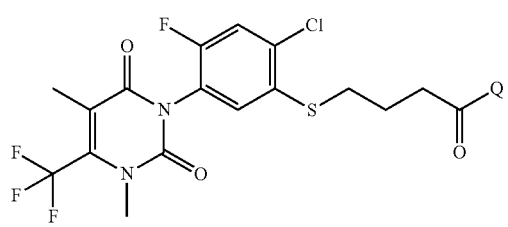
(I.57)

Table I.57: Preferred compounds of the formula (I.57) are the compounds I.57-1 to I.57-345 in which Q has the definitions from table 1 that are given in the respective line. The compounds I.57-1 to I.57-345 from table I.57 are thus defined by the meaning of the respective entries No. 1 to 345 for Q from table 1.

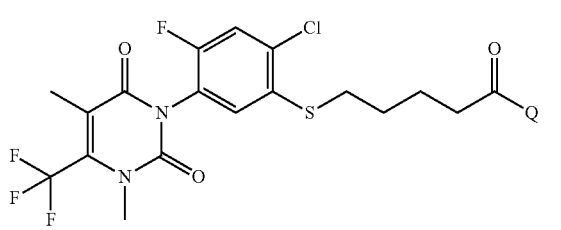
(I.58)

Table I.58: Preferred compounds of the formula (I.58) are the compounds I.58-1 to I.58-345 in which Q has the definitions from table 1 that are given in the respective line. The compounds I.58-1 to I.58-345 from table I.58 are thus defined by the meaning of the respective entries No. 1 to 345 for Q from table 1.

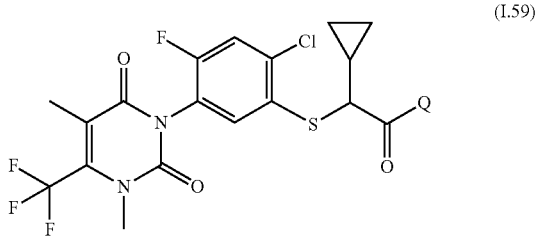

(I.59)

Table I.59: Preferred compounds of the formula (I.59) are the compounds I.59-1 to I.59-345 in which Q has the definitions from table 1 that are given in the respective line. The compounds I.59-1 to I.59-345 from table I.59 are thus defined by the meaning of the respective entries No. 1 to 345 for Q from table 1.

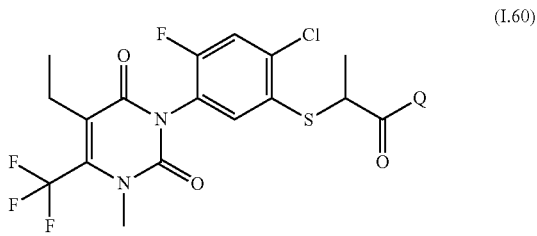

(I.60)

Table I.60: Preferred compounds of the formula (I.60) are the compounds I.60-1 to I.60-345 in which Q has the definitions from table 1 that are given in the respective line. The compounds I.60-1 to I.60-345 from table I.60 are thus defined by the meaning of the respective entries No. 1 to 345 for Q from table 1.

NMR Data of Selected Examples a) Conventional NMR Interpretation

Example No. I.12-91

$^1$H-NMR (CDCl$_3$ δ, ppm) 7.52 (m, 1H), 7.34 (m, 1H), 4.12-4.08 (m, 1H), 4.06-3.89 (m, 2H), 3.77-3.72 (m, 1H), 3.54 (s, 3H), 3.51-3.34 (m, 2H), 2.24-2.20 (m, 3H), 2.03-1.93 (m, 1H), 1.90-1.79 (m, 2H), 1.58-1.47 (m, 3H), 1.31-1.23 (m, 2H), 1.07 (t, 3H).

Example No. I.12-221

$^1$H-NMR (CDCl$_3$ δ, ppm) 7.33 (m, 1H), 7.19 (m, 1H), 6.72 (br. m, 1H, NH), 3.91-3.77 (m, 1H), 3.75-3.69 (m, 1H), 3.67-3.62 (m, 2H), 3.55 (s, 3H), 3.51-3.40 (m, 1H), 3.21-3.08 (m, 1H), 2.24-2.20 (m, 3H), 2.09-2.02 (m, 1H), 1.96-1.70 (m, 4H), 1.49/1.33 (m, 1H), 1.12 (t, 3H).

Example No. I.14-71

$^1$H-NMR (CDCl$_3$ δ, ppm) 7.51 (m, 1H), 7.34 (m, 1H), 4.16-4.10 (m, 1H), 4.07-3.85 (m, 3H), 3.81-3.67 (m, 2H), 3.54 (s, 3H), 2.24-2.21 (m, 3H), 1.96-1.80 (m, 4H), 1.78-1.74 (m, 1H), 1.69-1.65 (m, 1H), 1.53-1.48 (m, 1H), 0.97-0.93 (m, 6H).

Example No. I.48-127

$^1$H-NMR (CDCl$_3$ δ, ppm) 7.48 (m, 1H), 7.32 (m, 1H), 6.29 (m, 1H), 4.19-4.14 (m, 1H), 3.92-3.70 (m, 3H), 3.59-3.54 (m, 1H), 3.53 (s, 3H), 3.11 (s, 2H), 1.84-1.75 (m, 2H), 1.66-1.59 (m, 2H), 1.31 (s, 6H).

Example No. I.54-241

$^1$H-NMR (CDCl$_3$ δ, ppm) 7.33-7.27 (m, 2H), 6.73 (br. m, 1H, NH), 4.07-4.03 (m, 2H), 3.98-3.94 (m, 1H), 3.54 (s, 3H), 3.52-3.48 (m, 1H), 3.43-3.38 (m, 1H), 3.13 (s, 2H), 2.26-2.23 (m, 2H), 1.88-1.82 (m, 1H), 1.63-1.48 (m 4H), 1.39-1.31 (m 2H), 1.30 (s, 6H).

b) NMR Peak List Method

The $^1$H NMR data of selected examples are stated in the form of $^1$H NMR peak lists. For each signal peak, first the δ value in ppm and then the signal intensity in round brackets are listed. The δ value/signal intensity number pairs for different signal peaks are listed with separation from one another by semicolons. The peak list for an example therefore takes the following form:

δ$_1$ (intensity$_1$); δ$_2$ (intensity$_2$); . . . ; δ$_i$(intensity$_i$); . . . ; δ$_n$(intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum. For calibration of the chemical shifts of $^1$H NMR spectra we use tetramethylsilane and/or the chemical shift of the solvent, particularly in the case of spectra that are measured in DMSO. Therefore, the tetramethylsilane peak may, but need not, occur in NMR peak lists. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. In the reporting of compound signals in the delta range of solvents and/or water, our lists of $^1$H NMR peaks show the standard solvent peaks, for example peaks of DMSO in DMSO-D$_6$ and the peak of water, which usually have a high intensity on average. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation. Further details of $^1$H NMR peak lists can be found in Research Disclosure Database Number 564025.

Example No. I.1-1

$^1$H-NMR (400.0 MHz, d$_6$-DMSO): δ=7.8581 (5.0); 7.8343 (5.1); 7.7555 (4.4); 7.7521 (4.6); 7.7365 (4.4);

7.7330 (4.5); 6.6090 (7.8); 6.6018 (7.3); 4.1623 (1.3); 4.1529 (1.4); 4.1477 (1.6); 4.1380 (1.6); 4.1326 (3.0); 4.1234 (3.1); 4.1174 (3.8); 4.1082 (3.2); 4.0965 (2.2); 4.0861 (5.0); 4.0805 (6.1); 4.0760 (2.8); 4.0679 (4.8); 4.0629 (4.0); 4.0503 (2.0); 4.0461 (1.8); 4.0371 (0.7); 3.4700 (0.7); 3.4611 (1.1); 3.4410 (4.1); 3.4218 (22.0); 3.4092 (3.6); 3.4059 (2.9); 3.3896 (0.9); 3.3861 (0.9); 3.3670 (0.6); 3.3580 (1.4); 3.3420 (1.3); 3.3090 (340.3); 3.2586 (0.6); 3.1931 (66.1); 2.6739 (1.5); 2.6692 (2.1); 2.6648 (1.5); 2.5225 (11.0); 2.5092 (126.4); 2.5047 (249.2); 2.5002 (330.8); 2.4956 (234.6); 2.4912 (107.9); 2.3315 (1.5); 2.3270 (2.0); 2.3225 (1.4); 2.0719 (0.6); 1.4280 (16.0); 1.4108 (15.6); 1.2356 (1.4); 0.0079 (1.2); −0.0002 (23.5); −0.0086 (0.8).

Example No. I.1-2

$^1$H-NMR (400.0 MHz, CDCl$_3$): δ=7.5397 (3.3); 7.5341 (3.2); 7.5209 (3.4); 7.5153 (3.2); 7.3790 (3.7); 7.3772 (3.6); 7.3563 (3.7); 7.3545 (3.6); 7.2715 (0.6); 7.2691 (0.8); 7.2601 (121.6); 6.9961 (0.7); 6.3470 (6.9); 4.2477 (0.6); 4.2422 (0.6); 4.2387 (0.7); 4.2330 (0.7); 4.2315 (0.8); 4.2259 (0.7); 4.2223 (0.7); 4.2179 (1.4); 4.2125 (1.4); 4.2091 (1.3); 4.2035 (1.5); 4.2017 (1.7); 4.1961 (1.6); 4.1926 (1.3); 4.1871 (1.3); 4.1659 (2.0); 4.1570 (2.4); 4.1520 (2.2); 4.1432 (2.2); 4.1363 (1.0); 4.1272 (1.0); 4.1225 (1.1); 4.1135 (1.0); 3.9568 (0.8); 3.9541 (0.8); 3.9390 (2.9); 3.9362 (3.0); 3.9211 (3.0); 3.9184 (3.0); 3.9033 (0.8); 3.9006 (0.8); 3.5776 (0.8); 3.5754 (0.6); 3.5685 (0.8); 3.5663 (0.9); 3.5638 (0.9); 3.5615 (1.0); 3.5525 (14.7); 3.5493 (16.0); 3.5466 (7.3); 3.5400 (2.0); 3.5377 (2.0); 3.5352 (2.1); 3.5330 (2.0); 3.5240 (3.9); 3.5150 (2.9); 3.5075 (2.5); 3.4986 (2.5); 3.4955 (1.2); 3.4916 (2.0); 3.4883 (2.3); 3.4789 (1.2); 3.4741 (6.2); 3.4708 (7.4); 3.4566 (6.5); 3.4533 (7.1); 3.4391 (2.2); 3.4358 (2.3); 1.5468 (4.2); 1.5375 (11.9); 1.5344 (11.9); 1.5196 (10.7); 1.5165 (11.0); 1.1773 (6.8); 1.1744 (7.2); 1.1598 (13.9); 1.1569 (14.6); 1.1422 (6.7); 1.1394 (6.9); 0.0080 (1.5); 0.0063 (0.6); 0.0055 (0.6); 0.0046 (0.7); −0.0002 (45.4); −0.0051 (0.8); −0.0059 (0.6); −0.0068 (0.5); −0.0085 (1.3)

Example No. I.1-6

$^1$H-NMR (400.0 MHz, CDCl$_3$): δ=7.5328 (0.9); 7.5276 (0.9); 7.5181 (0.6); 7.5140 (0.9); 7.5088 (0.8); 7.3395 (0.9); 7.3367 (0.9); 7.3198 (2.1); 7.3173 (2.5); 7.3063 (2.3); 7.2982 (1.1); 7.2942 (2.2); 7.2800 (0.7); 7.2592 (78.8); 6.3060 (1.7); 4.4956 (2.9); 4.1932 (0.6); 4.1876 (0.6); 4.1792 (0.5); 3.9513 (0.6); 3.9463 (0.7); 3.9334 (0.7); 3.9284 (0.8); 3.6000 (0.6); 3.5914 (0.6); 3.5860 (0.6); 3.5774 (0.5); 3.5692 (0.6); 3.5607 (0.7); 3.5527 (0.6); 3.5442 (0.6); 3.5181 (3.4); 3.5148 (2.7); 1.5387 (3.1); 1.5363 (3.9); 1.5328 (16.0); 1.5209 (2.8); 1.5187 (2.8); 0.0080 (0.9); −0.0002 (28.4); −0.0085 (1.0)

Example No. I.1-23

$^1$H-NMR (400.0 MHz, CDCl$_3$): δ=7.5409 (1.6); 7.5320 (1.5); 7.5220 (1.6); 7.5197 (0.5); 7.5132 (1.5); 7.3815 (1.8); 7.3797 (1.7); 7.3587 (1.8); 7.3569 (1.7); 7.2606 (50.8); 6.3467 (2.5); 6.3433 (2.6); 4.2511 (0.5); 4.2372 (0.6); 4.2307 (0.6); 4.2284 (0.6); 4.2212 (1.0); 4.2144 (0.8); 4.2119 (0.6); 4.2053 (0.6); 4.1845 (0.7); 4.1756 (0.8); 4.1745 (0.9); 4.1706 (0.6); 4.1616 (0.8); 3.9293 (1.3); 3.9244 (1.4); 3.9114 (1.3); 3.9065 (1.4); 3.6225 (0.7); 3.6192 (0.8); 3.6135 (0.7); 3.6100 (0.9); 3.6087 (0.9); 3.6052 (0.8); 3.5994 (0.7); 3.5962 (0.7); 3.5904 (1.1); 3.5861 (1.0); 3.5817 (2.0); 3.5794 (1.3); 3.5758 (2.1); 3.5720 (2.5); 3.5687 (2.6); 3.5644 (2.6); 3.5622 (3.1); 3.5579 (3.1); 3.5522 (7.2); 3.5492 (7.2); 3.5460 (3.2); 3.5093 (2.8); 3.5079 (2.9); 3.5019 (1.6); 3.4986 (1.4); 3.4952 (2.2); 3.4860 (1.3); 3.3571 (15.3); 3.3552 (16.0); 1.5520 (13.3); 1.5348 (5.1); 1.5322 (5.3); 1.5169 (5.0); 1.5143 (5.2); 0.0080 (0.6); −0.0002 (19.0); −0.0085 (0.6)

Example No. I.1-26

$^1$H-NMR (400.0 MHz, CDCl$_3$): δ=7.4990 (1.2); 7.4958 (1.2); 7.4803 (1.2); 7.4771 (1.2); 7.3772 (2.2); 7.3545 (2.2); 7.2599 (53.8); 6.3496 (3.4); 4.1628 (0.9); 4.1463 (1.9); 4.1422 (0.6); 4.1298 (1.7); 4.1261 (1.0); 4.1135 (0.5); 3.8961 (1.1); 3.8940 (1.1); 3.8783 (1.1); 3.8761 (1.1); 3.5553 (5.0); 3.5522 (5.2); 3.5491 (2.1); 3.3709 (2.2); 3.3551 (4.7); 3.3394 (2.2); 3.2888 (16.0); 1.8226 (1.1); 1.8197 (0.7); 1.8179 (0.7); 1.8067 (1.7); 1.8035 (1.0); 1.7909 (1.1); 1.7873 (0.7); 1.5428 (2.4); 1.5304 (4.5); 1.5290 (4.6); 1.5125 (4.4); 1.5112 (4.4); 0.0080 (0.7); −0.0002 (21.3); −0.0085 (0.6)

Example No. I.1-27

$^1$H-NMR (400.0 MHz, CDCl$_3$): δ=7.5187 (1.0); 7.4987 (2.9); 7.4955 (2.9); 7.4799 (3.0); 7.4767 (2.9); 7.3753 (5.5); 7.3525 (5.4); 7.2598 (178.1); 6.9958 (1.0); 6.3486 (8.0); 4.2021 (0.6); 4.1857 (1.3); 4.1749 (2.0); 4.1694 (0.5); 4.1585 (3.8); 4.1521 (1.3); 4.1490 (1.2); 4.1422 (2.1); 4.1361 (2.4); 4.1329 (2.3); 4.1200 (1.3); 4.1168 (1.2); 4.1089 (0.8); 4.1057 (0.8); 3.9141 (0.7); 3.9104 (0.7); 3.8963 (2.4); 3.8924 (2.4); 3.8784 (2.4); 3.8746 (2.4); 3.8605 (0.7); 3.8567 (0.7); 3.5549 (12.8); 3.5519 (13.0); 3.4574 (3.1); 3.4399 (9.7); 3.4223 (10.0); 3.4127 (5.1); 3.4048 (3.6); 3.3969 (10.8); 3.3811 (5.2); 1.8436 (0.7); 1.8277 (2.5); 1.8247 (1.8); 1.8118 (3.6); 1.8086 (2.6); 1.7959 (2.4); 1.7923 (1.7); 1.7798 (0.6); 1.5391 (48.0); 1.5282 (11.1); 1.5271 (11.2); 1.5104 (10.8); 1.5093 (10.8); 1.1833 (8.1); 1.1657 (16.0); 1.1483 (7.7); 0.0080 (2.6); −0.0002 (68.8); −0.0085 (1.9)

Example No. I.1-30

$^1$H-NMR (400.0 MHz, CDCl$_3$): δ=7.4874 (2.6); 7.4843 (2.6); 7.4687 (2.6); 7.4656 (2.6); 7.3539 (0.9); 7.3482 (5.1); 7.3367 (1.8); 7.3324 (3.3); 7.3297 (3.5); 7.3254 (5.4); 7.3144 (8.6); 7.3083 (7.4); 7.2897 (2.2); 7.2858 (1.7); 7.2828 (1.2); 7.2753 (1.1); 7.2679 (2.5); 7.2589 (80.3); 6.3305 (4.0); 6.3262 (4.0); 4.4641 (13.0); 4.2120 (0.7); 4.2013 (1.0); 4.1992 (1.0); 4.1846 (2.0); 4.1775 (1.0); 4.1731 (1.0); 4.1687 (1.2); 4.1615 (1.9); 4.1571 (1.8); 4.1455 (1.2); 4.1410 (0.9); 4.1343 (0.6); 4.1299 (0.6); 3.8943 (0.5); 3.8880 (0.5); 3.8765 (1.8); 3.8701 (1.9); 3.8586 (1.9); 3.8523 (2.0); 3.8409 (0.6); 3.8345 (0.5); 3.5320 (5.7); 3.5290 (5.9); 3.5252 (3.6); 3.5209 (5.8); 3.5179 (5.8); 3.4740 (3.5); 3.4584 (7.6); 3.4428 (3.7); 1.8671 (1.3); 1.8640 (1.5); 1.8588 (1.2); 1.8513 (1.9); 1.8482 (2.1); 1.8429 (1.7); 1.8355 (1.3); 1.8325 (1.4); 1.8266 (1.1); 1.5396 (16.0); 1.5037 (9.4); 1.4858 (9.2); 0.0080 (0.9); −0.0002 (28.4); −0.0085 (1.1)

Example No. I.1-41

$^1$H-NMR (400.0 MHz, CDCl$_3$): δ=7.5027 (2.8); 7.4969 (2.7); 7.4839 (2.8); 7.4781 (2.6); 7.3968 (4.7); 7.3741 (4.7); 7.2601 (75.4); 6.3476 (4.2); 6.3359 (4.5); 4.2864 (0.5);

4.2768 (0.5); 4.2691 (0.6); 4.2625 (1.2); 4.2552 (1.3); 4.2456 (1.4); 4.2380 (1.4); 4.2290 (0.7); 4.2205 (1.2); 4.2074 (1.4); 4.1987 (0.9); 4.1762 (0.5); 4.0936 (0.6); 4.0891 (0.7); 4.0858 (0.7); 4.0806 (0.8); 4.0758 (0.6); 4.0721 (0.5); 4.0648 (1.2); 4.0602 (1.4); 4.0571 (1.3); 4.0518 (1.7); 4.0462 (1.1); 4.0433 (1.1); 4.0392 (1.0); 4.0184 (1.3); 4.0158 (1.3); 4.0114 (1.2); 4.0080 (1.3); 4.0012 (1.3); 3.9991 (1.3); 3.9936 (2.0); 3.9819 (0.8); 3.9746 (3.3); 3.9569 (3.0); 3.9393 (1.0); 3.5485 (9.6); 3.5456 (13.2); 3.5424 (9.5); 1.5641 (16.0); 1.5510 (10.5); 1.5489 (10.7); 1.5331 (9.8); 1.5311 (10.0); 0.0080 (1.0); −0.0002 (28.5); −0.0084 (1.1)

Example No. I.1-48

$^1$H-NMR (400.0 MHz, CDCl$_3$): δ=7.4827 (3.6); 7.4756 (3.6); 7.4640 (3.7); 7.4569 (3.6); 7.3941 (6.3); 7.3714 (6.3); 7.2601 (69.5); 6.3516 (6.0); 6.3465 (6.1); 4.1836 (0.6); 4.1683 (0.9); 4.1641 (0.9); 4.1556 (1.4); 4.1514 (1.6); 4.1401 (2.1); 4.1361 (2.3); 4.1247 (2.4); 4.1206 (1.8); 4.1188 (1.7); 4.1091 (2.3); 4.1033 (2.1); 4.0938 (1.6); 4.0881 (1.4); 4.0810 (0.9); 4.0753 (0.9); 4.0600 (0.5); 3.9536 (0.9); 3.9482 (0.9); 3.9357 (3.1); 3.9304 (3.2); 3.9179 (3.2); 3.9126 (3.3); 3.9001 (0.9); 3.8948 (0.9); 3.5521 (16.0); 2.8422 (2.3); 2.8233 (4.3); 2.8052 (2.6); 1.9510 (0.9); 1.9339 (2.6); 1.9170 (3.7); 1.9006 (2.5); 1.8826 (0.7); 1.5430 (9.4); 1.5355 (14.1); 1.5333 (14.2); 1.5177 (13.0); 1.5155 (13.3); 0.0080 (1.4); −0.0002 (41.0); −0.0085 (1.3)

Example No. I.1-51

$^1$H-NMR (400.0 MHz, CDCl$_3$): δ=7.5376 (1.7); 7.5324 (1.7); 7.5189 (1.8); 7.5132 (3.6); 7.4940 (2.3); 7.3769 (3.6); 7.3724 (2.8); 7.3541 (3.6); 7.3496 (2.8); 7.2609 (45.7); 6.3468 (6.2); 4.1354 (0.6); 4.1307 (0.7); 4.1257 (0.7); 4.1207 (0.6); 4.1067 (0.9); 4.1020 (0.9); 4.0969 (0.9); 4.0920 (0.9); 4.0259 (2.8); 4.0221 (3.5); 4.0150 (1.9); 4.0108 (2.8); 4.0085 (2.3); 3.9867 (1.0); 3.9839 (1.1); 3.9722 (1.1); 3.9693 (1.6); 3.9581 (0.8); 3.9552 (0.9); 3.9512 (2.2); 3.9428 (2.0); 3.9333 (2.2); 3.9267 (1.6); 3.9246 (1.6); 3.9155 (0.7); 3.5506 (12.7); 3.4955 (0.6); 3.4856 (0.6); 3.4804 (0.8); 3.4702 (0.8); 3.4648 (0.7); 3.4548 (0.6); 3.4459 (0.6); 3.4315 (0.9); 3.4301 (0.9); 3.4179 (0.8); 3.4157 (0.9); 3.4020 (0.5); 3.3119 (11.2); 3.3079 (11.9); 3.2969 (16.0); 3.2954 (15.9); 3.2888 (1.2); 1.5673 (3.6); 1.5440 (12.3); 1.5261 (12.0); 1.0981 (9.4); 1.0819 (11.4); 1.0685 (4.4); 1.0647 (4.6); 0.0080 (0.5); −0.0002 (18.6); −0.0085 (0.6)

Example No. I.1-71

$^1$H-NMR (400.0 MHz, CDCl$_3$): δ=7.5648 (2.1); 7.5583 (2.1); 7.5460 (2.2); 7.5394 (2.2); 7.5304 (3.9); 7.5195 (0.7); 7.5116 (3.9); 7.3735 (5.1); 7.3507 (5.1); 7.3107 (0.6); 7.2687 (0.6); 7.2679 (0.6); 7.2671 (0.7); 7.2663 (0.9); 7.2654 (1.1); 7.2646 (1.4); 7.2606 (89.1); 7.2542 (1.4); 7.2533 (1.2); 7.2525 (1.0); 7.2517 (0.9); 7.2509 (0.9); 7.2501 (0.8); 7.2493 (0.7); 7.2485 (0.7); 7.2477 (0.6); 7.2469 (0.6); 7.2461 (0.6); 7.2453 (0.6); 7.2445 (0.5); 7.2437 (0.5); 6.9965 (0.5); 6.3436 (7.1); 4.1548 (1.0); 4.1460 (1.3); 4.1445 (1.2); 4.1358 (1.2); 4.1270 (1.3); 4.1180 (1.8); 4.1082 (1.5); 4.0605 (0.9); 4.0522 (1.6); 4.0444 (1.5); 4.0346 (2.2); 4.0286 (2.3); 4.0216 (2.0); 4.0178 (2.5); 4.0117 (2.3); 4.0080 (2.6); 4.0015 (2.7); 3.9908 (3.0); 3.9877 (3.0); 3.9805 (1.7); 3.9784 (1.9); 3.9755 (2.6); 3.9722 (1.7); 3.9676 (0.9); 3.9632 (1.9); 3.9593 (3.6); 3.9476 (1.2); 3.9441 (1.5); 3.9412 (3.5); 3.9235 (3.8); 3.9057 (3.1); 3.8879 (0.9); 3.8365 (0.5); 3.8324 (0.5); 3.8292 (0.5); 3.8274 (0.6); 3.8196 (0.8); 3.8154 (1.6); 3.8117 (1.7); 3.8063 (1.2); 3.8033 (0.7); 3.7989 (1.6); 3.7946 (1.8); 3.7912 (1.9); 3.7892 (1.7); 3.7826 (0.8); 3.7783 (0.7); 3.7748 (0.9); 3.7571 (0.6); 3.7533 (0.7); 3.7421 (1.2); 3.7372 (1.5); 3.7242 (1.6); 3.7214 (1.9); 3.7194 (1.9); 3.7086 (0.7); 3.7033 (1.4); 3.6985 (0.8); 3.5505 (14.1); 3.5475 (16.0); 3.5442 (9.5); 1.9589 (0.6); 1.9549 (0.6); 1.9512 (0.6); 1.9468 (0.8); 1.9422 (0.9); 1.9390 (0.8); 1.9294 (1.1); 1.9257 (1.2); 1.9212 (1.1); 1.9124 (0.8); 1.9085 (1.6); 1.9018 (1.3); 1.8974 (1.1); 1.8883 (1.6); 1.8853 (1.4); 1.8821 (1.6); 1.8801 (1.6); 1.8729 (1.5); 1.8701 (2.0); 1.8665 (2.0); 1.8622 (1.6); 1.8578 (1.6); 1.8534 (2.0); 1.8497 (2.3); 1.8459 (1.6); 1.8368 (1.8); 1.8323 (1.6); 1.8281 (1.0); 1.8237 (0.9); 1.8190 (1.1); 1.8110 (0.7); 1.8023 (0.7); 1.5444 (7.3); 1.5401 (14.1); 1.5367 (8.6); 1.5265 (8.0); 1.5222 (14.2); 1.5189 (8.9); 1.5093 (1.5); 1.5068 (1.5); 1.5008 (1.4); 1.4894 (1.1); 1.4827 (0.8); 1.4718 (0.6); 0.0079 (1.0); −0.0002 (34.7); −0.0051 (0.8); −0.0060 (0.7); −0.0068 (0.6); −0.0085 (1.3)

Example No. I.1-72

$^1$H-NMR (400.0 MHz, CDCl$_3$): δ=7.5183 (2.8); 7.4878 (2.2); 7.4839 (4.0); 7.4690 (2.2); 7.4652 (4.0); 7.3851 (4.2); 7.3789 (0.5); 7.3624 (4.3); 7.3095 (0.6); 7.2780 (0.8); 7.2772 (0.8); 7.2755 (1.0); 7.2748 (1.1); 7.2740 (1.1); 7.2731 (1.3); 7.2724 (1.4); 7.2715 (1.6); 7.2707 (1.9); 7.2699 (2.3); 7.2692 (2.6); 7.2684 (2.9); 7.2675 (3.4); 7.2667 (4.1); 7.2659 (5.1); 7.2651 (6.2); 7.2594 (494.5); 7.2481 (1.6); 7.2474 (1.5); 7.2466 (1.3); 7.2458 (1.0); 7.2450 (1.0); 7.2442 (0.9); 7.2434 (0.8); 7.2426 (0.8); 7.2418 (0.7); 7.2402 (0.6); 7.2379 (0.7); 7.2313 (0.5); 7.2290 (0.6); 7.2100 (1.2); 6.9954 (2.9); 6.3491 (8.5); 4.1065 (0.7); 4.0954 (0.7); 4.0900 (0.8); 4.0790 (1.4); 4.0684 (1.0); 4.0629 (1.1); 4.0584 (0.7); 4.0516 (1.1); 4.0423 (0.6); 4.0379 (0.6); 4.0315 (1.2); 4.0271 (1.3); 4.0153 (1.2); 4.0108 (1.2); 3.9912 (1.8); 3.9716 (1.8); 3.9643 (0.9); 3.9524 (1.2); 3.9496 (1.3); 3.9452 (1.3); 3.9331 (1.4); 3.9280 (2.1); 3.9250 (2.5); 3.9191 (2.7); 3.9100 (1.8); 3.9068 (2.3); 3.9014 (2.9); 3.8890 (0.6); 3.8833 (0.7); 3.8324 (0.7); 3.8116 (1.8); 3.7979 (1.8); 3.7776 (1.1); 3.7698 (1.4); 3.7521 (1.9); 3.7476 (1.7); 3.7351 (2.1); 3.7304 (2.1); 3.7165 (2.2); 3.7129 (2.3); 3.6993 (1.3); 3.6927 (1.3); 3.6723 (0.5); 3.5527 (15.6); 3.5498 (16.0); 3.4694 (1.4); 3.4561 (2.8); 3.4470 (1.4); 3.4425 (1.8); 3.4340 (2.5); 3.4205 (1.3); 2.4781 (0.7); 2.4607 (1.1); 2.4446 (1.1); 2.4253 (0.8); 2.0052 (0.5); 1.9926 (0.6); 1.9854 (0.6); 1.9719 (1.1); 1.9592 (1.0); 1.9530 (1.0); 1.9404 (1.1); 1.9271 (0.6); 1.9206 (0.6); 1.7155 (0.6); 1.5875 (4.4); 1.5610 (2.2); 1.5356 (17.2); 1.5178 (16.6); 1.4932 (0.5); 0.1462 (0.6); 0.0080 (6.1); 0.0064 (2.8); −0.0002 (180.8); −0.0067 (2.5); −0.0085 (5.4); −0.1495 (0.6)

Example No. I.1-73

$^1$H-NMR (400.0 MHz, CDCl$_3$): δ=7.5193 (0.8); 7.4895 (0.9); 7.4869 (1.1); 7.4844 (1.8); 7.4795 (3.2); 7.4708 (1.0); 7.4682 (1.1); 7.4657 (1.8); 7.4607 (3.2); 7.3851 (4.5); 7.3814 (1.9); 7.3624 (4.4); 7.3585 (1.9); 7.2750 (0.5); 7.2742 (0.6); 7.2734 (0.6); 7.2726 (0.7); 7.2718 (0.8); 7.2710 (0.8); 7.2702 (0.9); 7.2694 (1.0); 7.2686 (1.1); 7.2677 (1.3); 7.2670 (1.5); 7.2661 (1.8); 7.2603 (139.3); 6.9964 (0.8); 6.3486 (9.3); 4.1031 (0.5); 4.0985 (0.5);

4.0877 (0.8); 4.0760 (0.9); 4.0713 (0.8); 4.0590 (1.0); 4.0521 (0.6); 4.0406 (0.6); 4.0361 (0.7); 4.0325 (0.5); 4.0250 (1.7); 4.0092 (2.1); 3.9949 (2.6); 3.9840 (0.8); 3.9767 (2.3); 3.9683 (0.7); 3.9637 (1.1); 3.9579 (1.5); 3.9530 (1.1); 3.9498 (1.2); 3.9450 (0.9); 3.9362 (2.8); 3.9314 (2.1); 3.9271 (1.5); 3.9245 (1.8); 3.9225 (2.5); 3.9182 (3.5); 3.9094 (1.8); 3.9066 (2.2); 3.9046 (2.8); 3.9004 (3.4); 3.8940 (1.0); 3.8896 (1.2); 3.8857 (1.9); 3.8828 (1.4); 3.8679 (0.6); 3.6971 (0.6); 3.6843 (0.6); 3.6787 (0.8); 3.5981 (0.8); 3.5911 (0.7); 3.5848 (0.9); 3.5765 (1.0); 3.5686 (0.7); 3.5534 (15.6); 3.5505 (16.0); 3.3818 (0.6); 3.3786 (0.6); 3.3674 (1.0); 3.3627 (0.7); 3.3595 (0.6); 3.3543 (0.8); 3.3448 (0.8); 3.3404 (0.6); 3.3313 (0.6); 2.5282 (0.5); 2.5223 (0.6); 2.5073 (0.7); 2.4890 (0.6); 1.7064 (0.7); 1.6903 (0.8); 1.6868 (0.7); 1.6746 (1.1); 1.6702 (0.6); 1.6580 (0.6); 1.5762 (0.9); 1.5595 (7.6); 1.5442 (1.5); 1.5322 (15.1); 1.5144 (14.7); 1.2426 (6.2); 1.2399 (3.3); 1.2275 (6.1); 1.2248 (3.3); 1.2021 (8.5); 1.1992 (5.0); 1.1869 (8.4); 1.1839 (4.9); 1.0629 (0.6); 1.0432 (0.6); 1.0403 (0.5); 0.0079 (1.6); −0.0002 (54.8); −0.0085 (1.6)

Example No. I.1-81

$^1$H-NMR (400.0 MHz, CDCl$_3$): δ=7.5311 (2.7); 7.5180 (2.7); 7.5118 (4.1); 7.4916 (1.8); 7.3745 (5.4); 7.3517 (5.4); 7.3093 (1.6); 7.2594 (297.8); 7.2136 (0.9); 6.9955 (1.6); 6.3558 (5.1); 6.3475 (5.4); 4.1135 (1.2); 4.0857 (2.7); 4.0666 (2.5); 4.0176 (2.3); 4.0013 (2.4); 3.9901 (2.4); 3.9772 (1.4); 3.9613 (0.9); 3.9427 (0.6); 3.9253 (1.6); 3.9068 (2.0); 3.8960 (1.8); 3.8879 (2.1); 3.8777 (1.6); 3.8699 (1.8); 3.5557 (16.0); 3.5111 (1.5); 3.4935 (2.1); 3.4817 (1.6); 2.8256 (2.4); 2.8090 (2.1); 2.7901 (2.6); 1.9569 (5.4); 1.9482 (5.7); 1.6795 (1.9); 1.6640 (1.8); 1.6533 (1.6); 1.5497 (49.4); 1.5290 (13.9); 0.1467 (0.6); −0.0002 (129.8); −0.1494 (0.7)

Example No. I.1-82

$^1$H-NMR (400.0 MHz, CDCl$_3$): δ=7.5179 (1.1); 7.4941 (2.9); 7.4756 (3.0); 7.3892 (3.7); 7.3666 (3.6); 7.2595 (165.1); 6.9954 (0.9); 6.3516 (6.1); 4.1319 (0.5); 4.1180 (0.8); 4.1045 (1.1); 4.0908 (1.3); 4.0744 (0.8); 4.0547 (1.6); 4.0419 (2.1); 4.0245 (2.2); 3.9976 (1.4); 3.9690 (0.6); 3.9377 (1.6); 3.9213 (2.5); 3.9036 (1.9); 3.8870 (0.5); 3.5556 (16.0); 2.8500 (3.8); 2.8339 (6.8); 2.8171 (5.2); 2.5355 (1.4); 2.5181 (1.8); 2.4916 (1.3); 2.4363 (0.9); 2.4180 (1.5); 2.4008 (1.3); 2.3827 (0.9); 2.0651 (1.0); 2.0502 (1.3); 2.0365 (1.4); 2.0204 (1.1); 1.6453 (1.4); 1.5544 (27.5); 1.5408 (13.6); 1.5226 (10.6); −0.0002 (71.3)

Example No. I.1-89

$^1$H-NMR (400.0 MHz, CDCl$_3$): δ=7.5182 (2.0); 7.5134 (2.7); 7.5047 (2.6); 7.4945 (2.7); 7.4861 (2.6); 7.3909 (5.0); 7.3682 (4.8); 7.3098 (0.6); 7.2595 (347.3); 7.2263 (0.5); 7.2100 (0.7); 6.9954 (1.8); 6.3503 (4.3); 6.3446 (4.4); 4.7259 (1.4); 4.7202 (1.6); 4.7104 (2.8); 4.7062 (3.1); 4.6949 (1.7); 4.6906 (2.9); 4.6866 (1.8); 4.6753 (1.4); 4.3843 (2.1); 4.3689 (4.1); 4.3591 (1.5); 4.3534 (2.2); 4.3467 (2.7); 4.3435 (2.6); 4.3281 (1.4); 4.3121 (0.9); 4.3031 (0.8); 4.2948 (0.8); 4.2837 (1.6); 4.2749 (1.8); 4.2674 (1.7); 4.2584 (1.8); 4.2433 (1.7); 4.2392 (1.7); 4.2276 (1.8); 4.2236 (1.8); 4.2153 (0.8); 4.1956 (0.8); 3.9493 (0.6); 3.9346 (2.0); 3.9311 (2.4); 3.9168 (2.2); 3.9132 (2.2); 3.8990 (0.7); 3.5515 (12.5); 3.5487 (12.5); 3.1880 (1.0); 3.1724 (1.5); 3.1563 (0.9); 1.5667 (5.0); 1.5452 (16.0); 1.5274 (14.7); 1.2669 (0.8); 0.8820 (1.0); 0.1460 (0.6); 0.0080 (4.0); −0.0002 (126.5); −0.0084 (3.8); −0.1496 (0.6)

Example No. I.1-91

$^1$H-NMR (400.0 MHz, CDCl$_3$): δ=7.5528 (1.1); 7.5434 (1.2); 7.5330 (2.3); 7.5265 (2.1); 7.5181 (1.8); 7.5083 (1.4); 7.3756 (1.9); 7.3656 (2.5); 7.3526 (2.2); 7.3431 (2.1); 7.3130 (0.8); 7.2595 (197.6); 7.2135 (1.0); 6.9954 (1.1); 6.3487 (7.2); 4.0925 (0.8); 4.0837 (0.9); 4.0641 (1.5); 4.0550 (1.8); 4.0285 (0.9); 4.0203 (0.9); 4.0092 (0.9); 3.9982 (1.5); 3.9819 (1.4); 3.9662 (2.0); 3.9615 (2.1); 3.9529 (2.9); 3.9434 (3.2); 3.9258 (3.2); 3.9072 (2.1); 3.5538 (16.0); 3.4639 (0.8); 3.4354 (0.8); 3.3991 (1.7); 3.3722 (2.0); 3.3463 (0.9); 1.8363 (1.4); 1.5449 (26.8); 1.5223 (8.9); 1.5142 (7.9); 1.4866 (6.0); 1.4542 (2.1); 1.2517 (1.0); 1.2373 (1.0); −0.0002 (85.0)

Example No. I.1-92

$^1$H-NMR (400.0 MHz, CDCl$_3$): δ=7.5181 (1.6); 7.4892 (2.8); 7.4703 (2.8); 7.3852 (4.0); 7.3621 (3.6); 7.2594 (272.3); 7.2084 (0.7); 7.1515 (0.6); 6.9953 (1.5); 6.3492 (7.7); 4.0194 (0.7); 4.0045 (0.7); 3.9914 (1.0); 3.9773 (1.1); 3.9379 (1.5); 3.9261 (2.0); 3.9099 (3.0); 3.8903 (3.0); 3.8588 (1.2); 3.8120 (3.2); 3.7833 (3.1); 3.5527 (16.0); 3.3939 (1.0); 3.3671 (1.5); 3.1633 (1.2); 3.1414 (2.0); 3.1126 (1.0); 1.8568 (1.1); 1.7483 (1.2); 1.7243 (1.3); 1.5854 (4.1); 1.5751 (4.6); 1.5470 (45.8); 1.5325 (14.5); 1.5145 (11.1); 1.2355 (1.0); 0.1470 (0.6); −0.0002 (115.4); −0.1493 (0.5)

Example No. I.1-94

$^1$H-NMR (400.0 MHz, CDCl$_3$): δ=7.5301 (1.6); 7.5254 (1.6); 7.5186 (1.7); 7.5162 (1.8); 7.5114 (1.7); 7.5067 (1.7); 7.4975 (1.7); 7.3653 (3.8); 7.3425 (3.8); 7.3095 (0.6); 7.2783 (0.5); 7.2759 (0.6); 7.2751 (0.7); 7.2743 (0.7); 7.2735 (0.8); 7.2727 (0.8); 7.2719 (1.0); 7.2711 (1.0); 7.2703 (1.2); 7.2695 (1.3); 7.2687 (1.5); 7.2679 (1.7); 7.2671 (1.9); 7.2663 (2.1); 7.2655 (2.5); 7.2647 (3.0); 7.2639 (4.0); 7.2630 (5.6); 7.2598 (228.0); 7.2549 (3.3); 7.2541 (2.4); 7.2533 (1.7); 7.2525 (1.2); 7.2517 (0.8); 7.2509 (0.6); 7.2501 (0.6); 7.2493 (0.6); 7.2485 (0.6); 6.9957 (1.3); 6.3491 (5.8); 5.0568 (0.6); 5.0518 (1.1); 5.0464 (0.7); 5.0407 (0.9); 5.0358 (1.2); 5.0297 (0.7); 5.0255 (0.9); 3.9219 (0.9); 3.9155 (0.9); 3.9040 (1.0); 3.8976 (1.1); 3.8943 (0.7); 3.8761 (2.1); 3.8581 (2.2); 3.8401 (0.6); 3.5522 (10.4); 3.4128 (0.6); 3.3966 (2.0); 3.3869 (1.3); 3.3813 (1.3); 3.3698 (3.4); 3.3545 (2.0); 3.3453 (0.6); 3.3407 (1.3); 3.3370 (1.8); 3.3297 (1.0); 3.3273 (1.0); 3.3063 (10.9); 3.3039 (11.5); 3.2975 (16.0); 3.2950 (15.8); 3.2905 (1.5); 3.2856 (1.3); 3.2800 (1.1); 3.2755 (1.2); 3.2635 (0.7); 3.2589 (0.8); 3.2534 (0.7); 3.2486 (0.8); 2.0223 (0.6); 1.5634 (6.4); 1.5379 (5.7); 1.5356 (6.0); 1.5319 (4.4); 1.5296 (4.3); 1.5200 (5.6); 1.5177 (5.8); 1.5140 (4.2); 1.5118 (4.0); 1.2572 (0.5); 1.2408 (0.8); 1.2244 (0.6); 1.1974 (5.6); 1.1937 (5.8); 1.1812 (5.5); 1.1775 (5.7); 1.1180 (7.3); 1.1018 (7.3); 0.2376 (0.6); 0.1262 (0.8); 0.0079 (2.9); 0.0063 (1.0); 0.0054 (1.1); 0.0046 (1.3); −0.0002 (93.0); −0.0052 (1.4); −0.0060 (1.1); −0.0068 (0.9); −0.0085 (2.6)

Example No. I.1-115

$^1$H-NMR (400.0 MHz, CDCl$_3$): δ=7.8084 (0.6); 7.5230 (4.8); 7.5183 (2.4); 7.5153 (4.8); 7.5092 (0.9); 7.5042 (4.8);

7.4965 (4.6); 7.4017 (9.3); 7.3790 (9.4); 7.3597 (0.9); 7.3085 (1.1); 7.2595 (339.3); 6.9955 (1.9); 6.3673 (0.7); 6.3552 (7.8); 6.3496 (7.6); 5.3758 (0.6); 5.3679 (1.4); 5.3647 (1.7); 5.3599 (1.6); 5.3519 (2.9); 5.3471 (3.1); 5.3389 (1.6); 5.3345 (1.9); 5.3313 (1.6); 5.3233 (0.8); 4.8455 (2.8); 4.8293 (4.9); 4.8127 (4.3); 4.7994 (1.6); 4.5397 (1.6); 4.5271 (3.1); 4.5249 (3.1); 4.5204 (1.6); 4.5147 (1.8); 4.5077 (2.9); 4.4915 (3.0); 4.4811 (2.9); 4.4713 (2.2); 4.4591 (1.4); 3.9656 (1.2); 3.9558 (1.1); 3.9476 (3.7); 3.9380 (3.9); 3.9298 (3.8); 3.9201 (4.0); 3.9121 (1.1); 3.9023 (1.2); 3.5543 (16.0); 3.5495 (13.0); 2.0790 (0.9); 2.0688 (1.2); 2.0047 (3.4); 1.5836 (3.5); 1.5508 (25.8); 1.5329 (25.1); 0.3306 (0.6); 0.1573 (0.6); 0.0080 (3.5); −0.0002 (134.8); −0.0085 (4.5)

Example No. I.1-117

$^1$H-NMR (400.0 MHz, CDCl$_3$): δ=7.5259 (0.6); 7.5186 (0.6); 7.5072 (0.6); 7.4956 (0.6); 7.4870 (0.6); 7.4826 (0.6); 7.4769 (0.6); 7.4684 (0.6); 7.4640 (0.6); 7.4392 (1.1); 7.4329 (0.7); 7.4163 (1.0); 7.4104 (0.7); 7.2597 (104.1); 6.9957 (0.6); 6.3581 (1.0); 6.3453 (1.6); 6.3306 (1.0); 5.2985 (8.4); 3.9819 (0.6); 3.9787 (0.6); 3.9687 (0.6); 3.9641 (0.7); 3.9613 (0.9); 3.9508 (0.6); 3.9441 (1.0); 3.9357 (1.0); 3.9211 (0.8); 3.5511 (5.3); 3.5487 (5.1); 2.8421 (0.5); 2.1697 (1.1); 2.0958 (0.5); 2.0862 (0.6); 1.5467 (2.1); 1.5352 (16.0); 1.5292 (3.0); 1.5218 (3.5); 1.5174 (2.1); 0.0080 (1.3); −0.0002 (40.8); −0.0085 (1.4)

Example No. I.1-123

$^1$H-NMR (400.0 MHz, CDCl$_3$): δ=7.5966 (0.8); 7.5854 (0.8); 7.5779 (0.9); 7.5665 (0.9); 7.5255 (0.9); 7.5216 (1.2); 7.5183 (1.8); 7.5071 (0.9); 7.5031 (1.0); 7.3788 (1.7); 7.3703 (1.2); 7.3561 (1.7); 7.3477 (1.1); 7.2930 (0.6); 7.2593 (294.4); 6.9954 (1.6); 6.3536 (2.2); 6.3470 (2.8); 3.9044 (0.7); 3.8941 (0.7); 3.8865 (0.7); 3.8762 (0.8); 3.8534 (0.7); 3.8459 (0.8); 3.8353 (0.7); 3.8282 (0.8); 3.5519 (7.0); 3.0675 (0.6); 3.0488 (0.7); 3.0371 (0.9); 3.0189 (0.6); 2.8549 (1.9); 2.8464 (1.3); 2.8428 (1.2); 2.8346 (1.9); 2.8257 (1.3); 2.8052 (1.0); 2.7905 (0.5); 2.7743 (0.6); 1.5551 (3.6); 1.5477 (4.5); 1.5367 (16.0); 1.5134 (4.3); 1.2655 (1.1); 0.8988 (0.6); 0.8819 (1.6); 0.8641 (0.6); 0.0079 (3.7); −0.0002 (107.4); −0.0085 (4.1)

Example No. I.1-126

$^1$H-NMR (400.0 MHz, CDCl3): δ=7.5920 (2.0); 7.5867 (1.9); 7.5736 (1.9); 7.5181 (2.0); 7.5107 (1.2); 7.4945 (2.0); 7.4761 (1.4); 7.3759 (3.3); 7.3532 (3.6); 7.2594 (316.3); 7.2141 (0.7); 6.9955 (1.8); 6.3441 (10.1); 4.7357 (1.6); 3.9424 (2.3); 3.9244 (3.0); 3.9096 (1.8); 3.6768 (1.3); 3.6471 (2.2); 3.6068 (2.5); 3.5905 (3.6); 3.5715 (4.9); 3.5506 (16.0); 3.5289 (6.2); 3.4839 (0.8); 3.4396 (0.9); 3.4249 (0.6); 1.8265 (1.6); 1.8031 (1.6); 1.7739 (2.0); 1.7149 (1.4); 1.5630 (9.0); 1.5470 (55.4); 1.5208 (10.0); 0.1458 (0.7); −0.0002 (137.6); −0.1497 (0.7)

Example No. I.1-132

$^1$H-NMR (400.0 MHz, CDCl$_3$): δ=7.5182 (1.4); 7.5010 (2.2); 7.4896 (2.3); 7.4827 (2.3); 7.4715 (2.1); 7.3819 (3.6); 7.3591 (3.8); 7.3124 (1.6); 7.2594 (213.2); 7.2153 (1.1); 6.9956 (1.1); 6.3504 (7.4); 4.7940 (1.4); 4.7811 (1.5); 3.9550 (1.0); 3.9373 (3.0); 3.9193 (3.0); 3.9020 (1.0); 3.5544 (16.0); 2.7431 (0.8); 2.7181 (1.9); 2.6910 (2.2); 2.5674 (2.0); 2.5412 (2.4); 2.5096 (1.5); 2.1702 (0.5); 2.0291 (1.2); 2.0198 (1.1); 2.0070 (1.5); 1.9725 (0.9); 1.9404 (1.3); 1.9205 (1.1); 1.8450 (0.7); 1.8253 (1.3); 1.8131 (1.0); 1.8012 (1.2); 1.7709 (0.8); 1.7230 (1.2); 1.5587 (29.7); 1.5392 (14.2); 1.5214 (12.4); 0.0528 (0.7); −0.0002 (92.1); −0.0454 (0.6)

Example No. I.1-142

$^1$H-NMR (400.0 MHz, CDCl$_3$): δ=7.5184 (1.3); 7.4905 (2.1); 7.4812 (2.2); 7.4720 (2.2); 7.4627 (2.2); 7.4273 (2.2); 7.4205 (2.2); 7.4048 (2.2); 7.3979 (2.2); 7.3096 (0.6); 7.2595 (226.6); 7.2254 (0.8); 6.9955 (1.3); 6.3472 (3.7); 6.3422 (3.6); 5.2984 (12.2); 4.9774 (1.2); 3.9975 (0.6); 3.9796 (2.0); 3.9769 (1.9); 3.9617 (2.0); 3.9590 (1.9); 3.9440 (0.6); 3.5489 (10.1); 3.0588 (0.6); 3.0466 (0.6); 3.0242 (1.4); 3.0099 (1.1); 3.0000 (1.1); 2.9869 (1.0); 2.9305 (0.9); 2.8930 (1.2); 2.8673 (0.5); 2.8547 (0.5); 2.2702 (0.8); 2.2610 (1.2); 2.2445 (1.8); 2.2342 (1.8); 2.2057 (0.6); 2.1947 (1.0); 2.1836 (1.5); 2.1695 (4.0); 2.1586 (1.3); 1.5737 (6.8); 1.5695 (6.8); 1.5558 (7.3); 1.5516 (7.4); 1.5356 (16.0); 0.0079 (3.3); −0.0002 (88.9); −0.0085 (3.5)

Example No. I.1-151

$^1$H-NMR (400.0 MHz, CDCl$_3$): δ=7.3604 (2.4); 7.3586 (2.3); 7.3379 (2.4); 7.3361 (2.3); 7.2630 (22.6); 7.2368 (1.9); 7.2187 (1.9); 7.2114 (1.9); 7.1932 (1.9); 6.7339 (0.5); 6.3406 (3.2); 6.3333 (3.2); 3.8154 (1.4); 3.8079 (1.4); 3.7973 (1.4); 3.7897 (1.4); 3.5487 (4.7); 3.5456 (6.0); 3.5422 (6.1); 3.5390 (4.8); 3.4893 (1.0); 3.4764 (1.1); 3.4388 (0.6); 3.4239 (0.5); 3.4159 (0.8); 3.4098 (0.8); 3.4057 (0.6); 3.3974 (0.6); 3.3916 (0.6); 3.3854 (0.6); 3.3806 (1.2); 3.3668 (1.6); 3.3581 (0.7); 3.3563 (0.7); 3.3499 (1.1); 3.3469 (1.0); 3.3411 (1.3); 3.3251 (1.2); 3.3223 (0.9); 3.3112 (1.7); 3.3082 (1.5); 3.3053 (1.0); 3.2987 (1.5); 3.2917 (1.1); 3.2482 (16.0); 3.2424 (15.6); 2.9549 (1.0); 2.8831 (0.8); 1.6180 (1.5); 1.6002 (5.8); 1.5967 (6.0); 1.5820 (5.8); 1.5785 (5.9); −0.0002 (8.3)

Example No. I.1-180

$^1$H-NMR (400.0 MHz, CDCl$_3$): δ=7.5182 (3.6); 7.3517 (1.1); 7.3442 (2.5); 7.3320 (3.1); 7.3156 (5.2); 7.3092 (4.5); 7.2941 (7.2); 7.2903 (7.2); 7.2766 (4.7); 7.2593 (628.6); 7.2325 (0.6); 7.1698 (1.8); 7.1518 (2.0); 7.1418 (2.0); 7.1237 (1.9); 6.9953 (4.0); 6.3321 (3.4); 6.3235 (3.2); 4.4545 (5.6); 4.4451 (5.7); 3.7489 (1.6); 3.7334 (1.6); 3.7120 (0.6); 3.5363 (5.1); 3.5335 (5.1); 3.5249 (5.1); 3.5221 (4.8); 3.4862 (0.8); 3.4815 (1.0); 3.4687 (1.5); 3.4567 (1.7); 3.4430 (0.9); 3.4358 (0.9); 3.3465 (1.6); 3.3321 (2.2); 3.3165 (1.8); 3.3014 (0.8); 1.7126 (1.6); 1.5514 (16.0); 1.5474 (13.1); 1.5331 (7.9); 1.5291 (7.2); 0.1460 (0.9); 0.0846 (0.7); 0.0496 (1.2); 0.0079 (8.1); −0.0002 (232.9); −0.0084 (8.3); −0.1497 (0.9)

Example No. I.1-181

$^1$H-NMR (400.0 MHz, d$_6$-DMSO): δ=8.2272 (0.6); 7.8121 (1.4); 7.7883 (1.5); 7.6150 (0.8); 7.6036 (0.8); 7.5961 (0.8); 7.5847 (0.7); 6.6143 (1.5); 6.6049 (1.4); 3.9203 (0.7); 3.9036 (0.7); 3.4277 (2.8); 3.4247 (2.8); 3.3787 (6.5); 3.2158 (1.0); 3.1992 (1.0); 2.6693 (0.6); 2.5556 (0.6); 2.5509 (0.6); 2.5227 (2.1); 2.5181 (2.9); 2.5093 (32.0); 2.5048 (66.7); 2.5002 (92.3); 2.4956 (64.0); 2.4910 (29.3); 2.4733 (0.9); 2.4629 (1.4); 2.4550 (1.8);

2.4461 (0.9); 2.4369 (0.5); 2.3270 (0.5); 2.0451 (0.9); 2.0405 (0.9); 2.0278 (16.0); 1.3933 (2.6); 1.3760 (2.6); −0.0002 (6.3)

Example No. I.1-221

$^1$H-NMR (400.0 MHz, CDCl$_3$): δ=7.5185 (2.2); 7.3604 (2.6); 7.3575 (2.7); 7.3494 (3.2); 7.3467 (3.0); 7.3378 (2.8); 7.3349 (2.9); 7.3268 (3.1); 7.3241 (3.1); 7.3201 (2.5); 7.3018 (2.4); 7.2921 (2.9); 7.2738 (3.6); 7.2596 (403.9); 7.2444 (4.0); 7.2280 (2.2); 7.2096 (3.0); 7.2023 (2.4); 7.1844 (2.3); 6.9957 (2.3); 6.7335 (1.3); 6.3348 (9.2); 6.3301 (4.8); 3.8860 (0.8); 3.8797 (0.9); 3.8700 (1.1); 3.8612 (1.2); 3.8429 (2.0); 3.8370 (1.7); 3.8317 (3.4); 3.8244 (3.9); 3.8191 (2.9); 3.8138 (3.5); 3.8062 (3.6); 3.8010 (2.7); 3.7948 (2.4); 3.7881 (1.3); 3.7778 (1.0); 3.7717 (0.6); 3.7507 (0.9); 3.7377 (1.5); 3.7199 (1.3); 3.7048 (1.1); 3.6884 (2.2); 3.6706 (2.5); 3.6533 (1.5); 3.6347 (0.7); 3.5429 (16.0); 3.5118 (0.6); 3.5035 (0.8); 3.4956 (1.0); 3.4879 (0.8); 3.4779 (0.8); 3.4698 (1.0); 3.4614 (1.2); 3.4534 (1.5); 3.4446 (1.2); 3.4384 (0.8); 3.4337 (0.7); 3.4292 (0.7); 3.4229 (0.8); 3.4187 (0.9); 3.4143 (0.8); 3.4090 (1.1); 3.4042 (0.9); 3.3993 (0.8); 3.3951 (0.7); 3.2932 (0.6); 3.2111 (0.7); 3.1970 (0.9); 3.1830 (0.9); 3.1690 (0.7); 3.1652 (0.7); 3.1486 (0.7); 3.1339 (1.0); 3.1289 (0.7); 3.1209 (0.7); 3.1156 (1.0); 3.1103 (0.7); 3.0983 (1.1); 3.0865 (0.6); 3.0818 (0.8); 3.0760 (0.6); 3.0637 (0.6); 2.0049 (6.1); 1.9298 (0.6); 1.9133 (0.8); 1.8966 (1.1); 1.8768 (2.0); 1.8632 (3.2); 1.8466 (3.6); 1.8299 (2.3); 1.8193 (1.7); 1.8082 (1.4); 1.7885 (1.3); 1.7699 (1.1); 1.7455 (1.2); 1.7376 (1.4); 1.7212 (1.4); 1.6105 (7.7); 1.6056 (7.9); 1.5925 (11.0); 1.5887 (11.1); 1.5758 (7.3); 1.5709 (7.2); 1.4915 (0.6); 1.4743 (0.8); 1.4493 (2.0); 1.4435 (1.6); 1.4361 (0.7); 1.4257 (1.1); 1.3507 (0.5); 1.3390 (0.8); 1.3301 (0.8); 1.3212 (0.9); 1.3120 (0.9); 0.1461 (0.6); 0.0080 (4.6); −0.0002 (146.7); −0.0085 (5.7); −0.1497 (0.5)

Example No. I.1-222

$^1$H-NMR (400.0 MHz, CDCl$_3$): δ=7.5209 (0.6); 7.4303 (4.1); 7.4120 (4.0); 7.3730 (3.7); 7.3694 (3.3); 7.3505 (3.8); 7.3468 (3.2); 7.2621 (97.4); 6.9980 (0.5); 6.3663 (4.8); 6.3577 (4.0); 3.7016 (16.0); 3.6618 (5.5); 3.6482 (10.5); 3.5606 (8.9); 3.5500 (11.6); 3.4938 (1.6); −0.0002 (27.1)

Example No. I.1-224

$^1$H-NMR (400.0 MHz, CDCl$_3$): δ=7.5181 (9.0); 7.3541 (3.7); 7.3396 (3.5); 7.3365 (4.1); 7.3316 (3.8); 7.3172 (3.5); 7.3142 (3.4); 7.3090 (1.3); 7.2936 (2.5); 7.2887 (1.2); 7.2755 (5.9); 7.2592 (1610.0); 7.2327 (3.2); 7.2269 (2.2); 7.2085 (1.3); 7.2006 (0.9); 7.1809 (2.7); 7.1631 (2.5); 7.1547 (2.9); 7.1370 (2.9); 7.1095 (0.7); 6.9952 (9.0); 6.8058 (1.0); 6.7098 (0.9); 6.3363 (9.4); 6.3286 (5.2); 3.8605 (2.1); 3.8521 (2.2); 3.8421 (2.4); 3.8374 (2.3); 3.8336 (2.8); 3.8246 (2.1); 3.8192 (2.3); 3.8089 (3.9); 3.7915 (3.8); 3.7876 (3.1); 3.7750 (2.4); 3.7700 (2.2); 3.7545 (1.0); 3.6924 (0.9); 3.6748 (1.8); 3.6607 (1.8); 3.6396 (1.5); 3.5446 (14.4); 3.5383 (14.2); 3.5351 (9.6); 3.3360 (1.0); 3.3205 (1.0); 3.3068 (1.9); 3.2910 (2.0); 3.2862 (1.7); 3.2725 (2.2); 3.2572 (4.7); 3.2414 (2.7); 3.2322 (2.1); 3.2278 (2.0); 3.2192 (2.0); 3.2144 (2.1); 3.1979 (1.1); 3.1937 (1.2); 3.1852 (1.1); 3.1806 (1.2); 2.0047 (1.0); 1.9330 (1.5); 1.9132 (1.1); 1.8977 (1.5); 1.8794 (1.6); 1.8615 (1.5); 1.6739 (1.8); 1.6553 (2.8); 1.6470 (2.2); 1.6265 (10.7); 1.6216 (9.6); 1.6083 (10.7); 1.6039 (13.5); 1.6007 (10.3); 1.5864 (8.9); 1.5824 (8.7); 1.5378 (51.6); 1.4866 (1.7); 1.4655 (1.3); 1.1149 (15.4); 1.1110 (16.0); 1.0587 (13.3); 1.0517 (13.3); 0.1460 (1.9); 0.0340 (0.9); 0.0079 (17.2); −0.0002 (597.4); −0.0085 (18.7); −0.1498 (2.1)

Example No. I.1-227

$^1$H-NMR (400.0 MHz, CDCl$_3$): δ=7.5182 (1.1); 7.4992 (1.8); 7.4891 (1.8); 7.4803 (1.8); 7.4705 (1.8); 7.3781 (3.4); 7.3553 (3.2); 7.3148 (0.6); 7.2595 (177.5); 7.2132 (0.8); 6.9955 (1.0); 6.3498 (5.8); 4.8970 (1.0); 4.8868 (1.3); 4.8764 (1.1); 3.9641 (0.8); 3.9461 (2.5); 3.9284 (2.6); 3.9113 (0.9); 3.8431 (1.1); 3.8164 (2.1); 3.7886 (1.4); 3.5528 (13.3); 3.5149 (1.7); 3.4911 (2.5); 3.4626 (1.4); 1.8719 (0.8); 1.8465 (1.0); 1.7559 (1.1); 1.6113 (16.0); 1.5405 (10.3); 1.5227 (10.4); 1.4937 (1.2); 1.4743 (1.0); 1.4598 (0.8); −0.0002 (76.1)

Example No. I.1-241

$^1$H-NMR (400.0 MHz, CDCl$_3$): δ=7.5185 (1.4); 7.3553 (5.1); 7.3328 (5.1); 7.3093 (1.3); 7.2733 (7.2); 7.2596 (233.2); 7.2135 (1.0); 7.1941 (2.1); 7.1763 (0.9); 6.9955 (1.3); 6.9223 (0.7); 6.7481 (1.3); 6.3368 (7.6); 3.9230 (1.2); 3.8965 (1.4); 3.8472 (1.8); 3.8266 (3.2); 3.8086 (2.7); 3.7907 (1.7); 3.5429 (16.0); 3.4835 (0.8); 3.4256 (0.9); 3.3906 (1.6); 3.3627 (1.3); 3.2808 (1.3); 3.1977 (0.9); 3.1730 (1.0); 3.0580 (0.6); 3.0462 (0.9); 3.0268 (1.2); 3.0120 (1.2); 2.9457 (0.6); 2.9137 (0.8); 1.7080 (6.4); 1.5959 (11.4); 1.5777 (11.1); 1.4638 (7.3); 1.1952 (0.7); 1.1670 (0.6); 1.0793 (0.8); 0.0495 (0.6); −0.0002 (98.6); −0.1489 (0.5)

Example No. I.1-271

$^1$H-NMR (400.0 MHz, CDCl$_3$): δ=7.5210 (0.9); 7.3722 (9.6); 7.3690 (4.8); 7.3497 (9.7); 7.3466 (4.6); 7.2766 (0.5); 7.2693 (1.4); 7.2620 (147.4); 7.2554 (4.4); 7.2435 (4.0); 7.2372 (4.0); 7.2254 (3.9); 7.2132 (4.0); 7.1951 (3.9); 7.1748 (3.5); 7.1568 (3.5); 6.9980 (0.8); 6.5734 (0.9); 6.5584 (1.5); 6.5408 (1.8); 6.3483 (8.5); 6.3410 (6.4); 6.3339 (5.7); 4.4303 (0.6); 4.4219 (1.3); 4.4098 (1.9); 4.4031 (2.4); 3.9969 (2.2); 4.3908 (2.4); 4.3835 (1.7); 4.3721 (1.1); 3.8823 (0.7); 3.8748 (0.6); 3.8596 (1.2); 3.8422 (1.4); 3.8348 (1.4); 3.8239 (1.0); 3.8166 (1.0); 3.8112 (1.0); 3.8070 (1.0); 3.8037 (1.0); 3.7930 (3.4); 3.7890 (3.5); 3.7855 (3.1); 3.7783 (6.0); 3.7752 (4.5); 3.7708 (3.8); 3.7672 (3.7); 3.7651 (3.2); 3.7626 (3.3); 3.7600 (5.3); 3.7546 (5.6); 3.7524 (4.6); 3.7439 (4.3); 3.7411 (6.8); 3.7388 (8.2); 3.7304 (6.1); 3.7240 (3.6); 3.7175 (6.1); 3.7117 (2.5); 3.7063 (3.1); 3.7032 (2.4); 3.6975 (1.9); 3.6934 (1.1); 3.6816 (0.6); 3.5687 (1.6); 3.5617 (2.0); 3.5548 (9.0); 3.5517 (12.3); 3.5486 (14.4); 3.5456 (15.3); 3.5434 (14.7); 3.5403 (16.0); 3.5382 (13.9); 3.5351 (10.5); 3.5250 (1.3); 3.5180 (1.2); 3.5090 (1.5); 3.5015 (2.6); 3.4930 (1.5); 3.4850 (1.2); 3.4773 (2.0); 3.4693 (1.1); 2.2303 (0.7); 2.2264 (0.8); 2.2220 (0.6); 2.2159 (0.7); 2.2099 (1.3); 2.2035 (0.8); 2.1924 (1.8); 2.1764 (1.9); 2.1742 (2.2); 2.1705 (1.6); 2.1590 (1.6); 2.1558 (1.7); 2.1534 (1.6); 2.1434 (1.3); 2.1408 (1.7); 2.1381 (1.2); 2.1225 (1.7); 2.1201 (1.2); 2.1043 (0.6); 2.0051 (8.9); 1.8061 (2.2); 1.7015 (0.7); 1.6931 (0.8); 1.6870 (0.8); 1.6847 (0.8); 1.6791 (1.0); 1.6738 (1.2); 1.6712 (1.2); 1.6680 (1.2); 1.6596 (1.8); 1.6517 (1.5); 1.6493 (1.5); 1.6455 (1.6); 1.6408 (1.7); 1.6387 (1.6); 1.6330 (1.4); 1.6263 (1.5); 1.6186 (1.2); 1.6119 (0.8);

1.5956 (11.7); 1.5925 (13.2); 1.5857 (14.8); 1.5840 (14.9); 1.5775 (12.1); 1.5743 (13.0); 1.5676 (14.1); 1.5659 (13.9); 0.0080 (1.7); −0.0002 (62.9); −0.0085 (1.8)

Example No. I.1-275

¹H-NMR (400.0 MHz, d₆-DMSO): δ=8.5920 (2.3); 8.5750 (2.3); 8.5121 (4.5); 8.4952 (4.7); 8.1667 (0.6); 7.8379 (7.0); 7.8300 (6.0); 7.8257 (6.2); 7.8140 (7.1); 7.8062 (5.9); 7.8020 (5.9); 7.6412 (9.2); 7.6223 (9.2); 7.5547 (4.2); 7.5359 (4.3); 7.4605 (4.5); 7.4419 (4.6); 6.6232 (9.5); 6.6102 (10.1); 6.5991 (10.2); 6.5745 (8.9); 5.4346 (0.5); 4.3828 (3.4); 4.3662 (3.1); 4.3485 (1.6); 4.2309 (0.5); 4.1917 (0.5); 3.9383 (1.0); 3.9211 (3.6); 3.9138 (1.3); 3.9037 (4.5); 3.8967 (3.9); 3.8869 (5.0); 3.8793 (4.0); 3.8693 (5.0); 3.8500 (3.9); 3.8326 (1.3); 3.7251 (2.5); 3.4269 (33.0); 3.3945 (1.9); 3.3840 (2.0); 3.3738 (2.8); 3.3625 (2.5); 3.3508 (2.8); 3.3403 (3.0); 3.3302 (3.4); 3.3196 (1.8); 3.3108 (1.9); 3.2959 (2.0); 3.2766 (1.8); 3.2354 (2.3); 3.2227 (2.6); 3.2111 (2.8); 3.2018 (2.9); 3.1903 (2.6); 3.1639 (1.4); 3.1433 (3.1); 3.1237 (3.0); 3.1134 (3.3); 3.1059 (2.2); 3.0988 (2.1); 3.0921 (2.8); 3.0827 (1.6); 3.0714 (0.8); 3.0642 (0.8); 2.8798 (1.6); 2.8707 (1.8); 2.8628 (1.6); 2.8523 (1.7); 2.8463 (1.5); 2.8361 (1.5); 2.8301 (1.4); 2.8190 (1.4); 2.7602 (1.6); 2.7527 (1.6); 2.7450 (1.7); 2.7359 (1.5); 2.7265 (1.6); 2.7196 (1.5); 2.7108 (1.4); 2.7020 (1.4); 2.6788 (0.8); 2.6742 (1.6); 2.6695 (2.3); 2.6648 (1.6); 2.5505 (1.4); 2.5230 (8.0); 2.5183 (11.2); 2.5096 (132.9); 2.5050 (280.5); 2.5004 (387.5); 2.4959 (269.5); 2.4913 (124.7); 2.4557 (1.6); 2.4511 (1.6); 2.3934 (0.8); 2.3764 (1.1); 2.3577 (1.6); 2.3320 (3.4); 2.3271 (3.7); 2.3226 (3.5); 2.3182 (3.2); 2.2996 (2.5); 2.2921 (1.7); 2.2854 (2.1); 2.2764 (1.7); 2.2583 (1.2); 2.2431 (0.6); 2.0721 (10.6); 2.0646 (0.7); 2.0447 (1.5); 2.0253 (1.5); 2.0161 (1.6); 1.9936 (1.8); 1.9812 (2.3); 1.9618 (2.7); 1.9444 (2.3); 1.9253 (1.6); 1.9099 (1.2); 1.4221 (11.9); 1.4080 (13.9); 1.4047 (15.9); 1.4000 (16.0); 1.3956 (15.4); 1.3908 (13.6); 1.3826 (14.2); 1.3783 (13.0); 1.2705 (0.5); 1.2527 (1.2); 1.2349 (0.7); 1.1612 (1.1); 1.1435 (0.6); 0.0080 (4.7); −0.0002 (168.4); −0.0085 (5.5)

Example No. I.1-276

¹H-NMR (400.0 MHz, CDCl₃): δ=7.5187 (2.0); 7.3627 (5.7); 7.3403 (5.8); 7.2595 (306.4); 7.2057 (2.1); 7.1626 (0.8); 6.9952 (1.7); 6.7496 (1.8); 6.3370 (6.7); 3.8891 (2.5); 3.8386 (2.5); 3.8230 (3.1); 3.8049 (2.1); 3.6435 (3.6); 3.6145 (4.8); 3.5373 (16.0); 3.3089 (1.8); 3.2946 (1.7); 3.2802 (1.6); 1.7587 (15.0); 1.6054 (14.6); 1.5873 (14.5); 1.5571 (4.4); 1.5387 (3.5); 1.4486 (1.1); 0.1441 (0.7); −0.0002 (130.4); −0.0539 (1.0); −0.1484 (0.7)

Example No. I.1-331

¹H-NMR (400.0 MHz, CDCl₃): δ=7.5183 (1.7); 7.3706 (4.3); 7.3484 (4.4); 7.3141 (1.1); 7.2596 (282.3); 7.2140 (2.3); 7.1995 (1.7); 6.9957 (1.6); 6.8010 (0.8); 6.6923 (1.2); 6.3433 (7.3); 3.8646 (0.8); 3.8471 (2.3); 3.8303 (3.0); 3.8127 (1.8); 3.7504 (1.0); 3.7183 (2.9); 3.6879 (4.4); 3.6618 (5.9); 3.6412 (4.8); 3.5946 (1.6); 3.5485 (16.0); 3.4991 (2.0); 3.4750 (1.5); 3.4477 (1.1); 3.4087 (1.2); 3.3932 (1.5); 3.3579 (1.2); 3.3487 (1.1); 3.2593 (0.9); 3.2501 (0.8); 3.2338 (1.1); 3.2245 (1.1); 3.1960 (0.7); 3.1528 (1.5); 3.1435 (1.4); 3.1229 (2.2); 3.1015 (1.4); 3.0899 (1.6); 3.0704 (1.2); 3.0578 (1.1); 3.0387 (0.9); 3.0236 (0.7); 3.0060 (0.6); 1.7893 (6.1); 1.6064 (8.8); 1.6010 (10.0); 1.5886 (8.8); 1.5828 (9.5); 0.1462 (0.6); −0.0002 (122.0); −0.1489 (0.6)

Example No. I.1-333

Diastereomer 1—¹H-NMR (400.0 MHz, CDCl₃): δ=7.5190 (1.6); 7.3798 (4.2); 7.3780 (4.1); 7.3740 (4.1); 7.3700 (3.4); 7.3574 (4.2); 7.3557 (4.2); 7.3517 (4.2); 7.3478 (3.4); 7.3097 (0.5); 7.2944 (0.6); 7.2810 (3.4); 7.2601 (295.8); 7.2436 (3.2); 7.2070 (3.0); 7.1892 (5.6); 7.1714 (2.7); 6.9961 (1.6); 6.8738 (0.9); 6.8310 (1.4); 6.3514 (4.9); 6.3468 (5.3); 6.3364 (5.3); 6.3287 (5.5); 4.4755 (0.8); 4.4676 (0.8); 4.4566 (1.5); 4.4489 (1.7); 4.4388 (2.0); 4.4325 (1.8); 4.4269 (2.6); 4.4138 (2.6); 4.4071 (2.4); 4.3991 (1.5); 4.3891 (1.2); 4.3804 (1.3); 4.1426 (1.1); 4.1362 (1.1); 4.1253 (1.3); 4.1176 (2.6); 4.1127 (1.7); 4.1004 (1.5); 4.0970 (1.4); 4.0938 (1.7); 4.0883 (2.0); 4.0736 (1.1); 4.0673 (1.0); 4.0576 (1.9); 4.0488 (2.7); 4.0385 (3.2); 4.0288 (3.1); 4.0241 (3.4); 4.0160 (2.2); 4.0092 (1.9); 4.0040 (2.4); 3.9983 (2.6); 3.9879 (1.0); 3.9798 (0.9); 3.9693 (0.8); 3.8650 (0.6); 3.8470 (2.6); 3.8286 (4.2); 3.8103 (3.0); 3.7986 (2.4); 3.7945 (2.2); 3.7801 (2.2); 3.7624 (0.7); 3.6491 (0.5); 3.6259 (0.7); 3.6022 (0.9); 3.5851 (1.0); 3.5710 (1.2); 3.5431 (16.0); 3.5373 (11.9); 3.5340 (11.1); 3.5315 (10.2); 3.4965 (0.7); 3.4826 (0.9); 3.4646 (0.7); 3.4513 (0.6); 3.4384 (0.8); 3.4198 (0.8); 3.4066 (0.6); 3.3967 (0.9); 3.3776 (0.9); 3.3590 (1.1); 3.3431 (1.4); 3.3256 (1.2); 3.3094 (0.8); 3.2903 (0.6); 3.1851 (0.6); 3.1672 (5.8); 3.1626 (5.5); 3.1540 (6.1); 3.1444 (7.2); 3.1374 (5.5); 3.1306 (1.9); 3.1242 (1.5); 3.1190 (2.5); 3.0880 (0.5); 2.7364 (0.5); 2.1212 (0.5); 2.1105 (0.9); 2.0909 (1.3); 2.0842 (1.3); 2.0726 (1.6); 2.0604 (1.5); 2.0350 (1.0); 2.0227 (0.8); 1.9712 (0.7); 1.9511 (2.0); 1.9380 (1.9); 1.9324 (2.5); 1.9187 (1.8); 1.9137 (2.0); 1.9002 (1.5); 1.8949 (1.4); 1.8809 (0.9); 1.7487 (0.7); 1.7432 (0.8); 1.7389 (2.5); 1.7311 (0.7); 1.7256 (0.8); 1.7214 (2.4); 1.6147 (15.3); 1.6015 (14.0); 1.5965 (16.4); 1.5835 (12.5); 1.2552 (3.3); 0.8819 (0.8); 0.0079 (2.6); −0.0002 (85.0); −0.0085 (2.7). Diastereomer 2—¹H-NMR (400.0 MHz, CDCl₃): δ=7.5186 (2.9); 7.3809 (3.6); 7.3775 (5.4); 7.3715 (3.4); 7.3585 (4.0); 7.3552 (5.6); 7.3493 (3.2); 7.3092 (3.5); 7.2908 (2.0); 7.2718 (6.8); 7.2597 (481.0); 7.2514 (4.8); 7.2326 (4.2); 7.2097 (5.5); 7.2038 (4.6); 7.1857 (4.3); 7.1652 (3.0); 6.9957 (6.8); 6.7862 (0.8); 6.7723 (1.0); 6.7067 (0.9); 6.3508 (4.7); 6.3464 (4.8); 6.3390 (5.0); 6.3320 (5.0); 4.4773 (0.7); 4.4690 (0.6); 4.4508 (1.5); 4.4382 (1.8); 4.4291 (1.9); 4.4190 (1.6); 4.4111 (2.7); 4.4014 (2.2); 4.3937 (1.6); 4.3843 (1.6); 4.1443 (0.8); 4.1373 (0.8); 4.1267 (0.9); 4.1187 (1.8); 4.1020 (0.9); 4.0945 (1.5); 4.0896 (1.4); 4.0750 (0.8); 4.0683 (1.0); 4.0591 (2.2); 4.0489 (2.0); 4.0428 (3.4); 4.0314 (3.9); 4.0193 (2.7); 4.0104 (2.4); 3.9995 (2.0); 3.9944 (1.1); 3.9901 (0.9); 3.9758 (0.8); 3.8401 (0.7); 3.8220 (2.0); 3.8062 (2.6); 3.7892 (3.1); 3.7723 (3.4); 3.7545 (2.5); 3.7362 (0.7); 3.6119 (0.6); 3.5977 (1.0); 3.5767 (1.3); 3.5459 (16.0); 3.5430 (14.9); 3.5008 (2.9); 3.4831 (2.8); 3.4656 (1.5); 3.4478 (0.7); 3.4289 (1.0); 3.4112 (0.9); 3.3963 (0.9); 3.3832 (1.0); 3.3644 (1.1); 3.3552 (1.1); 3.3425 (1.3); 3.3364 (1.3); 3.3299 (1.0); 3.3234 (1.3); 3.3078 (0.9); 3.2887 (0.8); 3.1848 (0.6); 3.1660 (5.5); 3.1625 (5.6); 3.1534 (5.7); 3.1449 (7.7); 3.1381 (5.1); 3.1301 (1.8); 3.1234 (1.7); 3.1195 (2.5); 3.0883 (0.7); 2.3954 (2.0); 2.1167 (0.7); 2.0980 (1.0); 2.0844 (1.3); 2.0686 (1.5); 2.0607 (1.4); 2.0487 (1.4); 2.0379 (1.3); 1.9693 (0.8); 1.9500 (1.8); 1.9307 (2.0); 1.9128 (2.0); 1.8938 (1.3); 1.8775 (0.8); 1.6103 (12.0); 1.5992 (9.6);

1.5970 (10.1); 1.5921 (12.8); 1.5811 (8.9); 1.5789 (8.7); 1.5496 (1.3); 1.5314 (1.0); 1.4320 (2.1); 1.2562 (0.6); 1.2290 (2.0); 1.2114 (3.9); 1.1939 (2.0); 0.1463 (0.7); 0.0494 (0.9); 0.0079 (6.5); −0.0002 (188.2); −0.0085 (6.4); −0.0502 (2.2); −0.1494 (0.8)

Example No. I.1-334

$^1$H-NMR (400.0 MHz, CDCl$_3$): δ=7.5183 (1.9); 7.3597 (5.2); 7.3375 (5.3); 7.3091 (1.8); 7.2595 (311.0); 7.2334 (4.5); 7.2164 (1.4); 6.9954 (1.8); 6.7778 (1.7); 6.3373 (6.4); 6.3278 (3.1); 4.1573 (1.2); 4.1084 (1.2); 3.9764 (1.3); 3.9557 (1.9); 3.9383 (1.2); 3.9031 (1.0); 3.8821 (1.9); 3.8522 (2.1); 3.8340 (2.4); 3.8226 (1.8); 3.5404 (16.0); 3.5145 (1.2); 3.4614 (0.8); 3.4369 (1.0); 3.4265 (1.3); 3.4126 (1.2); 3.4037 (1.6); 3.3817 (3.6); 3.3689 (3.4); 3.3271 (0.6); 3.3128 (1.3); 3.2985 (1.4); 3.2775 (1.0); 3.2640 (0.9); 1.6105 (13.7); 1.5923 (13.9); 1.5386 (73.1); 1.4280 (13.7); 1.3900 (12.4); 1.2875 (9.3); 1.2784 (11.6); 0.1466 (0.7); 0.0494 (0.8); −0.0002 (132.0); −0.1499 (0.6)

Example No. I.1-335

$^1$H-NMR (400.0 MHz, CDCl$_3$): δ=7.5863 (2.0); 7.5816 (0.7); 7.5732 (0.8); 7.5689 (2.5); 7.5675 (2.6); 7.5627 (0.8); 7.5542 (0.7); 7.5502 (2.0); 7.3850 (3.3); 7.3753 (1.2); 7.3622 (3.3); 7.3525 (1.1); 7.2615 (54.0); 6.3544 (3.6); 6.3474 (4.5); 5.7911 (0.6); 5.7802 (0.6); 5.7643 (0.5); 5.7500 (0.5); 5.1598 (1.4); 5.1576 (1.2); 5.1524 (1.1); 5.1477 (1.6); 5.1192 (2.6); 5.0780 (0.6); 4.7494 (0.6); 4.7371 (0.7); 4.7318 (1.0); 4.7196 (1.0); 4.7143 (0.7); 4.7019 (0.6); 4.0587 (1.4); 4.0542 (1.4); 4.0418 (1.5); 4.0373 (1.4); 3.9475 (0.5); 3.9349 (0.8); 3.9310 (0.8); 3.9182 (0.5); 3.8959 (0.7); 3.8917 (0.7); 3.8870 (0.6); 3.8820 (0.7); 3.8780 (0.5); 3.8286 (0.7); 3.8230 (0.9); 3.8178 (0.9); 3.8120 (0.7); 3.7770 (0.6); 3.7719 (0.5); 3.5565 (6.8); 3.5535 (8.6); 3.5500 (8.2); 3.4250 (1.0); 3.4231 (1.0); 3.4071 (0.9); 3.4048 (1.0); 3.3993 (1.6); 3.3974 (1.6); 3.3814 (1.5); 3.3792 (1.4); 3.3394 (1.4); 3.3341 (1.4); 3.3271 (2.0); 3.3220 (1.6); 3.3135 (1.1); 3.3107 (1.1); 3.3085 (1.1); 3.3015 (1.0); 3.2961 (0.9); 3.2897 (0.5); 3.2776 (15.6); 3.2742 (16.0); 3.2616 (4.1); 3.2572 (4.1); 1.5084 (1.4); 1.5033 (1.5); 1.4911 (1.5); 1.4859 (1.6); 1.4682 (5.3); 1.4634 (5.4); 1.4514 (5.4); 1.4465 (5.3); 1.4347 (0.8); 1.3881 (0.7); 1.2161 (2.7); 1.1990 (2.6); 1.1092 (5.3); 1.1003 (5.5); 1.0918 (5.4); 1.0828 (5.3); 0.0080 (0.6); −0.0002 (20.4); −0.0085 (0.6)

Example No. I.1-340

$^1$H-NMR (400.0 MHz, CDCl$_3$): δ=7.5183 (5.2); 7.4046 (3.2); 7.3992 (3.2); 7.3960 (3.0); 7.3929 (2.9); 7.3822 (3.4); 7.3769 (3.4); 7.3735 (3.1); 7.3708 (2.9); 7.3530 (2.9); 7.3349 (3.1); 7.3171 (2.8); 7.2990 (3.0); 7.2881 (5.1); 7.2700 (8.4); 7.2595 (876.8); 7.2497 (2.1); 7.2441 (0.9); 7.2330 (0.6); 7.2100 (0.9); 6.9954 (5.0); 6.6946 (1.2); 6.6696 (1.3); 6.5432 (1.4); 6.5145 (1.4); 6.3435 (8.1); 6.3390 (5.4); 6.3287 (4.0); 3.8262 (1.7); 3.8137 (1.9); 3.8079 (1.9); 3.7957 (2.1); 3.7790 (2.4); 3.7677 (2.3); 3.7608 (2.2); 3.7496 (2.3); 3.7427 (0.7); 3.7314 (0.6); 3.5503 (11.8); 3.5475 (12.2); 3.5326 (9.3); 3.3944 (2.4); 3.3731 (1.9); 3.3677 (3.1); 3.3643 (3.2); 3.3430 (2.1); 3.3318 (2.1); 3.1469 (1.9); 3.1343 (1.7); 3.1171 (1.5); 3.1071 (1.5); 3.0927 (1.3); 3.0665 (2.3); 3.0363 (1.6); 3.0246 (1.1); 3.0164 (1.4); 3.0079 (1.4); 2.9969 (1.4); 2.9862 (0.8); 2.9373 (1.5); 2.9285 (0.9); 2.9179 (1.0); 2.9089 (1.6); 2.9012 (1.2); 2.8899 (1.1); 2.8812 (1.1); 2.8229 (0.8); 2.8146 (0.8); 2.8055 (1.0); 2.7949 (1.3); 2.7860 (0.9); 2.7771 (1.2); 2.7691 (0.8); 2.7493 (1.0); 2.7016 (0.8); 2.6179 (0.7); 2.6021 (1.0); 2.5846 (1.2); 2.5704 (0.8); 2.4438 (1.5); 2.4228 (2.1); 2.4119 (1.9); 2.4038 (1.5); 2.3997 (1.4); 2.3930 (1.6); 2.3785 (1.5); 2.3173 (0.6); 2.2968 (0.8); 2.2843 (1.2); 2.2624 (1.0); 2.2504 (0.7); 2.0052 (0.7); 1.7338 (2.9); 1.6305 (9.5); 1.6169 (9.6); 1.6119 (16.0); 1.5989 (8.5); 1.5934 (8.8); 0.1460 (1.7); 0.0080 (15.6); −0.0002 (517.3); −0.0085 (15.6); −0.0497 (0.8); −0.1497 (1.8)

Example No. I.1-341

$^1$H-NMR (400.0 MHz, CDCl$_3$): δ=7.5177 (9.7); 7.5104 (2.9); 7.4971 (6.4); 7.4916 (2.7); 7.4134 (6.0); 7.3908 (6.1); 7.2923 (1.7); 7.2590 (1346.6); 7.2089 (1.9); 6.9950 (7.2); 6.3591 (7.7); 6.3446 (8.8); 3.9555 (3.5); 3.9379 (5.0); 3.9204 (3.4); 3.8697 (3.4); 3.8499 (4.0); 3.8317 (1.8); 3.7377 (2.0); 3.7261 (2.1); 3.7174 (2.5); 3.7044 (2.8); 3.6964 (2.4); 3.6913 (2.3); 3.6744 (4.0); 3.6577 (3.8); 3.6486 (5.0); 3.6431 (4.9); 3.6356 (3.4); 3.6200 (3.5); 3.5529 (16.0); 1.9935 (1.6); 1.9741 (1.6); 1.7158 (1.6); 1.5591 (15.5); 1.5565 (12.9); 1.5413 (15.1); 1.5387 (12.6); 0.0080 (14.4); −0.0002 (499.6); −0.0085 (14.4); −0.1498 (1.6)

Example No. I.2-71

Diastereomer 1—$^1$H-NMR (400.0 MHz, CDCl$_3$): δ=7.5532 (1.4); 7.5465 (1.4); 7.5344 (1.4); 7.5278 (1.4); 7.5181 (2.5); 7.5138 (1.6); 7.4985 (1.4); 7.4951 (1.5); 7.3611 (3.9); 7.3383 (3.9); 7.2594 (306.1); 7.2465 (0.6); 6.9954 (1.7); 6.3443 (6.1); 6.3392 (2.3); 4.1684 (0.7); 4.1596 (0.7); 4.1545 (0.7); 4.1460 (0.8); 4.1405 (0.8); 4.1317 (1.1); 4.1269 (0.9); 4.1183 (0.9); 4.0813 (0.6); 4.0681 (0.8); 4.0623 (1.2); 4.0500 (1.3); 4.0444 (1.2); 4.0351 (0.8); 4.0284 (1.3); 4.0174 (1.0); 4.0129 (1.5); 4.0004 (1.3); 3.9922 (2.1); 3.9861 (1.7); 3.9767 (1.3); 3.9701 (1.0); 3.9649 (1.0); 3.9583 (1.1); 3.9490 (0.7); 3.9422 (0.7); 3.8278 (0.5); 3.8149 (0.6); 3.8109 (1.5); 3.8075 (1.2); 3.7942 (1.3); 3.7903 (1.8); 3.7737 (0.9); 3.7654 (0.9); 3.7469 (1.4); 3.7347 (1.6); 3.7308 (1.8); 3.7181 (1.7); 3.7146 (2.4); 3.7114 (1.4); 3.6982 (1.1); 3.6946 (1.0); 3.5519 (9.2); 3.5488 (10.6); 3.5461 (6.8); 2.0048 (2.5); 1.9846 (1.0); 1.9818 (1.1); 1.9648 (1.4); 1.9463 (1.3); 1.9348 (0.8); 1.9304 (0.8); 1.9134 (0.8); 1.9051 (0.8); 1.9012 (1.0); 1.8922 (0.9); 1.8845 (1.5); 1.8687 (2.1); 1.8663 (2.1); 1.8569 (1.6); 1.8519 (2.1); 1.8480 (2.1); 1.8314 (1.5); 1.8150 (0.8); 1.5660 (2.0); 1.5426 (1.2); 1.5368 (1.0); 1.5230 (0.9); 1.5129 (0.7); 1.5058 (0.9); 1.4938 (0.7); 1.4889 (0.7); 1.0816 (7.2); 1.0631 (16.0); 1.0447 (6.6); 0.3307 (0.6); 0.2375 (0.6); 0.1263 (0.7); 0.0080 (3.8); −0.0002 (127.1); −0.0085 (3.8).

Diastereomer 2—$^1$H-NMR (400.0 MHz, CDCl$_3$): δ=7.5535 (1.6); 7.5469 (1.6); 7.5346 (1.7); 7.5281 (1.6); 7.5177 (1.3); 7.5142 (1.3); 7.4990 (1.2); 7.4955 (1.3); 7.3612 (3.9); 7.3384 (3.9); 7.2606 (53.4); 6.3440 (6.8); 6.3390 (2.2); 4.1679 (0.7); 4.1591 (0.8); 4.1541 (0.8); 4.1456 (0.8); 4.1400 (1.0); 4.1312 (1.1); 4.1266 (1.0); 4.1180 (1.0); 4.0812 (0.5); 4.0681 (0.7); 4.0622 (1.0); 4.0590 (0.9); 4.0502 (1.4); 4.0430 (1.2); 4.0345 (1.1); 4.0284 (1.0); 4.0174 (1.1); 4.0130 (1.3); 4.0008 (1.2); 3.9923 (2.0); 3.9863 (1.9); 3.9773 (1.4); 3.9703 (1.1); 3.9651 (1.2); 3.9584 (1.2); 3.9492 (0.7); 3.9424 (0.7); 3.8272 (0.6); 3.8142 (0.7); 3.8102 (1.6); 3.8066 (1.3); 3.7935 (1.5); 3.7895 (1.8); 3.7729 (0.9); 3.7661 (0.8); 3.7463 (1.3); 3.7343 (1.6); 3.7310 (2.0); 3.7251 (1.0); 3.7183 (2.2);

3.7147 (2.5); 3.7115 (1.6); 3.7071 (0.8); 3.6982 (1.5); 3.6947 (1.3); 3.5515 (10.1); 3.5485 (11.4); 2.0002 (0.8); 1.9844 (1.1); 1.9817 (1.2); 1.9646 (1.6); 1.9462 (1.4); 1.9341 (0.8); 1.9303 (0.9); 1.9263 (0.8); 1.9170 (0.6); 1.9130 (1.0); 1.9082 (0.8); 1.9049 (0.9); 1.9007 (1.0); 1.8924 (1.1); 1.8838 (1.5); 1.8738 (1.4); 1.8686 (2.2); 1.8662 (1.9); 1.8568 (1.8); 1.8518 (2.3); 1.8480 (2.0); 1.8384 (1.4); 1.8355 (1.7); 1.8222 (0.8); 1.8174 (0.9); 1.5559 (11.0); 1.5425 (0.6); 1.5369 (0.5); 1.5236 (0.7); 1.5144 (0.6); 1.5057 (0.9); 1.4967 (0.6); 1.4890 (0.7); 1.2565 (0.5); 1.0817 (7.4); 1.0632 (16.0); 1.0448 (6.8); 0.0692 (2.1); 0.0080 (0.7); −0.0002 (22.2); −0.0085 (0.6)

Example No. I.2-73

$^1$H-NMR (400.0 MHz, CDCl$_3$): δ=7.5451 (1.5); 7.5341 (1.5); 7.5263 (1.6); 7.5189 (0.9); 7.5150 (3.3); 7.5103 (2.0); 7.4961 (1.9); 7.4916 (1.9); 7.3631 (3.0); 7.3521 (3.6); 7.3403 (3.1); 7.3293 (3.6); 7.2601 (108.8); 6.9961 (0.6); 6.3483 (8.6); 4.1122 (0.7); 4.1076 (0.8); 4.1032 (0.8); 4.0987 (0.8); 4.0833 (1.2); 4.0787 (1.3); 4.0743 (1.3); 4.0698 (1.3); 4.0652 (0.6); 4.0476 (0.5); 4.0364 (1.1); 4.0268 (1.1); 4.0187 (1.2); 4.0091 (1.3); 4.0058 (1.4); 3.9998 (1.3); 3.9929 (1.3); 3.9888 (2.1); 3.9835 (2.2); 3.9794 (1.4); 3.9772 (1.0); 3.9709 (0.8); 3.9641 (0.6); 3.9600 (1.2); 3.9544 (1.1); 3.9506 (0.6); 3.9332 (1.3); 3.9288 (1.2); 3.9100 (1.0); 3.9050 (1.2); 3.8996 (1.3); 3.7563 (1.0); 3.7536 (1.0); 3.7498 (1.0); 3.7368 (2.1); 3.7334 (2.2); 3.7298 (1.2); 3.7195 (1.0); 3.7169 (1.1); 3.7132 (1.0); 3.5531 (14.1); 3.5188 (0.5); 3.4630 (0.7); 3.4543 (0.5); 3.4467 (0.7); 3.4412 (0.6); 3.4375 (0.6); 3.4326 (0.6); 3.3960 (1.0); 3.3897 (1.2); 3.3680 (1.4); 3.3627 (1.5); 3.3414 (0.7); 3.3348 (0.6); 2.0144 (0.6); 1.9964 (1.1); 1.9790 (1.5); 1.9609 (1.7); 1.9427 (1.0); 1.8932 (0.6); 1.8896 (0.6); 1.8752 (1.1); 1.8582 (1.5); 1.8547 (1.2); 1.8402 (2.1); 1.8224 (1.5); 1.8052 (1.2); 1.5470 (43.7); 1.5035 (2.2); 1.4856 (4.2); 1.4529 (1.2); 1.4432 (1.0); 1.2545 (0.9); 1.2422 (0.8); 1.2325 (0.6); 1.2238 (0.8); 1.2136 (0.7); 1.0753 (7.5); 1.0569 (16.0); 1.0384 (6.9); 0.0080 (1.2); −0.0002 (39.9); −0.0085 (1.2)

Example No. I.2-81

$^1$H-NMR (400.0 MHz, CDCl$_3$): δ=8.0511 (1.1); 8.0299 (1.3); 7.6910 (0.9); 7.6701 (1.3); 7.5891 (0.7); 7.5868 (0.7); 7.5718 (0.8); 7.5694 (0.9); 7.5509 (0.6); 7.5486 (0.6); 7.5188 (1.1); 7.5132 (2.4); 7.5112 (2.6); 7.4944 (4.4); 7.4925 (4.6); 7.4826 (0.6); 7.4755 (2.1); 7.4737 (2.2); 7.4512 (0.8); 7.4487 (0.8); 7.4338 (0.6); 7.4303 (0.9); 7.4275 (0.7); 7.4128 (0.5); 7.4102 (0.6); 7.3630 (7.3); 7.3403 (7.6); 7.3342 (0.7); 7.2924 (0.5); 7.2599 (156.9); 6.9959 (0.9); 6.3558 (3.8); 6.3528 (3.7); 6.3457 (5.1); 6.2805 (0.8); 6.2266 (9.4); 4.1334 (1.0); 4.1134 (1.4); 4.1057 (2.1); 4.0936 (0.8); 4.0863 (2.9); 4.0778 (1.2); 4.0665 (1.2); 4.0594 (1.3); 4.0249 (1.5); 4.0097 (2.5); 3.9979 (2.3); 3.9936 (1.6); 3.9815 (2.5); 3.9707 (1.0); 3.9663 (1.0); 3.9540 (0.9); 3.7273 (0.9); 3.7242 (1.0); 3.7109 (1.1); 3.7074 (1.8); 3.7037 (1.2); 3.7001 (1.1); 3.6926 (1.3); 3.6873 (1.1); 3.6836 (1.2); 3.6795 (1.3); 3.6766 (1.4); 3.6726 (1.2); 3.6630 (1.0); 3.6561 (1.0); 3.5578 (10.1); 3.5521 (11.4); 3.5489 (10.3); 3.5189 (2.6); 3.5030 (1.6); 3.4862 (1.2); 3.4750 (0.9); 2.8589 (0.7); 2.8473 (1.1); 2.8412 (1.1); 2.8346 (1.6); 2.8249 (1.5); 2.8221 (1.6); 2.8066 (1.8); 2.7900 (2.2); 2.7737 (1.3); 2.7646 (1.0); 2.7481 (0.5); 2.0165 (1.0); 1.9983 (1.7); 1.9851 (2.2); 1.9816 (3.3); 1.9776 (2.2); 1.9614 (4.9); 1.9510 (4.8); 1.9460 (4.5); 1.9427 (3.9); 1.9275 (1.8); 1.9165 (1.1); 1.8943 (1.0); 1.8860 (0.8); 1.8757 (1.4); 1.8680 (1.3); 1.8572 (1.3); 1.8499 (1.2); 1.8407 (1.0); 1.8329 (0.9); 1.8222 (0.5); 1.6925 (0.8); 1.6797 (1.3); 1.6644 (1.4); 1.6512 (1.2); 1.6371 (0.9); 1.5488 (14.4); 1.2557 (1.2); 1.0842 (8.0); 1.0659 (16.0); 1.0475 (7.2); 0.0080 (1.9); −0.0002 (66.2); −0.0085 (2.3)

Example No. I.2-221

$^1$H-NMR (400.0 MHz, CDCl$_3$): δ=7.5187 (2.0); 7.4538 (0.6); 7.4308 (0.6); 7.3512 (2.0); 7.3489 (2.1); 7.3403 (2.1); 7.3387 (2.1); 7.3285 (2.1); 7.3262 (2.2); 7.3213 (2.0); 7.3180 (2.3); 7.3162 (2.2); 7.3102 (0.9); 7.3030 (1.9); 7.2936 (1.8); 7.2888 (0.8); 7.2879 (0.8); 7.2872 (0.8); 7.2863 (0.8); 7.2856 (0.8); 7.2839 (0.9); 7.2832 (1.0); 7.2824 (1.0); 7.2816 (1.0); 7.2808 (1.0); 7.2800 (1.0); 7.2792 (1.2); 7.2784 (1.2); 7.2776 (1.4); 7.2753 (3.0); 7.2737 (2.0); 7.2729 (1.9); 7.2721 (2.0); 7.2712 (2.0); 7.2704 (2.2); 7.2696 (2.5); 7.2689 (2.7); 7.2681 (2.9); 7.2672 (3.3); 7.2664 (3.9); 7.2656 (4.6); 7.2648 (5.7); 7.2640 (7.2); 7.2598 (352.2); 7.2535 (2.7); 7.2527 (2.1); 7.2519 (1.5); 7.2511 (0.9); 7.2503 (0.6); 7.2185 (1.6); 7.2104 (0.6); 7.2004 (1.5); 7.1961 (1.6); 7.1782 (1.4); 6.9958 (2.0); 6.7325 (0.8); 6.3583 (0.7); 6.3328 (5.3); 3.8618 (0.6); 3.8482 (0.7); 3.8311 (0.8); 3.8240 (1.0); 3.8051 (1.4); 3.7881 (1.4); 3.7722 (0.5); 3.7458 (0.6); 3.7332 (1.0); 3.7177 (0.7); 3.7154 (0.8); 3.7002 (0.6); 3.6795 (1.5); 3.6695 (1.2); 3.6636 (2.4); 3.6519 (1.5); 3.6425 (2.8); 3.6350 (0.9); 3.6257 (1.4); 3.5603 (1.4); 3.5570 (1.7); 3.5438 (9.0); 3.5406 (10.4); 3.5378 (9.4); 3.5347 (6.0); 3.5133 (0.6); 3.5050 (0.7); 3.4976 (0.6); 3.4791 (0.5); 3.4725 (0.6); 3.4635 (0.9); 3.4559 (0.9); 3.4499 (0.8); 3.4245 (0.5); 3.4215 (0.5); 3.4155 (0.8); 3.4098 (0.5); 3.2038 (0.6); 3.1865 (0.6); 3.1697 (0.5); 3.1527 (0.5); 3.1382 (0.7); 3.1325 (0.6); 3.1255 (0.6); 3.1197 (0.9); 3.1141 (0.5); 3.1068 (0.5); 3.1017 (0.7); 3.0982 (0.5); 3.0854 (0.7); 2.4455 (3.9); 2.0791 (0.8); 2.0624 (1.4); 2.0439 (2.3); 2.0257 (1.9); 2.0087 (1.4); 1.9402 (0.7); 1.9296 (1.0); 1.9220 (1.3); 1.9128 (1.2); 1.9036 (1.4); 1.8947 (1.5); 1.8864 (1.4); 1.8765 (1.7); 1.8680 (1.6); 1.8594 (2.0); 1.8509 (1.5); 1.8399 (2.0); 1.8273 (1.3); 1.8224 (1.3); 1.8120 (1.0); 1.8018 (0.7); 1.7819 (0.6); 1.5445 (16.0); 1.4716 (0.5); 1.4503 (0.5); 1.4411 (0.8); 1.4225 (0.7); 1.3328 (0.7); 1.3199 (0.6); 1.3106 (0.8); 1.3015 (0.8); 1.2930 (0.6); 1.2843 (0.9); 1.2560 (2.5); 1.1214 (5.6); 1.1029 (11.4); 1.0846 (5.1); 0.8802 (0.6); 0.0144 (0.5); 0.0136 (0.6); 0.0127 (0.6); 0.0120 (0.7); 0.0112 (0.8); 0.0103 (0.9); 0.0080 (4.4); 0.0064 (1.7); 0.0056 (1.8); 0.0048 (2.2); 0.0039 (2.8); −0.0002 (135.1); −0.0050 (2.4); −0.0058 (1.8); −0.0067 (1.5); −0.0084 (3.9); −0.0106 (0.6)

Example No. I.2-224

$^1$H-NMR (400.0 MHz, CDCl$_3$): δ=7.3473 (2.3); 7.3458 (2.3); 7.3312 (2.2); 7.3290 (2.3); 7.3248 (2.5); 7.3233 (2.4); 7.3088 (2.1); 7.3067 (2.2); 7.2817 (1.9); 7.2610 (80.2); 7.2385 (1.8); 7.1814 (1.6); 7.1635 (1.7); 7.1584 (1.8); 7.1405 (1.6); 6.7717 (0.5); 6.3343 (6.0); 6.3274 (3.4); 3.8225 (1.1); 3.8052 (1.5); 3.7995 (0.9); 3.7946 (1.0); 3.7892 (1.9); 3.7824 (1.9); 3.7775 (1.9); 3.7706 (1.1); 3.7649 (1.1); 3.7606 (1.2); 3.7565 (1.0); 3.7499 (0.5); 3.7028 (0.8); 3.6990 (0.8); 3.6855 (1.7); 3.6684 (1.9); 3.6646 (2.6); 3.6545 (1.2); 3.6474 (3.5); 3.6368 (0.6); 3.6301 (1.9); 3.5453 (8.9); 3.5423 (8.2); 3.5392 (8.2); 3.5364 (9.0); 3.5336 (6.4); 3.3588 (0.7); 3.3422 (0.7); 3.3248 (1.1); 3.3082 (1.0); 3.2649 (4.4); 3.2501 (4.4);

3.2218 (1.0); 3.2168 (1.1); 3.2089 (1.1); 3.2041 (1.0); 3.1878 (0.6); 3.1829 (0.7); 3.1749 (0.6); 3.1701 (0.6); 2.0897 (0.6); 2.0854 (0.5); 2.0727 (1.0); 2.0689 (1.0); 2.0545 (1.6); 2.0503 (1.6); 2.0361 (1.4); 2.0337 (1.3); 2.0319 (1.3); 2.0193 (0.9); 2.0151 (1.0); 1.9572 (0.6); 1.9498 (0.7); 1.9387 (1.2); 1.9314 (1.4); 1.9203 (1.3); 1.9126 (1.6); 1.9096 (1.7); 1.9019 (1.3); 1.8913 (1.8); 1.8848 (1.2); 1.8743 (1.7); 1.8665 (1.0); 1.8569 (1.4); 1.8529 (1.0); 1.8482 (0.8); 1.8406 (1.0); 1.8271 (0.7); 1.8218 (0.7); 1.6718 (0.8); 1.6539 (1.7); 1.6460 (1.6); 1.6305 (1.6); 1.6245 (1.7); 1.6150 (0.9); 1.6095 (1.2); 1.6018 (0.6); 1.5986 (0.7); 1.5935 (0.7); 1.5744 (16.0); 1.5553 (0.6); 1.5438 (1.3); 1.5309 (0.9); 1.5236 (1.0); 1.5101 (0.8); 1.4876 (0.8); 1.4724 (0.7); 1.3039 (0.5); 1.2845 (0.8); 1.2647 (2.6); 1.1361 (3.6); 1.1170 (9.2); 1.1141 (10.9); 1.1100 (10.4); 1.1028 (8.9); 1.0846 (3.5); 1.0525 (9.5); 1.0452 (9.4); 0.8987 (1.3); 0.8818 (4.3); 0.8641 (1.7); 0.0691 (0.9); 0.0079 (1.0); −0.0002 (33.6); −0.0085 (1.1)

Example No. I.2-336

$^1$H-NMR (400.0 MHz, CDCl$_3$): δ=7.5184 (1.9); 7.3794 (0.6); 7.3726 (1.2); 7.3652 (4.9); 7.3499 (1.9); 7.3428 (3.2); 7.3286 (3.6); 7.3066 (3.8); 7.2596 (324.2); 7.1146 (0.7); 7.0983 (2.1); 7.0928 (2.2); 7.0807 (1.6); 7.0750 (1.6); 6.9955 (1.6); 6.8893 (0.8); 6.8643 (0.9); 6.3413 (4.9); 6.3341 (2.6); 6.3186 (2.8); 4.5861 (0.6); 4.5598 (0.8); 4.5393 (0.7); 4.4760 (0.7); 4.2233 (0.8); 4.2053 (1.1); 4.1806 (1.1); 4.1571 (1.0); 4.1387 (0.9); 3.8751 (1.1); 3.8576 (2.1); 3.8501 (1.0); 3.8399 (1.1); 3.8356 (1.2); 3.8310 (1.2); 3.8078 (1.6); 3.7945 (1.6); 3.7773 (0.9); 3.7583 (1.0); 3.7466 (0.9); 3.7381 (1.0); 3.7283 (1.2); 3.7109 (1.6); 3.7060 (1.6); 3.6939 (0.8); 3.6887 (0.7); 3.6235 (0.7); 3.6044 (0.7); 3.5917 (0.8); 3.5737 (0.8); 3.5468 (8.0); 3.5438 (7.8); 3.5325 (4.1); 3.5297 (4.2); 2.0958 (0.5); 2.0775 (0.8); 2.0600 (1.1); 2.0434 (1.5); 2.0182 (1.9); 2.0006 (2.6); 1.9818 (1.9); 1.9636 (0.6); 1.9265 (0.5); 1.9089 (0.8); 1.8943 (1.2); 1.8761 (1.6); 1.8559 (1.6); 1.8361 (1.4); 1.6563 (0.7); 1.5420 (16.0); 1.3768 (0.9); 1.2551 (1.6); 1.1528 (3.4); 1.1340 (7.0); 1.1157 (3.3); 1.1018 (3.9); 1.0833 (8.1); 1.0650 (3.7); 1.0483 (0.7); 1.0253 (0.7); 0.9935 (0.6); 0.3306 (0.8); 0.2374 (0.8); 0.1569 (0.6); 0.1262 (0.7); 0.0688 (3.7); 0.0079 (3.7); −0.0002 (128.2); −0.0085 (4.4)

Example No. I.4-71

$^1$H-NMR (400.0 MHz, CDCl$_3$): δ=7.5634 (0.6); 7.5592 (0.7); 7.5499 (1.9); 7.5440 (2.2); 7.5407 (1.1); 7.5311 (2.0); 7.5251 (1.8); 7.5193 (0.9); 7.5117 (1.6); 7.5058 (1.6); 7.4930 (1.5); 7.4871 (1.6); 7.3673 (2.1); 7.3637 (4.8); 7.3550 (1.1); 7.3443 (2.2); 7.3409 (4.8); 7.3323 (1.2); 7.2742 (0.5); 7.2726 (0.6); 7.2702 (0.8); 7.2694 (0.9); 7.2669 (1.4); 7.2604 (126.2); 6.9964 (0.7); 6.3424 (8.0); 6.3372 (3.0); 6.3242 (0.6); 4.1500 (0.9); 4.1408 (1.0); 4.1335 (1.0); 4.1243 (1.3); 4.1217 (1.3); 4.1126 (1.4); 4.1053 (1.2); 4.0962 (1.4); 4.0509 (0.6); 4.0430 (0.8); 4.0346 (1.2); 4.0275 (1.5); 4.0194 (1.1); 4.0159 (1.5); 4.0116 (1.5); 4.0079 (2.0); 3.9987 (2.3); 3.9928 (0.9); 3.9889 (1.2); 3.9847 (2.2); 3.9727 (1.5); 3.9667 (0.5); 3.9583 (1.1); 3.9552 (0.9); 3.9467 (1.3); 3.9380 (1.8); 3.9306 (1.8); 3.9224 (1.4); 3.9148 (2.3); 3.9099 (1.3); 3.9023 (1.4); 3.8971 (2.0); 3.8945 (2.4); 3.8867 (1.2); 3.8803 (2.3); 3.8767 (0.8); 3.8630 (1.2); 3.8597 (0.8); 3.8562 (1.2); 3.8423 (1.2); 3.8387 (1.2); 3.8315 (0.5); 3.8230 (0.7); 3.8174 (1.0); 3.8146 (0.8); 3.8062 (0.8); 3.8008 (1.4); 3.7971 (1.7); 3.7896 (0.6); 3.7849 (1.5); 3.7801 (2.1); 3.7767 (1.2); 3.7689 (0.9); 3.7633 (1.3); 3.7471 (0.8); 3.7375 (0.5); 3.7269 (1.0); 3.7229 (0.7); 3.7148 (1.2); 3.7122 (1.2); 3.7091 (1.1); 3.7056 (0.9); 3.6993 (0.8); 3.6938 (1.0); 3.6880 (0.5); 3.5492 (11.8); 3.5463 (13.6); 3.5431 (9.6); 1.9568 (0.5); 1.9484 (0.6); 1.9402 (0.8); 1.9352 (0.9); 1.9269 (0.9); 1.9231 (0.9); 1.9182 (1.2); 1.9065 (1.4); 1.8948 (2.2); 1.8898 (1.7); 1.8860 (1.8); 1.8764 (2.5); 1.8695 (2.2); 1.8602 (2.6); 1.8523 (2.0); 1.8449 (2.8); 1.8311 (1.6); 1.8272 (2.6); 1.8147 (1.4); 1.8106 (1.5); 1.8061 (1.0); 1.7979 (1.2); 1.7942 (1.4); 1.7813 (1.3); 1.7781 (1.4); 1.7616 (1.2); 1.7454 (0.7); 1.7142 (0.8); 1.7090 (0.9); 1.7065 (0.9); 1.7025 (0.9); 1.6964 (0.8); 1.6915 (1.2); 1.6853 (1.2); 1.6813 (0.8); 1.6736 (1.0); 1.6686 (1.1); 1.6638 (0.7); 1.6588 (0.9); 1.6561 (0.9); 1.6523 (1.0); 1.6391 (0.6); 1.6354 (0.6); 1.5558 (4.6); 1.5296 (0.6); 1.5180 (0.7); 1.5064 (0.6); 1.5004 (1.0); 1.4885 (0.8); 1.4801 (1.0); 1.4711 (0.8); 1.4631 (0.7); 1.4536 (0.6); 0.9687 (2.0); 0.9578 (9.4); 0.9542 (9.8); 0.9445 (16.0); 0.9399 (9.8); 0.9287 (12.7); 0.9117 (1.3); 0.9091 (1.2); 0.8879 (1.7); 0.8720 (1.7); 0.8627 (1.0); 0.8540 (1.1); 0.8495 (2.1); 0.8382 (1.3); 0.8340 (1.9); 0.0079 (1.7); −0.0002 (54.9); −0.0085 (1.5)

Example No. I.4-72

$^1$H-NMR (400.0 MHz, CDCl$_3$): δ=7.5197 (1.0); 7.4709 (2.4); 7.4659 (2.6); 7.4522 (2.4); 7.4471 (2.6); 7.3790 (4.7); 7.3563 (4.8); 7.3396 (0.9); 7.2722 (0.5); 7.2714 (0.5); 7.2706 (0.6); 7.2698 (0.7); 7.2690 (0.8); 7.2682 (0.9); 7.2674 (1.0); 7.2666 (1.2); 7.2658 (1.5); 7.2650 (1.9); 7.2608 (110.5); 7.2536 (0.5); 6.9968 (0.6); 6.3465 (8.9); 6.3365 (1.2); 4.0936 (0.8); 4.0818 (0.8); 4.0771 (0.8); 4.0663 (1.2); 4.0548 (1.0); 4.0500 (1.0); 4.0377 (0.9); 3.9838 (1.4); 3.9798 (1.3); 3.9676 (2.8); 3.9632 (1.5); 3.9501 (1.5); 3.9482 (1.6); 3.9209 (0.6); 3.8988 (1.2); 3.8944 (1.2); 3.8851 (1.0); 3.8785 (1.9); 3.8747 (1.5); 3.8723 (1.6); 3.8684 (1.4); 3.8618 (1.5); 3.8561 (2.3); 3.8508 (1.7); 3.8473 (1.8); 3.8396 (1.4); 3.8346 (1.2); 3.8216 (1.1); 3.8111 (1.0); 3.8004 (1.8); 3.7862 (1.7); 3.7799 (1.2); 3.7658 (1.2); 3.7619 (1.2); 3.7445 (1.7); 3.7399 (1.5); 3.7345 (1.0); 3.7309 (1.6); 3.7268 (2.1); 3.7233 (2.3); 3.7138 (1.5); 3.7067 (2.0); 3.6950 (1.2); 3.6904 (1.1); 3.6876 (1.1); 3.5500 (14.8); 3.5470 (15.8); 3.4470 (0.9); 3.4318 (1.0); 3.4270 (1.8); 3.4128 (1.9); 3.4053 (1.3); 3.3910 (1.3); 2.4534 (0.5); 2.4354 (0.8); 2.4168 (0.8); 2.3998 (0.5); 1.9800 (0.7); 1.9728 (0.5); 1.9598 (1.0); 1.9478 (0.9); 1.9399 (0.9); 1.9277 (1.1); 1.9153 (0.8); 1.9087 (0.6); 1.8989 (1.0); 1.8831 (1.3); 1.8774 (1.0); 1.8657 (1.4); 1.8614 (1.3); 1.8505 (1.4); 1.8441 (1.2); 1.8283 (1.5); 1.7724 (0.6); 1.7558 (1.1); 1.7388 (1.4); 1.7227 (1.3); 1.7069 (0.8); 1.6879 (1.5); 1.6716 (1.8); 1.6549 (1.5); 1.6385 (1.3); 1.6205 (0.7); 1.5600 (11.4); 1.5376 (1.2); 1.5212 (1.0); 1.5042 (1.0); 1.4891 (0.7); 1.4331 (1.4); 0.9720 (2.4); 0.9569 (15.4); 0.9511 (16.0); 0.9414 (13.9); 0.9350 (15.2); 0.9193 (1.0); 0.9150 (1.0); 0.8954 (2.1); 0.8795 (2.0); 0.8708 (0.8); 0.8653 (0.9); 0.8580 (2.1); 0.8492 (1.0); 0.8422 (2.0); 0.0079 (1.3); −0.0002 (47.2); −0.0085 (1.3)

Example No. I.4-221

$^1$H-NMR (400.6 MHz, CDCl$_3$): δ=7.3505 (0.9); 7.3476 (1.0); 7.3399 (1.7); 7.3381 (1.3); 7.3279 (1.0); 7.3251 (1.1); 7.3216 (1.0); 7.3174 (1.1); 7.3154 (1.2); 7.3128 (1.0); 7.2944 (1.0); 7.2720 (0.5); 7.2714 (0.6); 7.2706 (0.6);

7.2697 (0.7); 7.2689 (0.8); 7.2682 (0.8); 7.2673 (0.9); 7.2623 (69.0); 7.2439 (0.7); 7.2257 (0.8); 7.2214 (0.8); 7.2033 (0.8); 6.3397 (1.4); 6.3341 (2.5); 6.3307 (1.6); 3.8158 (0.5); 3.7995 (0.7); 3.7941 (0.6); 3.7769 (1.1); 3.7600 (1.2); 3.7547 (0.8); 3.7440 (0.6); 3.7408 (0.8); 3.6741 (0.5); 3.6558 (0.7); 3.5512 (2.2); 3.5483 (2.9); 3.5461 (2.8); 3.5430 (2.5); 3.5386 (2.9); 3.5356 (3.5); 3.5328 (2.6); 2.0082 (0.7); 1.8773 (0.8); 1.8654 (1.2); 1.8613 (1.2); 1.8497 (1.4); 1.8447 (1.4); 1.8360 (1.3); 1.8280 (1.4); 1.8199 (1.1); 1.8101 (0.9); 1.8012 (0.6); 1.7131 (0.5); 1.7064 (0.6); 1.6949 (0.6); 1.6927 (0.6); 1.6882 (0.7); 1.6824 (0.6); 1.6674 (0.6); 1.5855 (16.0); 1.2584 (0.6); 0.9780 (3.7); 0.9652 (5.5); 0.9621 (5.8); 0.9515 (2.8); 0.9494 (3.0); 0.9468 (2.6); −0.0002 (4.5)

Example No. I.5-71

$^{1}$H-NMR (400.0 MHz, CDCl$_{3}$): δ=7.5347 (1.6); 7.5249 (1.6); 7.5192 (1.8); 7.5158 (1.8); 7.5121 (1.2); 7.5061 (1.6); 7.5009 (1.1); 7.4932 (0.9); 7.4719 (2.0); 7.4678 (0.9); 7.4625 (0.8); 7.4532 (2.0); 7.4492 (0.9); 7.4438 (0.8); 7.3494 (4.6); 7.3266 (4.7); 7.2601 (137.4); 6.9960 (0.8); 6.3397 (11.1); 6.3345 (3.8); 4.1565 (0.8); 4.1514 (0.6); 4.1476 (0.8); 4.1396 (0.8); 4.1309 (1.2); 4.1232 (0.8); 4.1193 (1.1); 4.1117 (1.0); 4.1027 (1.2); 4.0703 (0.7); 4.0634 (0.7); 4.0545 (1.2); 4.0514 (1.3); 4.0458 (1.5); 4.0373 (2.4); 4.0299 (2.0); 4.0214 (2.1); 4.0130 (1.3); 4.0038 (0.8); 3.9943 (1.6); 3.9863 (1.0); 3.9814 (1.7); 3.9773 (1.4); 3.9672 (1.9); 3.9531 (1.9); 3.9480 (1.6); 3.9399 (1.0); 3.9373 (1.2); 3.9325 (1.5); 3.9246 (1.4); 3.9197 (1.0); 3.9120 (0.7); 3.9091 (0.8); 3.9042 (1.1); 3.8206 (0.7); 3.8036 (1.9); 3.7998 (1.9); 3.7830 (2.4); 3.7664 (1.1); 3.7340 (3.2); 3.7125 (5.7); 3.7063 (3.4); 3.6934 (2.8); 3.6901 (2.2); 3.6864 (3.2); 3.5468 (16.0); 2.0360 (0.9); 2.0193 (1.2); 2.0066 (1.2); 1.9894 (0.8); 1.9567 (0.6); 1.9376 (1.0); 1.9246 (1.2); 1.9180 (1.2); 1.9055 (1.8); 1.8937 (1.6); 1.8846 (1.4); 1.8781 (2.0); 1.8601 (2.2); 1.8430 (2.2); 1.8302 (1.8); 1.8258 (1.5); 1.8128 (1.1); 1.8089 (1.1); 1.7986 (0.8); 1.7914 (0.8); 1.7830 (0.7); 1.7652 (0.6); 1.6167 (0.6); 1.5999 (0.8); 1.5814 (1.3); 1.5602 (8.8); 1.5350 (1.3); 1.5141 (1.2); 1.4979 (1.4); 1.4886 (1.2); 1.4816 (1.1); 1.4702 (0.7); 1.3924 (0.5); 1.3735 (0.8); 1.3514 (1.2); 1.3326 (1.4); 1.3169 (1.1); 1.3110 (1.1); 1.2983 (1.1); 1.2767 (0.9); 1.2565 (1.3); 1.1424 (6.4); 1.1386 (7.1); 1.1255 (6.3); 1.1217 (6.8); 1.0625 (7.0); 1.0456 (6.7); 0.9503 (3.6); 0.9441 (7.1); 0.9318 (7.1); 0.9256 (13.7); 0.9133 (3.3); 0.9071 (5.6); 0.8542 (0.5); 0.0080 (1.7); −0.0002 (55.0); −0.0084 (1.8)

Example No. I.5-72

$^{1}$H-NMR (400.0 MHz, CDCl$_{3}$): δ=7.5188 (1.0); 7.4487 (1.2); 7.4439 (2.0); 7.4387 (2.5); 7.4346 (1.2); 7.4300 (1.5); 7.4252 (2.0); 7.4199 (2.5); 7.3650 (4.1); 7.3422 (4.1); 7.2598 (168.6); 6.9959 (0.9); 6.3440 (8.0); 4.1024 (0.7); 4.0935 (0.7); 4.0860 (0.8); 4.0759 (1.5); 4.0664 (1.0); 4.0588 (1.0); 4.0495 (1.0); 4.0001 (0.9); 3.9952 (1.0); 3.9840 (1.1); 3.9786 (2.0); 3.9758 (2.2); 3.9566 (1.5); 3.9078 (0.7); 3.9030 (0.7); 3.8884 (0.7); 3.8830 (0.8); 3.8765 (0.7); 3.8612 (0.6); 3.8563 (0.6); 3.8242 (0.9); 3.8095 (1.3); 3.8036 (2.1); 3.7893 (2.2); 3.7833 (1.5); 3.7693 (2.3); 3.7501 (1.6); 3.7367 (1.9); 3.7333 (1.8); 3.7289 (1.9); 3.7159 (2.2); 3.7062 (1.8); 3.6947 (2.6); 3.6891 (2.6); 3.6847 (3.3); 3.6745 (2.2); 3.6688 (1.7); 3.6643 (2.2); 3.5470 (16.0); 3.4565 (1.1); 3.4390 (1.3); 3.4241 (1.7); 3.4180 (1.5); 3.4026 (1.3); 2.4742 (0.7); 2.4577 (1.0); 2.4398 (1.1); 2.4227 (0.7); 2.0161 (0.8); 2.0051 (1.1); 1.9987 (1.3); 1.9888 (1.4); 1.9793 (1.3); 1.9679 (1.6); 1.9553 (1.2); 1.9484 (1.1); 1.9348 (1.1); 1.9245 (0.7); 1.5912 (0.7); 1.5526 (6.1); 1.5288 (2.5); 1.5141 (1.6); 1.4977 (1.1); 1.3756 (0.6); 1.3573 (0.6); 1.3416 (0.6); 1.3294 (0.8); 1.3111 (1.1); 1.2900 (1.0); 1.2770 (0.9); 1.2558 (1.9); 1.1431 (11.4); 1.1261 (11.0); 1.0483 (6.6); 1.0315 (6.4); 0.9594 (3.3); 0.9472 (6.0); 0.9409 (7.3); 0.9288 (11.8); 0.9224 (3.5); 0.9102 (4.7); 0.0690 (0.8); 0.0080 (2.1); −0.0002 (70.1); −0.0085 (2.4)

Example No. I.5-91

$^{1}$H-NMR (400.0 MHz, CDCl$_{3}$): δ=7.5349 (1.3); 7.5212 (1.6); 7.5187 (1.7); 7.5160 (1.5); 7.5079 (1.0); 7.5023 (1.5); 7.4891 (1.0); 7.4794 (2.6); 7.4685 (1.7); 7.4607 (2.6); 7.4498 (1.7); 7.3498 (2.9); 7.3388 (3.3); 7.3271 (3.0); 7.3159 (3.3); 7.3087 (0.6); 7.2927 (0.6); 7.2598 (206.5); 7.2220 (0.6); 7.2094 (1.0); 6.9958 (1.1); 6.3446 (8.4); 4.1110 (0.7); 4.1078 (0.7); 4.1004 (0.9); 4.0912 (0.9); 4.0823 (1.0); 4.0789 (1.0); 4.0707 (1.2); 4.0627 (1.0); 4.0431 (0.5); 4.0348 (0.5); 4.0259 (0.5); 4.0170 (1.0); 4.0144 (1.1); 4.0057 (1.2); 3.9970 (1.2); 3.9885 (1.4); 3.9832 (1.2); 3.9734 (1.7); 3.9674 (2.3); 3.9629 (0.9); 3.9552 (1.6); 3.9499 (1.4); 3.9445 (1.3); 3.9383 (1.4); 3.9351 (1.4); 3.9265 (2.1); 3.9210 (1.9); 3.9062 (1.4); 3.8987 (1.5); 3.8896 (1.6); 3.7220 (2.4); 3.7155 (3.0); 3.7004 (3.1); 3.6958 (3.0); 3.5497 (16.0); 3.5190 (0.8); 3.4460 (0.9); 3.4202 (1.0); 3.3835 (1.6); 3.3761 (1.4); 3.3563 (1.8); 3.3489 (1.5); 3.3358 (0.7); 3.3279 (0.9); 2.0371 (0.8); 2.0200 (1.1); 2.0100 (1.2); 1.8310 (1.5); 1.8004 (1.4); 1.7770 (0.7); 1.6047 (0.8); 1.5481 (14.7); 1.4797 (5.5); 1.4415 (1.4); 1.4095 (0.7); 1.3876 (0.6); 1.3680 (0.8); 1.3496 (1.2); 1.3314 (1.2); 1.3095 (1.1); 1.2908 (1.1); 1.2755 (1.0); 1.2568 (1.6); 1.2354 (1.1); 1.2219 (1.0); 1.1340 (9.4); 1.1171 (9.3); 1.0628 (4.5); 1.0571 (4.2); 1.0460 (4.4); 1.0402 (4.0); 0.9437 (4.9); 0.9285 (8.0); 0.9253 (9.4); 0.9226 (8.3); 0.9098 (4.0); 0.9067 (4.2); 0.0080 (3.1); −0.0002 (80.3); −0.0058 (1.7); −0.0085 (2.8)

Example No. I.5-221

$^{1}$H-NMR (400.0 MHz, CDCl$_{3}$): δ=7.3403 (3.2); 7.3303 (3.8); 7.3177 (3.4); 7.3080 (5.6); 7.2896 (2.1); 7.2762 (2.7); 7.2614 (66.2); 7.1829 (1.9); 7.1648 (2.1); 7.1591 (2.0); 7.1410 (2.0); 6.8890 (0.7); 6.8741 (0.8); 6.8567 (1.0); 6.8420 (1.1); 6.8286 (0.8); 6.8164 (0.8); 6.3342 (4.8); 6.3287 (9.1); 3.8612 (1.0); 3.8482 (0.9); 3.8269 (0.6); 3.8193 (1.1); 3.8018 (2.5); 3.7931 (1.7); 3.7840 (2.9); 3.7756 (1.5); 3.7661 (1.3); 3.7571 (0.7); 3.7409 (1.0); 3.7280 (1.5); 3.7127 (1.5); 3.7022 (1.4); 3.6961 (1.3); 3.6822 (1.6); 3.6632 (5.7); 3.6549 (3.1); 3.6476 (5.6); 3.6400 (2.6); 3.6299 (1.6); 3.6102 (0.8); 3.5420 (10.4); 3.5330 (13.0); 3.5171 (0.9); 3.5123 (0.8); 3.5081 (0.8); 3.5003 (0.8); 3.4957 (0.8); 3.4912 (0.8); 3.4826 (0.9); 3.4778 (0.9); 3.4689 (1.4); 3.4611 (1.6); 3.4532 (1.4); 3.4462 (1.0); 3.4351 (0.8); 3.4266 (1.1); 3.4192 (1.0); 3.4119 (1.0); 3.4035 (0.5); 3.2025 (0.6); 3.1883 (1.2); 3.1723 (1.2); 3.1540 (1.1); 3.1379 (1.0); 3.1236 (0.6); 3.1083 (0.7); 3.1032 (0.7); 3.0964 (0.7); 3.0906 (1.0); 3.0844 (0.6); 3.0733 (1.0); 3.0622 (0.6); 3.0563 (0.8); 3.0502 (0.5); 3.0430 (0.5); 2.1401 (0.9); 2.1337 (1.2); 2.1241 (1.4); 2.1177 (1.6); 2.1115 (1.4); 2.1016 (1.3); 2.0950 (1.0); 2.0853 (0.6); 1.9187 (0.6); 1.9060 (0.9); 1.9016 (0.9); 1.8847 (1.4); 1.8655 (2.0); 1.8606 (2.2); 1.8506 (2.2); 1.8437 (2.4); 1.8315 (2.7); 1.8255 (2.7);

1.8142 (2.0); 1.7950 (1.4); 1.7767 (1.2); 1.7579 (0.9); 1.7356 (1.1); 1.7255 (1.5); 1.7171 (1.8); 1.7013 (2.1); 1.6916 (1.7); 1.6825 (2.0); 1.6725 (1.5); 1.6539 (0.9); 1.5910 (7.0); 1.4842 (0.6); 1.4623 (0.8); 1.4549 (0.8); 1.4447 (0.9); 1.4363 (1.3); 1.4276 (0.6); 1.4180 (1.0); 1.3861 (0.8); 1.3739 (1.0); 1.3680 (1.1); 1.3514 (1.6); 1.3453 (1.3); 1.3335 (1.8); 1.3162 (1.6); 1.2987 (1.5); 1.2805 (1.1); 1.2577 (1.4); 1.1228 (11.1); 1.1147 (11.3); 1.1059 (11.2); 1.0977 (10.5); 1.0780 (1.2); 1.0703 (0.6); 1.0599 (1.5); 1.0408 (0.8); 0.9614 (8.3); 0.9431 (16.0); 0.9246 (7.2); 0.0079 (1.4); −0.0002 (26.5); −0.0076 (1.1)

Example No. I.6-71

Diastereomer 1—$^1$H-NMR (400.0 MHz, CDCl$_3$): δ=7.5305 (2.5); 7.5216 (2.6); 7.5117 (2.5); 7.5029 (2.4); 7.4791 (1.9); 7.4750 (2.0); 7.4604 (1.9); 7.4564 (1.9); 7.3733 (0.7); 7.3510 (6.3); 7.3282 (6.4); 7.3159 (1.4); 7.3100 (1.4); 7.2932 (1.5); 7.2604 (113.3); 6.9964 (0.6); 6.3411 (10.3); 6.3363 (3.9); 6.3192 (0.6); 4.7508 (0.6); 4.7392 (0.5); 4.1649 (1.3); 4.1559 (1.5); 4.1472 (1.4); 4.1369 (2.0); 4.1277 (1.9); 4.1192 (1.6); 4.1102 (1.8); 4.0775 (1.3); 4.0589 (2.1); 4.0522 (1.7); 4.0426 (3.1); 4.0352 (2.2); 4.0266 (2.3); 4.0181 (1.4); 4.0096 (1.6); 3.9945 (2.2); 3.9785 (2.6); 3.9650 (1.6); 3.9613 (1.5); 3.9554 (2.2); 3.9479 (2.2); 3.9395 (1.3); 3.9317 (1.5); 3.9275 (1.4); 3.9197 (1.4); 3.9114 (1.0); 3.9035 (1.1); 3.8478 (0.6); 3.8278 (1.1); 3.8233 (1.2); 3.8105 (1.5); 3.8063 (2.6); 3.8025 (2.3); 3.7897 (2.4); 3.7854 (2.9); 3.7734 (1.0); 3.7688 (1.6); 3.7473 (1.1); 3.7289 (1.6); 3.7199 (1.6); 3.7139 (2.1); 3.7024 (1.3); 3.6959 (1.5); 3.6815 (0.6); 3.6719 (0.6); 3.6156 (3.4); 3.5942 (3.9); 3.5896 (3.5); 3.5848 (3.4); 3.5684 (3.8); 3.5637 (3.9); 3.5480 (16.0); 2.2721 (0.5); 2.2567 (0.8); 2.2408 (1.4); 2.2234 (1.9); 2.2057 (1.8); 2.1886 (1.1); 1.9616 (1.0); 1.9439 (1.5); 1.9293 (1.7); 1.9225 (1.6); 1.9103 (2.1); 1.8983 (2.0); 1.8934 (2.1); 1.8810 (2.6); 1.8623 (2.3); 1.8489 (2.3); 1.8317 (1.8); 1.8193 (0.9); 1.8148 (1.1); 1.7980 (0.5); 1.5731 (6.5); 1.5505 (1.5); 1.5394 (1.3); 1.5187 (1.4); 1.5104 (1.2); 1.5020 (1.4); 1.4926 (1.1); 1.4851 (1.1); 1.4735 (0.7); 1.2566 (1.4); 1.1983 (2.5); 1.1813 (3.0); 1.1681 (14.0); 1.1512 (12.4); 1.1261 (1.8); 1.0874 (15.4); 1.0707 (14.6); 0.9742 (1.1); 0.9653 (1.1); 0.9567 (1.2); 0.9515 (1.3); 0.9450 (1.3); 0.9343 (1.0); 0.9278 (1.1); 0.8902 (1.1); 0.8844 (1.1); 0.8731 (1.2); 0.8673 (1.5); 0.8525 (1.0); 0.0691 (2.2); 0.0495 (0.6); 0.0080 (2.2); −0.0002 (47.6); −0.0085 (1.4). 2—Diastereomer$^1$H-NMR (400.0 MHz, CDCl$_3$): δ=7.5306 (1.0); 7.5218 (1.0); 7.5190 (0.8); 7.5118 (1.0); 7.5030 (0.8); 7.4792 (0.7); 7.4751 (0.7); 7.4605 (0.7); 7.4563 (0.7); 7.3511 (2.4); 7.3283 (2.6); 7.3159 (0.8); 7.2930 (0.9); 7.2600 (87.8); 6.3414 (3.8); 6.3366 (1.4); 4.1561 (0.5); 4.1371 (0.7); 4.1277 (0.6); 4.1193 (0.6); 4.1103 (0.7); 4.0776 (0.5); 4.0592 (0.8); 4.0522 (0.6); 4.0428 (1.1); 4.0354 (0.8); 4.0265 (0.9); 4.0096 (0.6); 3.9946 (0.8); 3.9786 (1.0); 3.9650 (0.6); 3.9556 (0.8); 3.9481 (0.8); 3.9396 (0.5); 3.9318 (0.5); 3.9277 (0.5); 3.8063 (1.0); 3.8025 (0.9); 3.7898 (0.9); 3.7856 (1.1); 3.7688 (0.6); 3.7288 (0.6); 3.7137 (0.8); 3.6958 (0.6); 3.6156 (1.3); 3.5942 (1.4); 3.5896 (1.2); 3.5849 (1.2); 3.5685 (1.3); 3.5637 (1.4); 3.5482 (6.0); 2.2407 (0.5); 2.2235 (0.7); 2.2056 (0.7); 1.9436 (0.5); 1.9304 (0.6); 1.9098 (0.7); 1.8987 (0.8); 1.8936 (0.8); 1.8812 (1.0); 1.8653 (0.9); 1.8490 (0.9); 1.8317 (0.7); 1.5451 (16.0); 1.5117 (0.6); 1.5019 (0.6); 1.2561 (0.5); 1.1978 (0.8); 1.1810 (1.0); 1.1682 (5.2); 1.1512 (4.7); 1.1424 (1.0); 1.1254 (0.8); 1.0875 (5.8); 1.0708 (5.5); 0.9504 (0.5); 0.8669 (0.6); 0.0079 (1.6); −0.0002 (36.7); −0.0085 (1.3)

Example No. I.6-72

$^1$H-NMR (400.0 MHz, CDCl$_3$): δ=7.4494 (0.8); 7.4422 (0.9); 7.4313 (0.9); 7.4234 (0.8); 7.3668 (1.7); 7.3440 (1.6); 7.2600 (52.6); 7.2486 (4.5); 6.3444 (2.9); 3.9972 (0.5); 3.9828 (1.0); 3.9637 (0.6); 3.8045 (0.8); 3.7905 (0.9); 3.7701 (0.8); 3.7381 (0.8); 3.7293 (0.9); 3.7169 (0.8); 3.6896 (0.6); 3.5670 (1.2); 3.5476 (7.5); 3.4456 (0.7); 3.4240 (0.7); 2.4434 (0.5); 2.2053 (0.6); 2.1849 (0.6); 1.5447 (16.0); 1.5014 (0.5); 1.1698 (5.2); 1.1530 (4.8); 1.0714 (4.6); 1.0548 (4.6); 0.8641 (0.6); −0.0002 (21.5)

Example No. I.8-1

$^1$H-NMR (400.0 MHz, CDCl$_3$): δ=7.5183 (1.0); 7.4509 (1.8); 7.4325 (1.8); 7.3573 (1.8); 7.3347 (1.8); 7.2595 (177.5); 6.9955 (1.0); 6.3526 (2.7); 4.2560 (1.9); 4.2480 (0.9); 4.2444 (1.7); 4.2404 (1.0); 4.2326 (2.0); 3.6814 (7.7); 3.5542 (5.0); 3.5493 (1.9); 3.5426 (1.7); 3.5390 (1.0); 3.5309 (1.9); 3.3345 (15.6); 1.5447 (16.0); 0.0079 (2.0); −0.0002 (66.1); −0.0085 (1.8)

Example No. I.8-71

$^1$H-NMR (400.0 MHz, CDCl$_3$): δ=7.4556 (3.8); 7.4533 (3.8); 7.4373 (3.8); 7.4350 (3.8); 7.3539 (6.5); 7.3313 (6.4); 7.2612 (22.7); 6.3513 (5.6); 6.3468 (5.7); 4.1694 (1.5); 4.1634 (3.1); 4.1439 (3.9); 4.1371 (2.3); 4.0831 (1.2); 4.0732 (1.3); 4.0661 (1.8); 4.0598 (1.6); 4.0562 (1.7); 4.0501 (4.1); 4.0468 (4.1); 4.0413 (1.6); 4.0389 (1.7); 4.0333 (0.9); 4.0239 (2.5); 4.0222 (2.5); 4.0071 (1.2); 4.0052 (1.1); 3.8570 (1.4); 3.8399 (2.5); 3.8359 (2.4); 3.8232 (1.6); 3.8189 (3.6); 3.8026 (1.6); 3.7669 (1.6); 3.7492 (2.3); 3.7335 (2.0); 3.7284 (1.7); 3.7129 (0.9); 3.6874 (14.5); 3.6848 (15.2); 3.6468 (0.6); 3.5553 (11.1); 3.5523 (16.0); 3.5491 (11.7); 1.9827 (0.5); 1.9758 (0.6); 1.9653 (0.9); 1.9541 (0.9); 1.9444 (1.1); 1.9392 (0.8); 1.9325 (1.2); 1.9248 (1.1); 1.9182 (1.0); 1.9142 (1.3); 1.9027 (1.5); 1.8991 (1.5); 1.8941 (1.0); 1.8839 (2.8); 1.8790 (1.5); 1.8666 (2.8); 1.8631 (2.1); 1.8534 (0.9); 1.8492 (1.3); 1.8460 (1.4); 1.8370 (0.5); 1.8286 (0.7); 1.5678 (0.6); 1.5579 (5.6); 1.5515 (1.4); 1.5424 (0.8); 1.5380 (0.8); 1.5339 (1.0); 1.5300 (1.1); 1.5206 (0.8); 1.5167 (0.8); 1.5024 (0.6); 1.2561 (0.7); 0.0080 (1.0); −0.0002 (28.3); −0.0084 (1.0)

Example No. I.8-72

$^1$H-NMR (400.0 MHz, CDCl$_3$): δ=7.4132 (1.8); 7.4110 (1.8); 7.3949 (1.8); 7.3927 (1.8); 7.3672 (3.1); 7.3446 (3.1); 7.2602 (33.7); 6.3546 (4.8); 4.1376 (0.7); 4.1212 (0.8); 4.1106 (1.2); 4.0943 (1.2); 4.0203 (1.6); 4.0007 (1.7); 3.9932 (1.1); 3.9736 (1.1); 3.8260 (0.9); 3.8125 (1.0); 3.8055 (0.7); 3.7916 (0.6); 3.7776 (1.2); 3.7596 (1.4); 3.7554 (1.6); 3.7378 (2.2); 3.7194 (1.3); 3.7015 (1.1); 3.6804 (0.7); 3.6561 (11.2); 3.5559 (7.3); 3.5529 (7.3); 3.5036 (1.2); 3.4900 (1.3); 3.4813 (1.1); 3.4679 (1.0); 2.5140 (0.6); 2.0444 (0.8); 1.9916 (0.6); 1.9711 (0.6); 1.9581 (0.5); 1.5876 (0.5); 1.5705 (0.7); 1.5534 (0.7); 1.5403 (16.0); 1.2590 (0.9); 0.8818 (1.1); 0.0079 (1.4); −0.0002 (42.1); −0.0085 (1.5)

Example No. I.8-271

$^1$H-NMR (400.0 MHz, CDCl$_3$): δ=7.5191 (1.1); 7.3651 (7.4); 7.3428 (7.2); 7.2603 (202.8); 7.2103 (1.2); 7.1112

(4.1); 7.0928 (6.0); 7.0745 (3.8); 6.9962 (1.1); 6.7496 (1.2); 6.7299 (1.2); 6.3497 (6.8); 6.3426 (6.4); 5.2988 (5.1); 4.9359 (1.3); 4.4655 (1.2); 4.4591 (1.3); 4.4534 (1.3); 4.4469 (1.2); 3.8564 (0.7); 3.8523 (0.7); 3.8345 (2.2); 3.8162 (2.5); 3.7981 (1.2); 3.7939 (1.2); 3.7863 (2.1); 3.7804 (2.2); 3.7728 (2.1); 3.7669 (2.4); 3.7625 (4.8); 3.7563 (2.9); 3.7487 (4.9); 3.7420 (4.7); 3.7272 (3.7); 3.7195 (1.6); 3.7054 (1.5); 3.6196 (15.1); 3.6167 (16.0); 3.5822 (2.6); 3.5759 (2.2); 3.5517 (10.6); 3.5484 (11.9); 3.5446 (12.3); 3.5413 (10.3); 2.2411 (1.0); 2.2232 (1.7); 2.2200 (1.2); 2.2079 (1.3); 2.2054 (1.3); 2.2019 (1.7); 2.1902 (2.0); 2.1868 (1.5); 2.1842 (1.2); 2.1721 (1.3); 2.1688 (1.9); 2.1509 (1.1); 2.0053 (0.5); 1.7305 (0.7); 1.7228 (0.8); 1.7173 (0.8); 1.7117 (1.1); 1.7036 (1.1); 1.6971 (1.0); 1.6897 (1.0); 1.6841 (0.8); 1.6779 (0.7); 1.6699 (0.6); 1.5550 (4.8); 1.2554 (1.8); 0.0689 (14.7); 0.0080 (2.4); −0.0002 (85.2); −0.0085 (2.4); −0.0501 (0.6)

Example No. I.12-71

$^1$H-NMR (400.0 MHz, CDCl$_3$): δ=7.5355 (0.6); 7.5317 (0.6); 7.5176 (0.6); 7.5129 (0.5); 7.3540 (1.2); 7.3311 (1.2); 7.2598 (43.5); 4.1310 (0.6); 4.0497 (0.6); 4.0064 (0.7); 3.9911 (0.6); 3.9883 (0.5); 3.9809 (0.5); 3.7488 (0.6); 3.7325 (1.0); 3.7156 (1.0); 3.6957 (0.6); 3.5474 (3.2); 3.5421 (3.5); 3.5370 (1.9); 2.2520 (1.0); 2.2405 (2.6); 2.2290 (2.5); 2.2175 (0.9); 1.9789 (0.5); 1.9605 (0.6); 1.9435 (0.5); 1.9129 (0.5); 1.8807 (0.7); 1.8627 (0.8); 1.8516 (0.8); 1.8460 (0.7); 1.8335 (0.6); 1.5402 (16.0); 1.0789 (2.0); 1.0605 (3.8); 1.0421 (1.7); 0.0075 (1.4); −0.0002 (15.4); −0.0084 (0.6)

Example No. I.12-72

$^1$H-NMR (400.0 MHz, CDCl$_3$): δ=7.4641 (0.9); 7.4595 (0.9); 7.4454 (0.8); 7.4407 (0.8); 7.3689 (1.3); 7.3462 (1.2); 7.2599 (46.1); 5.2985 (1.5); 3.9504 (0.6); 3.8097 (0.6); 3.7957 (0.6); 3.7761 (0.7); 3.7589 (0.6); 3.7545 (0.6); 3.7381 (0.9); 3.7304 (0.5); 3.7251 (0.8); 3.7209 (1.2); 3.7092 (1.0); 3.7043 (1.0); 3.6886 (0.6); 3.5533 (1.8); 3.5482 (4.1); 3.5427 (4.1); 3.5373 (1.6); 3.4568 (0.7); 3.4347 (0.5); 2.2518 (1.3); 2.2404 (3.5); 2.2288 (3.5); 2.2173 (1.2); 1.9843 (0.5); 1.9679 (0.7); 1.9642 (0.7); 1.9495 (0.8); 1.9290 (0.6); 1.8624 (0.6); 1.8458 (0.6); 1.5585 (0.7); 1.5414 (16.0); 1.0712 (2.2); 1.0528 (4.3); 1.0344 (1.9); 0.0078 (1.1); −0.0002 (17.5); −0.0085 (0.7)

Example No. I.14-72

$^1$H-NMR (400.0 MHz, CDCl$_3$): δ=7.2595 (57.5); 6.2266 (1.7); 3.5467 (1.2); 3.5415 (1.1); 2.2410 (1.0); 2.2292 (1.0); 1.5330 (16.0); 1.4813 (0.6); 0.9650 (0.7); 0.9536 (1.4); 0.9485 (1.0); 0.9399 (1.9); 0.9250 (1.3); 0.0078 (0.8); −0.0002 (22.0); −0.0080 (1.0)

Example No. I.14-91

$^1$H-NMR (400.0 MHz, CDCl$_3$): δ=7.2594 (42.0); 3.5396 (0.5); 1.5350 (16.0); 0.9566 (0.6); 0.9511 (0.6); 0.9406 (0.7); 0.9350 (0.6); −0.0002 (14.2); −0.0084 (0.6)

Example No. I.42-71

$^1$H-NMR (400.0 MHz, CDCl$_3$): δ=7.5184 (0.9); 7.3265 (2.4); 7.3038 (2.4); 7.2907 (2.2); 7.2758 (0.6); 7.2720 (2.6); 7.2686 (1.1); 7.2678 (1.1); 7.2670 (1.3); 7.2662 (1.4); 7.2595 (171.6); 7.2092 (1.3); 6.9956 (1.0); 6.3599 (3.3); 4.0376 (2.5); 4.0274 (1.6); 4.0230 (1.9); 3.5622 (4.7); 3.5595 (4.8); 3.3916 (0.6); 3.3884 (0.6); 3.1374 (3.5); 3.1325 (3.4); 1.5744 (0.7); 1.5387 (15.2); 1.5151 (0.7); 1.5038 (1.4); 1.4951 (1.1); 1.4631 (0.5); 1.3242 (16.0); 1.2841 (0.6); 1.2701 (1.1); 1.2567 (0.5); 1.2341 (0.8); 1.2195 (0.7); 1.2097 (0.8); 1.2059 (1.2); 0.0080 (2.0); −0.0002 (71.0); −0.0085 (2.2); −0.0506 (0.6)

Example No. I.42-72

$^1$H-NMR (400.0 MHz, CDCl$_3$): δ=7.3060 (3.0); 7.2836 (3.0); 7.2690 (0.5); 7.2599 (81.8); 6.9494 (2.9); 6.9312 (2.9); 6.3268 (4.4); 4.0856 (0.6); 4.0680 (0.6); 4.0582 (1.0); 4.0423 (1.0); 3.9787 (0.9); 3.9756 (0.9); 3.9594 (1.0); 3.9560 (0.9); 3.9518 (0.6); 3.9486 (0.6); 3.9324 (0.6); 3.9290 (0.6); 3.7782 (0.8); 3.7636 (0.8); 3.7578 (0.6); 3.7437 (0.5); 3.7096 (0.9); 3.7063 (0.8); 3.6889 (1.5); 3.6734 (1.0); 3.6663 (0.9); 3.5364 (6.2); 3.5334 (6.5); 3.3840 (0.8); 3.3698 (0.8); 3.3630 (0.7); 3.3494 (0.7); 2.4233 (0.5); 2.2017 (16.0); 2.1577 (14.4); 1.5484 (1.4); 1.4985 (0.6); 1.4827 (0.6); 1.4668 (0.6); 1.2560 (2.7); 0.8802 (0.6); 0.8531 (0.6); 0.0080 (1.0); −0.0002 (35.4); −0.0085 (1.0)

Example No. I.48-71

$^1$H-NMR (400.0 MHz, CDCl$_3$): δ=7.3292 (2.2); 7.3067 (3.9); 7.2888 (2.0); 7.2608 (27.8); 6.3583 (3.2); 4.1147 (0.8); 4.1055 (1.2); 4.0965 (0.6); 4.0888 (1.0); 4.0831 (1.6); 4.0740 (0.8); 4.0704 (0.6); 4.0394 (0.9); 4.0211 (1.0); 4.0081 (0.9); 3.8519 (0.8); 3.8481 (0.8); 3.8311 (1.3); 3.8147 (0.6); 3.7679 (0.7); 3.7508 (0.6); 3.5589 (4.3); 3.1366 (3.6); 3.1328 (3.8); 1.8940 (0.9); 1.8895 (0.6); 1.8774 (0.8); 1.8735 (0.8); 1.8565 (0.6); 1.5567 (2.0); 1.3283 (16.0); 1.2700 (0.8); 1.2410 (0.6); 1.2195 (0.6); 1.2103 (0.6); 1.2058 (0.8); −0.0002 (10.8)

Example No. I.48-72

$^1$H-NMR (400.0 MHz, CDCl$_3$): δ=7.3382 (1.7); 7.3155 (1.7); 7.2963 (1.6); 7.2779 (1.7); 7.2651 (0.6); 7.2642 (0.8); 7.2601 (41.8); 6.3600 (2.5); 4.0840 (0.6); 4.0677 (0.6); 4.0569 (0.9); 4.0405 (0.9); 3.9738 (1.0); 3.9542 (1.0); 3.9467 (0.6); 3.9271 (0.6); 3.8456 (0.6); 3.8327 (0.9); 3.8156 (0.6); 3.8116 (1.0); 3.7938 (0.6); 3.7425 (0.7); 3.7235 (0.5); 3.5614 (4.0); 3.5586 (4.0); 3.5467 (0.6); 3.5384 (0.5); 3.1124 (5.6); 3.0120 (0.6); 1.3111 (16.0); 1.2929 (1.9); 1.2705 (0.7); 1.2196 (0.6); 1.2080 (0.7); 0.0079 (0.5); −0.0002 (16.4); −0.0085 (0.5)

Example No. I.48-73

$^1$H-NMR (400.0 MHz, CDCl$_3$): δ=7.3371 (0.6); 7.3145 (0.6); 7.2942 (0.7); 7.2755 (1.0); 7.2593 (74.0); 6.3593 (1.3); 3.5591 (2.1); 3.1085 (2.5); 1.5314 (16.0); 1.3083 (7.0); 1.2623 (1.1); 1.2471 (0.9); 1.2224 (1.5); 1.2071 (1.6); 0.0080 (1.0); −0.0002 (28.2); −0.0084 (1.1)

Example No. I.48-81

$^1$H-NMR (400.0 MHz, CDCl$_3$): δ=7.3323 (1.9); 7.3094 (1.9); 7.3040 (1.5); 7.2856 (1.5); 7.2664 (0.6); 7.2656 (0.7); 7.2648 (0.8); 7.2639 (1.1); 7.2598 (65.4); 6.3605 (2.7); 4.1032 (0.8); 4.0835 (0.7); 4.0760 (1.1); 4.0563 (1.2); 4.0142 (1.2); 3.9978 (1.3); 3.9870 (0.6); 3.9705 (0.7); 3.5633 (4.1); 3.5603 (4.3); 3.1239 (3.7); 3.1224 (3.9); 2.8527 (0.6); 2.8378 (0.6); 2.0039 (0.8); 1.9975 (0.7);

Example No. I.48-82

¹H-NMR (400.0 MHz, CDCl3): δ=7.3366 (1.2); 7.2593 (67.6); 7.2564 (64.9); 7.2508 (34.0); 6.3598 (1.6); 4.0843 (0.7); 4.0355 (0.6); 3.5596 (3.8); 3.1158 (2.7); 2.8813 (1.0); 2.8630 (1.4); 2.5976 (0.6); 2.1008 (0.6); 1.5306 (16.0); 1.5277 (15.3); 1.5221 (8.1); 1.3151 (7.9); −0.0002 (24.0); −0.0031 (23.2); −0.0087 (12.6)

Example No. I.48-91

¹H-NMR (400.0 MHz, CDCl3): δ=7.5184 (0.9); 7.3265 (2.4); 7.3038 (2.4); 7.2907 (2.2); 7.2758 (0.6); 7.2720 (2.6); 7.2686 (1.1); 7.2678 (1.1); 7.2670 (1.3); 7.2662 (1.4); 7.2595 (171.6); 7.2092 (1.3); 6.9956 (1.0); 6.3599 (3.3); 4.0376 (2.5); 4.0274 (1.6); 4.0230 (1.9); 3.5622 (4.7); 3.5595 (4.8); 3.3916 (0.6); 3.3884 (0.6); 3.1374 (3.5); 3.1325 (3.4); 1.5744 (0.7); 1.5387 (15.2); 1.5151 (0.7); 1.5038 (1.4); 1.4951 (1.1); 1.4631 (0.5); 1.3242 (16.0); 1.2841 (0.6); 1.2701 (1.1); 1.2567 (0.5); 1.2341 (0.8); 1.2195 (0.7); 1.2097 (0.8); 1.2059 (1.2); 0.0080 (2.0); −0.0002 (71.0); −0.0085 (2.2); −0.0506 (0.6)

Example No. I.48-93

¹H-NMR (400.0 MHz, CDCl3): δ=7.5183 (0.7); 7.3344 (1.5); 7.3117 (1.6); 7.2861 (1.7); 7.2594 (115.4); 6.9954 (0.6); 6.3597 (2.6); 3.9796 (0.6); 3.9694 (0.6); 3.9501 (0.7); 3.9418 (0.7); 3.9197 (2.6); 3.9036 (2.6); 3.5617 (4.0); 3.5591 (3.9); 3.4026 (0.6); 3.3973 (0.7); 3.3731 (1.2); 3.3681 (1.2); 3.3437 (0.6); 3.3387 (0.6); 3.1160 (5.2); 2.0436 (1.1); 1.6081 (0.6); 1.5766 (0.8); 1.5325 (15.9); 1.3793 (0.6); 1.3676 (0.6); 1.3464 (0.6); 1.3345 (0.7); 1.3177 (16.0); 1.2897 (0.5); 1.2765 (0.5); 1.2587 (1.3); 0.0080 (1.7); −0.0002 (44.1); −0.0085 (1.4)

Example No. I.48-121

¹H-NMR (400.0 MHz, CDCl₃): δ=7.5182 (0.5); 7.3372 (1.1); 7.3281 (0.6); 7.3234 (0.6); 7.3145 (1.1); 7.3051 (0.6); 7.2594 (86.1); 6.3602 (1.6); 3.8787 (0.6); 3.8738 (0.6); 3.8675 (0.6); 3.8352 (0.5); 3.5596 (2.7); 3.1196 (1.0); 3.1166 (1.0); 3.1113 (1.1); 3.1080 (1.0); 3.0915 (0.6); 1.5312 (16.0); 1.3010 (7.9); 1.2943 (2.5); 1.2586 (0.5); 1.2026 (2.0); 0.8819 (0.6); 0.0079 (1.0); −0.0002 (33.9); −0.0085 (1.4)

Example No. I.48-221

¹H-NMR (400.0 MHz, CDCl₃): δ=7.3103 (0.9); 7.2876 (1.0); 7.2594 (77.1); 6.3567 (1.2); 3.5597 (1.8); 3.5569 (1.8); 3.1559 (0.5); 3.1446 (0.5); 3.1241 (0.5); 1.5359 (16.0); 1.3178 (3.1); 1.3132 (2.1); 1.3074 (1.7); 0.0079 (1.1); −0.0002 (28.7); −0.0085 (1.0)

Example No. I.49-71

¹H-NMR (400.0 MHz, CDCl₃): δ=7.5196 (0.7); 7.4294 (4.1); 7.4269 (4.4); 7.4107 (4.2); 7.4082 (4.4); 7.3731 (8.2); 7.3501 (8.2); 7.2728 (0.5); 7.2721 (0.6); 7.2712 (0.6); 7.2705 (0.7); 7.2696 (0.8); 7.2689 (0.9); 7.2680 (1.1); 7.2672 (1.2); 7.2664 (1.4); 7.2656 (1.7); 7.2648 (2.2); 7.2607 (122.4); 6.9966 (0.7); 6.3693 (1.3); 6.3586 (6.3); 6.3546 (6.2); 4.1857 (1.4); 4.1770 (1.7); 4.1735 (1.1); 4.1709 (1.0); 4.1651 (1.1); 4.1626 (1.2); 4.1579 (1.7); 4.1492 (2.6); 4.1461 (1.4); 4.1436 (1.2); 4.1376 (1.8); 4.1353 (1.8); 4.1282 (0.5); 4.1207 (0.7); 4.1113 (1.5); 4.1039 (1.7); 4.0943 (1.6); 4.0863 (1.8); 4.0792 (1.3); 4.0690 (0.8); 4.0621 (0.6); 4.0365 (2.1); 4.0203 (3.9); 4.0090 (1.4); 4.0034 (1.9); 3.9925 (2.8); 3.9756 (1.4); 3.8871 (0.8); 3.8832 (0.7); 3.8700 (1.6); 3.8662 (2.5); 3.8627 (1.2); 3.8535 (3.0); 3.8492 (3.0); 3.8455 (2.0); 3.8325 (1.1); 3.8284 (1.0); 3.7965 (1.0); 3.7927 (0.9); 3.7764 (2.0); 3.7586 (1.8); 3.7422 (0.6); 3.7042 (1.1); 3.6887 (1.7); 3.6835 (1.4); 3.6719 (1.5); 3.6682 (1.8); 3.6514 (1.2); 3.5631 (11.1); 3.5600 (16.0); 3.5569 (11.6); 2.7333 (1.6); 2.7185 (1.7); 2.6938 (2.6); 2.6790 (2.6); 2.5796 (3.0); 2.5764 (1.6); 2.5589 (2.8); 2.5557 (1.5); 2.5401 (1.8); 2.5370 (1.0); 2.5194 (1.7); 2.5163 (0.9); 2.0187 (0.7); 2.0140 (0.8); 2.0016 (1.3); 1.9944 (0.9); 1.9896 (0.8); 1.9808 (1.7); 1.9730 (0.8); 1.9683 (1.3); 1.9512 (1.2); 1.9363 (0.7); 1.9331 (0.8); 1.9246 (1.1); 1.9163 (1.4); 1.9072 (3.1); 1.9034 (1.8); 1.9001 (1.7); 1.8907 (2.8); 1.8871 (2.4); 1.8728 (1.4); 1.8699 (2.1); 1.8524 (0.8); 1.6316 (0.5); 1.6236 (0.8); 1.6134 (1.1); 1.6096 (0.9); 1.6015 (1.1); 1.5919 (1.5); 1.5833 (1.2); 1.5743 (1.3); 1.5572 (8.3); 1.3735 (16.0); 1.3566 (15.6); 1.2562 (0.9); 0.0080 (1.5); −0.0002 (47.8); −0.0085 (1.3)

Example No. I.49-72

¹H-NMR (400.0 MHz, CDCl₃): δ=7.4106 (1.7); 7.4041 (2.3); 7.4005 (2.0); 7.3919 (1.8); 7.3854 (2.5); 7.3803 (6.7); 7.3573 (6.1); 7.2683 (0.5); 7.2674 (0.6); 7.2666 (0.7); 7.2658 (0.9); 7.2650 (1.2); 7.2642 (1.6); 7.2608 (84.6); 7.2544 (0.8); 7.2536 (0.6); 7.2528 (0.5); 6.3611 (5.5); 4.1353 (0.6); 4.1308 (0.6); 4.1189 (0.7); 4.1145 (1.5); 4.1082 (1.0); 4.1036 (1.0); 4.0983 (1.0); 4.0917 (1.0); 4.0874 (2.4); 4.0712 (1.5); 4.0250 (1.1); 4.0216 (1.1); 4.0054 (1.2); 4.0011 (1.5); 3.9971 (1.5); 3.9770 (1.4); 3.9697 (0.8); 3.9531 (0.7); 3.9496 (0.7); 3.8716 (0.9); 3.8576 (1.0); 3.8508 (2.0); 3.8366 (3.3); 3.8302 (1.5); 3.8170 (3.7); 3.7955 (1.9); 3.7629 (1.2); 3.7437 (2.6); 3.7244 (2.0); 3.7051 (0.9); 3.6919 (1.1); 3.6751 (1.5); 3.6715 (1.4); 3.6548 (1.6); 3.6393 (1.1); 3.5730 (2.8); 3.5637 (9.4); 3.5603 (14.9); 3.5571 (10.6); 3.5533 (4.2); 3.5372 (2.2); 2.7027 (0.6); 2.6980 (0.8); 2.6926 (0.6); 2.6879 (0.6); 2.6835 (0.8); 2.6775 (0.6); 2.6633 (1.0); 2.6587 (1.3); 2.6533 (1.1); 2.6486 (1.0); 2.6439 (1.3); 2.6383 (0.9); 2.5794 (0.9); 2.5615 (1.1); 2.5423 (2.0); 2.5389 (2.5); 2.5354 (1.4); 2.5219 (1.4); 2.5184 (2.1); 2.5147 (1.2); 2.5030 (0.8); 2.4996 (1.3); 2.4961 (0.8); 2.4827 (0.8); 2.4791 (1.3); 2.4754 (0.8); 2.0520 (0.8); 2.0389 (1.1); 2.0296 (0.8); 2.0201 (1.2); 2.0070 (0.8); 1.6590 (0.7); 1.6413 (1.1); 1.6271 (1.4); 1.6074 (1.4); 1.5925 (1.1); 1.5748 (2.4); 1.3725 (16.0); 1.3555 (15.6); 1.2557 (0.8); 0.0080 (1.0); −0.0002 (35.6); −0.0085 (1.0)

Example No. I.49-91

¹H-NMR (400.0 MHz, CDCl₃): δ=7.5192 (1.1); 7.4199 (3.9); 7.4168 (3.7); 7.4122 (0.8); 7.4012 (3.9); 7.3981 (3.6); 7.3894 (0.6); 7.3718 (6.7); 7.3489 (6.7); 7.2748 (0.5); 7.2740 (0.6); 7.2732 (0.6); 7.2717 (0.8); 7.2708 (0.9); 7.2701 (1.0); 7.2692 (1.1); 7.2685 (1.3); 7.2677 (1.4); 7.2668 (1.7); 7.2660 (2.0); 7.2652 (2.5); 7.2644 (3.2); 7.2603 (192.6); 7.2539 (1.5); 7.2514 (0.5); 6.9963 (1.1); 6.4032 (0.6); 6.3602 (5.9); 6.3561 (6.0); 5.9753 (1.4); 4.1184 (1.2); 4.1100 (1.4); 4.0981 (0.7); 4.0894 (2.4); 4.0810 (2.5); 4.0781 (1.9); 4.0691 (1.6); 4.0522 (2.6);

4.0355 (2.7); 4.0323 (1.6); 4.0302 (1.5); 4.0231 (0.9); 4.0147 (1.5); 4.0127 (1.5); 4.0064 (1.5); 4.0009 (1.7); 3.9951 (1.4); 3.9859 (1.4); 3.9714 (1.3); 3.9671 (1.3); 3.9612 (1.2); 3.7055 (1.0); 3.6905 (1.5); 3.6735 (1.4); 3.6694 (1.6); 3.6529 (1.1); 3.5949 (0.9); 3.5917 (1.0); 3.5642 (10.4); 3.5610 (15.2); 3.5576 (11.4); 3.5298 (1.1); 3.5210 (1.0); 3.5036 (1.0); 3.4972 (0.7); 3.4451 (1.1); 3.4407 (1.0); 3.4174 (1.9); 3.4127 (1.5); 3.3889 (0.9); 2.7355 (1.2); 2.7226 (1.2); 2.6957 (2.0); 2.6813 (1.9); 2.5817 (2.3); 2.5607 (2.2); 2.5422 (1.5); 2.5213 (1.4); 1.8716 (1.1); 1.8589 (0.9); 1.8426 (0.9); 1.7458 (1.0); 1.7284 (1.0); 1.5951 (1.4); 1.5627 (4.3); 1.5527 (4.0); 1.5347 (4.4); 1.5247 (3.8); 1.5179 (4.0); 1.5098 (3.1); 1.4869 (1.8); 1.4780 (1.5); 1.4685 (0.7); 1.4474 (0.5); 1.3679 (16.0); 1.3510 (15.7); 1.3238 (1.0); 1.3092 (0.9); 1.2951 (0.8); 1.2846 (0.7); 1.2558 (1.6); 0.0080 (2.6); 0.0064 (0.9); 0.0056 (1.0); 0.0048 (1.2); 0.0039 (1.5); −0.0002 (78.4); −0.0067 (0.7); −0.0084 (2.1)

Example No. I.54-71

$^1$H-NMR (400.0 MHz, CDCl$_3$): $^1$H-NMR (400.0 MHz, CDCl$_3$): δ=7.3208 (1.3); 7.2979 (1.7); 7.2912 (1.7); 7.2726 (2.6); 7.2593 (70.2); 4.0864 (0.7); 3.5567 (1.6); 3.5515 (1.5); 3.1329 (1.5); 3.1297 (1.5); 2.2606 (0.5); 2.2492 (1.4); 2.2378 (1.5); 2.2262 (0.5); 1.5330 (16.0); 1.3269 (6.7); −0.0002 (24.8); −0.0084 (0.8)

Example No. I.54-82

$^1$H-NMR (400.0 MHz, CDCl$_3$): δ=7.5183 (0.5); 7.3313 (1.4); 7.3086 (1.5); 7.2883 (1.4); 7.2697 (1.9); 7.2594 (89.8); 5.2984 (0.6); 4.0886 (0.6); 4.0728 (0.6); 4.0707 (0.6); 4.0401 (0.6); 4.0245 (0.6); 3.5636 (1.1); 3.5585 (3.1); 3.5531 (3.2); 3.5477 (1.2); 3.1156 (4.8); 2.9201 (0.6); 2.9102 (0.6); 2.8940 (0.6); 2.8830 (1.3); 2.8686 (1.5); 2.8636 (1.5); 2.8492 (1.3); 2.6274 (0.6); 2.6084 (0.7); 2.5822 (0.7); 2.2619 (0.8); 2.2504 (2.7); 2.2389 (2.9); 2.2274 (1.0); 1.5303 (16.0); 1.3159 (14.4); 0.0080 (1.1); −0.0002 (35.1); −0.0085 (1.4)

Example No. I.54-221

Diastereomer 1—$^1$H-NMR (400.0 MHz, CDCl$_3$): δ=7.3038 (3.1); 7.2871 (1.2); 7.2813 (2.5); 7.2599 (71.2); 5.2983 (2.7); 3.9383 (0.5); 3.8513 (0.7); 3.8472 (0.6); 3.8308 (0.9); 3.7432 (0.9); 3.7266 (0.6); 3.7227 (0.6); 3.5559 (4.7); 3.5505 (4.9); 3.5451 (1.9); 3.1943 (0.6); 3.1787 (0.8); 3.1742 (0.7); 3.1486 (1.5); 3.1439 (1.6); 3.1151 (1.5); 3.1107 (1.4); 3.0847 (0.6); 3.0805 (0.6); 2.2599 (1.2); 2.2485 (3.9); 2.2369 (4.1); 2.2254 (1.4); 1.9451 (0.5); 1.9179 (0.8); 1.9023 (1.2); 1.8833 (1.3); 1.8662 (0.8); 1.5497 (16.0); 1.3156 (8.3); 1.3076 (7.1); 1.2954 (0.5); 1.1850 (0.5); 0.0080 (0.8); −0.0002 (26.3); −0.0084 (0.9). Diastereomer 2—$^1$H-NMR (400.0 MHz, CDCl$_3$): δ=7.3105 (0.7); 7.3038 (5.6); 7.2870 (2.3); 7.2837 (2.7); 7.2812 (4.5); 7.2601 (82.6); 6.1429 (0.8); 5.2984 (6.5); 3.9465 (0.9); 3.9382 (0.9); 3.9292 (0.9); 3.9207 (0.9); 3.8682 (0.7); 3.8512 (1.4); 3.8472 (1.2); 3.8349 (0.9); 3.8307 (1.8); 3.8144 (0.9); 3.7606 (0.9); 3.7433 (1.7); 3.7266 (1.1); 3.7230 (1.1); 3.7062 (0.6); 3.5608 (3.0); 3.5558 (8.8); 3.5504 (9.1); 3.5450 (3.6); 3.5344 (0.6); 3.5236 (0.6); 3.5210 (0.6); 3.5152 (0.7); 3.5125 (0.7); 3.5083 (0.7); 3.5058 (0.6); 3.4999 (0.6); 3.4972 (0.6); 3.2110 (0.6); 3.2072 (0.6); 3.1983 (0.6); 3.1941 (1.1); 3.1899 (0.6); 3.1786 (1.5); 3.1742 (1.4); 3.1637 (0.6); 3.1596 (0.9); 3.1552 (0.6); 3.1485 (2.8); 3.1438 (3.0); 3.1151 (2.8); 3.1106 (2.6); 3.0848 (1.0); 3.0803 (1.1); 2.2598 (2.2); 2.2484 (7.3); 2.2368 (7.7); 2.2253 (2.6); 2.0434 (1.8); 1.9626 (0.7); 1.9452 (1.0); 1.9332 (0.8); 1.9178 (1.6); 1.9022 (2.4); 1.8833 (2.5); 1.8663 (1.5); 1.5585 (9.3); 1.5390 (0.9); 1.5198 (0.7); 1.3155 (16.0); 1.3075 (12.5); 1.2764 (0.7); 1.2585 (1.5); 1.2407 (0.6); 0.0080 (1.0); −0.0002 (30.8); −0.0083 (1.2)

Example No. I.60-72

$^1$H-NMR (400.0 MHz, CDCl$_3$): δ=7.4902 (1.0); 7.4720 (1.0); 7.3788 (1.2); 7.3563 (1.2); 7.2601 (25.5); 3.9388 (0.6); 3.9266 (0.7); 3.9208 (0.6); 3.9086 (0.7); 3.9023 (0.6); 3.8099 (0.7); 3.7955 (0.7); 3.7748 (0.8); 3.7559 (0.8); 3.7347 (0.9); 3.7166 (0.8); 3.5418 (3.1); 3.5362 (3.0); 3.4569 (0.6); 3.4343 (0.5); 2.7202 (0.7); 2.7131 (0.8); 2.7030 (0.8); 2.6947 (0.7); 1.5374 (16.0); 1.5144 (3.9); 1.1448 (1.8); 1.1265 (3.4); 1.1080 (1.6); −0.0002 (31.4); −0.0083 (1.2)

Example No. I.60-91

$^1$H-NMR (400.0 MHz, CDCl$_3$): δ=7.5351 (0.7); 7.3697 (0.8); 7.3570 (0.8); 7.3456 (0.8); 7.3351 (0.9); 7.2601 (21.1); 7.2584 (18.4); 4.0615 (0.5); 3.9939 (0.7); 3.9325 (1.0); 3.5401 (3.4); 3.3978 (0.5); 3.3753 (0.6); 2.7173 (0.9); 1.8352 (0.5); 1.5375 (16.0); 1.5185 (2.7); 1.5086 (2.4); 1.4872 (1.8); 1.2587 (0.6); 1.1470 (1.7); 1.1285 (2.9); 1.1109 (1.3); −0.0002 (25.4); −0.0019 (21.9)

Example No. I.60-221

$^1$H-NMR (400.0 MHz, CDCl$_3$): δ=7.3528 (0.6); 7.3419 (0.5); 7.3300 (0.6); 7.3202 (0.5); 7.2603 (26.0); 3.8155 (0.6); 3.7989 (0.6); 3.5293 (2.0); 3.5237 (1.3); 2.0449 (1.4); 1.6044 (1.6); 1.5879 (2.1); 1.5706 (1.7); 1.5435 (16.0); 1.2771 (0.5); 1.2592 (1.1); 1.1388 (0.6); 1.1257 (1.3); 1.1216 (1.2); 1.1075 (0.7); 0.8819 (0.6); 0.0080 (0.9); −0.0002 (30.9); −0.0085 (1.6)

The present invention further provides for the use of one or more inventive compounds of the formula (I) and/or salts thereof, as defined above, preferably in a configuration identified as preferred or particularly preferred, especially of one or more compounds of the formulae (I.1) to (I.60) and/or salts thereof, each as defined above, as herbicide and/or plant growth regulator, preferably in crops of useful plants and/or ornamentals.

The present invention further provides a method of controlling harmful plants and/or of regulating the growth of plants, characterized in that an effective amount of one or more inventive compounds of the formula (I) and/or salts thereof, as defined above, preferably in a configuration identified as preferred or particularly preferred, especially of one or more compounds of the formulae (I.1) to (I.60) and/or salts thereof, each as defined above, or a composition of the invention, as defined below, is applied to the (harmful) plants, (harmful) plant seeds, the soil in or on which the (harmful) plants grow, or the cultivation area.

The present invention also provides a method of controlling unwanted plants, preferably in crops of useful plants, characterized in that an effective amount of one or more compounds of the formula (I) and/or salts thereof, as defined above, preferably in a configuration identified as preferred or particularly preferred, especially of one or more compounds of the formulae (I.1) to (I.60) and/or salts thereof, each as defined above, or a composition of the invention, as defined below, is applied to unwanted plants (for example harmful plants such as mono- or dicotyledonous weeds or unwanted crop plants), the seed of the unwanted plants (i.e. plant seeds, e.g. grains, seeds or vegetative propagation organs such as tubers or parts of shoots with buds), the soil in or on which the unwanted plants grow (for example the soil of cropland or non-cropland), or the cultivation area (i.e. the area in which the unwanted plants will grow).

The present invention additionally also provides methods of controlling of regulating the growth of plants, preferably of useful plants, characterized in that an effective amount of one or more compounds of the formula (I) and/or salts thereof, as defined above, preferably in a configuration identified as preferred or particularly preferred, especially of one or more compounds of the formulae (I.1) to (I.60) and/or salts thereof, each as defined above, or a composition of the invention, as defined below, is applied the plant, the seed of the plant (i.e. plant seeds, e.g. grains, seeds or vegetative propagation organs such as tubers or parts of shoots with buds), the soil in or on which the plants grow (for example the soil of cropland or non-cropland), or the cultivation area (i.e. the area in which the plants will grow).

It is possible here for the compounds of the invention or the compositions of the invention to be deployed, for example, at the pre-seeding stage (possibly even by being incorporated into the soil), pre-emergence and/or post-emergence. Specific examples of some representatives of the monocotyledonous and dicotyledonous weed flora which can be controlled by the compounds of the invention are as follows, though there is no intention to restrict the enumeration to particular species.

In a method of the invention for controlling harmful plants or for regulating the growth of plants, preference is given to using one or more compounds of the formula (I) and/or salts thereof for controlling harmful plants or for regulating growth in crops of useful plants or ornamentals, wherein the useful plants or ornamentals in a preferred configuration are transgenic plants.

The inventive compounds formula (I) and/or salts thereof are suitable for controlling the following genera of mono- cotyledonous and dicotyledonous harmful plants:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds of the invention are applied to the soil surface before the germination of the harmful plants (weed grasses and/or broad-leaved weeds), either the emergence of the weed grass seedlings and/or broad-leaved weed seedlings is prevented completely or the weeds grow until they have reached the cotyledon stage, but then they stop growing and ultimately die completely after three to four weeks.

When the active ingredients are applied post-emergence to the green parts of the plants, growth stops after the treatment, and the harmful plants remain at the growth stage at the time of application, or they die completely after a certain time, such that competition by the weeds, which is harmful to the crop plants, is thus eliminated very early and in a lasting manner.

Although the compounds of the invention have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* will be damaged only insignificantly, if at all, depending on the structure of the particular compound of the invention and its application rate. For these reasons, the present compounds are of very good suitability for selective control of unwanted plant growth in plant crops such as plantations of agriculturally useful plants or ornamentals.

In addition, the compounds of the invention (depending on their particular structure and the application rate deployed) have excellent growth-regulating properties in crop plants. They intervene in the plants' own metabolism with regulatory effect, and can thus be used for controlled influencing of plant constituents and to facilitate harvesting, for example by triggering desiccation and stunted growth. In addition, they are also suitable for general control and inhibition of unwanted vegetative growth without killing the plants in the process. Inhibition of vegetative growth plays a major role for many mono- and dicotyledonous crops since, for example, this can reduce or completely prevent lodging.

Owing to their herbicidal and plant growth regulatory properties, the active ingredients can also be used to control harmful plants in crops of genetically modified plants or plants modified by conventional mutagenesis. In general, transgenic plants are notable for particular advantageous properties, for example for resistances to certain pesticides, in particular certain herbicides, resistances to plant diseases or pathogens of plant diseases, such as certain insects, or microorganisms such as fungi, bacteria or viruses. Other particular characteristics relate, for example, to the harvested material with regard to quantity, quality, storability, composition and specific constituents. For instance, there are known transgenic plants with an elevated starch content or altered starch quality, or with a different fatty acid composition of the harvested material.

With regard to transgenic crops, preference is given to the use of the inventive compounds and/or salts thereof in economically important transgenic crops of useful plants and ornamentals, for example of cereal such as wheat, barley, rye, oats, millet/sorghum, rice and corn, or else crops of sugar beet, cotton, soybean, oilseed rape, potatoes, tomatoes, peas and other vegetables.

The compounds of the invention can preferably also be used as herbicides in crops of useful plants that are resistant, or have been made resistant by recombinant means, to the phytotoxic effects of the herbicides.

Owing to their herbicidal and plant growth regulatory properties, the active ingredients can also be used to control harmful plants in crops of genetically modified plants that are known or yet to be developed. In general, transgenic plants are notable for particular advantageous properties, for example for resistances to certain pesticides, in particular certain herbicides, resistances to plant diseases or pathogens of plant diseases, such as certain insects, or microorganisms such as fungi, bacteria or viruses.

Other particular characteristics relate, for example, to the harvested material with regard to quantity, quality, storability, composition and specific constituents. For instance, there are known transgenic plants with an elevated starch content or altered starch quality, or with a different fatty acid composition of the harvested material. Further particular properties may be tolerance or resistance to abiotic stress factors, for example heat, cold, drought, salinity and ultraviolet radiation.

Preference is given to the use of the inventive compounds of the formula (I) or salts thereof in economically important transgenic crops of useful plants and ornamentals, for example of cereal such as wheat, barley, rye, oats, triticale, millet/sorghum, rice, cassava and corn, or else crops of sugar beet, cotton, soybean, oilseed rape, potatoes, tomatoes, peas and other vegetables.

The compounds of the formula (I) can preferably also be used as herbicides in crops of useful plants that are resistant, or have been made resistant by recombinant means, to the phytotoxic effects of the herbicides.

Conventional ways of producing novel plants which have modified properties compared to existing plants involve, for example, conventional cultivation methods and the generation of mutants. Alternatively, novel plants with altered properties can be generated with the aid of recombinant methods.

Numerous molecular biology techniques by which novel transgenic plants with modified properties can be produced are known to the person skilled in the art. For such recombinant manipulations, nucleic acid molecules which allow mutagenesis or sequence alteration by recombination of DNA sequences can be introduced into plasmids. With the aid of standard methods, it is possible, for example, to undertake base exchanges, remove part sequences, or add natural or synthetic sequences. For the connection of the DNA fragments to one another, it is possible to add adapters or linkers to the fragments.

For example, the production of plant cells with a reduced activity of a gene product can be achieved by the expression of at least one corresponding antisense RNA, or a sense RNA for achieving a cosuppression effect, or the expression of at least one appropriately constructed ribozyme which specifically cleaves transcripts of the abovementioned gene product.

To this end, it is firstly possible to use DNA molecules which encompass the entire coding sequence of a gene product including any flanking sequences that may be present, and also DNA molecules which encompass only portions of the coding sequence, in which case it is necessary for these portions to be long enough to have an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, in order to achieve localization in a particular compartment, it is possible, for example, to join the coding region to DNA sequences which assure localization in a particular compartment. Such sequences are known to those skilled in the art (see, for example, Braun et al., EMBO J. 11 (1992), 3219-3227). The nucleic acid molecules can also be expressed in the organelles of the plant cells.

The transgenic plant cells can be regenerated by known techniques to give rise to whole plants. In principle, the transgenic plants may be plants of any desired plant species, i.e. not only monocotyledonous but also dicotyledonous plants.

In this way, transgenic plants having properties altered by overexpression, suppression or inhibition of homologous (=natural) genes or gene sequences or expression of heterologous (=foreign) genes or gene sequences are obtainable.

The inventive compounds (I) can be used with preference in transgenic crops that are resistant to growth regulators, for example dicamba, or to herbicides that inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

When the active ingredients of the invention are used in transgenic crops, not only do the effects toward harmful plants that are to be observed in other crops occur, but often also effects that are specific to application in the particular transgenic crop, for example an altered or specifically widened spectrum of weeds that can be controlled, altered application rates that can be used for the application, preferably good combinability with the herbicides to which the transgenic crop is resistant, and influencing of growth and yield of the transgenic crop plants.

The invention therefore also provides for the use of the inventive compounds of the formula (I) and/or salts thereof as herbicides for controlling harmful plants in crops of useful plants or ornamentals, if appropriate in transgenic crop plants.

Preference is given to using cereal, preferably corn, wheat, barley, rye, oats, millet/sorghum, or rice, pre- or post-emergence.

Preference is also given to use in soybean, pre- or post-emergence.

The inventive use for control of harmful plants or for regulation of plant growth also includes the case in which the active ingredient of the formula (I) or salt thereof is formed only after deployment on the plant, in the plant or in the soil from a precursor substance ("prodrug").

The invention also provides for use of one or more compounds of the formula (I) or salts thereof or of an inventive composition (as defined below) (in a method) for control of harmful plants or for regulating the growth of plants, characterized in that an effective amount of one or more compounds of the formula (I) or salts thereof is applied to the plants (harmful plants, if appropriate together with the crop plants), plant seeds, the soil in or on which the plants grow, or the cultivation area.

The invention also provides a herbicidal and/or plant growth-regulating composition, characterized in that the composition comprises
(a) one or more compounds of the formula (I) and/or salts thereof, as defined above, preferably in a configuration identified as preferred or particularly preferred, especially of one or more compounds of the formulae (I.1) to (I.XX) and/or salts thereof, each as defined above, and (b) one or more further substances selected from the groups (i) and/or (ii):
(i) one or more further active agrochemical ingredients, preferably selected from the group consisting of insecticides, acaricides, nematicides, further herbicides (i.e. those that do not conform to the above-defined formula (I)), fungicides, safeners, fertilizers and/or further growth regulators,
(ii) one or more formulation auxiliaries customary in crop protection.

The further active agrochemical ingredients of constituent (i) of a composition of the invention are preferably selected from the group of substances specified in "The Pesticide Manual", 16th edition, The British Crop Protection Council and the Royal Soc. of Chemistry, 2012.

A herbicidal or plant growth-regulating composition of the invention preferably comprises one, two, three or more formulation auxiliaries (ii) that are customary in crop protection, selected from the group consisting of surfactants, emulsifiers, dispersants, film formers, thickeners, inorganic salts, dusting agents, carriers that are solid at 25° C. and 1013 mbar, preferably adsorptive granulated inert materials, wetting agents, antioxidants, stabilizers, buffer substances, antifoams, water, organic solvents, preferably organic solvents that are miscible with water in any desired ratio at 25° C. and 1013 mbar.

The inventive compounds (I) may be employed in the form of wettable powders, emulsifiable concentrates, sprayable solutions, dusting products or granules in the customary formulations. The invention therefore also provides herbicidal and plant-growth-regulating compositions comprising the compounds of the formula (I) and/or salts thereof.

The compounds of the formula (I) and/or salts thereof can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dustable powders (DP), seed dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types and the formulation auxiliaries such as inert materials, surfactants, solvents and further additives are known to the person skilled in the art, and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-Active Ethylene Oxide Adducts], Wiss. Verlagsgesellschaft, Stuttgart 1976; Winnacker-Küichler, "Chemische Technologie" [Chemical Technology], volume 7, C. Hanser Verlag Munich, 4th ed. 1986.

Wettable powders are preparations that are dispersible uniformly in water and, in addition to the active ingredient, apart from a diluent or inert substance, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. The wettable powders are produced by finely grinding the active herbicidal ingredients, for example in customary apparatuses such as hammer mills, blower mills and air jet mills, and simultaneously or subsequently mixing with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers that may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely divided solid materials, for example talc, natural clays such as kaolin, bentonite and pyrophyllite, or diatomaceous earth.

Suspension concentrates may be water- or oil-based. They may be produced, for example, by wet grinding by means of commercial bead mills and optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of stickers, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan, fluidized-bed, extruder and spray granules, see, for example, processes in "Spray Drying Handbook" 3rd Ed. 1979, G. Goodwin Ltd., London, J. E. Browning, "Agglomeration", Chemical and Engineering 1967, pages 147 ff; "Perry's Chemical Engineer's Handbook", 5th ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations, preferably herbicidal or plant growth-regulating compositions of the present invention, preferably contain a total amount of 0.1 to 99% by weight, preferably 0.5% to 95% by weight, further preferably 1% to 90% by weight, especially preferably 2% to 80% by weight, of active ingredients of the formula (I) and salts thereof.

In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Formulations in dustable form contain 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is in liquid or solid form and on which granulation auxiliaries, fillers, etc., are used. In water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreezes and solvents, fillers, carriers and dyes, defoamers, evaporation inhibitors, and pH and viscosity modifiers. Examples of formulation auxiliaries are described inter alia in "Chemistry and Technology of Agrochemical Formulations", ed. D. A. Knowles, Kluwer Academic Publishers (1998).

The compounds of the formula (I) or salts thereof may be used as such or in combination in the form of their preparations (formulations) with other pesticidally substances, for example insecticides, acaricides, nematicides, herbicides, fungicides, safeners, fertilizers and/or growth regulators, for example as a ready-made formulation or in the form of tankmixes. The combined formulations may be produced here on the basis of the abovementioned formulations, taking account of the physical properties and stabilities of the active ingredients to be combined.

Combination partners usable for the inventive compounds of the formula (I) in mixed formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as described, for example, in Weed Research 26 (1986) 441-445 or "The Pesticide Manual", 16th edition, The British Crop Protection Council and the Royal Soc. of Chemistry, 2012 and the literature cited therein.

Of particular interest is the selective control of harmful plants in crops of useful plants and ornamentals. Although the inventive compounds (I) already have very good to adequate selectivity in many crops, it is possible in principle for phytotoxicities on the crop plants to occur in some crops, and particularly also in the case of mixtures with other herbicides that are less selective. Of particular interest in this regard are combinations of inventive compounds (I) that comprise the compounds (I) or combinations thereof with other herbicides or pesticides and safeners. The safeners, which are used in an antidotically effective content, reduce the phytotoxic side effects of the herbicides/pesticides used, for example in economically important crops such as cereal (wheat, barley, rye, corn, rice, millet/sorghum), sugar beet, sugar cane, oilseed rape, cotton and soybean, preferably cereal.

The weight ratios of (herbicide) mixture to safener generally depend on the application rate of herbicide and the efficacy of the respective safener, and may vary within broad limits, for example in the range from 200:1 to 1:200, preferably 100:1 to 1:100, especially 20:1 to 1:20. The safeners may be formulated analogously to the compounds (I) or mixtures thereof with further herbicides/pesticides, and be provided and applied as a ready-made formulation or tankmix with the herbicides.

For application, the herbicide or herbicide-safener formulations in commercial form are diluted if appropriate by means of water, for example in the case of wettable powders, emulsifiable concentrates, dispersions and water-dispersible granules. Dustable formulations, granules for soil application or scattering, and sprayable solutions are typically not diluted with further inert substances prior to application.

External conditions such as temperature, humidity etc. affect the application rate of the compounds of the formula (I) and/or salts thereof to a certain degree. The application rate may vary within broad limits. For application as herbicide for control of harmful plants, the total amount of compounds of the formula (I) and salts thereof is preferably in the range from 0.001 to 10.0 kg/ha, preferably in the range from 0.005 to 5 kg/ha, further preferably in the range from 0.01 to 1.5 kg/ha, especially preferably in the range from 0.05 to 1 kg/ha. This applies to application both pre- and post-emergence.

When compounds of the formula (I) and/or salts thereof are used as plant growth regulators, for example as stem shortener in the case of crop plants as specified above, preferably in the case of cereal plants such as wheat, barley, rye, triticale, millet/sorghum, rice or corn, the total application rate is preferably in the range from 0.001 to 2 kg/ha, preferably in the range from 0.005 to 1 kg/ha, especially in the range from 10 to 500 g/ha, most preferably in the range from 20 to 250 g/ha. This applies to application both pre- and post-emergence.

Application as a stem shortener can be effected at various stages of the growth of the plant. Preference is given, for example, to application after tillering at the start of linear growth.

An alternative option in the case of use as plant growth regulator is also the treatment of the seed, which includes different seed dressing and coating techniques. The application rate depends on the individual techniques and can be ascertained in preliminary tests.

Combination partners usable for the inventive compounds of the formula (I) in compositions of the invention (for example mixed formulations or in a tankmix) are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as described, for example, from Weed Research 26 (1986) 441-445 or "The Pesticide Manual", 16th edition, The British Crop Protection Council and the Royal Soc. of Chemistry, 2012 and literature cited therein. Specified hereinafter by way of example are known herbicides or plant growth regulators that can be combined with the compounds of the invention, with designation of these active ingredients either by their common name in the English-language variant according to the International Organization for Standardization (ISO) or by the chemical name or by the code number. These always include all use forms, for example acids, salts, esters and all isomeric forms such as stereoisomers and optical isomers, even if these are not mentioned explicitly.

Combination partners usable for the compounds of the invention in mixed formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as described, for example, from Weed Research 26 (1986) 441-445 or "The Pesticide Manual", 16th edition, The British Crop Protection Council and the Royal Soc. of Chemistry, 2,006 and literature cited therein. Specified hereinafter by way of example are known herbicides or plant growth regulators that can be combined with the compounds of the invention, with designation of these active ingredients either by their common name in the English-language variant according to the International Organization for Standardization (ISO) or by the chemical name or by the code number. These always include all use forms, for example acids, salts, esters and all isomeric forms such as stereoisomers and optical isomers, even if these are not mentioned explicitly.

Examples of such herbicidal mixing partners are: acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammonium-sulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]-phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, florpyrauxifen, florpyrauxifen-benzyl, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)-O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-[3-chloro-4-(1-methylethyl)-phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxotrione (lancotrione), oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrione, sulfentrazone, sulfometuron, sulfometuron-methyl, sulfosulfuron, SYN-523, SYP-249, i.e. 1-ethoxy-3-methyl-1-oxobut-3-en-2-yl5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline, and the following compounds:

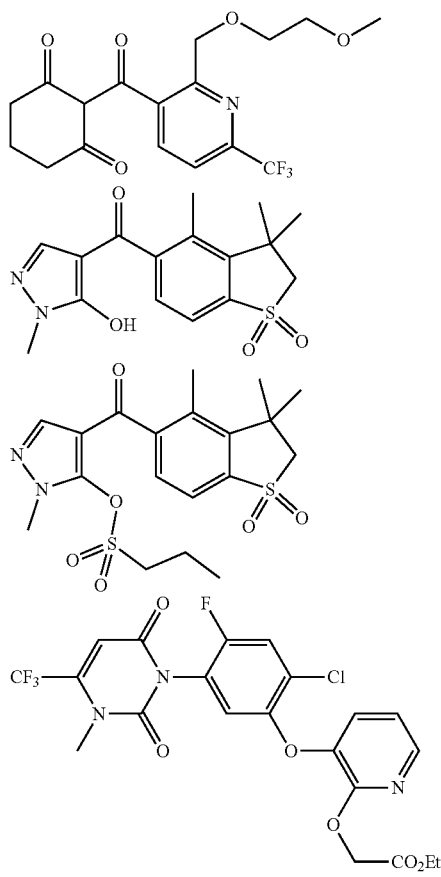

Examples of plant growth regulators as possible mixing partners are:
acibenzolar, acibenzolar-S-methyl, 5-aminolevulic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4[(2-phenylethyl)amino]butyric acid, paclobutrazol, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Likewise possible as combination partners for the inventive compounds of the formula (I) include, for example, the following safeners:
S1) Compounds from the group of heterocyclic carboxylic acid derivatives:
S1$^a$) Compounds of the dichlorophenylpyrazoline-3-carboxylic acid type (Sla), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;
S1$^b$) Derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;
S1$^c$) Derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268 554;
S1$^d$) Compounds of the triazolecarboxylic acid type (S1$^d$), preferably compounds such as fenchlorazole (ethyl ester), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;
S1$^e$) Compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.
S2) Compounds from the group of the 8-quinolinoxy derivatives (S2):
S2$^a$) Compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop- 2-yl (5-chloro-8-quinolinoxy)acetate (S2-4), ethyl (5-chloro-8-quinolinoxy)acetate (S2-5), methyl 5-chloro-8-quinolinoxyacetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) Compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Active ingredients of the dichloroacetamide type (S3), which are frequently used as pre-emergence safeners (soil-acting safeners), for example "dichlormid" (N,N-diallyl-2,2-dichloroacetamide) (S3-1),
"R-29148" (3-dichloroacetyl-2,2,5-trimethyl-1,3-oxazolidine) from Stauffer (S3-2),
"R-28725" (3-dichloroacetyl-2,2-dimethyl-1,3-oxazolidine) from Stauffer (S3-3),
"benoxacor" (4-dichloroacetyl-3,4-dihydro-3-methyl-2H-1,4-benzoxazine) (S3-4),
"PPG-1292" (N-allyl-N-[(1,3-dioxolan-2-yl)methyl]dichloroacetamide) from PPG Industries (S3-5),
"DKA-24" (N-allyl-N-[(allylaminocarbonyl)methyl]dichloroacetamide) from Sagro-Chem (S3-6),
"AD-67" or "MON 4660" (3-dichloroacetyl-1-oxa-3-azaspiro[4.5]decane) from Nitrokemia or Monsanto (S3-7),
"TI-35" (1-dichloroacetylazepane) from TRI-Chemical RT (S3-8),
"Diclonon" (dicyclonon) or "BAS145138" or "LAB145138" (S3-9),
((RS)-1-dichloroacetyl-3,3,8a-trimethylperhydropyrrolo[1,2-a]pyrimidin-6-one) from BASF,
"furilazole" or "MON 13900" ((RS)-3-dichloroacetyl-5-(2-furyl)-2,2-dimethyloxazolidine) (S3-10), and the (R) isomer thereof (S3-11).

S4) Compounds from the class of the acylsulfonamides (S4):

S4$^a$) N-Acylsulfonamides of the formula (S4$^a$) and salts thereof, as described in WO-A-97/45016,

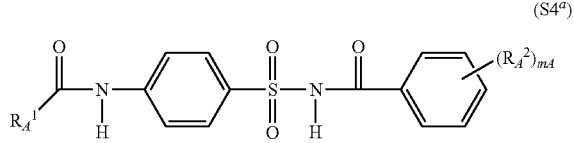

(S4$^a$)

in which
$R_A^1$ is $(C_1-C_6)$alkyl, $(C_3-C_6)$cycloalkyl, where the 2 latter radicals are substituted by $v_A$ substituents from the group of halogen, $(C_1-C_4)$alkoxy, $(C_1-C_6)$haloalkoxy and $(C_1-C_4)$alkylthio and, in the case of cyclic radicals, also by $(C_1-C_4)$alkyl and $(C_1-C_4)$haloalkyl;
$R_A^2$ is halogen, $(C_1-C_4)$alkyl, $(C_1-C_4)$alkoxy, $CF_3$;
$m_A$ is 1 or 2;
$v_A$ is 0, 1, 2 or 3;

S4$^a$) Compounds of the 4-(benzoylsulfamoyl)benzamide type of the formula (S4$^b$) and salts thereof, as described in WO-A-99/16744,

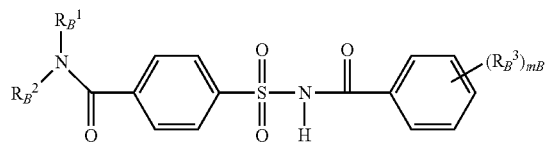

(S4$^b$)

in which
$R_B^1$, $R_B^2$ are, independently, hydrogen, $(C_1-C_6)$alkyl, $(C_3-C_6)$cycloalkyl, $(C_3-C_6)$alkenyl, $(C_3-C_6)$alkynyl,
$R_B^3$ is halogen, $(C_1-C_4)$alkyl, $(C_1-C_4)$haloalkyl or $(C_1-C_4)$alkoxy and
$m_B$ is 1 or 2,
for example those in which
$R_B^1$=cyclopropyl, $R_B^2$=hydrogen and $(R_B^3)$=2-OMe ("cyprosulfamide", S4-1),
$R_B^1$=cyclopropyl, $R_B^2$=hydrogen and $(R_B^3)$=5-Cl-2-OMe (S4-2),
$R_B^1$=ethyl, $R_B^2$=hydrogen and $(R_B^3)$=2-OMe (S4-3),
$R_B^1$=isopropyl, $R_B^2$=hydrogen and $(R_B^3)$=5-Cl-2-OMe (S4-4) and
$R_B^1$=isopropyl, $R_B^2$=hydrogen and $(R_B^3)$=2-OMe (S4-5).

S4$^c$) Compounds from the class of the benzoylsulfamoylphenylureas of the formula (S4$^c$), as described in EP-A-365 484,

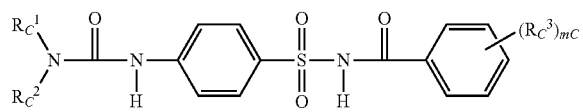

(S4$^c$)

in which
$R_C^1$, $R_C^2$ are independently hydrogen, $(C_1-C_8)$alkyl, $(C_3-C_8)$cycloalkyl, $(C_3-C_6)$alkenyl, $(C_3-C_6)$alkynyl,
$R_C^3$ is halogen, $(C_1-C_4)$alkyl, $(C_1-C_4)$alkoxy, $CF_3$ and
$m_C$ is 1 or 2;
for example:
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea;

S4$^d$) Compounds of the N-phenylsulfonylterephthalamide type of the formula (S4$^d$) and salts thereof, which are known, for example, from CN 101838227,

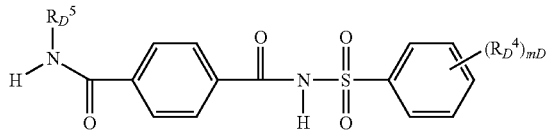

(S4$^d$)

in which $R_D^4$ is halogen, $(C_1-C_4)$alkyl, $(C_1-C_4)$alkoxy, $CF_3$;

$m_D$ is 1 or 2;

$R_D^5$ is hydrogen, $(C_1-C_6)$alkyl, $(C_3-C_6)$cycloalkyl, $(C_2-C_6)$alkenyl, $(C_2-C_6)$alkynyl, $(C_5-C_6)$cycloalkenyl.

S5) Active ingredients from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicyclic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), for example methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8), as described in WO-A-98/27049,

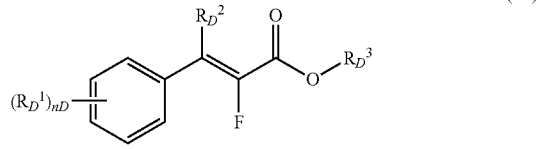

(S8)

in which the symbols and indices are defined as follows:

$R_D^1$ is halogen, $(C_1-C_4)$alkyl, $(C_1-C_4)$haloalkyl, $(C_1-C_4)$alkoxy, $(C_1-C_4)$haloalkoxy, $R_D^2$ is hydrogen or $(C_1-C_4)$alkyl, $R_D^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy; or salts thereof, $n_D$ is an integer from 0 to 2.

s9) Active ingredients from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formula (S10$^a$) or (S10$^b$)

as described in WO-A-2007/023719 and WO-A-2007/023764,

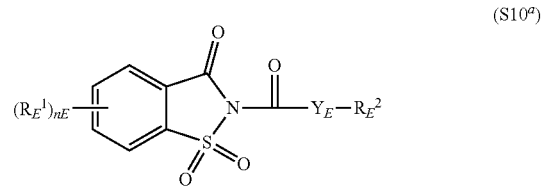

(S10$^a$)

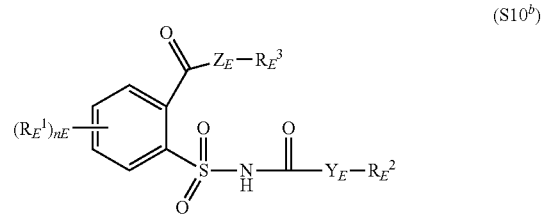

(S10$^b$)

in which $R_E^1$ is halogen, $(C_1-C_4)$alkyl, methoxy, nitro, cyano, $CF_3$, $OCF_3$ $Y_E, Z_E$ are independently O or S, $n_E$ is an integer from 0 to 4, $R_E^2$ is $(C_1-C_{16})$alkyl, $(C_2-C_6)$alkenyl, $(C_3-C_6)$cycloalkyl, aryl; benzyl, halobenzyl, $R_E^3$ is hydrogen or $(C_1-C_6)$alkyl.

S11) Active ingredients of the oxyimino compound type (S11) that are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino(phenyl)acetonitrile) (S11-3), which is known as a seed-dressing safener for millet/sorghum against metolachlor damage.

S12) Active ingredients from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (S13-5) from Nitrokemia, which is known as a safener for corn, "MG 838" (CAS Reg. No. 133993-74-5), (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).

S14) Active ingredients which, in addition to herbicidal action against weeds, also have safener action on crop plants such as rice, for example
"dimepiperate" or "MY-93" (S-1-methyl 1-phenylethylpiperidine-1-carbothioate), which is known as a safener for rice against damage by the herbicide molinate,
"daimuron" or "SK 23" (1-(1-methyl-1-phenylethyl)-3-p-tolylurea), which is known as safener for rice against imazosulfuron herbicide damage,
"cumyluron"="JC-940" (3-(2-chlorophenylmethyl)-1-(1-methyl-1-phenylethyl)urea, see JP-A-60087254), which is known as safener for rice against damage by some herbicides,
"methoxyphenone" or "NK 049" (3,3'-dimethyl-4-methoxybenzophenone), which is known as a safener for rice against damage by some herbicides,
"CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

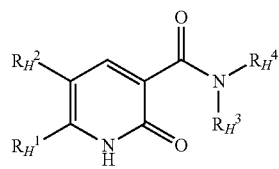

(S15)

as described in WO-A-2008/131861 and WO-A-2008/131860,
in which
$R_H^1$ is a $(C_1-C_6)$haloalkyl radical and
$R_H^2$ is hydrogen or halogen and
$R_H^3$, $R_H^4$ are independently hydrogen, $(C_1-C_6)$alkyl, $(C_2-C_{16})$alkenyl or $(C_2-C_{16})$alkynyl,
where each of the 3 latter radicals is unsubstituted or substituted by one or more radicals from the group of halogen, hydroxyl, cyano, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted,
or $(C_3-C_6)$cycloalkyl, $(C_4-C_6)$cycloalkenyl, $(C_3-C_6)$cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring,
where each of the 4 latter radicals is unsubstituted or substituted by one or more radicals from the group of halogen, hydroxyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted,
or
$R_H^3$ is $(C_1-C_4)$alkoxy, $(C_2-C_4)$alkenyloxy, $(C_2-C_6)$alkynyloxy or $(C_2-C_4)$haloalkoxy and
$R_H^4$ is hydrogen or $(C_1-C_4)$-alkyl or
$R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

S16) Active ingredients which are used primarily as herbicides but also have safener action on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Preferred safeners in combination with the inventive compounds of the formula (I) and/or salts thereof, especially with the compounds of the formulae (I.1) to (I.60) and/or salts thereof, are: cloquintocet-mexyl, cyprosulfamide, fenchlorazole-ethyl ester, isoxadifen-ethyl, mefenpyr-diethyl, fenclorim, cumyluron, S4-1 and S4-5, and particularly preferred safeners are: cloquintocet-mexyl, cyprosulfamide, isoxadifen-ethyl and mefenpyr-diethyl.

Biological Examples

A. Herbicidal Action and Crop Compatibility Post-Emergence

Seeds of mono- and dicotyledonous weed plants and crop plants are laid out in sandy loam soil in plastic or wood-fiber pots, covered with earth and grown under controlled growth conditions in a greenhouse. 2 to 3 weeks after sowing, the trial plants are treated at the one-leaf stage. The compounds of the invention formulated in the form of wettable powders (WP) or emulsion concentrates (EC) were then sprayed onto the green parts of the plant as an aqueous suspension or emulsion with addition of 0.5% additive at a water application rate equivalent to 600 L/ha. After the trial plants had stood for about 3 weeks in the greenhouse, under optimal growth conditions, the effect of the preparations was scored visually by comparison with untreated controls. For example, 100% efficacy=plants have died, 0% efficacy=like control plants.

Crop plant compatibilities were also scored correspondingly.

Tables A1 to A15 below show the efficacies of selected compounds of the general formula (I) according to tables I.1 to I.60 on various harmful plants and an application rate corresponding to 80 g/ha or lower that were obtained by the aforementioned trial method.

TABLE A1

| Compound Example No. | Alopecurus myosuroides (Efficacy in %) | Application rate [g/ha] |
|---|---|---|
| I.2-72 | 90 | 80 |
| I.1-73 | 90 | 80 |
| I.48-71 | 90 | 80 |
| I.1-26 | 80 | 80 |
| I.1-222 | 90 | 80 |
| I.1-221 | 90 | 80 |
| I.1-341 | 90 | 80 |
| I.1-27 | 90 | 80 |
| I.48-72 | 90 | 80 |
| I.8-271 | 100 | 80 |
| I.1-2 | 90 | 80 |
| I.1-271 | 100 | 80 |
| I.1-1 | 80 | 80 |
| I.1-275 | 90 | 80 |
| I.1-224 | 80 | 80 |
| I.1-115 | 80 | 20 |
| I.2-336 | 80 | 20 |
| I.2-92 | 80 | 20 |
| I.2-91 | 90 | 20 |
| I.6-71 | 80 | 20 |
| I.6-221 | 90 | 20 |
| I.12-91 | 80 | 20 |
| I.48-93 | 80 | 20 |
| I.48-121 | 80 | 20 |
| I.1-181 | 80 | 80 |
| I.1-51 | 80 | 20 |

TABLE A2

| Compound Example No. | Echinochloa crus-galli (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 80 | 80 |
| I.1-2 | 100 | 80 |
| I.1-72 | 100 | 80 |
| I.1-271 | 90 | 80 |
| I.1-71 | 100 | 80 |
| I.1-1 | 100 | 80 |
| I.1-275 | 90 | 80 |
| I.8-1 | 100 | 80 |
| I.1-6 | 90 | 20 |
| I.1-30 | 100 | 20 |
| I.2-71 | 80 | 20 |
| I.48-81 | 90 | 20 |
| I.48-91 | 100 | 20 |
| I.42-72 | 90 | 20 |
| I.2-92 | 100 | 20 |
| I.2-91 | 100 | 20 |
| I.2-81 | 100 | 20 |
| I.6-71 | 90 | 20 |
| I.6-72 | 80 | 20 |
| I.5-71 | 90 | 20 |
| I.5-72 | 90 | 20 |
| I.5-221 | 80 | 20 |
| I.5-91 | 80 | 20 |
| I.6-221 | 80 | 20 |
| I.4-221 | 80 | 20 |
| I.12-71 | 100 | 20 |
| I.12-91 | 100 | 20 |
| I.12-72 | 100 | 20 |
| I.54-71 | 80 | 20 |
| I.1-181 | 100 | 20 |
| I.1-82 | 100 | 20 |
| I.1-92 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A3

| Compound Example No. | Setaria viridis (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-115 | 100 | 20 |
| I.2-71 | 90 | 20 |
| I.1-6 | 100 | 20 |
| I.1-30 | 100 | 20 |
| I.2-73 | 90 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 90 | 20 |
| I.5-71 | 90 | 20 |
| I.5-72 | 80 | 20 |
| I.5-221 | 100 | 20 |
| I.5-91 | 90 | 20 |
| I.6-221 | 100 | 20 |
| I.4-221 | 100 | 20 |
| I.12-91 | 80 | 20 |
| I.14-72 | 100 | 20 |
| I.54-71 | 100 | 20 |
| I.54-241 | 100 | 20 |
| I.48-92 | 100 | 20 |
| I.1-181 | 100 | 20 |
| I.1-151 | 100 | 20 |
| I.1-82 | 80 | 20 |
| I.1-241 | 100 | 20 |
| I.1-334 | 90 | 20 |
| I.1-126 | 100 | 20 |
| I.1-92 | 100 | 20 |
| I.1-276 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |
| I.1-340 | 80 | 80 |

TABLE A4

| Compound Example No. | Abutilon theophrasti (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 100 | 80 |
| I.1-340 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-221 | 100 | 20 |
| I.48-91 | 100 | 20 |
| I.48-81 | 100 | 20 |
| I.49-71 | 100 | 20 |
| I.49-72 | 100 | 20 |
| I.49-221 | 100 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 100 | 20 |
| I.5-221 | 100 | 20 |
| I.5-91 | 100 | 20 |
| I.6-221 | 100 | 20 |
| I.4-221 | 100 | 20 |
| I.12-221 | 100 | 20 |
| I.12-71 | 100 | 20 |
| I.12-91 | 100 | 20 |
| I.12-72 | 100 | 20 |
| I.14-221 | 90 | 20 |
| I.14-71 | 100 | 20 |
| I.14-91 | 100 | 20 |
| I.14-72 | 80 | 20 |
| I.54-221 | 100 | 20 |
| I.54-71 | 100 | 20 |
| I.54-241 | 100 | 20 |
| I.54-82 | 100 | 20 |
| I.48-82 | 100 | 20 |
| I.48-73 | 100 | 20 |
| I.48-93 | 100 | 20 |
| I.48-121 | 100 | 20 |
| I.48-92 | 100 | 20 |
| I.48-127 | 100 | 20 |
| I.1-181 | 100 | 20 |
| I.1-151 | 100 | 20 |
| I.1-81 | 100 | 20 |
| I.1-82 | 100 | 20 |
| I.1-132 | 100 | 20 |
| I.1-241 | 100 | 20 |
| I.1-334 | 100 | 20 |
| I.1-331 | 100 | 20 |
| I.1-227 | 100 | 20 |
| I.1-126 | 100 | 20 |
| I.1-91 | 100 | 20 |
| I.1-92 | 100 | 20 |
| I.1-276 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A5

| Compound Example No. | Amaranthus retroflexus (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-221 | 90 | 20 |
| I.48-91 | 100 | 20 |
| I.48-81 | 100 | 20 |
| I.49-71 | 100 | 20 |
| I.49-72 | 100 | 20 |
| I.49-221 | 100 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 100 | 20 |
| I.5-221 | 100 | 20 |
| I.5-91 | 100 | 20 |
| I.6-221 | 100 | 20 |
| I.4-221 | 100 | 20 |
| I.12-221 | 100 | 20 |
| I.12-71 | 100 | 20 |
| I.12-91 | 100 | 20 |
| I.12-72 | 100 | 20 |
| I.14-221 | 100 | 20 |
| I.14-71 | 100 | 20 |
| I.14-91 | 100 | 20 |
| I.14-72 | 100 | 20 |
| I.54-221 | 100 | 20 |
| I.54-71 | 100 | 20 |
| I.54-241 | 100 | 20 |
| I.54-82 | 100 | 20 |
| I.48-82 | 100 | 20 |
| I.48-73 | 100 | 20 |
| I.48-93 | 100 | 20 |
| I.48-121 | 100 | 20 |
| I.48-92 | 100 | 20 |
| I.48-127 | 100 | 20 |

TABLE A5-continued

| Compound Example No. | Amaranthus retroflexus (Efficacy in %) | Application rate [g/ha] |
|---|---|---|
| I.1-181 | 100 | 20 |
| I.1-151 | 100 | 20 |
| I.1-81 | 100 | 20 |
| I.1-82 | 100 | 20 |
| I.1-132 | 100 | 20 |
| I.1-241 | 100 | 20 |
| I.1-334 | 100 | 20 |
| I.1-331 | 100 | 20 |
| I.1-227 | 100 | 20 |
| I.1-126 | 100 | 20 |
| I.1-91 | 100 | 20 |
| I.1-92 | 100 | 20 |
| I.1-276 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A6

| Compound Example No. | Matricaria inodora (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 100 | 80 |
| I.1-340 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-221 | 80 | 20 |
| I.48-91 | 100 | 20 |
| I.48-81 | 100 | 20 |
| I.49-71 | 100 | 20 |
| I.49-72 | 90 | 20 |
| I.49-221 | 90 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 90 | 20 |
| I.5-221 | 100 | 20 |
| I.5-91 | 90 | 20 |
| I.6-221 | 100 | 20 |
| I.4-221 | 100 | 20 |
| I.12-221 | 100 | 20 |
| I.12-71 | 80 | 20 |
| I.12-91 | 80 | 20 |
| I.12-72 | 100 | 20 |

TABLE A6-continued

| Compound Example No. | Matricaria inodora (Efficacy in %) | Application rate [g/ha] |
|---|---|---|
| I.14-221 | 80 | 20 |
| I.14-72 | 80 | 20 |
| I.54-221 | 100 | 20 |
| I.48-73 | 80 | 20 |
| I.48-121 | 100 | 20 |
| I.48-127 | 90 | 20 |
| I.1-181 | 100 | 20 |
| I.1-151 | 100 | 20 |
| I.1-81 | 90 | 20 |
| I.1-82 | 100 | 20 |
| I.1-132 | 100 | 20 |
| I.1-241 | 100 | 20 |
| I.1-334 | 100 | 20 |
| I.1-331 | 90 | 20 |
| I.1-227 | 100 | 20 |
| I.1-126 | 90 | 20 |
| I.1-91 | 100 | 20 |
| I.1-92 | 80 | 20 |
| I.1-276 | 100 | 20 |
| I.1-123 | 100 | 20 |
| I.1-41 | 90 | 20 |
| I.1-121 | 100 | 20 |
| I.1-51 | 100 | 20 |
| I.1-48 | 100 | 20 |

TABLE A7

| Compound Example No. | Polygonum convolvulus (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 100 | 80 |
| I.1-340 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-91 | 100 | 20 |
| I.48-81 | 100 | 20 |
| I.49-71 | 100 | 20 |
| I.49-221 | 100 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 90 | 20 |
| I.5-221 | 100 | 20 |
| I.5-91 | 90 | 20 |
| I.6-221 | 100 | 20 |
| I.4-221 | 100 | 20 |

TABLE A7-continued

| Compound Example No. | Polygonum convolvulus (Efficacy in %) | Application rate [g/ha] |
|---|---|---|
| I.12-221 | 100 | 20 |
| I.12-71 | 80 | 20 |
| I.12-91 | 80 | 20 |
| I.12-72 | 100 | 20 |
| I.14-221 | 80 | 20 |
| I.14-72 | 80 | 20 |
| I.54-221 | 100 | 20 |
| I.54-71 | 100 | 20 |
| I.54-241 | 100 | 20 |
| I.48-82 | 100 | 20 |
| I.48-93 | 80 | 20 |
| I.48-73 | 80 | 20 |
| I.48-92 | 80 | 20 |
| I.48-121 | 100 | 20 |
| I.48-127 | 90 | 20 |
| I.1-181 | 100 | 20 |
| I.1-151 | 100 | 20 |
| I.1-81 | 90 | 20 |
| I.1-82 | 100 | 20 |
| I.1-132 | 100 | 20 |
| I.1-241 | 100 | 20 |
| I.1-334 | 90 | 20 |
| I.1-227 | 100 | 20 |
| I.1-91 | 100 | 20 |
| I.1-92 | 100 | 20 |
| I.1-276 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A8

| Compound Example No. | Stellaria media (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 80 | 80 |
| I.1-115 | 100 | 20 |
| I.2-71 | 100 | 20 |
| I.1-180 | 90 | 20 |
| I.1-6 | 90 | 20 |
| I.1-30 | 90 | 20 |
| I.2-73 | 100 | 20 |
| I.48-221 | 100 | 20 |
| I.48-91 | 100 | 20 |
| I.48-81 | 100 | 20 |
| I.49-71 | 100 | 20 |
| I.49-221 | 90 | 20 |
| I.42-72 | 90 | 20 |
| I.2-92 | 100 | 20 |
| I.2-91 | 80 | 20 |
| I.2-81 | 100 | 20 |
| I.6-71 | 100 | 20 |
| I.6-72 | 90 | 20 |
| I.5-71 | 80 | 20 |

TABLE A8-continued

| Compound Example No. | Stellaria media (Efficacy in %) | Application rate [g/ha] |
|---|---|---|
| I.5-221 | 90 | 20 |
| I.6-221 | 80 | 20 |
| I.4-221 | 80 | 20 |
| I.12-221 | 80 | 20 |
| I.12-71 | 100 | 20 |
| I.12-91 | 100 | 20 |
| I.12-72 | 100 | 20 |
| I.54-221 | 80 | 20 |
| I.54-71 | 80 | 20 |
| I.54-241 | 80 | 20 |
| I.48-93 | 100 | 20 |
| I.48-73 | 100 | 20 |
| I.48-92 | 100 | 20 |
| I.48-121 | 80 | 20 |
| I.48-127 | 100 | 20 |
| I.1-181 | 100 | 20 |
| I.1-151 | 100 | 20 |
| I.1-82 | 80 | 20 |
| I.1-132 | 80 | 20 |
| I.1-241 | 100 | 20 |
| I.1-334 | 90 | 20 |
| I.1-331 | 80 | 20 |
| I.1-126 | 100 | 20 |
| I.1-276 | 100 | 20 |
| I.1-123 | 100 | 20 |
| I.1-121 | 100 | 20 |
| I.1-51 | 80 | 20 |
| I.1-48 | 100 | 20 |

TABLE A9

| Compound Example No. | Viola tricolor (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 100 | 80 |
| I.1-340 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-221 | 100 | 20 |
| I.48-91 | 100 | 20 |
| I.48-81 | 100 | 20 |
| I.49-71 | 100 | 20 |
| I.49-72 | 100 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |

TABLE A9-continued

| Compound Example No. | *Viola tricolor* (Efficacy in %) | Application rate [g/ha] |
| --- | --- | --- |
| I.5-72 | 100 | 20 |
| I.5-221 | 100 | 20 |
| I.5-91 | 100 | 20 |
| I.6-221 | 100 | 20 |
| I.4-221 | 100 | 20 |
| I.12-221 | 100 | 20 |
| I.12-71 | 100 | 20 |
| I.12-91 | 100 | 20 |
| I.12-72 | 100 | 20 |
| I.14-221 | 100 | 20 |
| I.14-91 | 100 | 20 |
| I.14-72 | 100 | 20 |
| I.54-71 | 100 | 20 |
| I.54-82 | 90 | 20 |
| I.48-73 | 100 | 20 |
| I.48-93 | 100 | 20 |
| I.48-121 | 100 | 20 |
| I.48-92 | 100 | 20 |
| I.48-127 | 100 | 20 |
| I.1-181 | 100 | 20 |
| I.1-151 | 100 | 20 |
| I.1-81 | 100 | 20 |
| I.1-82 | 100 | 20 |
| I.1-132 | 100 | 20 |
| I.1-241 | 100 | 20 |
| I.1-334 | 100 | 20 |
| I.1-331 | 100 | 20 |
| I.1-227 | 80 | 20 |
| I.1-126 | 100 | 20 |
| I.1-91 | 100 | 20 |
| I.1-92 | 100 | 20 |
| I.1-276 | 100 | 20 |
| I.1-123 | 100 | 20 |
| I.1-41 | 100 | 20 |
| I.1-51 | 100 | 20 |
| I.1-48 | 100 | 20 |

TABLE A10

| Compound Example No. | *Veronica persica* (Efficacy in %) | Application rate [g/ha] |
| --- | --- | --- |
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 80 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.2-73 | 100 | 20 |
| I.48-221 | 100 | 20 |
| I.48-91 | 100 | 20 |
| I.48-81 | 100 | 20 |
| I.49-71 | 100 | 20 |
| I.49-72 | 100 | 20 |
| I.49-221 | 100 | 20 |

TABLE A10-continued

| Compound Example No. | *Veronica persica* (Efficacy in %) | Application rate [g/ha] |
| --- | --- | --- |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 100 | 20 |
| I.5-221 | 100 | 20 |
| I.5-91 | 100 | 20 |
| I.6-221 | 100 | 20 |
| I.4-221 | 100 | 20 |
| I.12-221 | 100 | 20 |
| I.12-71 | 100 | 20 |
| I.12-91 | 100 | 20 |
| I.12-72 | 100 | 20 |
| I.14-221 | 100 | 20 |
| I.14-71 | 100 | 20 |
| I.14-91 | 100 | 20 |
| I.14-72 | 100 | 20 |
| I.54-221 | 80 | 20 |
| I.54-71 | 100 | 20 |
| I.54-241 | 100 | 20 |
| I.54-82 | 80 | 20 |
| I.48-73 | 100 | 20 |
| I.48-93 | 100 | 20 |
| I.48-121 | 100 | 20 |
| I.48-92 | 100 | 20 |
| I.48-127 | 100 | 20 |
| I.1-181 | 100 | 20 |
| I.1-151 | 100 | 20 |
| I.1-81 | 100 | 20 |
| I.1-82 | 100 | 20 |
| I.1-132 | 100 | 20 |
| I.1-241 | 100 | 20 |
| I.1-334 | 100 | 20 |
| I.1-331 | 100 | 20 |
| I.1-227 | 100 | 20 |
| I.1-126 | 100 | 20 |
| I.1-91 | 100 | 20 |
| I.1-92 | 100 | 20 |
| I.1-276 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A11

| Compound Example No. | *Pharbitis purpurea* (Efficacy in %) | Application rate [g/ha] |
| --- | --- | --- |
| I.2-72 | 100 | 80 |
| I.1-73 | 100 | 80 |
| I.48-71 | 100 | 80 |
| I.1-26 | 100 | 80 |
| I.1-222 | 100 | 80 |
| I.1-221 | 100 | 80 |
| I.1-341 | 100 | 80 |
| I.1-27 | 100 | 80 |
| I.48-72 | 100 | 80 |
| I.8-271 | 100 | 80 |
| I.1-2 | 100 | 80 |
| I.1-72 | 100 | 80 |
| I.1-271 | 100 | 80 |
| I.1-71 | 100 | 80 |
| I.1-1 | 100 | 80 |
| I.1-275 | 100 | 80 |
| I.1-335 | 100 | 80 |
| I.8-1 | 100 | 80 |
| I.1-224 | 100 | 80 |
| I.1-333 | 80 | 80 |

TABLE A11-continued

| Compound Example No. | Pharbitis purpurea (Efficacy in %) | Application rate [g/ha] |
|---|---|---|
| I.1-340 | 100 | 80 |
| I.1-115 | 100 | 20 |
| I.2-71 | 100 | 20 |
| I.1-180 | 100 | 20 |
| I.1-6 | 100 | 20 |
| I.1-30 | 100 | 20 |
| I.48-91 | 100 | 20 |
| I.48-81 | 100 | 20 |
| I.49-71 | 100 | 20 |
| I.49-221 | 100 | 20 |
| I.42-72 | 100 | 20 |
| I.2-336 | 100 | 20 |
| I.2-92 | 100 | 20 |
| I.2-91 | 100 | 20 |
| I.2-81 | 100 | 20 |
| I.6-71 | 100 | 20 |
| I.6-72 | 100 | 20 |
| I.5-71 | 100 | 20 |
| I.5-72 | 100 | 20 |
| I.5-221 | 100 | 20 |
| I.5-91 | 100 | 20 |
| I.6-221 | 100 | 20 |
| I.4-221 | 100 | 20 |
| I.12-71 | 100 | 20 |
| I.12-91 | 100 | 20 |
| I.14-221 | 100 | 20 |
| I.14-71 | 100 | 20 |
| I.14-91 | 80 | 20 |
| I.14-72 | 80 | 20 |
| I.54-221 | 100 | 20 |
| I.54-71 | 100 | 20 |
| I.48-73 | 100 | 20 |
| I.48-93 | 100 | 20 |
| I.48-121 | 100 | 20 |
| I.48-127 | 90 | 20 |
| I.1-151 | 100 | 20 |
| I.1-82 | 100 | 20 |
| I.1-132 | 100 | 20 |
| I.1-227 | 100 | 20 |
| I.1-126 | 100 | 20 |
| I.1-91 | 100 | 20 |
| I.1-92 | 100 | 20 |
| I.1-123 | 100 | 20 |
| I.1-41 | 100 | 20 |
| I.1-121 | 100 | 20 |
| I.1-51 | 100 | 20 |
| I.1-48 | 100 | 20 |

TABLE A12

| Compound Example No. | Hordeum murinum (Efficacy in %) | Application rate [g/ha] |
|---|---|---|
| I.2-72 | 80 | 80 |
| I.1-73 | 80 | 80 |
| I.48-71 | 80 | 80 |
| I.1-26 | 90 | 80 |
| I.1-221 | 80 | 80 |
| I.1-341 | 90 | 80 |
| I.1-27 | 80 | 80 |
| I.1-72 | 80 | 80 |
| I.1-71 | 80 | 80 |
| I.1-115 | 100 | 20 |
| I.2-336 | 80 | 20 |
| I.6-71 | 80 | 20 |
| I.4-221 | 80 | 20 |
| I.1-121 | 80 | 20 |
| I.1-48 | 80 | 20 |

TABLE A13

| Compound Example No. | Avena fatua (Efficacy in %) | Application rate [g/ha] |
|---|---|---|
| I.2-72 | 80 | 80 |
| I.1-222 | 80 | 80 |
| I.1-221 | 80 | 80 |
| I.1-341 | 90 | 80 |
| I.8-271 | 90 | 80 |
| I.1-72 | 80 | 80 |
| I.1-72 | 80 | 80 |
| I.1-115 | 80 | 20 |
| I.1-121 | 80 | 20 |

TABLE A14

| Compound Example No. | Digitaria sanguinalis (Efficacy in %) | Application rate [g/ha] |
|---|---|---|
| I.2-72 | 100 | 80 |
| I.1-73 | 100 | 80 |
| I.48-71 | 100 | 80 |
| I.1-26 | 100 | 80 |
| I.1-27 | 100 | 80 |
| I.48-72 | 100 | 80 |
| I.1-2 | 100 | 80 |
| I.1-115 | 100 | 20 |
| I.2-71 | 100 | 20 |
| I.1-6 | 100 | 20 |
| I.1-30 | 100 | 20 |
| I.48-91 | 100 | 20 |
| I.48-81 | 100 | 20 |
| I.42-72 | 100 | 20 |
| I.2-92 | 100 | 20 |
| I.2-81 | 100 | 20 |
| I.4-221 | 100 | 20 |
| I.6-71 | 100 | 20 |
| I.6-72 | 100 | 20 |
| I.5-71 | 100 | 20 |
| I.5-72 | 100 | 20 |
| I.5-221 | 80 | 20 |
| I.6-221 | 100 | 20 |
| I.54-71 | 80 | 20 |
| I.54-241 | 80 | 20 |
| I.48-121 | 80 | 20 |
| I.1-151 | 80 | 20 |
| I.1-82 | 100 | 20 |
| I.1-241 | 100 | 20 |
| I.1-126 | 80 | 20 |
| I.1-123 | 80 | 20 |
| I.1-41 | 100 | 20 |
| I.1-121 | 100 | 20 |
| I.1-51 | 100 | 20 |
| I.1-48 | 100 | 20 |

TABLE A15

| Compound Example No. | Lolium rigidum (Efficacy in %) | Application rate [g/ha] |
|---|---|---|
| I.2-72 | 80 | 80 |
| I.1-73 | 90 | 80 |
| I.48-71 | 80 | 80 |
| I.1-26 | 90 | 80 |
| I.1-222 | 90 | 80 |
| I.1-221 | 90 | 80 |
| I.1-341 | 100 | 80 |
| I.1-27 | 80 | 80 |
| I.48-72 | 80 | 80 |
| I.1-2 | 100 | 80 |
| I.1-72 | 100 | 80 |
| I.1-271 | 100 | 80 |
| I.1-1 | 90 | 80 |
| I.1-275 | 80 | 80 |
| I.5-221 | 80 | 20 |
| I.6-221 | 80 | 20 |

TABLE A15-continued

| Compound Example No. | Lolium rigidum (Efficacy in %) | Application rate [g/ha] |
|---|---|---|
| I.1-181 | 80 | 20 |
| I.1-121 | 80 | 20 |

Tables A16 to A20 below show the crop compatibilities of selected compounds of the general formula (I) according to tables I.1 to I.60 at an application rate corresponding to 80 g/ha or lower that were observed in trials according to the aforementioned trial method. The effects observed are reported here on selected crop plants by comparison with the untreated controls (values in %).

TABLE A16

| Compound Example No. | Oryza sativa (Efficacy in %) | Application rate [g/ha] |
|---|---|---|
| I.1-271 | 10 | 20 |
| I.1-222 | 20 | 80 |
| I.1-221 | 0 | 20 |
| I.1-335 | 10 | 20 |
| I.1-1 | 20 | 5 |
| I.8-1 | 10 | 5 |
| I.1-71 | 20 | 5 |
| I.1-115 | 0 | 5 |
| I.2-71 | 20 | 20 |
| I.1-180 | 0 | 20 |
| I.1-6 | 0 | 5 |
| I.1-30 | 0 | 20 |
| I.2-72 | 20 | 5 |
| I.2-73 | 10 | 20 |
| I.48-72 | 10 | 20 |
| I.48-71 | 20 | 20 |
| I.48-221 | 10 | 20 |
| I.49-71 | 10 | 20 |
| I.49-72 | 10 | 20 |
| I.49-221 | 10 | 20 |
| I.2-336 | 0 | 5 |
| I.12-221 | 20 | 20 |
| I.12-71 | 0 | 20 |
| I.12-91 | 0 | 20 |
| I.12-72 | 20 | 20 |
| I.14-221 | 10 | 20 |
| I.14-71 | 0 | 20 |
| I.14-91 | 0 | 20 |
| I.14-72 | 0 | 20 |
| I.54-221 | 20 | 20 |
| I.54-71 | 0 | 5 |
| I.54-241 | 0 | 20 |
| I.54-82 | 0 | 20 |
| I.48-72 | 0 | 5 |
| I.48-73 | 0 | 20 |
| I.48-93 | 0 | 20 |
| I.48-121 | 0 | 20 |
| I.48-92 | 10 | 20 |
| I.48-127 | 0 | 20 |
| I.1-333 | 0 | 80 |
| I.1-181 | 10 | 80 |
| I.1-224 | 10 | 20 |
| I.1-275 | 20 | 20 |
| I.1-340 | 10 | 20 |
| I.1-341 | 10 | 5 |
| I.1-151 | 20 | 20 |
| I.1-81 | 0 | 20 |
| I.1-82 | 10 | 20 |
| I.1-132 | 0 | 20 |
| I.1-241 | 10 | 20 |
| I.1-334 | 10 | 20 |
| I.1-331 | 10 | 20 |
| I.1-227 | 0 | 20 |
| I.1-126 | 0 | 20 |
| I.1-91 | 10 | 20 |
| I.1-92 | 0 | 20 |
| I.1-276 | 10 | 5 |
| I.1-26 | 10 | 5 |

TABLE A16-continued

| Compound Example No. | Oryza sativa (Efficacy in %) | Application rate [g/ha] |
|---|---|---|
| I.1-27 | 10 | 5 |
| I.1-23 | 10 | 5 |
| I.1-73 | 5 | 20 |

TABLE A17

| Compound Example No. | Zea mays (Efficacy in %) | Application rate [g/ha] |
|---|---|---|
| I.1-271 | 10 | 20 |
| I.8-271 | 20 | 80 |
| I.1-222 | 20 | 20 |
| I.1-221 | 10 | 5 |
| I.1-335 | 10 | 80 |
| I.1-1 | 20 | 20 |
| I.8-1 | 20 | 5 |
| I.1-71 | 20 | 80 |
| I.1-72 | 20 | 20 |
| I.1-115 | 20 | 5 |
| I.2-71 | 0 | 5 |
| I.48-221 | 20 | 80 |
| I.12-221 | 0 | 5 |
| I.12-71 | 0 | 5 |
| I.12-91 | 0 | 5 |
| I.12-72 | 0 | 5 |
| I.14-71 | 0 | 20 |
| I.14-91 | 20 | 20 |
| I.54-221 | 00 | 20 |
| I.54-82 | 20 | 5 |
| I.48-92 | 10 | 5 |
| I.48-127 | 20 | 5 |
| I.1-333 | 0 | 80 |
| I.1-181 | 20 | 80 |
| I.1-224 | 20 | 80 |
| I.1-340 | 0 | 80 |
| I.1-341 | 10 | 20 |
| I.1-151 | 20 | 5 |
| I.1-81 | 10 | 20 |
| I.1-82 | 20 | 20 |
| I.1-132 | 20 | 20 |
| I.1-334 | 20 | 20 |
| I.1-227 | 20 | 20 |
| I.1-126 | 20 | 20 |
| I.1-91 | 20 | 20 |
| I.1-92 | 20 | 20 |

TABLE A18

| Compound Example No. | Brassica napis (Efficacy in %) | Application rate [g/ha] |
|---|---|---|
| I.1-271 | 20 | 5 |
| I.2-71 | 20 | 5 |
| I.12-221 | 0 | 5 |
| I.54-241 | 0 | 5 |
| I.54-82 | 0 | 5 |
| I.48-82 | 20 | 5 |
| I.48-121 | 20 | 5 |
| I.1-333 | 0 | 20 |
| I.1-224 | 20 | 20 |
| I.1-340 | 10 | 20 |
| I.1-341 | 0 | 5 |
| I.1-81 | 10 | 5 |
| I.1-82 | 0 | 5 |
| I.1-227 | 0 | 5 |
| I.1-126 | 10 | 5 |
| I.1-91 | 10 | 5 |

TABLE A19

| Compound Example No. | Glycine max (Efficacy in %) | Application rate [g/ha] |
|---|---|---|
| I.1-271 | 20 | 5 |
| I.8-1 | 20 | 5 |
| I.1-71 | 20 | 20 |
| I.1-72 | 10 | 20 |
| I.54-82 | 0 | 5 |
| I.4-221 | 20 | 5 |
| I.12-91 | 0 | 5 |
| I.12-72 | 20 | 5 |
| I.14-71 | 0 | 20 |
| I.14-91 | 20 | 20 |
| I.14-72 | 20 | 20 |
| I.54-82 | 20 | 5 |
| I.1-333 | 20 | 20 |
| I.1-181 | 20 | 20 |
| I.1-340 | 20 | 20 |
| I.1-341 | 10 | 25 |
| I.1-227 | 20 | 5 |

TABLE A20

| Compound Example No. | Triticum aestivum (Efficacy in %) | Application rate [g/ha] |
|---|---|---|
| I.1-271 | 20 | 20 |
| I.1-222 | 20 | 80 |
| I.1-221 | 20 | 20 |
| I.1-335 | 20 | 80 |
| I.1-1 | 20 | 5 |
| I.1-71 | 20 | 80 |
| I.1-72 | 0 | 20 |
| I.2-71 | 20 | 20 |
| I.1-180 | 20 | 20 |
| I.1-30 | 20 | 20 |
| I.2-72 | 20 | 80 |
| I.48-72 | 20 | 20 |
| I.48-71 | 20 | 20 |
| I.48-91 | 20 | 5 |
| I.48-81 | 20 | 20 |
| I.49-71 | 20 | 20 |
| I.42-72 | 20 | 20 |
| I.2-92 | 20 | 5 |
| I.2-91 | 20 | 5 |
| I.2-81 | 20 | 20 |
| I.6-71 | 20 | 20 |
| I.6-72 | 20 | 5 |
| I.5-71 | 10 | 20 |
| I.5-72 | 20 | 20 |
| I.5-221 | 20 | 20 |
| I.5-91 | 10 | 20 |
| I.12-221 | 20 | 20 |
| I.12-71 | 0 | 5 |
| I.12-91 | 0 | 5 |
| I.12-72 | 0 | 20 |
| I.14-221 | 20 | 20 |
| I.14-71 | 0 | 20 |
| I.14-91 | 20 | 20 |
| I.14-72 | 20 | 20 |
| I.54-221 | 0 | 20 |
| I.54-71 | 20 | 5 |
| I.54-241 | 0 | 20 |
| I.54-82 | 0 | 5 |
| I.48-82 | 0 | 5 |
| I.48-73 | 0 | 20 |
| I.48-93 | 0 | 20 |
| I.48-121 | 0 | 20 |
| I.48-92 | 0 | 20 |
| I.48-127 | 10 | 20 |
| I.1-333 | 10 | 20 |
| I.1-181 | 20 | 20 |
| I.1-224 | 20 | 20 |
| I.1-275 | 20 | 20 |
| I.1-340 | 20 | 20 |
| I.1-341 | 10 | 20 |
| I.1-151 | 20 | 5 |
| I.1-81 | 20 | 20 |
| I.1-82 | 0 | 5 |
| I.1-132 | 10 | 5 |
| I.1-241 | 20 | 5 |
| I.1-227 | 10 | 5 |
| I.1-126 | 20 | 20 |
| I.1-91 | 10 | 5 |
| I.1-92 | 10 | 20 |
| I.1-2 | 20 | 5 |
| I.1-26 | 20 | 5 |
| I.1-27 | 10 | 5 |
| I.1-73 | 20 | 80 |
| I.1-123 | 20 | 20 |
| I.1-41 | 20 | 20 |
| I.1-51 | 20 | 20 |
| I.1-48 | 10 | 5 |

As the results show, inventive compounds of the general formula (I) in the case of post-emergence treatment exhibit good herbicidal efficacy against harmful plants such as, for example, *Abutilon theophrasti, Alopecurus myosuroides, Amaranthus retroflexus, Avena fatua, Digitaria sanguinalis, Echinochloa crus-galli, Hordeum murinum, Lolium rigidum, Matricaria inodora, Pharbitis purpurea, Polygonum convolvulus, Setaria viridis, Stellaria media, Veronica persica* and *Viola tricolor* at an application rate 0.02 to 0.08 kg of active substance per hectare.

The tested crop plants *Brassica napus, Glycine max, Oryza sativa, Triticum aestivum* and *Zea mays* are impaired only to a minor degree, if at all, after application of inventive compounds of the general formula (I) at an application rate of 0.005 to 0.08 kg of active substance per hectare.

B. Herbicidal Action and Crop Compatibility Pre-Emergence

Seeds of mono- and dicotyledonous weeds and crop plants were laid out in plastic or organic plant pots and covered with soil. The compounds of the invention formulated in the form of wettable powders (WP) or emulsion concentrates (EC) were then applied to the surface of the covering soil as an aqueous suspension or emulsion with addition of 0.5% additive at a water application rate equivalent to 600 L/ha. After the treatment, the pots were placed in a greenhouse and kept under good growth conditions for the test plants. After about 3 weeks, the efficacy of the preparations was scored visually as a percentage by comparison with untreated controls. For example, 100% efficacy=plants have died, 0% efficacy=like control plants.

Crop compatibilities were also scored correspondingly.

Tables B1 to B16 below show the efficacies of selected compounds of the general formula (I) according to tables I.1 to I.60 on various harmful plants and an application rate corresponding to 320 g/ha or lower that were obtained by the aforementioned trial method.

TABLE B1

| Compound Example No. | Alopecurus myosuroides (Efficacy in %) | Application rate [g/ha] |
|---|---|---|
| I.1-271 | 100 | 320 |
| I.8-271 | 90 | 320 |
| I.1-222 | 100 | 320 |
| I.1-221 | 90 | 320 |
| I.1-335 | 90 | 320 |
| I.1-1 | 80 | 320 |
| I.1-27 | 80 | 320 |

TABLE B1-continued

| Compound Example No. | *Alopecurus myosuroides* (Efficacy in %) | Application rate [g/ha] |
| --- | --- | --- |
| I.1-71 | 100 | 320 |
| I.1-72 | 90 | 320 |
| I.2-72 | 100 | 320 |
| I.48-72 | 90 | 320 |
| I.48-71 | 100 | 320 |
| I.1-333 | 100 | 320 |
| I.1-224 | 100 | 320 |
| I.1-275 | 100 | 320 |
| I.1-340 | 90 | 320 |
| I.1-341 | 90 | 320 |
| I.1-2 | 80 | 320 |
| I.1-181 | 100 | 320 |

TABLE B2

| Compound Example No. | *Echinochloa crus-galli* (Efficacy in %) | Application rate [g/ha] |
| --- | --- | --- |
| I.1-271 | 100 | 320 |
| I.8-271 | 80 | 320 |
| I.1-222 | 100 | 320 |
| I.1-221 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.48-72 | 100 | 320 |
| I.48-71 | 100 | 320 |
| I.1-333 | 100 | 320 |
| I.1-224 | 100 | 320 |
| I.1-275 | 100 | 320 |
| I.1-340 | 100 | 320 |
| I.1-341 | 100 | 320 |
| I.1-2 | 100 | 320 |
| I.1-26 | 100 | 320 |
| I.1-27 | 100 | 320 |
| I.1-23 | 100 | 320 |
| I.1-73 | 100 | 320 |
| I.2-71 | 100 | 80 |
| I.1-181 | 100 | 320 |

TABLE B3

| Compound Example No. | *Setaria viridis* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 90 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |

TABLE B3-continued

| Compound Example No. | *Setaria viridis* (Efficacy in %) | Application rate [g/ha] |
| --- | --- | --- |
| I.1-181 | 100 | 320 |
| I.1-82 | 100 | 80 |

TABLE B4

| Compound Example No. | *Abutilon theophrasti* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |
| I.1-181 | 100 | 320 |
| I.1-81 | 100 | 80 |
| I.1-82 | 100 | 80 |
| I.1-132 | 100 | 80 |
| I.1-227 | 100 | 80 |
| I.1-126 | 100 | 80 |
| I.1-91 | 100 | 80 |
| I.1-92 | 100 | 80 |

TABLE B5

| Compound Example No. | *Amaranthus retroflexus* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |
| I.1-181 | 100 | 320 |
| I.1-81 | 100 | 80 |
| I.1-82 | 100 | 80 |
| I.1-132 | 100 | 80 |
| I.1-227 | 100 | 80 |

TABLE B5-continued

| Compound Example No. | *Amaranthus retroflexus* (Efficacy in %) | Application rate [g/ha] |
| --- | --- | --- |
| I.1-126 | 100 | 80 |
| I.1-91 | 100 | 80 |
| I.1-92 | 100 | 80 |

TABLE B6

| Compound Example No. | *Matricaria inodora* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |
| I.1-181 | 100 | 320 |
| I.1-81 | 80 | 80 |
| I.1-82 | 100 | 80 |
| I.1-132 | 100 | 80 |
| I.1-227 | 90 | 80 |
| I.1-126 | 100 | 80 |
| I.1-91 | 100 | 80 |
| I.1-92 | 100 | 80 |

TABLE B7

| Compound Example No. | *Polygonum convolvulus* (Efficacy in %) | Application rate [g/ha] |
| --- | --- | --- |
| I.1-271 | 320 | 100 |
| I.1-275 | 320 | 100 |
| I.1-27 | 320 | 100 |
| I.1-341 | 320 | 100 |
| I.1-335 | 320 | 100 |
| I.1-1 | 320 | 100 |
| I.8-1 | 320 | 100 |
| I.1-71 | 320 | 100 |
| I.1-72 | 320 | 100 |
| I.2-72 | 320 | 100 |
| I.1-73 | 320 | 100 |
| I.1-26 | 320 | 100 |
| I.1-333 | 320 | 100 |
| I.1-224 | 320 | 90 |
| I.8-271 | 320 | 100 |
| I.1-222 | 320 | 100 |
| I.1-221 | 320 | 100 |
| I.48-72 | 320 | 100 |
| I.48-71 | 320 | 100 |
| I.1-340 | 320 | 100 |
| I.1-2 | 320 | 100 |
| I.1-23 | 320 | 100 |
| I.2-71 | 100 | 80 |
| I.1-81 | 100 | 80 |

TABLE B8

| Compound Example No. | *Stellaria media* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 90 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.2-71 | 100 | 80 |
| I.1-181 | 100 | 320 |
| I.1-82 | 100 | 80 |

TABLE B9

| Compound Example No. | *Viola tricolor* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |
| I.1-181 | 100 | 320 |
| I.1-81 | 100 | 80 |
| I.1-82 | 100 | 80 |
| I.1-132 | 90 | 80 |
| I.1-227 | 80 | 80 |
| I.1-91 | 100 | 80 |

TABLE B10

| Compound Example No. | *Veronica persica* (Efficacy in %) | Application rate [g/ha] |
| --- | --- | --- |
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |

TABLE B10-continued

| Compound Example No. | Veronica persica (Efficacy in %) | Application rate [g/ha] |
|---|---|---|
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.48-72 | 100 | 320 |
| I.48-71 | 100 | 320 |
| I.1-340 | 100 | 320 |
| I.1-2 | 100 | 320 |
| I.2-71 | 100 | 80 |
| I.1-181 | 100 | 320 |
| I.1-81 | 80 | 80 |
| I.1-82 | 100 | 80 |
| I.1-91 | 100 | 80 |

TABLE B11

| Compound Example No. | Pharbitis purpurea (Efficacy in %) | Application rate [g/ha] |
|---|---|---|
| I.1-271 | 100 | 320 |
| I.1-275 | 100 | 320 |
| I.1-27 | 100 | 320 |
| I.1-341 | 100 | 320 |
| I.1-335 | 100 | 320 |
| I.1-1 | 100 | 320 |
| I.8-1 | 100 | 320 |
| I.1-71 | 100 | 320 |
| I.1-72 | 100 | 320 |
| I.2-72 | 100 | 320 |
| I.1-73 | 100 | 320 |
| I.1-26 | 100 | 320 |
| I.1-333 | 100 | 320 |
| I.1-224 | 100 | 320 |
| I.8-271 | 100 | 320 |
| I.1-222 | 100 | 320 |
| I.1-221 | 100 | 320 |
| I.48-72 | 100 | 320 |
| I.48-71 | 100 | 320 |
| I.1-340 | 100 | 320 |
| I.1-2 | 100 | 320 |
| I.1-23 | 100 | 320 |
| I.2-71 | 100 | 80 |
| I.1-181 | 100 | 320 |
| I.1-82 | 100 | 80 |

TABLE B12

| Compound Example No. | Hordeum murinum (Efficacy in %) | Application rate [g/ha] |
|---|---|---|
| I.1-271 | 100 | 320 |
| I.1-275 | 90 | 320 |
| I.1-27 | 80 | 320 |
| I.1-341 | 80 | 320 |
| I.1-335 | 90 | 320 |
| I.1-1 | 90 | 320 |
| I.8-1 | 90 | 320 |
| I.1-71 | 90 | 320 |
| I.1-72 | 90 | 320 |
| I.2-72 | 90 | 320 |
| I.1-73 | 90 | 320 |
| I.1-26 | 100 | 320 |
| I.1-333 | 100 | 320 |
| I.1-224 | 100 | 320 |
| I.1-222 | 90 | 320 |
| I.1-221 | 100 | 320 |
| I.1-181 | 90 | 320 |

TABLE B13

| Compound Example No. | Avena fatua (Efficacy in %) | Application rate [g/ha] |
|---|---|---|
| I.1-271 | 100 | 320 |
| I.8-271 | 90 | 320 |
| I.1-222 | 100 | 320 |
| I.1-221 | 100 | 320 |
| I.1-335 | 100 | 320 |
| I.1-1 | 90 | 320 |
| I.8-1 | 80 | 320 |
| I.1-71 | 90 | 320 |
| I.1-72 | 100 | 320 |
| I.2-72 | 80 | 320 |
| I.48-72 | 80 | 320 |
| I.48-71 | 80 | 320 |
| I.1-333 | 100 | 320 |
| I.1-224 | 100 | 320 |
| I.1-275 | 100 | 320 |
| I.1-340 | 80 | 320 |
| I.1-341 | 90 | 320 |
| I.1-2 | 90 | 320 |
| I.1-26 | 80 | 320 |
| I.1-73 | 90 | 320 |
| I.1-181 | 100 | 320 |

TABLE B14

| Compound Example No. | Digitaria sanguinalis (Efficacy in %) | Application rate [g/ha] |
|---|---|---|
| I.1-26 | 100 | 80 |
| I.1-27 | 100 | 80 |
| I.2-72 | 100 | 80 |
| I.48-72 | 100 | 80 |
| I.48-71 | 100 | 80 |
| I.1-73 | 100 | 80 |
| I.1-2 | 100 | 80 |
| I.2-71 | 100 | 80 |
| I.1-82 | 80 | 80 |

TABLE B15

| Compound Example No. | Lolium rigidum (Efficacy in %) | Application rate [g/ha] |
|---|---|---|
| I.1-271 | 100 | 320 |
| I.1-275 | 90 | 320 |
| I.1-27 | 90 | 320 |
| I.1-341 | 100 | 320 |
| I.1-335 | 100 | 320 |
| I.1-1 | 80 | 320 |
| I.8-1 | 90 | 320 |
| I.1-71 | 90 | 320 |
| I.1-72 | 100 | 320 |
| I.2-72 | 90 | 320 |
| I.1-73 | 100 | 320 |
| I.1-26 | 90 | 320 |
| I.1-333 | 100 | 320 |
| I.1-224 | 100 | 320 |
| I.1-222 | 100 | 320 |
| I.1-221 | 100 | 320 |
| I.48-72 | 80 | 320 |
| I.48-71 | 90 | 320 |
| I.1-340 | 100 | 320 |
| I.1-2 | 90 | 320 |
| I.1-181 | 100 | 80 |

TABLE B16

| Compound Example No. | *Cyperus esculentus* (Efficacy in %) | Application rate [g/ha] |
| --- | --- | --- |
| I.1-271 | 80 | 320 |
| I.1-224 | 90 | 320 |
| I.1-222 | 100 | 320 |
| I.1-221 | 100 | 320 |
| I.1-275 | 80 | 320 |
| I.1-1 | 100 | 320 |
| I.8-1 | 90 | 320 |
| I.1-71 | 80 | 320 |
| I.1-72 | 80 | 320 |
| I.1-333 | 80 | 320 |

Tables B17 to B19 below show the crop compatibilities of selected compounds of the general formula (I) according to tables I.1 to I.60 at an application rate corresponding to 320 g/ha or lower that were observed in trials according to the aforementioned trial method. The effects observed are reported here on selected crop plants by comparison with the untreated controls (values in %).

TABLE B17

| Compound Example No. | *Oryza sativa* (Efficacy in %) | Application rate [g/ha] |
| --- | --- | --- |
| I.1-271 | 20 | 20 |
| I.8-271 | 0 | 80 |
| I.2-71 | 0 | 20 |
| I.1-181 | 0 | 20 |
| I.1-224 | 0 | 20 |
| I.1-126 | 20 | 80 |
| I.1-92 | 10 | 80 |

TABLE B18

| Compound Example No. | *Zea mays* (Efficacy in %) | Application rate [g/ha] |
| --- | --- | --- |
| I.1-271 | 0 | 20 |
| I.8-271 | 20 | 80 |
| I.1-222 | 20 | 20 |
| I.1-221 | 0 | 20 |
| I.1-335 | 20 | 20 |
| I.1-1 | 20 | 20 |
| I.1-71 | 0 | 80 |
| I.1-72 | 20 | 80 |
| I.2-71 | 10 | 80 |
| I.2-72 | 10 | 80 |
| I.48-72 | 0 | 320 |
| I.48-71 | 20 | 320 |
| I.1-333 | 20 | 80 |
| I.1-181 | 0 | 20 |
| I.1-224 | 0 | 20 |
| I.1-340 | 0 | 80 |
| I.1-341 | 0 | 80 |
| I.1-81 | 0 | 80 |
| I.1-82 | 0 | 80 |
| I.1-227 | 0 | 80 |
| I.1-132 | 0 | 80 |
| I.1-126 | 0 | 80 |
| I.1-91 | 0 | 80 |
| I.1-92 | 0 | 80 |
| I.1-2 | 0 | 20 |
| I.1-26 | 10 | 80 |
| I.1-27 | 0 | 80 |
| I.1-23 | 10 | 80 |
| I.1-73 | 0 | 80 |

TABLE B19

| Compound Example No. | *Glycine max* (Efficacy in %) | Application rate [g/ha] |
| --- | --- | --- |
| I.1-271 | 10 | 20 |
| I.1-222 | 10 | 20 |
| I.1-71 | 0 | 80 |
| I.1-72 | 20 | 80 |
| I.2-71 | 0 | 80 |
| I.2-72 | 20 | 20 |
| I.48-72 | 10 | 320 |
| I.48-71 | 0 | 20 |
| I.1-333 | 0 | 80 |
| I.1-181 | 20 | 80 |
| I.1-224 | 0 | 20 |
| I.1-340 | 20 | 80 |
| I.1-81 | 0 | 80 |
| I.1-132 | 20 | 80 |
| I.1-126 | 10 | 80 |
| I.1-91 | 20 | 80 |
| I.1-26 | 0 | 20 |
| I.1-27 | 20 | 80 |
| I.1-23 | 0 | 80 |
| I.1-73 | 0 | 80 |

As the results show, inventive compounds of the general formula (I) in the case of pre-emergence treatment exhibit good herbicidal efficacy against harmful plants, for example against harmful plants such as *Abutilon theophrasti, Alopecurus myosuroides, Amaranthus retroflexus, Avena fatua, Cyperus esculentus, Digitaria sanguinalis, Echinocloa crusgalli, Hordeum murinum, Lolium rigidum, Matricaria inodora, Pharbitis purpurea, Polygonum convolvulus, Setaria viridis, Stellaria media, Veronica persica* and Viola tricolor at an application rate of 0.32 kg of active substance per hectare. The tested crop plants *Glycine max, Oryza sativa* and *Zea mays* are impaired only to a minor degree, if at all, after application of inventive compounds of the general formula (I) at an application rate of 0.02 to 0.32 kg of active substance per hectare.

The invention claimed is:

1. A substituted thiophenyluracil of formula (I) or salt thereof,

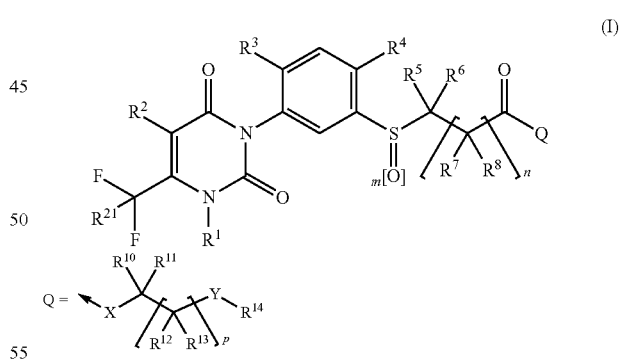

wherein
$R^1$ is methyl, ethyl, n-propyl, 1-methylethyl, n-butyl, 1-methylpropyl, 2-methylpropyl, 1,1-dimethylethyl, n-pentyl, amino, dimethylamino, or diethylamino,
$R^2$ is hydrogen, methyl, ethyl, n-propyl, or isopropyl,
$R^3$ is hydrogen, fluorine, chlorine, bromine, methoxy, or ethoxy,
$R^4$ is halogen, cyano, $C(O)NH_2$, $C(S)NH_2$, difluoromethyl, trifluoromethyl, ethynyl, or propyn-1-yl,
$R^5$ and $R^6$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, ethynyl, 1-propynyl, 2-propynyl, 1-butynyl, 2-butynyl, 3-butynyl, trifluoromethyl, pentafluoroethyl, 1,1,2,2-tetrafluoroethyl, heptafluoropropyl, nonafluorobutyl, difluoromethyl, 2,2-difluoroethyl, 2,2,2-trifluoroethyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, phenyl, 2-fluorophenyl, 3-fluorophenyl, 4-fluorophenyl, 2,4-difluorophenyl, 2-chlorophenyl, 3-chlorophenyl, 4-chlorophenyl, 2,4-dichlorophenyl, 2,5-dichlorophenyl, 3,4-dichlorophenyl, 3,5-dichlorophenyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, phenylethyl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, methylthiomethyl, ethylthiomethyl, ethylthioethyl, methylthioethyl, n-propylthiomethyl, isopropylthiomethyl, trifluoromethylthiomethyl, or trifluoromethylthioethyl, or $R^5$ and $R^6$ together with the carbon atom to which they are bonded form a double bond optionally substituted by $R^{22}$ and $R^{23}$, according to formula (I') below (I')

$R^7$ and $R^8$ are independently hydrogen, fluorine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, cyclohexylmethyl, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, trifluoromethyl, pentafluoroethyl, 1,1,2,2-tetrafluoroethyl, heptafluoropropyl, difluoromethyl, 2,2-difluoroethyl, 2,2,2-trifluoroethyl, difluoro-tert-butyl, methoxy, ethoxy, n-propyloxy, isopropyloxy, n-butyloxy, tert-butyloxy, methoxymethyl, ethoxymethyl, n-propyloxymethyl, isopropyloxymethyl, methoxyethyl, ethoxyethyl, n-propyloxyethyl, isopropyloxyethyl, methoxy-n-propyl, 2-fluorophenyl, 3-fluorophenyl, 4-fluorophenyl, 2,4-difluorophenyl, 2,5-difluorophenyl, 2,6-difluorophenyl, 2,3-difluorophenyl, 3,4-difluorophenyl, 3,5-difluorophenyl, 2,4,5-trifluorophenyl, 3,4,5-trifluorophenyl, 2-chlorophenyl, 3-chlorophenyl, 4-chlorophenyl, 2,4-dichlorophenyl, 2,5-dichlorophenyl, 2,6-dichlorophenyl, 2,3-dichlorophenyl, 3,4-dichlorophenyl, 3,5-dichlorophenyl, 2,4,5-trichlorophenyl, 3,4,5-trichlorophenyl, 2,4,6-trichlorophenyl, pyridin-2-yl, pyridin-3-yl, pyridin-4-yl, thiophen-2-yl, thiophen-3-yl, furan-2-yl, tetrahydrofuran-2-yl, tetrahydrofuran-3-yl, 1-(4-methylphenyl)ethyl, 1-(3-methylphenyl)ethyl, 1-(2-methylphenyl)ethyl, 1-(4-chlorophenyl)ethyl, 1-(3-chlorophenyl)ethyl, 1-(2-chlorophenyl)ethyl, benzyl, (4-fluorophenyl)methyl, (3-fluorophenyl)methyl, (2-fluorophenyl)methyl, (2,4-difluorophenyl)methyl, (3,5-difluorophenyl)methyl, (2,5-difluorophenyl)methyl, (2,6-difluorophenyl)methyl, (2,4,5-trifluorophenyl)methyl, (2,4,6-trifluorophenyl)methyl, (4-chlorophenyl)methyl, (3-chlorophenyl)methyl, (2-chlorophenyl)methyl, (2,4-dichlorophenyl)methyl, (3,5-dichlorophenyl)methyl, (2,5-dichlorophenyl)methyl, (2,6-dichlorophenyl)methyl, (2,4,5-trichlorophenyl)methyl, (2,4,6-trichlorophenyl)methyl, methylthiomethyl, ethylthiomethyl, ethylthioethyl, methylthioethyl, n-propylthiomethyl, isopropylthioethyl, trifluoromethylthiomethyl, or trifluoromethylthioethyl, or $R^7$ and $R^8$ together with the carbon atom to which they are bonded form a double bond optionally substituted by $R^{22}$ and $R^{23}$, according to formula (I″) below

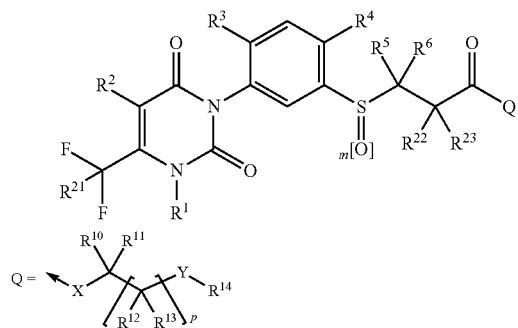

m is 0, 1, or 2, n is 0, 1, 2, or 3, $R^{21}$ is hydrogen, fluorine, chlorine, bromine, trifluoromethyl, methoxy, ethoxy, n-propyloxy, or n-butyloxy, $R^{22}$ and $R^{23}$ are independently hydrogen, fluorine, chlorine, bromine, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, cyclopropyl, cyclobutyl, cyclopentyl, cyclohexyl, trifluoromethyl, difluoromethyl, pentafluoroethyl, ethenyl, 1-propenyl, 1-methylethenyl, 1-butenyl, or phenyl, and Q is selected from the group consisting of Q-71, Q-72 and Q-73

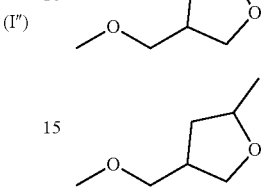

2. A compound of formula (I) and/or salts thereof as of claim 1, wherein the compound is used as a herbicide and/or plant growth regulator.

3. A herbicidal and/or plant growth-regulating composition, comprising one or more compounds of the formula (I) and/or salts thereof as defined in claim 1 and one or more further substances selected from groups (i) and/or (ii)
   (i) one or more further active agrochemical ingredients,
   (ii) one or more formulation auxiliaries customary in crop protection.

4. A method of controlling harmful plants or of regulating the growth of plants, wherein an effective amount of
   one or more compounds of the formula (I) and/or salts thereof as defined in claim 1 or
   a composition comprising one or more compounds of the formula(I) and/or salts as defined in claim 1
is applied to the plants, plant seeds, the soil in or on which the plants grow, or the cultivation area, wherein the composition optionally further comprises or more further substances selected from groups (i) and/or (ii):
   (i) one or more further active agrochemical ingredients,
   (ii) one or more formulation auxiliaries customary in crop protection.

* * * * *